(12) United States Patent
Rupley et al.

(10) Patent No.: US 12,121,295 B2
(45) Date of Patent: Oct. 22, 2024

(54) MAGNETICALLY COUPLED ABLATION COMPONENTS

(71) Applicant: AtriCure, Inc., Mason, OH (US)

(72) Inventors: Geni Giannotti Rupley, Cincinnati, OH (US); Salvatore Privitera, Mason, OH (US); Peter Joseph France, Fort Mitchell, KY (US); Adam Harp, Cincinnati, OH (US); Kenneth Lance Miller, Hamilton, OH (US); Matthew Monti, Cincinnati, OH (US); Jackson Thomas Romelli, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 18/345,010

(22) Filed: Jun. 30, 2023

(65) Prior Publication Data
US 2024/0050151 A1 Feb. 15, 2024

Related U.S. Application Data

(63) Continuation of application No. PCT/US2022/082057, filed on Dec. 20, 2022.
(Continued)

(51) Int. Cl.
*A61B 18/18* (2006.01)
*A61B 18/14* (2006.01)
(Continued)

(52) U.S. Cl.
CPC ............ *A61B 18/1492* (2013.01); *A61B 2017/00561* (2013.01); *A61B 2017/00876* (2013.01);
(Continued)

(58) Field of Classification Search
CPC ............ A61B 18/1492; A61B 18/18; A61B 2017/00876; A61B 2018/00023;
(Continued)

(56) References Cited

U.S. PATENT DOCUMENTS 8,048,072 B2  11/2011  Verin et al.
9,060,761 B2  6/2015  Hastings et al.
(Continued)

FOREIGN PATENT DOCUMENTS

WO PCT/US2022/082057  6/2024

*Primary Examiner* — Michael F Peffley
*Assistant Examiner* — Amanda L Zink
(74) *Attorney, Agent, or Firm* — Dorton & Willis LLP; Ryan Willis

(57) ABSTRACT

Ablation systems, components thereof, and related methods are disclosed. An example ablation system may include a first ablation component including a first ablation component end effector configured to be positioned on a first side of a target tissue and a second ablation component including a second ablation component end effector configured to be positioned on a second side of the target tissue. The first ablation component may include a first ablation component permanent magnet that is translationally repositionable between an engaged configuration and a disengaged configuration. The second ablation component may include a second ablation component permanent magnet that is freely rotatable and is configured to rotatably self-orient into a magnetically attractive orientation with the first ablation component permanent magnet.

43 Claims, 54 Drawing Sheets

Related U.S. Application Data

(60) Provisional application No. 63/383,004, filed on Nov. 9, 2022, provisional application No. 63/365,692, filed on Jun. 1, 2022, provisional application No. 63/294,191, filed on Dec. 28, 2021.

(51) Int. Cl.
*A61B 17/00* (2006.01)
*A61B 18/00* (2006.01)

(52) U.S. Cl.
CPC ......... *A61B 2018/00023* (2013.01); *A61B 2018/00577* (2013.01); *A61B 2218/002* (2013.01)

(58) Field of Classification Search
CPC ........... A61B 2018/00363; A61B 2018/00559; A61B 2018/00577; A61B 2018/00642; A61B 2018/00714; A61B 2018/00791; A61B 2018/00875; A61B 2018/00982; A61B 2018/126; A61B 2034/732; A61B 34/20; A61B 34/73; A61B 5/062; A61B 5/283; A61B 5/287; A61B 5/29
See application file for complete search history.

(56) References Cited

U.S. PATENT DOCUMENTS

| | | |
|---|---|---|
| 9,603,660 B2 | 3/2017 | Doty et al. |
| 2008/0091193 A1 | 4/2008 | Kauphusman et al. |
| 2009/0124847 A1* | 5/2009 | Doty ............... A61B 18/1442 606/50 |
| 2011/0288544 A1 | 11/2011 | Verin et al. |
| 2014/0142565 A1* | 5/2014 | Doty ..................... A61B 18/18 606/33 |
| 2022/0096174 A1 | 3/2022 | Harlev et al. |

\* cited by examiner

MAGNETICALLY COUPLED ABLATION COMPONENTS

CROSS REFERENCE TO RELATED APPLICATIONS

This application is a continuation of International Application No. PCT/US2022/082057, filed Dec. 20, 2022, titled "MAGNETICALLY COUPLED ABLATION COMPONENTS," which claims the benefit of U.S. Provisional Application No. 63/294,191, filed Dec. 28, 2021, titled "MAGNETICALLY COUPLED ABLATION COMPONENTS," U.S. Provisional Application No. 63/365,692, filed Jun. 1, 2022, titled "MAGNETICALLY COUPLED ABLATION COMPONENTS," and U.S. Provisional Application No. 63/383,004, filed Nov. 9, 2022, titled "MAGNETICALLY COUPLED ABLATION COMPONENTS," each of which is incorporated by reference herein in its entirety.

INTRODUCTION

The present disclosure is directed to medical devices and related methods, and, more specifically, to devices for ablating tissue and related methods.

The present disclosure contemplates that heart arrhythmias affect millions of people in the United States. For example, atrial fibrillation is a heart arrhythmia in which the electrical activity of the upper chambers of the heart is disorganized. Other common arrhythmias include ventricular tachycardia, and/or inappropriate sinus tachycardia.

The present disclosure contemplates that treatments for cardiac arrhythmias may include creating an anatomical based lesion pattern ("maze") of scar lesions and/or targeted spot or linear lesions per electrical mapping of a patient's heart to interrupt the errant electrical impulses in the heart tissue. The lesions may be created by cutting the cardiac tissue and sewing it back together. Alternatively, the lesions may be created by ablating the cardiac tissue using a variety of modalities, such as radiofrequency (RF) energy ablation, pulsed field ablation, cryoablation, ultrasound ablation, and/or laser ablation, for example. As used herein, "ablation" may refer to the removal or destruction of a function of a body part, such as cardiac tissue, regardless of the apparatus or process used to carry out the ablation.

The present disclosure contemplates that, in some circumstances, it may be desirable for cardiac ablation lesions to span the entire thickness of the heart tissue. Thus, some ablation apparatus and methods may be configured to create transmural lesions. As used herein, "transmural" may refer to through the wall or thickness, such as through the wall or thickness of a hollow organ or vessel.

The present disclosure contemplates that because RF ablation delivers energy between two electrodes to heat the target tissue, an effective electrode configuration for achieving transmural lesions with RF energy may include ablation electrodes positioned on either side of the tissue targeted for ablation. Similar approaches may be utilized with other ablation modalities.

The present disclosure contemplates that, in the context of cardiac ablation, catheter-based ablation devices may be used for accessing the endocardial (interior) surface of the heart, but may not have easy access to the epicardial (exterior) surface of the heart. Surgical-based ablation devices may easily access the epicardial surface, either through open-chest procedures or minimally invasive procedures, but may require atriotomies to directly access the endocardial surface. In other circumstances, epicardial access may be obtained percutaneously. Some devices may use vacuum to fold tissue so that the endocardial surfaces are between electrodes, but these devices may be limited by the size of tissue that can be engaged. RF clamp devices may include electrodes on opposing jaws and can be used epicardially by pinching together two walls or with one jaw endocardial and the opposing jaw epicardial.

The present disclosure contemplates that problems encountered in cardiac ablation procedures may include difficulty in precisely locating ablation apparatus on the target tissue and difficulties related to the ablation of the tissue. For example, in some circumstances, it may be difficult to create a sufficiently continuous, sufficiently deep (e.g., transmural) line of ablated tissue, which may be necessary to electrically isolate a portion of the heart.

While known devices have been used to ablate tissue (such as cardiac tissue), improvements in the construction and operation of devices for ablating tissue may be beneficial for users (e.g., surgeons, electrophysiologists, interventionalists) and patients. The present disclosure includes various improvements which may enhance the construction, operation, and methods of use of devices for ablating tissue, such as cardiac tissue.

It is an aspect of the present disclosure to provide an ablation system including a first ablation component and/or a second ablation component. The first ablation component may include a first ablation component end effector configured to be positioned on a first side of a target tissue, the first ablation component end effector including a first ablation component end effector housing, a first ablation component tissue contacting portion configured to engage the first side of the target tissue, a first ablation component ablation element, wherein the first ablation component ablation element is selectively operable to cause ablation of the target tissue, and/or a first ablation component permanent magnet, wherein the first ablation component permanent magnet is translationally repositionable relative to the first ablation component end effector housing between an engaged configuration and a disengaged configuration; and/or a mechanical linkage operatively coupled to translationally reposition the first ablation component permanent magnet relative to the first ablation component end effector housing between the engaged configuration and the disengaged configuration. The second ablation component may be configured for cooperative operation with the first ablation component. The second ablation component may include a second ablation component end effector configured to be positioned on a second side of the target tissue opposite the first side of the target tissue, the second ablation component end effector including a second ablation component end effector housing, a second ablation component tissue contacting portion configured to engage the second side of the target tissue, a second ablation component ablation element, wherein the second ablation component is selectively operable to cause ablation of the target tissue, and/or a second ablation component permanent magnet, wherein the second ablation component permanent magnet is freely rotatable about at least one axis of rotation relative to the second ablation component end effector housing without substantial translation relative to the second ablation component end effector housing, and wherein the second ablation component permanent magnet is configured to rotatably self-orient into a magnetically attractive orientation with the first ablation component permanent magnet. In the engaged configuration, the first ablation component permanent magnet may be configured to magnetically attract the second ablation component permanent magnet with the second ablation component end effector positioned on the second side of the target tissue substantially adjacent the first ablation component tissue contacting portion. In the disengaged configuration, with the second ablation component end effector positioned on the second side of the target tissue substantially adjacent the first ablation component tissue contacting portion, magnetic attraction between the first ablation component permanent magnet and the second ablation component permanent magnet may be reduced as compared to the engaged configuration.

In a detailed embodiment, the first ablation component permanent magnet may be translationally repositionable relative to the first ablation component end effector housing between the engaged configuration and the disengaged configuration without substantial rotation. The first ablation component permanent magnet may be translationally repositionable between the engaged configuration and the disengaged configuration along a longitudinal axis of the first ablation component permanent magnet.

In a detailed embodiment, in the engaged configuration, the first ablation component permanent magnet may be located substantially laterally adjacent to the first ablation component tissue contacting portion. In the disengaged configuration, the first ablation component permanent magnet may be located substantially not laterally adjacent to the first ablation component tissue contacting portion.

In a detailed embodiment, the first ablation component end effector may include at least one vacuum port disposed on the first ablation component tissue contacting portion, the vacuum port configured to be fluidically coupled to a vacuum source. The vacuum port may be configured so that, upon application of vacuum to the vacuum port, the vacuum port releasably secures the first ablation component tissue contacting portion to the target tissue. The first ablation component ablation element may be disposed substantially within a perimeter at least partially circumscribing the vacuum port.

In a detailed embodiment, the first ablation component ablation element may include a first ablation component ablation electrode. The first ablation component may be configured to deliver radio frequency ablation energy to the target tissue via the first ablation component ablation electrode. The first ablation component ablation electrode may include an elongated electrode having one dimension that is substantially greater than a perpendicular dimension.

In a detailed embodiment, a distal end portion of the first ablation component may be steerable.

In a detailed embodiment, the first ablation component end effector may include an outwardly extending, generally circumferential first ablation component end effector skirt. The first ablation component tissue contacting portion may include the first ablation component end effector skirt. The first ablation component ablation element may be disposed within a perimeter at least partially defined by the first ablation component end effector skirt.

In a detailed embodiment, the first ablation component end effector may include at least one opening configured to deliver an irrigation fluid to the first side of the target tissue proximate the first ablation component ablation element.

In a detailed embodiment, the first ablation component ablation element may include a first ablation component ablation electrode. The first ablation component ablation electrode may include at least one internal channel. The at least one internal channel may be operatively coupled to a source of cooling fluid.

In a detailed embodiment, the first ablation component may include a first ablation component connecting element. The first ablation component end effector may be disposed distally on the first ablation component connecting element. The first ablation component may include a first ablation component handle disposed proximally on the first ablation component connecting element. The first ablation component handle may include a first ablation component magnet actuator operatively connected to the first ablation component permanent magnet via the mechanical linkage to reposition the first ablation component permanent magnet between the engaged configuration and the disengaged configuration.

In a detailed embodiment, the first ablation component may include at least one first ablation component auxiliary electrode.

In a detailed embodiment, the second ablation component permanent magnet may be freely rotatable about three axes of rotation relative to the second ablation component end effector housing. The second ablation component permanent magnet may include a substantially spherical permanent magnet. The substantially spherical permanent magnet may be rotatably disposed within a substantially spherical interior of the second ablation component end effector housing. The second ablation component permanent magnet may be disposed in a substantially spherical mount. The substantially spherical mount may be rotatably disposed within a substantially spherical interior of the second ablation component end effector housing.

In a detailed embodiment, the second ablation component tissue contacting portion may be bulbous. The second ablation component tissue contacting portion may be at least partially generally spherical.

In a detailed embodiment, the second ablation component end effector housing may be constructed of a high magnetic permeability, non-ferrous, electrically conductive material. The second ablation component end effector housing may be constructed from copper.

In a detailed embodiment, the second ablation component ablation element may include a second ablation component ablation electrode. The second ablation component ablation electrode may form at least a portion of the second ablation component end effector housing.

In a detailed embodiment, the second ablation component may include at least one second ablation component auxiliary electrode. The at least one second ablation component auxiliary electrode may be disposed at a distal tip of the second ablation component end effector housing. The at least one second ablation component auxiliary electrode may be disposed laterally on the second ablation component end effector housing.

In a detailed embodiment, the second ablation component end effector housing may be at least partially generally spherical. The second ablation component end effector housing may include a distal portion constructed from a conductive material and a proximal portion constructed from a non-conductive material.

In a detailed embodiment, the second ablation component may include a second ablation component connecting element. The second ablation component end effector may be disposed distally on the second ablation component connecting element.

In a detailed embodiment, the second ablation component connecting element may include a generally tubular first connecting element, the first connecting element comprising a first connecting element distal portion; a second connecting element operatively coupled to the first connecting element distal portion, wherein the second ablation component end effector is disposed distally on the second connecting element; and/or an engagement element configured to selectively engage the second ablation component end effector with the first connecting element distal portion. The second connecting element may be selectively repositionable relative to the first connecting element distal portion between (i) a retracted configuration in which the second connecting element may be disposed substantially within the first connecting element and the engagement element may operatively couple the second ablation component end effector and the first connecting element distal portion, and (ii) a deployed configuration in which at least a portion of the second connecting element may extend from the first connecting element distal portion and the engagement element may be disengaged from at least one of the second ablation component end effector or the first connecting element distal portion. The second connecting element portion may have greater flexibility than the first connecting element distal portion.

In a detailed embodiment, the ablation system may include a second ablation component handle disposed proximally on the first connecting element. The second ablation component handle may include a deployment actuator operable to reposition the second connecting element relative to the first connecting element distal portion.

In a detailed embodiment, the first connecting element distal portion may be steerable. The second ablation component handle may include a steering actuator operable to steer the first connecting element distal portion.

In a detailed embodiment, the engagement element may be disposed at a distal end of the first connecting element distal portion. In the retracted configuration, the engagement element may be configured to receive at least a portion of the end effector therein. The engagement element may include a distally oriented opening. The opening may be generally conical.

It is an aspect of the present disclosure to provide a method of creating a lesion in a target tissue, the method including placing a first ablation component proximate a first surface of a target tissue, the first ablation component including a first ablation component end effector including a first ablation component end effector housing, a first ablation component permanent magnet which is translationally repositionable within the first ablation component end effector housing, and a first ablation component ablation element. The method may include placing a second ablation component proximate a second surface of the target tissue opposite the first surface of the target tissue, the second ablation component including a second ablation component end effector including a second ablation component end effector housing, a second ablation component permanent magnet which is freely rotatable about at least one axis of rotation relative to the second ablation component end effector housing, and a second ablation component ablation element. The method may include self-orienting the second ablation component permanent magnet into a magnetically attractive orientation with the first ablation component permanent magnet by allowing the second ablation component permanent magnet to rotate about the at least one axis of rotation without substantial translation relative to the second ablation component end effector housing. The method may include positioning one or both of the first ablation component end effector and the second ablation component end effector on the target tissue using attractive magnetic coupling between the first ablation component permanent magnet and the second ablation component permanent magnet.

The method may include creating a first lesion in the target tissue using at least one of the first ablation component ablation element and the second ablation component ablation element. The method may include reducing the attractive magnetic coupling between the first ablation component permanent magnet and the second ablation component permanent magnet by translationally repositioning the first ablation component permanent magnet within the first ablation component end effector housing from an engaged configuration to a disengaged configuration.

In a detailed embodiment, translationally repositioning the first ablation component permanent magnet within the first ablation component end effector housing may include translationally repositioning the first ablation component permanent magnet within the first ablation component end effector housing without substantial rotation of the first ablation component permanent magnet relative to the first ablation component end effector housing. Translationally repositioning the first ablation component permanent magnet within the first ablation component end effector housing may include translationally repositioning the first ablation component permanent magnet along a longitudinal axis of the first ablation component permanent magnet. Translationally repositioning the first ablation component permanent magnet within the first ablation component end effector housing may include translationally repositioning the first ablation component permanent magnet from substantially laterally adjacent to a first ablation component tissue contacting portion of the first ablation component end effector housing to substantially not laterally adjacent to the first ablation component tissue contacting portion.

In a detailed embodiment, the first ablation component may include a first ablation component connecting element, wherein the first ablation component end effector is disposed distally on the first ablation component connecting element. The first ablation component may include a first ablation component handle disposed proximally on the first ablation component connecting element. The first ablation component handle may include a first ablation component magnet actuator operatively connected to the first ablation component permanent magnet to translationally reposition the first ablation component permanent magnet within the first ablation component end effector housing between the engaged configuration and the disengaged configuration. Translationally repositioning the first ablation component permanent magnet within the first ablation component end effector housing from the engaged configuration to the disengaged configuration may include translationally repositioning the first ablation component permanent magnet within the first ablation component end effector housing from the engaged configuration to the disengaged configuration by operating the first ablation component magnet actuator.

In a detailed embodiment, the method may include securing the first ablation component end effector to the target tissue by applying vacuum to a vacuum port of the first ablation component end effector. The method may include discontinuing applying vacuum to the vacuum port.

In a detailed embodiment, the first ablation component ablation element may include a first ablation component ablation electrode. The second ablation component ablation element may include a second ablation component ablation electrode. Creating the first lesion in the target tissue using the at least one of the first ablation component ablation element and the second ablation component ablation element may include creating the first lesion in the target tissue by applying bipolar radiofrequency energy to the target tissue using the first ablation component ablation element and the second ablation component ablation element.

In a detailed embodiment, the first ablation component may include at least one electrode. The method may include at least one of pacing, sensing, stimulating, and mapping using the at least one electrode. The at least one electrode may include at least one of a first ablation component ablation electrode and a first ablation component auxiliary electrode. The at least one of pacing, sensing, stimulating, and mapping using the at least one electrode may include at least one of pacing, sensing, stimulating, and mapping using the at least one of the first ablation component ablation electrode and the first ablation component auxiliary electrode.

In a detailed embodiment, the second ablation component permanent magnet may be freely rotatable about three axes of rotation relative to the second ablation component end effector housing. Self-orienting the second ablation component permanent magnet into the magnetically attractive orientation with the first ablation component permanent magnet may include allowing the second ablation component permanent magnet to rotate about the three axes of rotation. The second ablation component permanent magnet may include a generally spherical second ablation component permanent magnet. The second ablation component end effector housing may include a generally spherical interior. Allowing the second ablation component permanent magnet to rotate about the three axes of rotation comprises allowing the generally spherical second ablation component permanent magnet to rotate about the three axes of rotation within the generally spherical interior of the second ablation component end effector housing.

In a detailed embodiment, positioning the one or both of the first ablation component end effector and the second ablation component end effector on the target tissue may include engaging a generally bulbous tissue contacting surface of the second ablation component end effector with the second surface of the target tissue.

In a detailed embodiment, the method may include removing at least one of the first ablation component end effector and the second ablation component end effector from the target tissue.

In a detailed embodiment, placing the first ablation component proximate the first surface of the target tissue may include steering a distal portion of a first ablation component connecting element, the first ablation component end effector disposed distally on the first ablation component connecting element.

In a detailed embodiment, the second ablation component may include at least one electrode. The method may include at least one of pacing, sensing, stimulating, and mapping using the at least one electrode. The at least one electrode may include at least one of a second ablation component ablation electrode and a second ablation component auxiliary electrode. The at least one of pacing, sensing, stimulating, and mapping using the at least one electrode may include at least one of pacing, sensing, stimulating, and mapping using the at least one of the second ablation component ablation electrode and the second ablation component auxiliary electrode.

In a detailed embodiment, placing the second ablation component proximate the second surface of the target tissue may include steering a distal portion of a second ablation component connecting element. The second ablation component end effector may be disposed distally on the second ablation component connecting element.

In a detailed embodiment, the second ablation component may include a second ablation component connecting element, the second ablation component connecting element comprising a generally tubular first connecting element comprising a first connecting element distal portion, and a second connecting element operatively coupled to the first connecting element distal portion. The second ablation component end effector may be disposed distally on the second connecting element. The method may include repositioning the second connecting element and the second ablation component end effector from a retracted configuration in which the second connecting element may be disposed substantially within the first connecting element to a deployed configuration in which at least a portion of the second connecting element may extend from the first connecting element distal portion. Creating the first lesion in the target tissue using the at least one of the first ablation component ablation element and the second ablation component ablation element may be performed while the second connecting element and the second ablation component end effector are in the deployed configuration.

In a detailed embodiment, the second ablation component may include a second ablation component handle disposed proximally on the first connecting element, the second ablation component handle comprising a deployment actuator operable to reposition the second connecting element relative to the first connecting element distal portion. Repositioning the second connecting element and the second ablation component end effector from the retracted configuration to the deployed configuration may include operating the deployment actuator. The method may include repositioning the second connecting element and the second ablation component end effector from the deployed configuration to the retracted configuration. Repositioning the second connecting element and the second ablation component end effector from the retracted configuration to the deployed configuration may include disengaging the second ablation component end effector from an engagement element configured to selectively engage the second ablation component end effector with the first connecting element distal portion. Repositioning the second connecting element and the second ablation component end effector from the deployed configuration to the retracted configuration may include engaging the second ablation component end effector with the engagement element.

It is an aspect of the present disclosure to provide an ablation component including a generally tubular first connecting element, the first connecting element comprising a first connecting element distal portion; a second connecting element operatively coupled to the first connecting element distal portion; an end effector disposed distally on the second connecting element, the end effector comprising an end effector housing, an ablation element, and a permanent magnet; and/or an engagement element configured to selectively engage the end effector with the first connecting element distal portion. The second connecting element may be selectively repositionable relative to the first connecting element distal portion between (i) a retracted configuration in which the second connecting element may be disposed substantially within the first connecting element and the engagement element operatively couples the end effector and the first connecting element distal portion, and (ii) a deployed configuration in which at least a portion of the second connecting element may extend from the first connecting element distal portion and the engagement element may be disengaged from at least one of the end effector or the first connecting element distal portion.

In a detailed embodiment, the second connecting element portion may have greater flexibility than the first connecting element distal portion. The permanent magnet may be freely rotatable about three axes of rotation relative to the end effector housing.

In a detailed embodiment, the permanent magnet may include a substantially spherical permanent magnet. The substantially spherical permanent magnet may be rotatably disposed within a substantially spherical interior of the end effector housing. The permanent magnet may be disposed in a substantially spherical mount. The substantially spherical mount may be rotatably disposed within a substantially spherical interior of the end effector housing.

In a detailed embodiment, the end effector may include a generally bulbous tissue contacting surface. The end effector may include a tissue contacting surface that is at least partially generally spherical. The end effector housing may be constructed of a high magnetic permeability, non-ferrous, electrically conductive material. The second ablation component end effector housing may be constructed from copper.

In a detailed embodiment, the ablation element may include an electrode. The end effector housing may include the electrode. The electrode may include two primary electrodes generally in the form of laterally arranged cooperating hemispheres separated by an insulator.

In a detailed embodiment, the ablation component may include a handle disposed proximally on the first connecting element, the handle comprising a deployment actuator operable to reposition the second connecting element relative to the first connecting element distal portion.

In a detailed embodiment, the first connecting element distal portion may be steerable. The first connecting element distal portion may be steerable at least about 180 degrees. The ablation component may include a handle disposed proximally on the first connecting element, the handle comprising a steering actuator operable to steer the first connecting element distal portion.

In a detailed embodiment, the engagement element may be disposed at a distal end of the first connecting element distal portion. In the retracted configuration, the engagement element may be configured to receive at least a portion of the end effector therein. The engagement element may include a distally oriented opening. The opening may be generally conical.

In a detailed embodiment, the ablation component may include at least one auxiliary electrode. The at least one auxiliary electrode may be disposed at a distal tip of the end effector housing. The at least one auxiliary electrode may be disposed laterally on the end effector housing. The at least one auxiliary electrode may include a generally circular circumferential ring, which may be disposed laterally on the end effector housing.

In a detailed embodiment, the end effector housing may be at least partially generally spherical. The end effector housing may include a distal portion constructed from a conductive material and a proximal portion constructed from a non-conductive material.

It is an aspect of the present disclosure to provide a method of creating a lesion in a target tissue, the method including placing an ablation component proximate a first surface of a target tissue, the ablation component comprising an end effector comprising an end effector housing, a permanent magnet which is freely rotatable about at least one axis of rotation relative to the end effector housing, and an ablation element. The method may include self-orienting the permanent magnet into a magnetically attractive orientation with a cooperating ablation component magnetic element of a cooperating ablation component disposed proximate a second surface of the target tissue opposite the first surface of the target tissue by allowing the permanent magnet to rotate about the at least one axis of rotation. The method may include positioning the end effector on the target tissue using attractive magnetic coupling between the permanent magnet and the cooperating ablation component magnetic element. The method may include creating a lesion in the target tissue using the ablation element.

In a detailed embodiment, the permanent magnet may be freely rotatable about three axes of rotation relative to the end effector housing. Self-orienting the permanent magnet into the magnetically attractive orientation with the cooperating ablation component magnetic element may include allowing the permanent magnet to rotate about the three axes of rotation.

In a detailed embodiment, the permanent magnet may include a generally spherical permanent magnet. The end effector housing may include a generally spherical interior. Allowing the permanent magnet to rotate about the three axes of rotation may include allowing the generally spherical permanent magnet to rotate about the three axes of rotation within the generally spherical interior of the end effector housing.

In a detailed embodiment, positioning the end effector on the target tissue may include engaging a generally bulbous tissue contacting surface of the end effector with the first surface of the target tissue.

In a detailed embodiment, placing the ablation component proximate the first surface of the target tissue may include steering a distal portion of a connecting element, the end effector disposed distally on the connecting element. Steering the distal portion of the connecting element may include operating a steering actuator disposed on a handle of the ablation component, the handle disposed proximally on the connecting element.

In a detailed embodiment, the ablation element may include an electrode. Creating the lesion in the target tissue using the ablation element may include applying radiofrequency ablation energy to the target tissue using the electrode. Applying radiofrequency ablation energy to the target tissue using the electrode may include applying bipolar radiofrequency ablation energy to the target tissue using the electrode and a cooperating electrode of the cooperating ablation component.

In a detailed embodiment, the end effector may include at least one electrode. The method may include at least one of pacing, sensing, stimulating, and mapping using the at least one electrode. The at least one electrode may include at least one of an ablation electrode and an auxiliary electrode. The at least one of pacing, sensing, stimulating, and mapping using the at least one electrode may include at least one of pacing, sensing, stimulating, and mapping using the at least one of the ablation electrode and the auxiliary electrode.

In a detailed embodiment, the ablation component may include a connecting element, the connecting element comprising a generally tubular first connecting element comprising a first connecting element distal portion, and a second connecting element operatively coupled to the first connecting element distal portion. The end effector may be disposed distally on the second connecting element. The method may include repositioning the second connecting element and the end effector from a retracted configuration in which the second connecting element is disposed substantially within the first connecting element to a deployed configuration in which at least a portion of the second connecting element extends from the first connecting element distal portion. Creating the lesion in the target tissue using the ablation element may be performed while the second connecting element and the end effector are in the deployed configuration.

In a detailed embodiment, the ablation component comprises a handle disposed proximally on the first connecting element, the handle may include a deployment actuator operable to reposition the second connecting element relative to the first connecting element distal portion. Repositioning the second connecting element and the end effector from the retracted configuration to the deployed configuration may include operating the deployment actuator. The method may include repositioning the second connecting element and the end effector from the deployed configuration to the retracted configuration. Repositioning the second connecting element and the end effector from the retracted configuration to the deployed configuration may include disengaging the end effector from an engagement element configured to selectively engage the end effector with the first connecting element distal portion. Repositioning the second connecting element and the end effector from the deployed configuration to the retracted configuration may include engaging the end effector with the engagement element.

It is an aspect of the present disclosure to provide an ablation system including a first ablation component and/or a second ablation component. The first ablation component may include a first ablation component end effector configured to be positioned on a first side of a target tissue, the first ablation component including a first ablation component end effector housing, a first ablation component tissue contacting portion configured to engage the first side of the target tissue, a first ablation component ablation element, wherein the first ablation component is selectively operable to cause ablation of the target tissue, and/or a first ablation component permanent magnet, wherein the first ablation component permanent magnet is freely rotatable about at least one axis of rotation relative to the first ablation component end effector housing without substantial translation relative to the first ablation component end effector housing, and wherein the first ablation component permanent magnet is configured to rotatably self-orient into a magnetically attractive orientation with a cooperating magnetic element. The second ablation component may be configured for cooperative operation with the first ablation component. The second ablation component may include a second ablation component end effector configured to be positioned on a second side of the target tissue opposite the first side of the target tissue, the second ablation component comprising a second ablation component end effector housing, a second ablation component tissue contacting portion configured to engage the second side of the target tissue, a second ablation component ablation element, wherein the second ablation component is selectively operable to cause ablation of the target tissue, and/or a second ablation component permanent magnet, the second ablation component permanent magnet comprising the cooperating magnetic element, wherein the second ablation component permanent magnet is freely rotatable about at least one axis of rotation relative to the second ablation component end effector housing without substantial translation relative to the second ablation component end effector housing, and wherein the second ablation component permanent magnet is configured to rotatably self-orient into a magnetically attractive orientation with the first ablation component permanent magnet.

In a detailed embodiment, the first ablation component permanent magnet may be freely rotatable about three axes of rotation relative to the first ablation component end effector housing. The second ablation component permanent magnet may be freely rotatable about three axes of rotation relative to the second ablation component end effector housing.

In a detailed embodiment, the first ablation component ablation element may include a first ablation component ablation electrode. The first ablation component ablation electrode may form at least a portion of the first ablation component end effector housing. The second ablation component ablation element may include a second ablation component ablation electrode. The second ablation component ablation electrode may form at least a portion of the second ablation component end effector housing.

In a detailed embodiment, the first ablation component may include at least one first ablation component auxiliary electrode. The second ablation component may include at least one second ablation component auxiliary electrode.

In a detailed embodiment, the first ablation component may include a first ablation component connecting element. The first ablation component end effector may be disposed distally on the first ablation component connecting element. The second ablation component may include a second ablation component connecting element. The second ablation component end effector may be disposed distally on the second ablation component connecting element.

In a detailed embodiment, the first ablation component connecting element may include a generally tubular first ablation component first connecting element, the first ablation component first connecting element including a first ablation component first connecting element distal portion; a first ablation component second connecting element operatively coupled to the first ablation component first connecting element distal portion, wherein the first ablation component end effector is disposed distally on the first ablation component second connecting element; and/or a first ablation component engagement element configured to selectively engage the first ablation component end effector with the first ablation component first connecting element distal portion. The first ablation component second connecting element may be selectively repositionable relative to the first ablation component first connecting element distal portion between (i) a retracted configuration in which the first ablation component second connecting element may be disposed substantially within the first ablation component first connecting element and the first ablation component engagement element may operatively couple the first ablation component end effector and the first ablation component first connecting element distal portion, and (ii) a deployed configuration in which at least a portion of the first ablation component second connecting element may extend from the first ablation component first connecting element distal portion and the first ablation component engagement element may be disengaged from at least one of the first ablation component end effector or the first ablation component first connecting element distal portion. The second ablation component connecting element may include a generally tubular second ablation component first connecting element, the second ablation component first connecting element comprising a second ablation component first connecting element distal portion; a second ablation component second connecting element operatively coupled to the second ablation component first connecting element distal portion, wherein the second ablation component end effector is disposed distally on the second ablation component second connecting element; and/or a second ablation component engagement element configured to selectively engage the second ablation component end effector with the second ablation component first connecting element distal portion. The second ablation component second connecting element may be selectively repositionable relative to the second ablation component first connecting element distal portion between (i) a retracted configuration in which the second ablation component second connecting element may be disposed substantially within the second ablation component first connecting element and the second ablation component engagement element may operatively couple the second ablation component end effector and the second ablation component first connecting element distal portion, and (ii) a deployed configuration in which at least a portion of the second ablation component second connecting element may extend from the second ablation component first connecting element distal portion and the second ablation component engagement element may be disengaged from at least one of the second ablation component end effector or the second ablation component first connecting element distal portion.

In a detailed embodiment, the first ablation component second connecting element portion may have greater flexibility than the first ablation component first connecting element distal portion. The second ablation component second connecting element portion may have greater flexibility than the second ablation component first connecting element distal portion.

In a detailed embodiment, the system may include a first ablation component handle disposed proximally on the first ablation component first connecting element, the second ablation component handle comprising a first ablation component deployment actuator operable to reposition the first ablation component second connecting element relative to the first ablation component first connecting element distal portion. The system may include a second ablation component handle disposed proximally on the second ablation component first connecting element, the second ablation component handle comprising a second ablation component deployment actuator operable to reposition the second ablation component second connecting element relative to the second ablation element first connecting element distal portion.

In a detailed embodiment, the first ablation component engagement element may be disposed at a distal end of the first ablation component first connecting element distal portion. In the retracted configuration, the first ablation component engagement element may be configured to receive at least a portion of the first ablation component end effector therein. The second ablation component engagement element may be disposed at a distal end of the second ablation component first connecting element distal portion. In the retracted configuration, the second ablation component engagement element may be configured to receive at least a portion of the second ablation component end effector therein.

In a detailed embodiment, the first ablation component engagement element may include a distally oriented opening. The second ablation component engagement element may include a distally oriented opening.

It is an aspect of the present disclosure to provide a method of creating a lesion in a target tissue, the method including placing a first ablation component proximate a first surface of a target tissue, the first ablation component including a first ablation component end effector including a first ablation component end effector housing, a first ablation component permanent magnet which is freely rotatable about at least one axis of rotation relative to the first ablation component end effector housing, and/or a first ablation component ablation element. The method may include placing a second ablation component proximate a second surface of a target tissue, the second ablation component including a second ablation component end effector including a second ablation component end effector housing, a second ablation component permanent magnet which is freely rotatable about at least one axis of rotation relative to the second ablation component end effector housing, and/or a second ablation component ablation element. The method may include self-orienting the first ablation component permanent magnet into a magnetically attractive orientation with the second ablation component permanent magnet by allowing the first ablation component permanent magnet to rotate freely and/or self-orienting the second ablation component permanent magnet into a magnetically attractive orientation with the first ablation component permanent magnet by allowing the second ablation component permanent magnet to rotate freely. The method may include positioning the first ablation component end effector and the second ablation component end effector on the target tissue using attractive magnetic coupling between the first ablation component permanent magnet and the second ablation component permanent magnet. The method may include creating a first lesion in the target tissue using at least one of the first ablation component ablation element and the second ablation component ablation element.

In a detailed embodiment, placing the first ablation component proximate the first surface of the target tissue may include steering a distal portion of a first ablation component connecting element, the first ablation component end effector disposed distally on the first ablation component connecting element. Placing the second ablation component proximate the second surface of the target tissue may include steering a distal portion of a second ablation component connecting element, the second ablation component end effector disposed distally on the second ablation component connecting element.

In a detailed embodiment, steering the distal portion of the first ablation component connecting element may include operating a first ablation component steering actuator disposed on a first ablation component handle of the first ablation component, the first ablation component handle disposed proximally on the first ablation component connecting element. Steering the distal portion of the second ablation component connecting element may include operating a second ablation component steering actuator disposed on a second ablation component handle of the second ablation component, the second ablation component handle disposed proximally on the second ablation component connecting element.

In a detailed embodiment, the first ablation component ablation element may include a first ablation component ablation electrode. The second ablation component ablation element may include a second ablation component ablation electrode. Creating the first lesion in the target tissue using at least one of the first ablation component ablation element and the second ablation component ablation element may include applying radiofrequency ablation energy to the target tissue using at least one of the first ablation component ablation element and the second ablation component ablation element. Applying radiofrequency ablation energy to the target tissue using at least one of the first ablation component ablation element and the second ablation component ablation element may include applying bipolar radiofrequency ablation energy to the target tissue using the first ablation component ablation element and the second ablation component ablation element.

In a detailed embodiment, the first ablation component end effector may include at least one first ablation component electrode. The second ablation component end effector may include at least one second ablation component electrode. The method may include at least one of pacing, sensing, stimulating, and mapping using at least one of the at least one first ablation component electrode and the at least one second ablation component electrode.

In a detailed embodiment, the first ablation component may include a first ablation component connecting element, the first ablation component connecting element comprising a generally tubular first ablation component first connecting element comprising a first ablation component first connecting element distal portion, and/or a first ablation component second connecting element operatively coupled to the first ablation component first connecting element distal portion. The first ablation component end effector may be disposed distally on the first ablation component second connecting element. The method may include repositioning the first ablation component second connecting element and the first ablation component end effector from a retracted configuration in which the first ablation component second connecting element may be disposed substantially within the first ablation component first connecting element to a deployed configuration in which at least a portion of the first ablation component second connecting element may extend from the first ablation component first connecting element distal portion.

In a detailed embodiment, creating the first lesion in the target tissue using at least one of the first ablation component ablation element and the second ablation component ablation element may be performed while the first ablation component second connecting element and the first ablation component end effector are in the deployed configuration.

In a detailed embodiment, the first ablation component may include a first ablation component handle disposed proximally on the first ablation component first connecting element, the first ablation component handle including a first ablation component deployment actuator operable to reposition the first ablation component second connecting element relative to the first ablation component first connecting element distal portion. Repositioning the first ablation component second connecting element and the first ablation component end effector from the retracted configuration to the deployed configuration may include operating the first ablation component deployment actuator.

In a detailed embodiment, the second ablation component may include a second ablation component connecting element, the second ablation component connecting element including a generally tubular second ablation component first connecting element comprising a second ablation component first connecting element distal portion, and/or a second ablation component second connecting element operatively coupled to the second ablation component first connecting element distal portion. The second ablation component end effector may be disposed distally on the second ablation component second connecting element. The method may include repositioning the second ablation component second connecting element and the second ablation component end effector from a retracted configuration in which the second ablation component second connecting element may be disposed substantially within the second ablation component first connecting element to a deployed configuration in which at least a portion of the second ablation component second connecting element may extend from the second ablation component first connecting element distal portion.

In a detailed embodiment, creating the first lesion in the target tissue using at least one of the first ablation component ablation element and the second ablation component ablation element may be performed while the first ablation component second connecting element and the first ablation component end effector are in the deployed configuration and while the second ablation component second connecting element and the second ablation component end effector are in the deployed configuration.

In a detailed embodiment, the second ablation component may include a second ablation component handle disposed proximally on the second ablation component first connecting element, the second ablation component handle including a second ablation component deployment actuator operable to reposition the second ablation component second connecting element relative to the second ablation component first connecting element distal portion. Repositioning the second ablation component second connecting element and the second ablation component end effector from the retracted configuration to the deployed configuration may include operating the second ablation component deployment actuator.

In a detailed embodiment, repositioning the first ablation component second connecting element and the first ablation component end effector from the retracted configuration to the deployed configuration may include disengaging the first ablation component end effector from a first ablation component engagement element configured to selectively engage the first ablation component end effector with the first ablation component first connecting element distal portion. Repositioning the first ablation component second connecting element and the first ablation component end effector from the deployed configuration to the retracted configuration may include engaging the first ablation component end effector with the first ablation component engagement element.

In a detailed embodiment, the target tissue may include a ventricular septum of a heart. The first surface of the target tissue may include a right ventricular surface of the ventricular septum. The second surface of the target tissue may include a left ventricular surface of the ventricular septum. Creating the first lesion in the target tissue may include ablating the ventricular septum using the first ablation component ablation element and the second ablation component ablation element.

It is an aspect of the present disclosure to provide a system including a first component including a first component end effector configured to be positioned on a first side of a heart tissue, the first component end effector including a first component electrode; and/or a second component including a second component end effector configured to be positioned on a second side of the heart tissue opposite the first side, the second component end effector including a second component electrode. The first component and the second component may be configured for cooperative use of the first component electrode and the second component electrode for at least one of sensing, pacing, stimulation, and mapping.

In a detailed embodiment, the system may include a control unit configured for cooperative use of the first component electrode and the second component electrode for at least one of sensing, pacing, stimulation, and mapping.

In a detailed embodiment, cooperative use of the first component electrode and the second component electrode for the at least one of sensing, pacing, stimulation, and mapping may include cooperative sensing using the first component electrode and the second component electrode. Cooperative use of the first component electrode and the second component electrode for the at least one of sensing, pacing, stimulation, and mapping may include cooperative pacing using the first component electrode and the second component electrode. Cooperative use of the first component electrode and the second component electrode for the at least one of sensing, pacing, stimulation, and mapping may include cooperative stimulation using the first component electrode and the second component electrode. Cooperative use of the first component electrode and the second component electrode for the at least one of sensing, pacing, stimulation, and mapping may include cooperative mapping using the first component electrode and the second component electrode.

In a detailed embodiment, cooperative use of the first component electrode and the second component electrode for the at least one of sensing, pacing, stimulation, and mapping may include delivery of an electrical current to the heart tissue using one of the first component electrode and the second component electrode and detection of at least one electrical parameter associated with the heart tissue using the other of the first component electrode and the second component electrode.

In a detailed embodiment, the first component end effector may be configured to be positioned on an epicardial surface of the heart. The first component end effector may be configured to be positioned on an endocardial surface of the heart. The second component end effector may be configured to be positioned on an epicardial surface of the heart. The second component end effector may be configured to be positioned on an endocardial surface of the heart.

In a detailed embodiment, at least one of the first component end effector and the second component end effector may include an ablation element.

In a detailed embodiment, the first component end effector may include a first component magnetic element, the second component end effector may include a second component magnetic element, and/or the first component magnetic element and the second component magnetic element may be configured for cooperative magnetic attraction across the heart tissue.

It is an aspect of the present disclosure to provide a method including placing a first component proximate a first surface of a heart tissue, the first component including a first component end effector including a first component electrode; placing a second component proximate a second surface of the heart tissue opposite the first surface, the second component including a second component end effector including a second component electrode; and/or cooperatively using the first component electrode and the second component electrode for at least one of sensing, pacing, stimulation, and mapping.

In a detailed embodiment, cooperatively using the first component electrode and the second component electrode for the at least one of sensing, pacing, stimulation, and mapping may include delivering an electrical current to the heart tissue using one of the first component electrode and the second component electrode and/or detecting at least one electrical parameter associated with the heart tissue using the other of the first component electrode and the second component electrode.

In a detailed embodiment, the method may include creating a lesion in the heart tissue. Creating the lesion in the heart tissue may include creating the lesion in the heart tissue using at least one of the first component end effector and the second component end effector. Creating the lesion in the heart tissue using the at least one of the first component end effector and the second component end effector comprises delivering ablation energy to the heart tissue using at least one of the first component electrode and the second component electrode.

In a detailed embodiment, cooperatively using the first component electrode and the second component electrode for the at least one of sensing, pacing, stimulation, and mapping may include identifying a target location in the heart tissue for a future ablation. In a detailed embodiment, cooperatively using the first component electrode and the second component electrode for the at least one of sensing, pacing, stimulation, and mapping may include assessing an ablation.

It is an aspect of the present disclosure to provide any method, operation, process, system, device, and/or apparatus associated with any preceding aspect or described elsewhere herein.

It is an aspect of the present disclosure to provide any combination of any one or more elements of any preceding aspect or described elsewhere herein.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, among other things, medical instruments and devices and related methods, and, more specifically, devices for ablating tissue and related methods. Some example embodiments according to at least some aspects of the present disclosure may be useful in connection with ablation of cardiac tissue, such as to treat cardiac arrhythmias like atrial fibrillation, ventricular tachycardia, and/or inappropriate sinus tachycardia, for the reasons discussed above in the Introduction section. Some example embodiments according to at least some aspects of the present disclosure may be configured to deliver ablation energy, such as through the heart wall to create an efficient transmural lesion, while minimizing collateral tissue trauma.

Figure 1:
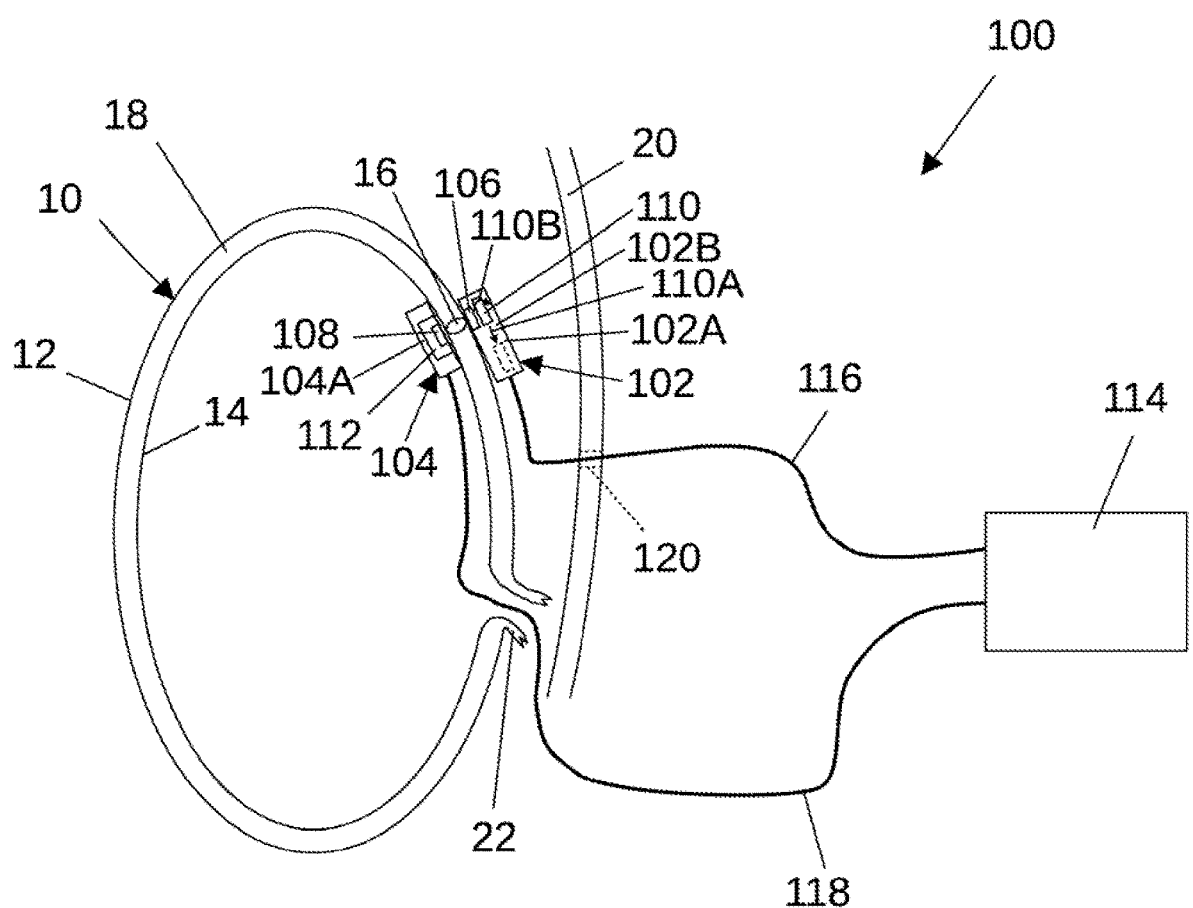
FIG. 1 is a simplified schematic view of an example ablation system in use on a heart.

FIG. 1 is a simplified schematic view of an example ablation system 100 in use on a heart 10, according to at least some aspects of the present disclosure. The following description of the ablation system 100 provides context for the description of various detailed example embodiments below. It is to be understood that although numerous features and aspects are described with reference to FIG. 1 and subsequent figures, each of these features and aspects is optional, and these features and aspects may be implemented in any combination.

The example ablation system 100 may include a first ablation component 102 configured to be positioned on a first side of a target tissue and/or a second ablation component 104 configured to be positioned on a second side of the target tissue. Generally, each of the ablation components 102, 104 may comprise any ablation component described herein. For example and without limitation, in some embodiments, the first ablation component 102 may comprise an ablation component such as those described herein with reference to FIGS. 2-20 and/or the second ablation component 104 may comprise an ablation component such as those described herein with reference to FIGS. 21-47. In some embodiments, each of the first ablation component 102 and the second ablation component 104 may comprise an ablation component such as those described herein with reference to FIGS. 2-20. In some embodiments, each of the first ablation component 102 and the second ablation component 104 may comprise an ablation component such as those described herein with reference to FIGS. 21-47.

Each ablation component 102, 104 may include a respective end effector 102A, 104A. The first and second sides of the target tissue may be opposite sides. For example, when a portion of a heart wall 18 is the target tissue, the first ablation component end effector 102A may be configured to be positioned on an epicardial (exterior) surface 12 of the heart 10. The second ablation component end effector 104A may be configured to be positioned on an endocardial (interior) surface 14 of the heart 10. In some circumstances, the first and second ablation components 102, 104 may be placed on opposite, endocardial sides of a target tissue (e.g., atrial septum, ventricular septum, papillary muscles). Generally, from the perspective of one ablation component 102, 104, the other ablation component 102, 104 may be referred to as a "cooperating" ablation component 102, 104, and constituent parts of the cooperating ablation components 102, 104 may be similarly referred to as "cooperating."

In the illustrated embodiment, the first ablation component 102 may include at least one ablation element 106, such as one or more electrodes configured to deliver ablation energy, and/or the second ablation component 104 may include at least one ablation element 108, such as one or more electrodes configured to deliver radiofrequency ablation energy. In some embodiments, the ablation elements 106, 108 may be configured to cooperate to create a lesion 16 in the target tissue, such as a transmural lesion extending through the full thickness of the heart wall 18. For example, the ablation elements 106, 108 may be configured to operate cooperatively to perform bipolar radiofrequency ablation. In other embodiments, only one of the first ablation component 102 and the second ablation component 104 may include an ablation element 106, 108, or only one of the ablation elements 106, 108 may be utilized at one time. For example, one or both of the ablation elements 106, 108 (if present) may be configured to operate independently to perform ablation.

It will be appreciated that various example embodiments are described herein in connection with creating a lesion in a target tissue. It is within the scope of this disclosure to perform ablation procedures forming lesions of any shape. Example lesion shapes include linear lesions (curved or straight), spot lesions, or custom shapes (e.g., oval, triangle, arc, etc.). It will be understood that the foregoing list is merely exemplary and is not to be considered limiting. Ablation elements may be configured to produce desired lesion shapes with single and/or multiple applications. For example, in some circumstances, it may be advantageous to create more than one lesion, or it may be advantageous to create a larger lesion comprising a plurality of smaller, overlapping lesions. Accordingly, it will be understood that various steps in the exemplary methods described herein may be repeated as desired to create any desired lesion or set of lesions. For example, one or both of the ablation components may be repositioned on the target tissue, or removed from the target tissue after a lesion is created, and then may be repositioned on the target tissue, to create a subsequent lesion.

It is within the scope of this disclosure to ablate tissue using any ablation suitable modalities, devices, and methods. Accordingly, in various alternative example embodiments, any ablation elements, such as the ablation element 106 and/or the ablation element 108, may be configured for any suitable ablation modality or modalities. For example, any ablation elements described herein in connection with any exemplary embodiment may be configured to deliver one or more of radiofrequency (RF) ablation energy (monopolar and/or bipolar), pulsed field energy, cryoablation energy, ultrasound energy, laser energy, and/or ablation chemicals (e.g., ethanol) for tissue ablation, individually and/or cooperatively. It will be understood that the foregoing list is merely exemplary and is not to be considered limiting.

In some example embodiments configured to perform radiofrequency (RF) ablation, known RF ablation equipment and/or algorithms may be used. For example, ablation components described herein may be connected to existing electrosurgical generators and suitable ablation pen algorithms and/or suitable ablation clamp algorithms may be used. In some example embodiments, electrosurgical generators may be configured to measure one or more parameters associated with the tissue being ablated (e.g., impedance), and the RF energy delivery may be adjusted based on the measured parameter. For example, some RF ablation algorithms may measure impedance and use the measured value to determine when RF energy delivery is terminated or changed.

In some example embodiments, bipolar radiofrequency ablation energy may be applied, followed by monopolar radiofrequency ablation energy. In other embodiments, monopolar radiofrequency ablation energy may be applied using one or more ablation components, followed by bipolar radiofrequency ablation energy. In some such embodiments, the bipolar and monopolar ablations may create overlapping lesions such that a combined transmural lesion of a desired shape is formed. Similarly, some example embodiments may utilize pulse field ablation in connection with monopolar and/or bipolar radiofrequency ablation. In some example embodiments configured for use with multiple ablation modalities applied via electrodes, various ablation components may be connected to one or more electrosurgical generators via one or more switching units, which may be operative to select among two or more ablation modalities. More generally, it is within the scope of the disclosure to utilize multiple energy modalities within an ablation procedure to create one or more lesions, which may overlap, providing a desired combined size and/or shape.

In various ablation systems comprising cooperating ablation components according to at least some aspects of the present disclosure, the size and/or shape of the ablation elements (e.g., electrodes) may be selected to create desired lesion geometry. In some embodiments, cooperating electrodes having similar geometries may be utilized. For example, in some embodiments, a linear electrode may be used cooperatively with another linear electrode or a spot electrode may be used cooperatively with another spot electrode. In alternative embodiments, electrodes of dissimilar geometries may be used cooperatively. For example, a linear electrode may be used cooperatively with a spot electrode.

In the illustrated embodiment, the first ablation component 102 includes at least one magnetic element 110 and the second ablation component 104 includes at least one magnetic element 112. Various example embodiments according to at least some aspects of the present disclosure may include one or more magnetic elements. Magnetic elements may comprise, for example, any combination of one or more permanent magnets, electromagnets, and/or ferromagnetic materials. Individual magnetic elements mentioned above may comprise one or more magnetic subcomponents, which may be shaped, arranged, configured, combined, and/or controlled to achieve desired magnetic and/or mechanical characteristics. In some example embodiments, electromagnets may be energized (with constant or varying electrical current) to attract and/or repel other magnetic elements, such as by reversing current direction to reverse magnetic polarity and/or varying current flow to adjust magnetic field strength. In some example embodiments, magnetic elements (such as permanent magnets) may be repositionable (e.g., translated and/or reoriented/rotated) to vary the location and/or orientation of the magnetic field.

In the illustrated embodiment, the magnetic elements 110, 112 are configured to cooperate to facilitate positioning the first ablation component 102 and/or the second ablation component 104. For example, the magnetic elements 110, 112 may be configured for mutual attraction, such as to align the ablation elements 106, 108 across the target tissue (e.g., heart wall 18) to create the lesion 16 at the desired location. Some example ablation components 102, 104 may be configured to at least partially compress tissue therebetween. For example, the magnetic elements 110, 112 may be configured to cooperate to compress the target tissue (e.g., heart wall 18) between the ablation components 102, 104 using the magnetic attraction of the magnetic elements 110, 112, which may improve ablation outcomes in some circumstances.

The present disclosure contemplates that the magnetic attractive force between two magnets may be estimated given certain information about each magnet, the separation between the magnetics, and the permeability of the intervening medium. Accordingly, various embodiments according to at least some aspects of the present disclosure may be configured for use in connection with specific target tissues, tissue thicknesses, and/or tissue types. For example, the size, shape, positioning, and/or strength of each magnetic element in an ablation system may be configured, in connection with the configuration of each ablation component, to provide desired tissue compression facilitating desired ablation characteristics. For example, ablation systems configured for use with relatively thicker target tissues may utilize magnetic elements configured to provide a relatively high compressive force across the greater separation of the thicker target tissue, while ablation systems configured for use with relatively thinner target tissues may utilize magnetic elements configured to provide a relatively smaller compressive force across the lesser separation of the thinner target tissue. Similarly, regardless of thickness, some target tissue types may require higher compression to achieve desired ablation results, and other target tissue types may be easily injured, thus requiring lesser compression forces.

In some example embodiments, one or more of the magnetic elements 110, 112 may be movable relative to other portions of the respective end effector 102A, 104A. For example, in some embodiments, one or more magnetic elements 110, 112 may be substantially freely rotatable relative to other portions of the respective end effector 102A, 104A. In some embodiments, one or more magnetic elements 110, 112 may be selectively repositionable (e.g., by and/or under the control of a user) relative to other portions of the respective end effector 102A, 104A.

In the illustrated embodiment, the magnetic element 110 is selectively repositionable as indicated by arrow 110A and/or arrow 110B (e.g., by and/or under the control of a user) relative to a housing 102B forming part of the first ablation component end effector 102A. For example, the magnetic element 110 may be moved relative to the housing 102B to facilitate decoupling of the magnetic element 110 from the magnetic element 112, such as when it may be desired to disengage one or both of the ablation components 102, 104 from the tissue 18. As described in more detail below, in various example embodiments, one or more magnetic elements 110, 112 may be translatable, rotatable, or both translatable and rotatable relative to respective ablation component housings 102B, 104B. As used herein, "translation" and related terms may be used to describe motion of an object in which all points in the object move substantially uniformly along the same line or direction. Translational movement may be linear or curvilinear, for example. As used herein, "rotation" and related terms may be used to describe motion of an object in which the object moves circularly about an axis of rotation. Some motions of objects may involve a combination of translation and rotation.

In some example embodiments comprising a magnetic element that is repositionable relative to an end effector housing, the repositioning of the magnetic element may be used to cause a cooperating magnetic element to move correspondingly. For example, translation of a repositionable permanent magnet in a first ablation component may be used to translate a cooperating end effector positioned on an opposite side of the target tissue. In some example embodiments, such motion may be used to create an elongated lesion of any desired shape.

In the illustrated embodiment, the example ablation system 100 may include a control unit 114. The control unit 114 may be operable to control the operation of one or more aspects of the ablation components 102, 104. In some example embodiments, the control unit 114 may be configured to selectively provide ablation energy (e.g., RF energy from an electrosurgical generator) to electrodes comprising the ablation elements 106, 108. In some alternative example embodiments, the control unit 114 may be configured to selectively provide a cryogenic fluid (e.g., nitrous oxide from a pressurized source) to one or more cryogenic elements comprising one or more of the ablation elements 106, 108. In some embodiments, a control unit 114 may include a vacuum source. In some example embodiments, the control unit 114 may be configured for sensing, pacing, stimulation, and/or mapping using one or both of the ablation components 102, 104, such as by using one or more electrodes associated with one or more of the ablation components 102, 104. Although the control unit 114 is illustrated as a single box for clarity, it will be understood that the ablation components 102, 104 may be operatively coupled to one or more separate or combined devices (e.g., electrosurgical generator, cryogenic unit, vacuum source, etc.) collectively providing the pertinent functionalities of the control unit 114 as described herein.

In the illustrated embodiment, the ablation components 102, 104 may include respective connecting elements 116, 118, which may operatively couple the ablation elements 106, 108 and/or the magnetic elements 110, 112 to the control unit 114. The connecting elements 116, 118 may include or be used in connection with one or more electrical conductors, fluidic conduits, mechanical force transmission components (e.g., mechanical linkages), catheters, wires, steerable portions, sheaths, trocars, hemostatic components, etc. For example, the connecting element 116, 118 may include one or more fluidic conduits for conveying a cooling fluid in a closed loop manner. In some embodiments, the connecting elements 116, 118 may include one or more fluidic conduits for conveying an irrigation fluid for open irrigation and/or cooling, such as for one or more of the ablation elements 106, 108 (e.g., electrodes). In such embodiments, portions of the end effectors 102A, 104A may be perforated to express the irrigation fluid at the desired locations.

In some example embodiments, the connecting elements 116, 118 may include user interfaces. For example, some ablation components may include rigidly configured handles and end effectors, rigid handles with steerable end effectors, and/or flexible or steerable devices (e.g., catheters). Some embodiments may include user-operated actuators, such as sliding or rotating elements, for manipulating end effector components (e.g., magnetic elements). Some embodiments may include substantially rigid connecting elements (e.g., shafts). It will be understood that the foregoing list is merely exemplary and is not to be considered limiting.

In some example embodiments, the example ablation system 100 may be configured to access the target tissue (e.g., heart wall 18) via a surgical approach (open-chest and/or minimally invasive) and/or via the patient's vascular system. For example, the first ablation component 102 may be positioned on the epicardial surface 12 via a percutaneous or surgical sub-xiphoid or intercostal access or incision 120, such as through the chest wall 20. The second ablation component 104 may be positioned on the endocardial surface 14 via a blood vessel 22 (e.g., the femoral vein or artery). In various circumstances, the routes used to obtain access to the epicardial and endocardial surfaces may be determined based at least in part upon factors such as the portion of the heart wall 18 that comprises the target tissue for the ablation, the patient's potential anatomical variations, previous surgeries, etc. More generally, in various exemplary embodiments, either or both of the first ablation component 102 or the second ablation component 104 may access the target tissue by any suitable route, such as open chest, thoracotomy, sub-xiphoid, trans-diaphragmatic, and/or vascular access. For example, endocardial access may be obtained using percutaneous approaches (e.g., arterial and/or venous) and/or surgical approaches (e.g., transapical, fem-fem bypass (venous), fem-fem bypass (arterial), bypass cannula traditional (arterial), bypass cannular traditional (venous), and/or atriotomy). Epicardial access may be obtained using percutaneous approaches (e.g., sub-xiphoid) and/or surgical approaches (e.g., lateral (right or left), surgical window, and/or sternotomy (full or partial)), for example. It will be understood that the foregoing list is merely exemplary and is not to be considered limiting.

Generally, some example embodiments may be operated as follows. Suitable access to the target tissue may be obtained. For example, access to the epicardial 12 and endocardial 14 surfaces may be obtained. The first ablation component 102 may positioned at a desired location on the epicardial surface 12. The magnetic elements 110, 112 may be utilized (e.g., magnetically coupled) to position and/or secure the second ablation component 104 on the endocardial surface 14. For example, the magnetic element 110 of the first ablation component 102 may magnetically attract the magnetic element 112 of the second ablation component 104. In other embodiments, the second ablation component 104 may be positioned at a desired location on the endocardial surface 14, and the magnetic elements 110, 112 may be utilized to position and/or secure the first ablation component 102 on the epicardial surface 12. One or more of the ablation elements 106, 108 may be operated to ablate the target tissue and create the lesion 16. The magnetic elements 110, 112 may be at least partially decoupled. In some example embodiments, the magnetic elements 110, 112 may be reconfigured into a less magnetically attractive arrangement and/or a magnetically repulsive arrangement, such as to disengage one or more of the first ablation component 102 and/or the second ablation component 104 from the target tissue 18. The first and second ablation components 102, 104 may be repositioned for subsequent ablations and/or may be withdrawn from the patient.

In some example embodiments, an ablation component 102, 104 may be passively oriented and/or located on the target tissue. For example, the ablation component 102, 104 may be generally positioned on the target tissue 18, such as by direct imaging and/or visualization through a scope. In some example embodiments, the ablation component 102, 104 may be releasably attached to the target tissue, such as by a vacuum anchor or other tissue anchor. Related elements associated with the ablation component 102, 104 may include a single lumen sheath, a multi lumen sheath, and/or an inflatable element, such as a space-making element.

In some example embodiments, an ablation component 102, 104 may be oriented and/or located on the target tissue using an image guided catheter and/or an electrophysiological mapping system. For example, one or more of the ablation components 102, 104 may include guidance features. In some example embodiments, an ablation component 102, 104 may include pacing features, sensing features, mapping features, and/or stimulation features and/or may be used in connection with a cooperating ablation component 102, 104 including pacing features, sensing features, mapping features, and/or stimulation features.

Some example embodiments may provide sensing capabilities for various parameters. For example, tissue impedance may be sensed between ablation electrodes 106, 108, such as to assess the extent of an ablation 16. In some example embodiments, measurements of magnetic fields may be utilized, such as to determine a distance between certain components. In some example embodiments, one or more temperatures may be measured.

The ablation elements 106, 108 and magnetic elements 110, 112 are illustrated as separate elements in FIG. 1 for clarity. However, in some example embodiments, one or more of the ablation elements 106, 108 and/or one or more of the magnetic elements 110, 112 may be combined into a single element. For example, at least a portion of a magnetic element 110, 112 may also act as an ablation element 106, 108 (e.g., an RF electrode), or a dedicated electrode material may be used around or adjacent to a magnetic element 110, 112.

The foregoing description of the example ablation system 100 provides context for various other example embodiments described below. The various detailed example embodiments described below may comprise components of the example ablation system 100, or may be utilized independently or in cooperation in alternative systems and circumstances. Any feature, component, or operation described in connection with any example embodiment herein may be utilized in connection with any other embodiment, in any combination, and repeated description of features, components, and operations is omitted for brevity.

Figure 2:
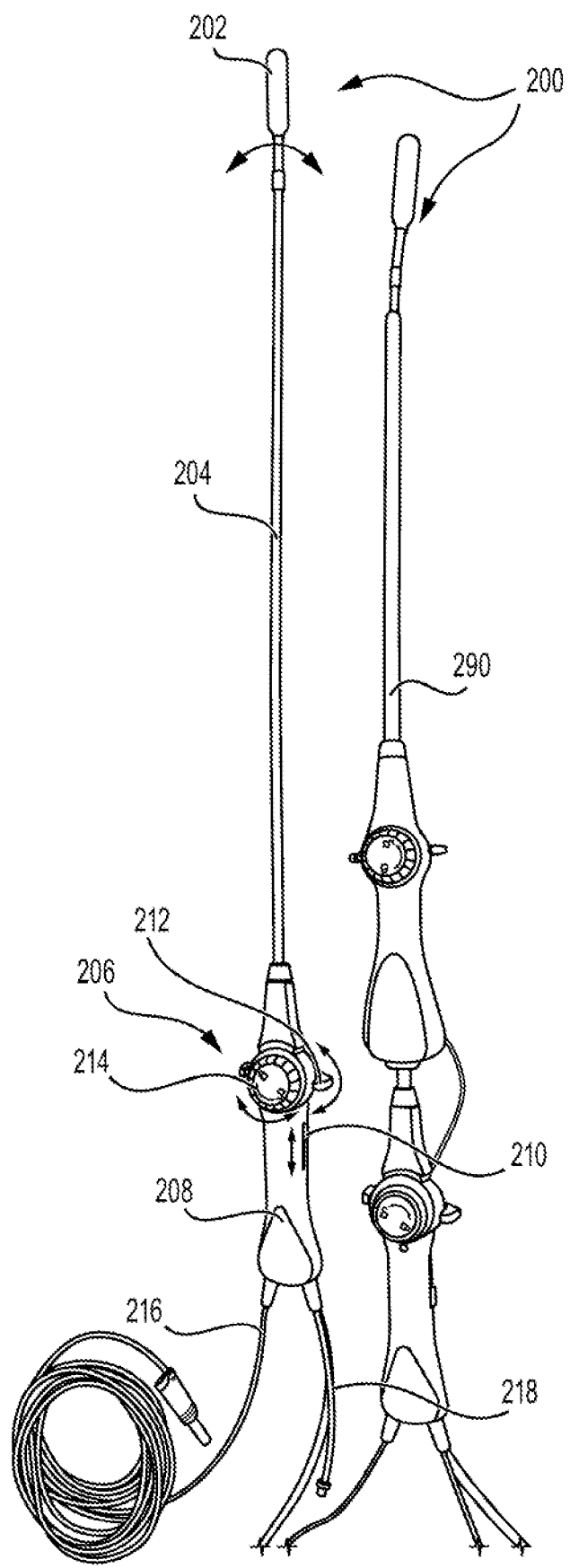
FIG. 2 is a perspective view of two example ablation components, one shown alone and one shown inserted through an example delivery device.

It will be appreciated that any example ablation component described herein may be utilized in connection with a delivery sheath (which may be steerable) or other similar device for directing the ablation component to the target tissue. For example, FIG. 2 is a perspective view of two example ablation components 200, one shown alone and one shown inserted through an example delivery device 290, according to at least some aspects of the present disclosure. The ablation component 200 may be generally similar in structure and operation to other ablation components described elsewhere herein, and repeated description is omitted for brevity. Likewise, any feature described in connection with ablation component 200 may be utilized in connection with any other embodiment described elsewhere herein. The ablation component 200 may be similar to and/or may be utilized as the first ablation component 102 of FIG. 1, for example. In some example embodiments, the delivery device 290 may be similar in construction and/or operation to those described in U.S. patent application Ser. No. 17/695,210, titled DELIVERY DEVICES AND RELATED METHODS, filed Mar. 15, 2022, which is hereby incorporated by reference in its entirety.

Referring to FIG. 2, the ablation component 200 may include a distally disposed end effector 202 configured to be positioned on a first side 12 of a target tissue 16 (FIG. 1), an elongated connecting element 204, and a proximally disposed handle 206. The handle 206 may include a grip portion 208 configured to be grasped by a user and/or one or more actuators 210, 212, 214 configured to operate other elements of the ablation component 200. Although actuators 210, 212, 214 are shown on one side of the handle 206 in FIG. 2, some alternative embodiments may include one or similar actuators on the opposite side or other portions of the handle 206, such as to facilitate ambidextrous operation. Various actuators described herein may be operatively coupled to the respective actuated elements by one or more mechanical connectors (e.g., linkages, rods, wires, cables, etc.), which may extend longitudinally through the connecting element 204.

In the illustrated embodiment, one or more magnet actuators 210 may be configured to reposition one or more magnetic elements, as described in more detail below. In this embodiment, the magnet actuator 210 is longitudinally slidable (e.g., distally and proximally); however, alternative embodiments may include magnet actuators configured for alternative actuation motions, such as those described elsewhere herein.

In the illustrated embodiment, one or more steering actuators 212 may be configured to articulate a distal end portion of the ablation component 200. For example, in the illustrated embodiment, the steering actuator 212 may be generally in the form of a rotatable tab configured to articulate the distal end portion of the ablation component 200 (e.g., including the end effector 202) as described in more detail below.

In the illustrated embodiment, one or more locking actuators 214 may be configured to secure the distal end portion of the ablation component 200 in a desired orientation. For example, the locking actuator 214 may be generally in the form of a rotatable knob configured to lock the steering actuator 212, thereby securing the distal end portion of the ablation component 200 in a desired orientation.

In the illustrated embodiment, an electrical connecting element 216 is operatively connected to the end effector 202 and is configured to electrically couple the ablation component 200 to a control unit 114 (FIG. 1), which may comprise an electrosurgical generator, such as via an electrical conductor extending longitudinally through the connecting element 216. In the illustrated embodiment, a vacuum connecting element 218 is operatively connected to the end effector 202 and is configured to fluidically couple the ablation component 200 a control unit 114 (FIG. 1), which may comprise a vacuum source, such as via a suction or vacuum lumen extending longitudinally through the connecting element 204. It will be appreciated that similar connecting elements, lumens, conductors, and/or connectors may be utilized in connection with other components and/or embodiments described herein. For example, an ablation component configured for irrigation may include a similar irrigation connecting element, an ablation component configured for closed loop cooling may include a cooling connecting element comprising supply and return conduits, etc. In some example embodiments, some connecting elements may extend individually from the ablation component 200, as is shown in FIG. 2 with separate the electrical connecting element 216 and vacuum connecting element 218. In other example embodiments, two or more connecting elements may be provided together, such as is generally shown with connecting element 116 in FIG. 1.

Figure 3:
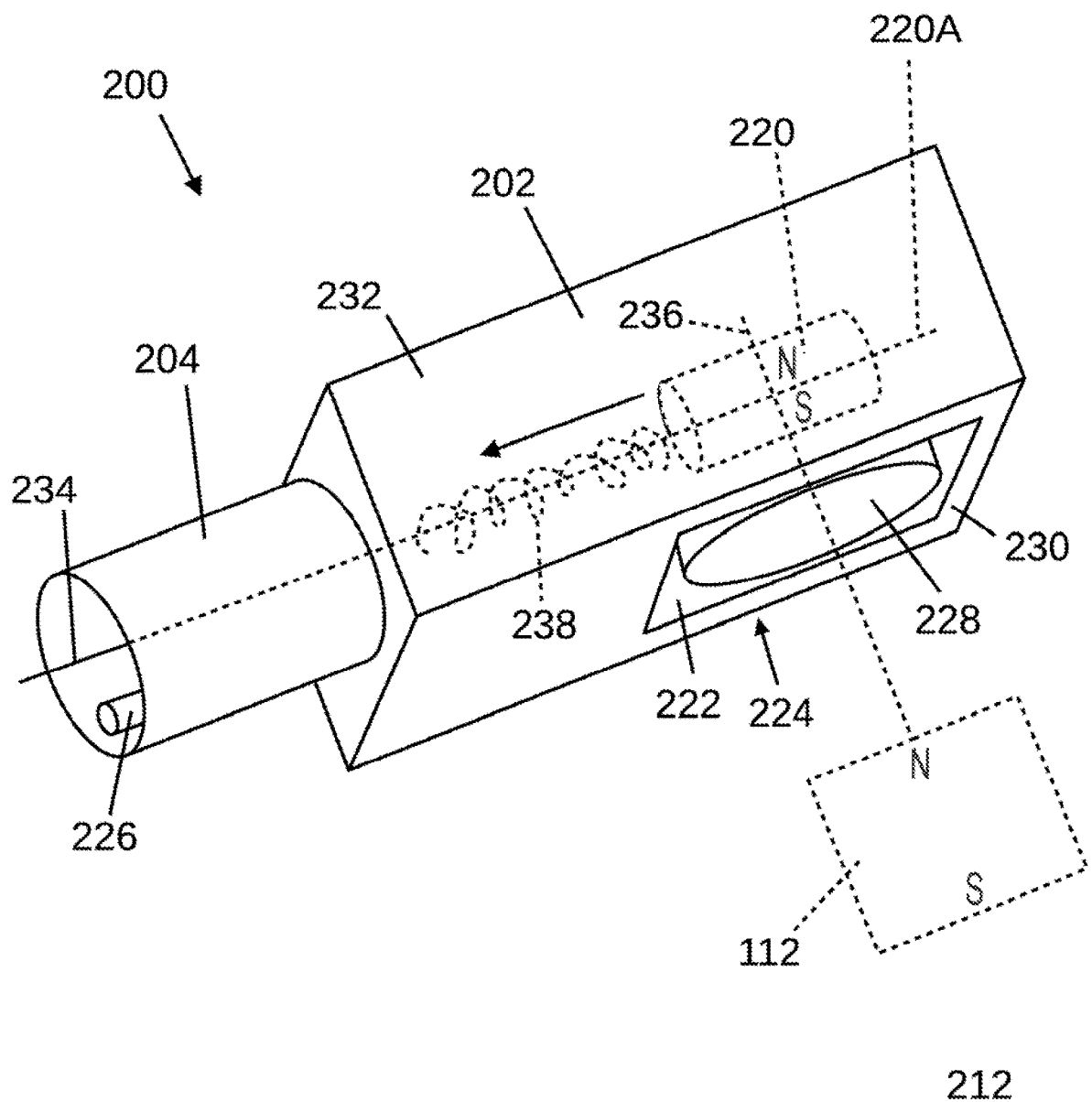
FIG. 3 is a simplified perspective view of a distal portion of the ablation component of FIG. 2.

FIG. 3 is a simplified perspective view of a distal portion of the ablation component 200, including a magnetic element comprising a repositionable permanent magnet 220, according to at least some aspects of the present disclosure. In the illustrated embodiment, the ablation component 200 is configured to utilize vacuum fixation to releasably couple the end effector 202 to the target tissue. The end effector 202 includes at least one vacuum port 222 on a tissue contacting portion 224. The vacuum port 222 is fluidically connected to a vacuum source by a vacuum conduit 226, which may extend longitudinally through the connecting element 204. An electrode 228 (or other ablation element) is configured to deliver ablation energy to the target tissue adjacent to the tissue contacting portion 224. In the illustrated embodiment, the electrode 228 is disposed substantially within a perimeter wall 230 defining the vacuum port 222; however, other suitable arrangements may be utilized in alternative embodiments. For example, other embodiments may include one or more ablation elements disposed adjacent to a vacuum port. Further, other example embodiments may include more than one vacuum port on the tissue contacting portion 224. It will be appreciated that similar vacuum ports may be utilized in connection with other embodiments described herein.

In the illustrated embodiment, the end effector 202 includes a housing 232, and the magnet 220 is disposed within the housing 232. The magnet 220 is configured to cooperate with a magnetic element of a corresponding ablation component, such as the magnetic element 112 of the second ablation component 104 (FIG. 1). In the illustrated embodiment, the magnet 220 is translatable (e.g., longitudinally repositionable) within the housing 232 generally along a longitudinal axis 220A of the magnet 220, which may be colinear with and/or parallel to a longitudinal axis of the end effector 202. For example, in the illustrated embodiment, the magnet actuator 210 (FIG. 2) may be operable to translate the magnet 220 proximally and distally, such as via a mechanical linkage 234, which may extend longitudinally through the connecting element 204. In other example embodiments, the magnet 220 may repositionable in other manners, such as translatable along other suitable axes.

In the illustrated embodiment, the magnet 220 is diametrically magnetized and is arranged so that the North and South poles are oriented substantially towards and away from the cooperating magnetic element 112. That is, one of the North pole and the South pole is oriented substantially toward the target tissue contacting portion 224 and the other of the North pole and the South pole is oriented substantially away from the tissue contacting portion 224. Accordingly, a magnetic (North-South) axis 236 of the magnet 220 is oriented substantially in line with and/or generally normal to the tissue contacting portion 224. In the illustrated embodiment, the rotational orientation of the magnet (e.g., the relative angular orientation of the magnetic axis 236 with respect to the end effector 202) remains substantially the same as the magnet 220 is repositioned proximally and/or distally by the magnet actuator 210 (FIG. 2). That is, the magnet 220 moves proximally and/or distally without substantial rotation relative to the housing 232.

Some example embodiments may include a magnet follower spring 238, which may include a helical compression spring disposed for compression as the magnet 220 is retracted proximally. In some embodiments, the magnet follower spring 238 may exert a distal force on the magnet 220, which may facilitate distal movement of the magnet 220 using the magnet actuator 210.

Figure 4:
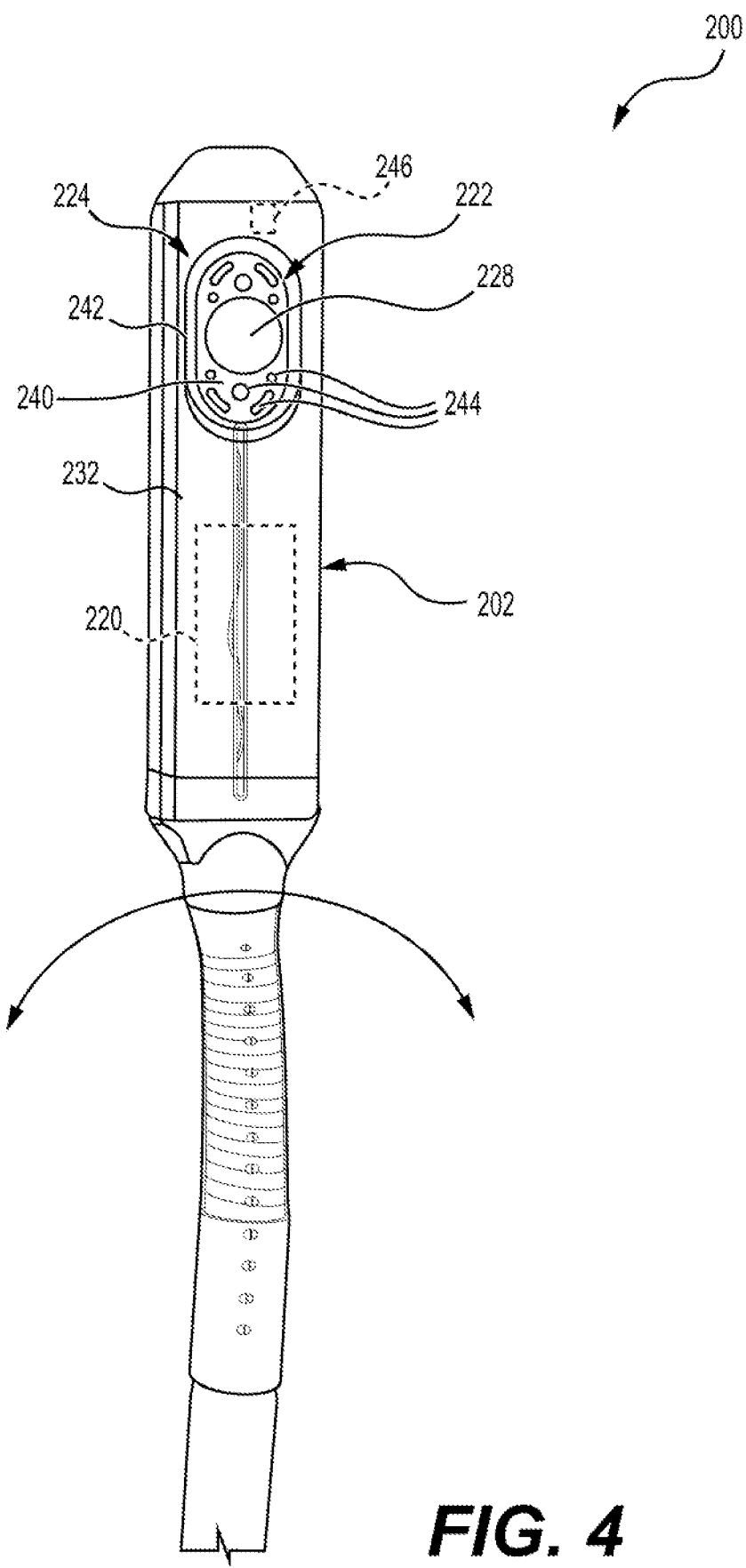
FIG. 4 is a detailed perspective view of a distal end portion of the ablation component of FIG. 2 in a generally straight orientation.
Figure 5:
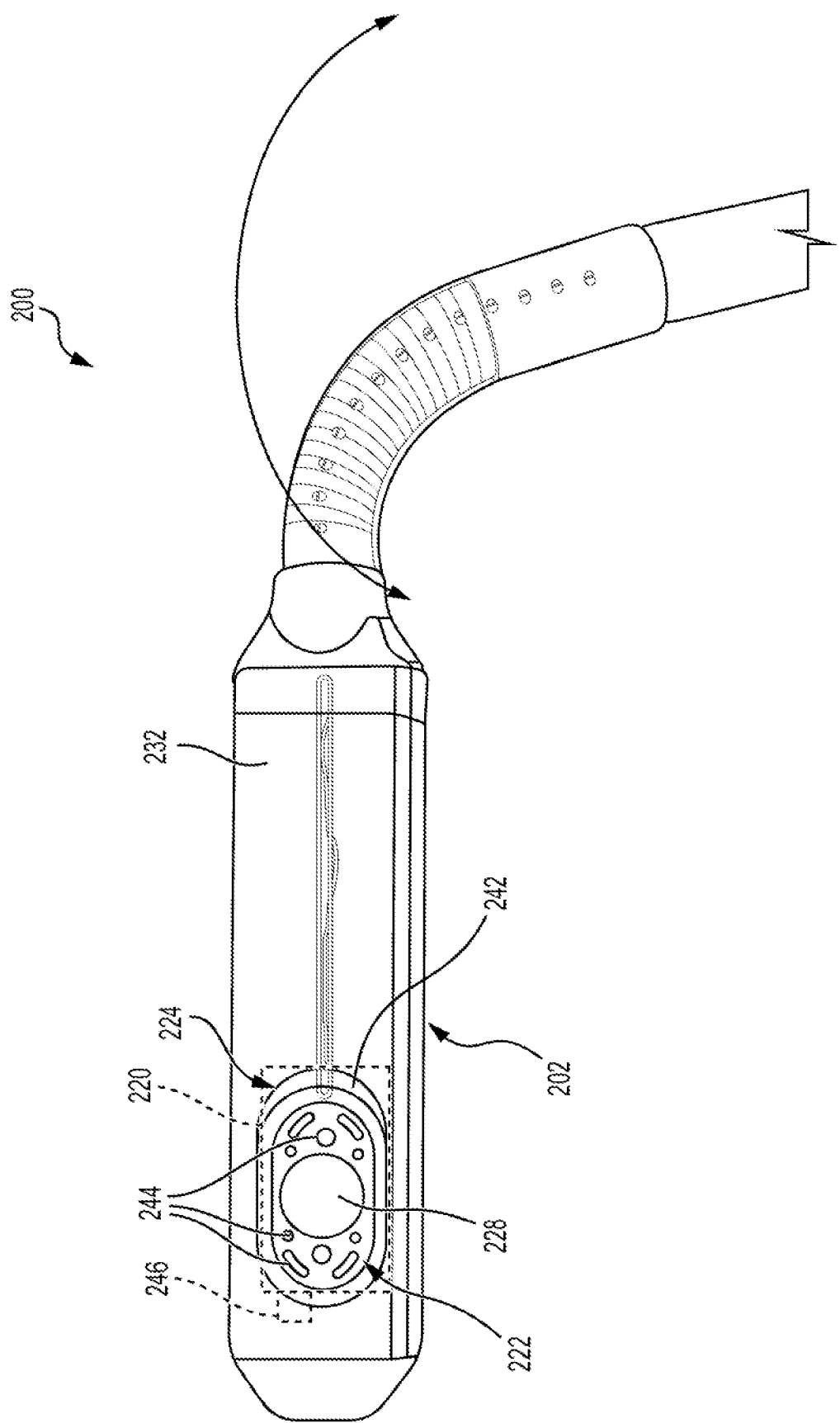
FIG. 5 is a detailed perspective view of the distal end portion of the ablation component of FIG. 2 in an articulated orientation.

FIG. 4 is a detailed perspective view of a distal end portion of ablation component 200 in a generally straight orientation, and FIG. 5 is a detailed perspective view of the distal end portion of ablation component 200 in an articulated orientation, all according to at least some aspects of the present disclosure.

Referring to FIGS. 2-5, in some example embodiments, the housing 232 may be constructed at least partially from a flexible material. For example, in some embodiments, the flexible material may be substantially fully encompassing. Alternatively, the flexible material may form a flexible exterior portion, which may be disposed over a more rigid interior portion. In some example embodiments, the housing 232 may include an electrode insulating portion 240 disposed at least partially generally around the ablation element (e.g., electrode 228). The electrode insulating portion 240 may act to electrically and/or thermally isolate the electrode 228 from nearby components, except where exposure of the electrode 228 is desired (e.g., to the target tissue).

In some embodiments, the tissue-contacting portion of the electrode 228 may extend through and/or project above the surrounding insulative portion 240, thus ensuring that only the desired portion of the electrode 228 (e.g., a raised circular portion) may contact the target tissue. In some embodiments, the electrode may include portions shielded by the insulative portion 240, such as additional mass for heat dissipation, heat transfer features such as fins, etc., that do not contact the target tissue. In some example embodiments, an irrigation conduit may extend within the housing 232, such as near the distal tip.

In the illustrated embodiment, the tissue contacting portion 224 faces generally laterally relative to the proximal-distal direction. The tissue contacting portion 224 may include a generally circumferential, outwardly projecting skirt 242 at least partially defining the vacuum port 222. The tissue contacting portion 224 may include one or more openings 244 disposed within the perimeter of the skirt 242 (e.g., through the insulative portion 240). The openings 244 may be configured to deliver irrigation fluid and/or may be fluidically coupled to a vacuum source, for example. Irrigation fluid may provide cooling for the target tissue, adjacent tissues, and/or the electrode 228, for example. Generally, the tissue contacting portion 224 of the illustrated embodiment may be shorter (e.g., longitudinally) than in other similar example embodiments described herein.

In the illustrated embodiment, the electrode 228 is generally circular such that it may act as a focal spot electrode for bipolar and/or monopolar radiofrequency ablation, for example. In the illustrated embodiment, the electrode 228 is generally longitudinally and/or laterally centrally disposed within the tissue contacting portion 224. Further, in the illustrated embodiment, the electrode 228 is recessed within the skirt 242 so that the skirt 242 projects laterally outwardly farther than the tissue contacting surface 224 of the electrode 228.

In the illustrated embodiment, the distal portion of the ablation component 200 may be steerable using the steering actuator 212. For example, the distal portion of the ablation component 200 may be steerable between the generally straight orientation shown in FIG. 4, the approximately 90 degree left orientation shown in FIG. 5, and a mirror-image approximately 90 right orientation. Although the illustrated embodiment is generally symmetrically bidirectionally steerable about 0-90 degrees left and about 0-90 degrees right (e.g., for a total of about 180 degrees), it will be understood that alternative embodiments may be unidirectionally steerable (e.g., 0-180 degrees in one direction) or bidirectionally steerable symmetrically or asymmetrically (e.g., 0-180 degrees in each direction, for a total of 0-360 degrees). In the illustrated embodiment, the distal end portion of the ablation component 200 is generally flexible in the up-down plane (e.g., generally perpendicular to the left-right plane in which the device is steerable). Some alternative embodiments may be generally rigid or steerable (unidirectionally or bidirectionally) in the up-down plane.

In the illustrated embodiment, the magnet 220 is selectively translatable (e.g., longitudinally repositionable) within the housing 232 generally between a distal, engaged position (FIG. 5) and a proximal, disengaged position (FIG. 4). In this embodiment, the housing 232 at least partially defines an internal cavity within which the magnet 220 is translatable. Generally, as described in more detail below, prior to ablation, the magnet 220 may be moved into (or may be verified to already be in) the engaged position generally adjacent the electrode 228. The magnet 220 may be used in connection with a cooperating magnet 112 (FIG. 1) to position the end effector 202 on the target tissue 18 (FIG. 1). In some embodiments, the magnetic attraction between the magnet 220 and the cooperating magnet 112 may at least partially compress the target tissue 18. After the desired ablation has been conducted, the magnet 220 may be repositioned, such as to the disengaged position generally proximal to the electrode 228 as shown in FIG. 4. Such retraction may facilitate discontinuing and/or reducing magnetic attraction between the magnet 220 and the cooperating magnet 112.

In alternative embodiments, the distal position may be the disengaged position and/or the proximal position may be the engaged position. In some such embodiments, the magnet 220 may be retracted into an engaged position proximate an electrode and/or may be extended into a disengaged position distal to the electrode.

Referring to FIGS. 4 and 5, some example embodiments may include one or more mechanical stops 246 configured to facilitate positioning of the permanent magnet 220. For example, in the illustrated embodiment, the mechanical stop 246 is disposed generally distally within the housing 232. The stop 246 acts as a distal stop for the permanent magnet 220, thereby ensuring that the permanent magnet 220 is positioned as desired in the distal, engaged position. For example, the stop 246 may ensure that the permanent magnet 220 is substantially centered relative to the ablation element 228 when the permanent magnet 220 is in the distal, engaged position. As a result, the cooperating magnetic element of a cooperating ablation component (e.g., on the opposite side of the target tissue) may be operative to align the respective ablation elements across the target tissue. In other embodiments, similar mechanical stops may be used in connection with other positions of magnetic elements, such as proximal, disengaged positions.

Figure 6:
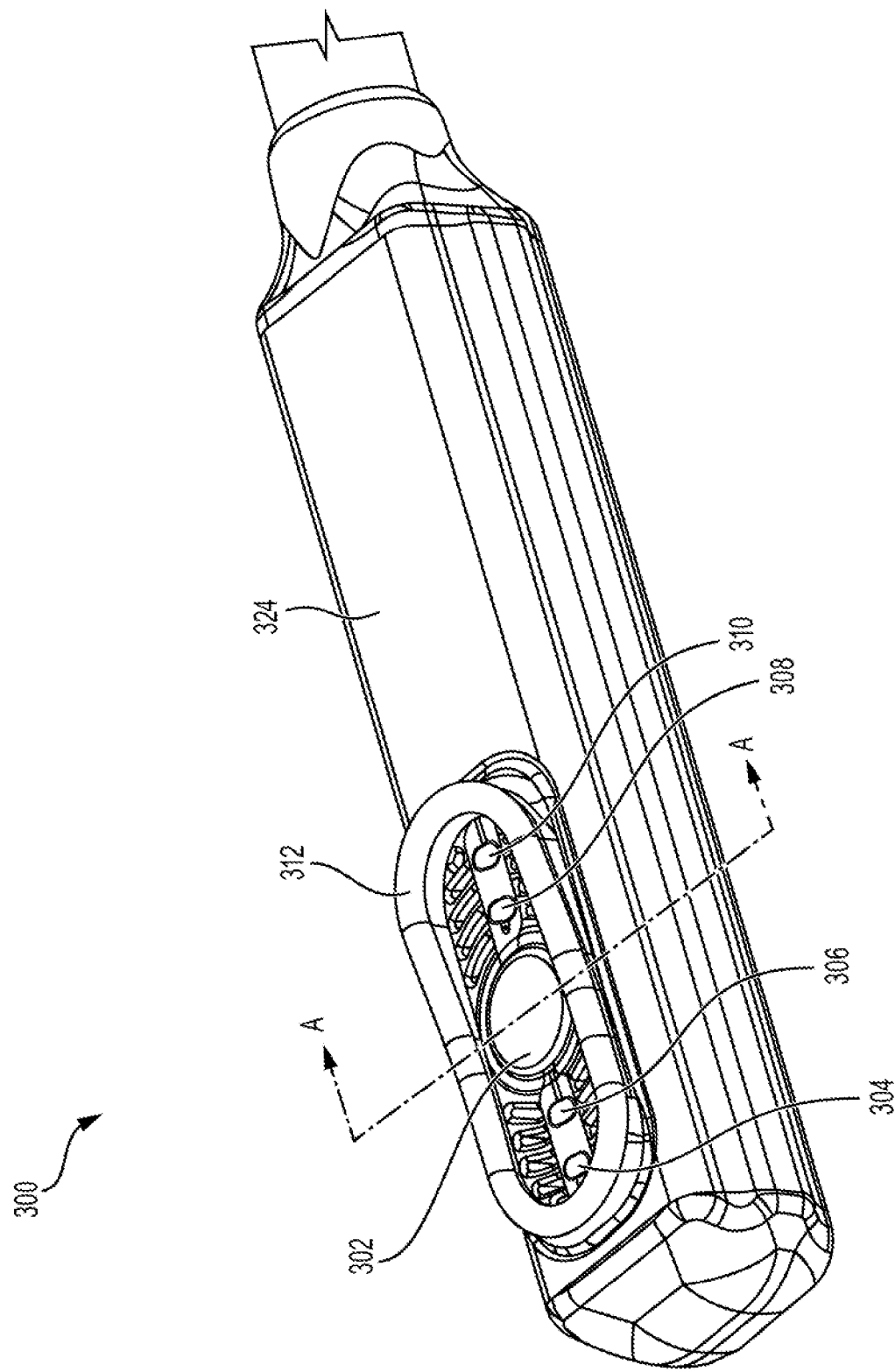
FIG. 6 is a perspective view of a distal end portion of an alternative example ablation component.
Figure 7:
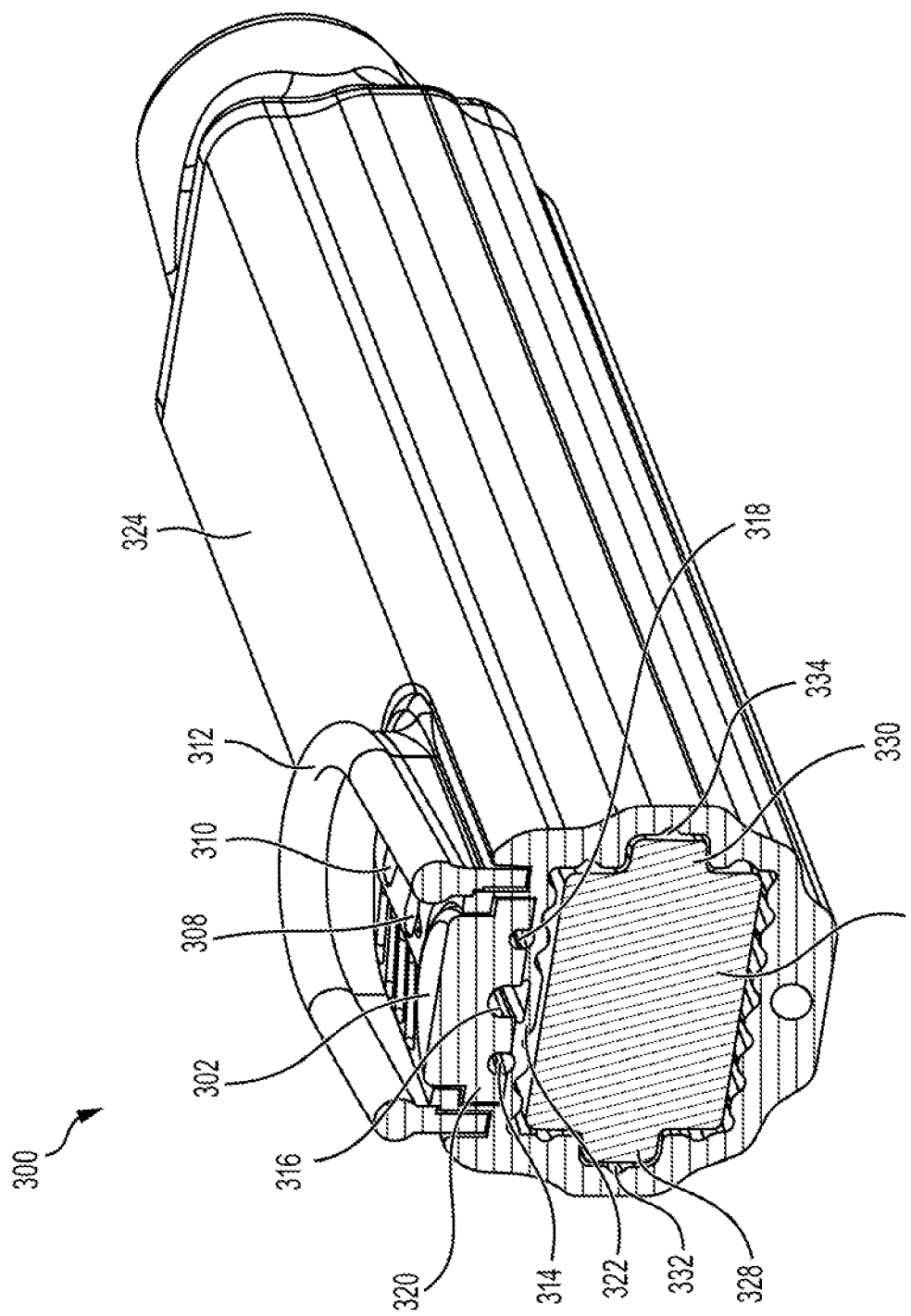
FIG. 7 is a perspective cross section view of the distal end portion of the ablation component of FIG. 6.

FIG. 6 is a perspective view of a distal end portion of an alternative example ablation component 300, and FIG. 7 is a perspective cross section view of the distal end portion of the ablation component 300 taken at line A-A in FIG. 6, all according to at least some aspects of the present disclosure. Ablation component 300 is generally similar in structure and operation to ablation components described elsewhere herein, including ablation component 200, and repeated description of similar elements is omitted for brevity. Likewise, any feature described in connection with ablation component 300 may be utilized in connection with any other embodiment described elsewhere herein. In the illustrated embodiment, the ablation element comprises a generally circular primary electrode 302. One or more auxiliary electrodes 304, 306, 308, 310 are provided in addition to the primary electrode 302. In this embodiment, both the primary electrode 302 and the auxiliary electrodes 304, 306, 308, 310 are disposed within the perimeter defined by the skirt 312.

The auxiliary electrodes 304, 306, 308, 310 may be used for sensing, stimulating, mapping, and/or pacing, for example. Such sensing, stimulating, mapping and/or pacing may be conducted, for example, in connection with identifying a target location for a future ablation and/or for assessing the effectiveness of a prior ablation, as well as solely for diagnostic purposes (e.g., not immediately preceding and/or following an ablation). In some example embodiments, the primary electrode 302 may be used for non-ablation purposes, such as sensing, stimulating, mapping and/or pacing, instead of or in addition to one or more auxiliary electrodes 304, 306, 308, 310. In some embodiments, one or more of the auxiliary electrodes 304, 306, 308, 310 may be used for ablation purposes, in addition to or instead of the primary electrode 302.

In this embodiment, two of the auxiliary electrodes 304, 306 are disposed distally relative to the primary electrode 302, and two of the auxiliary electrodes 308, 310 are disposed proximally relative to the primary electrode 302. In the illustrated embodiment, all five electrodes 302, 304, 306, 308, 310 are arranged generally in line in the longitudinal direction. That is, they form a one-dimensional array. In some alternative embodiments, one or more of the electrodes 302, 304, 306, 308, 310 may be disposed in alternative arrangements, such as in a two-dimensional array (e.g., a partial or complete grid arrangement). In some alternative embodiments, one or more of the auxiliary electrodes 304, 306, 308, 310 may be disposed laterally relative to the primary electrode 302. That is, in some embodiments, all five electrodes 302, 304, 306, 308, 310 may not be arranged generally in line. For example, one or more auxiliary electrodes 304, 306, 308, 310 may be disposed both longitudinally and laterally offset from the primary electrode 302, on one or both lateral sides of the primary electrode. In some embodiments, one or more auxiliary electrodes 304, 306, 308, 310 may be disposed laterally offset at the same (or about the same) longitudinal position as the primary electrode 302, on one or both lateral sides of the primary electrode 302.

Referring to FIG. 7, in the illustrated embodiment, the primary electrode 302 may at least partially define one or more internal channels 314, 316, 318. In this embodiment, the channels 314, 316, 318 extend generally longitudinally and generally in parallel, and are partially defined by a base portion 320 of the primary electrode 302. Specifically, in the orientation illustrated in FIG. 7, the primary electrode 302 defines the upper aspects of each of the channels 314, 316, 318 and a divider member 322, which may be formed as a part of the housing 324, defines the lower aspects of each of the channels 314, 316, 318. The channels 314, 316, 318 may be fluidically coupled to a source of cooling fluid, such as via one or more connecting elements 116, 118 (FIG. 1). For example, irrigation fluid may be conveyed to the target tissue via one or more of the channels 314, 316, 318. Accordingly, in some such embodiments, the primary electrode 302 may be cooled internally by irrigation fluid flowing through the channels 314, 316, 318 (e.g., in an open-loop configuration) as well as externally by irrigation fluid present within the area bounded by the skirt 312. In some alternative embodiments, one or more of the channels 314, 316, 318 may be fluidically connected to a source of cooling fluid in a closed-loop configuration.

Referring still to FIG. 7, this example embodiment may include a longitudinally repositionable magnetic element including a permanent magnet 326, which may include one or more projections, such as one or more longitudinal wings 328, 330, which may be arranged to slide longitudinally within one or more corresponding grooves 332, 334 on the interior of the housing. In this embodiment, the projections 328, 330 may be formed integrally with other portions of the magnet 326. For example, the magnet 326 may be substantially monolithically formed with the wings 328, 330. In other similar embodiments, the magnetic element may have other shapes. For example, some alternative embodiments may include a longitudinally repositionable permanent magnet generally in form of a rectangular solid (e.g., without projections) or generally in the form of a right circular cylindrical solid.

Figure 8:
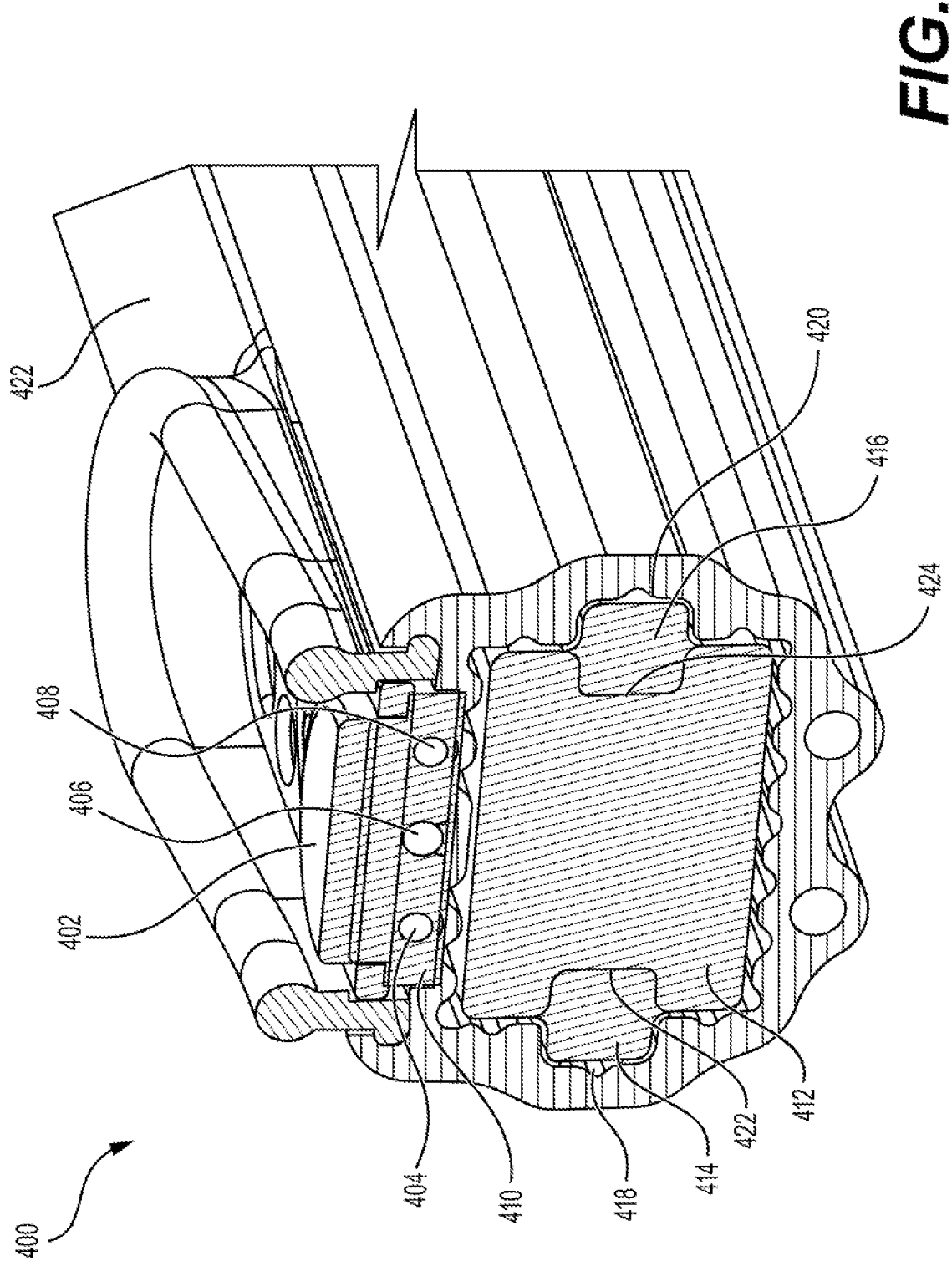
FIG. 8 is a perspective cross section view of the distal end portion of an alternative example ablation component.

FIG. 8 is a perspective cross section view of the distal end portion of an alternative example ablation component 400, according to at least some aspects of the present disclosure. Ablation component 400 may be generally similar to and/or may be used in a generally similar manner as various ablation components described elsewhere herein, including ablation components 300, described above, and repeated description of similar elements and operations is omitted for brevity. Likewise, any feature described in connection with ablation component 400 may be utilized in connection with any other embodiment described elsewhere herein.

In the embodiment of FIG. 8, the ablation element comprises an electrode 402, which may include one or more internal channels 404, 406, 408. In this embodiment, the channels 404, 406, 408 extend generally longitudinally and generally in parallel through a base portion 410 of the electrode 402. In the illustrated embodiment, and unlike the embodiment of FIG. 7, the channels 404, 406, 408 are substantially fully defined by the base portion 410. Accordingly, the embodiment of FIG. 8 may not include a divider member 322 as shown in FIG. 7. In other embodiments, the one or more internal channels 404, 406, 408 may be disposed in different positions and/or orientations. In the illustrated embodiment, the channels 404, 406, 408 may be fluidically coupled to a source of cooling fluid, such as via one or more connecting elements 116, 118 (FIG. 1). For example, irrigation fluid may be conveyed to the target tissue via one or more of the channels 404, 406, 408. Accordingly, in some such embodiments, the electrode 402 may be cooled internally by irrigation fluid flowing through the channels 404, 406, 408 (e.g., in an open-loop configuration) as well as externally by irrigation fluid present in the vicinity of the electrode 402. In some alternative embodiments, one or more of the channels 404, 406, 408 may be fluidically connected to a source of cooling fluid in a closed-loop configuration.

Referring still to FIG. 8, this example embodiment may include a magnetic element including a permanent magnet 412 including one or more projections, such as one or more longitudinal wings 414, 416, which may be arranged to slide longitudinally within one or more corresponding grooves 418, 420 on the interior of the housing 422. This configuration is generally similar to that described above with reference to FIG. 7; however, in the embodiment of FIG. 8, the projections 414, 416 may be separately formed and affixed to the magnet 412. The magnet 412 may be formed to accept the projections 414, 416, such as in respective longitudinal recesses 422, 424.

Figure 9:
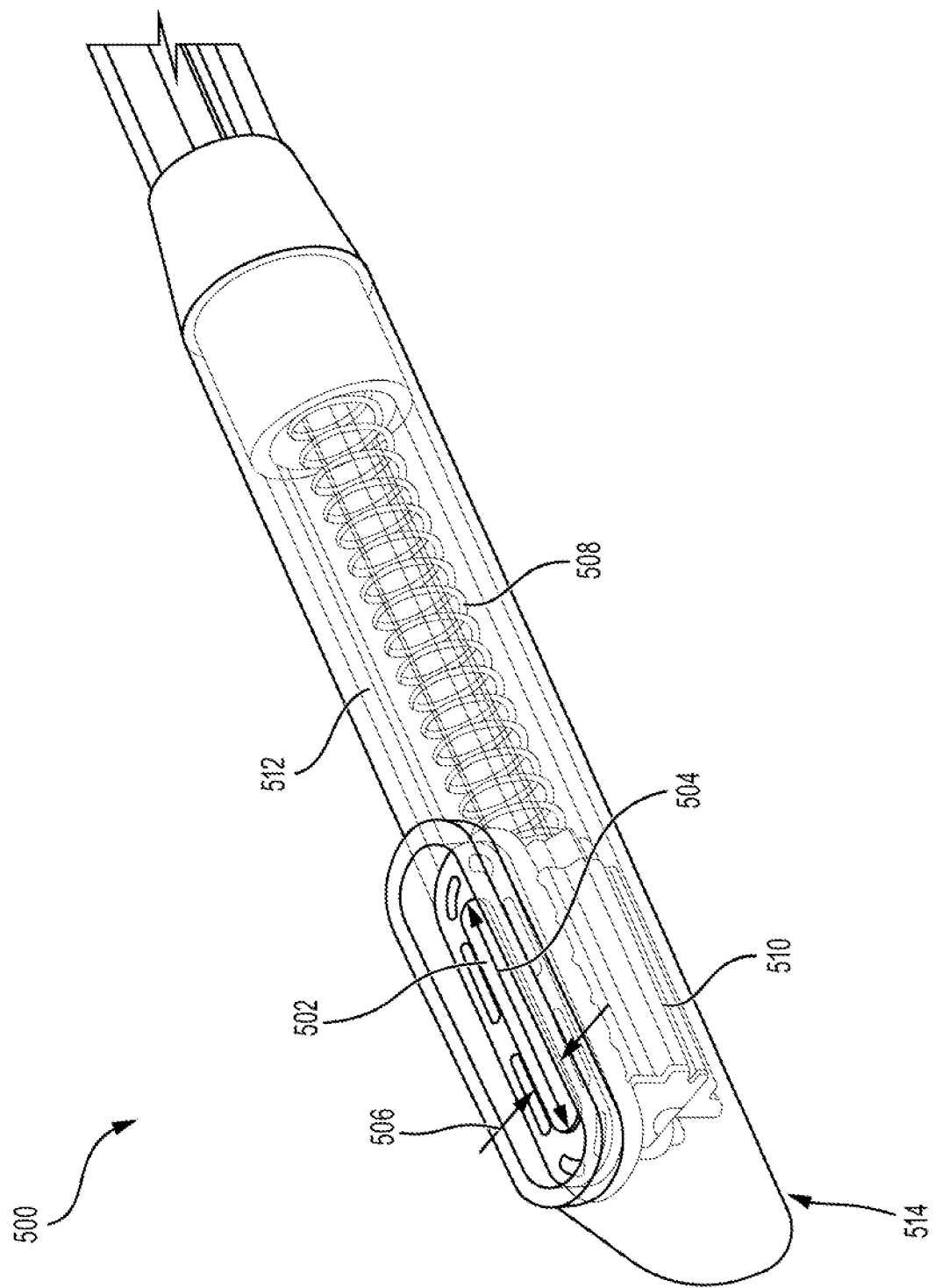
FIG. 9 is a perspective view of an alternative example ablation component including an ablation element comprising a linear electrode.

FIG. 9 is a perspective view of an alternative example ablation component 500 including an ablation element comprising a linear electrode, according to at least some aspects of the present disclosure. The ablation component 500 is generally similar in structure and operation to ablation components described elsewhere herein, including ablation component 300, and repeated description of similar elements is omitted for brevity. Likewise, any feature described in connection with ablation component 500 may be utilized in connection with any other embodiment described elsewhere herein. In the illustrated embodiment, the ablation element comprises an elongated electrode 502. In this embodiment, the electrode 502 has one dimension that is substantially greater than a perpendicular dimension. For example, the electrode 502 has a longitudinal length 504 that is about eight times a lateral width 506 of the electrode 502. In this embodiment, the electrode 502 is elongated in the longitudinal direction; however, in some alternative embodiments, the electrode may be elongated in another direction, such as in a lateral direction and/or a diagonal direction. In this embodiment, the electrode 502 is generally straight; however, other embodiments may include electrodes having one or more curves and/or angles. Further, in some embodiments, the width 506 may vary over the length 504 of the electrode 502.

Additionally, FIG. 9 illustrates a magnet follower spring 508, which may be a helical compression spring, disposed for compression as the magnet 510 is retracted proximally. In the illustrated embodiment, the spring 508 is configured to hold an inner lumen of a flexible portion 512 of the end effector 514 open to receive the magnet 510 therein upon retraction. Further, in some embodiments, compression of the spring 508 as the magnet 510 is retracted proximally may exert a distal force on the magnet 510, which may facilitate distal movement of the magnet 510 into an extended position.

Figure 10:
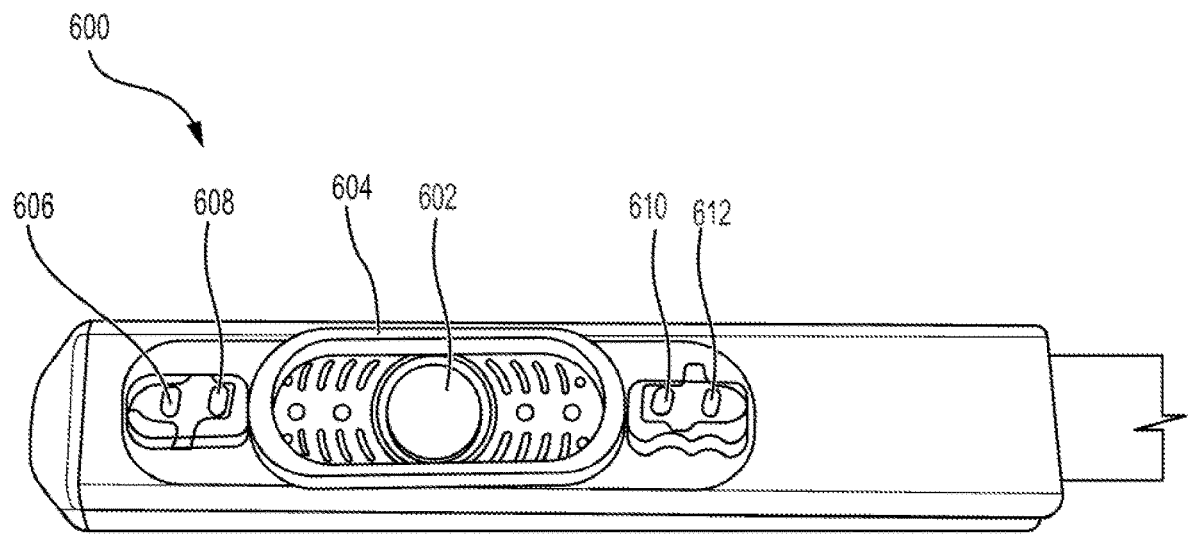
FIG. 10 is a perspective view of a distal end portion of an alternative example ablation component.
Figure 11:
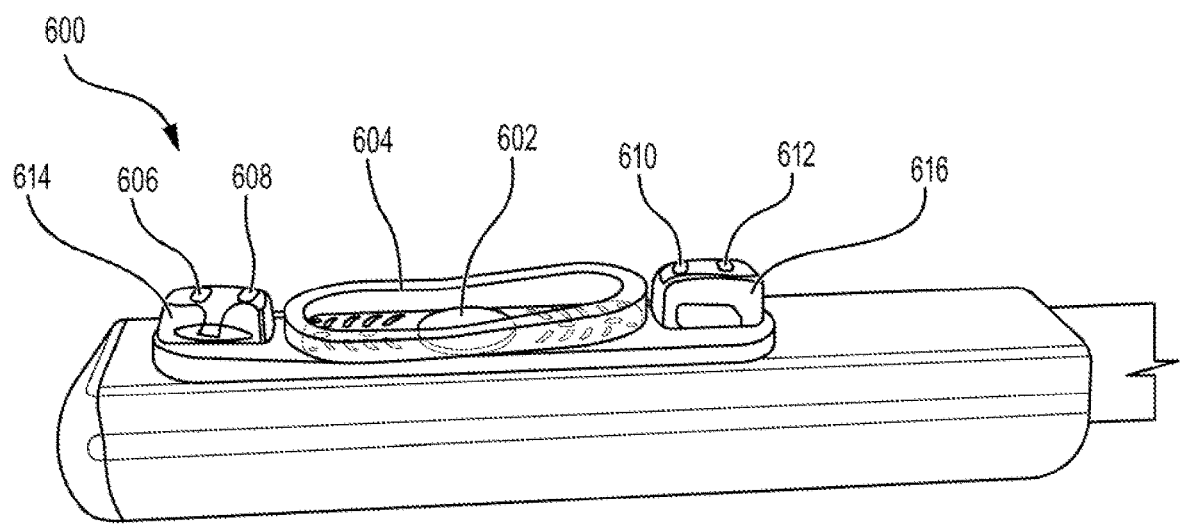
FIG. 11 is a perspective view of the distal end portion of the ablation component of FIG. 10.

FIGS. 10 and 11 are perspective views of a distal end portion of an alternative example ablation component 600, all according to at least some aspects of the present disclosure. Ablation component 600 is generally similar in structure and operation to ablation components described elsewhere herein, including ablation component 300, and repeated description of similar elements is omitted for brevity. Likewise, any feature described in connection with ablation component 600 may be utilized in connection with any other embodiment described elsewhere herein. Similar to ablation component 300, in ablation component 600, a primary electrode 602 is disposed within an outwardly extending skirt 604, and one or more auxiliary electrodes 606, 608, 610, 612 are provided in addition to the primary electrode 602. In this embodiment, however, one or more of the auxiliary electrodes 606, 608, 610, 612 are disposed outside of the perimeter defined by the skirt 604. Specifically, in the illustrated embodiment, two auxiliary electrodes 606, 608 are disposed distal to the skirt 604 and two auxiliary electrodes 610, 612 are disposed proximal to the skirt 604.

Referring to FIG. 11, in some example embodiments, one or more auxiliary electrodes 606, 608, 610, 612 may be disposed on one or more outwardly extending projections 614, 616, which may facilitate electrical contact between the auxiliary electrodes 606, 608, 610, 612 and anatomical tissues. For example, in the illustrated embodiment, distal auxiliary electrodes 606, 608 are disposed on a distal projection 614 and proximal auxiliary electrodes 610, 612 are disposed on a proximal projection 616.

Figure 12:
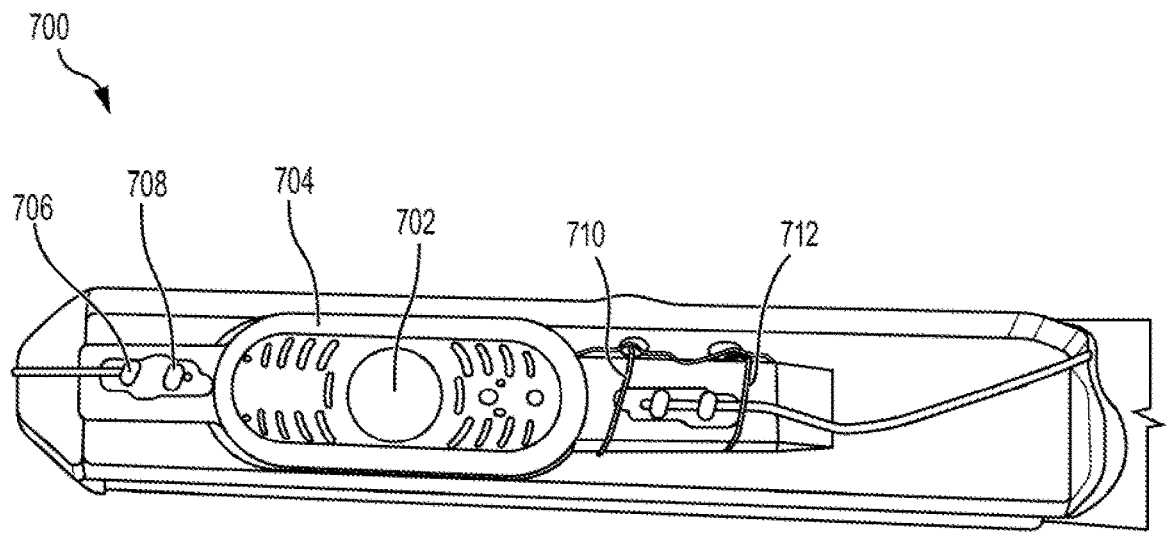
FIG. 12 is a perspective view of a distal end portion of an alternative example ablation component.
Figure 13:
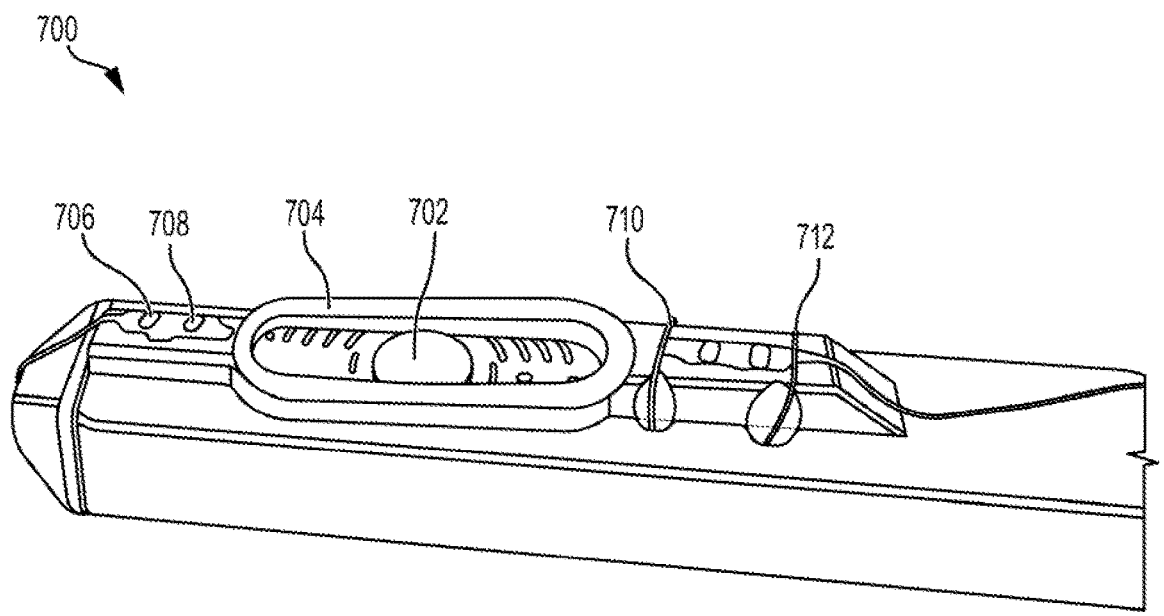
FIG. 13 is a perspective view of the distal end portion of the ablation component of FIG. 12.

FIGS. 12 and 13 are perspective views of a distal end portion of an alternative example ablation component 700, all according to at least some aspects of the present disclosure. Ablation component 700 is generally similar in structure and operation to ablation components described elsewhere herein, including ablation component 600, and repeated description of similar elements is omitted for brevity. Likewise, any feature described in connection with ablation component 700 may be utilized in connection with any other embodiment described elsewhere herein. Similar to ablation component 600, in ablation component 700, a primary electrode 702 is disposed within an outwardly extending skirt 704, and one or more auxiliary electrodes 706, 708, 710, 712 are provided on projections 714, 716 outside of the perimeter defined by the skirt 704.

In the embodiments of FIGS. 12 and 13, two of the auxiliary electrodes 706, 708 are in the form of spot electrodes, generally similar to those of ablation component 600, described above. Two of the auxiliary electrodes 710, 712 are elongated electrodes (e.g., each has a length that is substantially greater than its width). In the illustrated embodiment, the elongated auxiliary electrodes 710, 712 are oriented generally transversely (e.g., substantially perpendicular) to the longitudinal direction. More generally, any one or more of the auxiliary electrodes 706, 708, 710, 712 may be elongated, and elongated electrodes may be positioned in any desired position and/or orientation, such as within and/or outside of the skirt 704.

Figure 14:
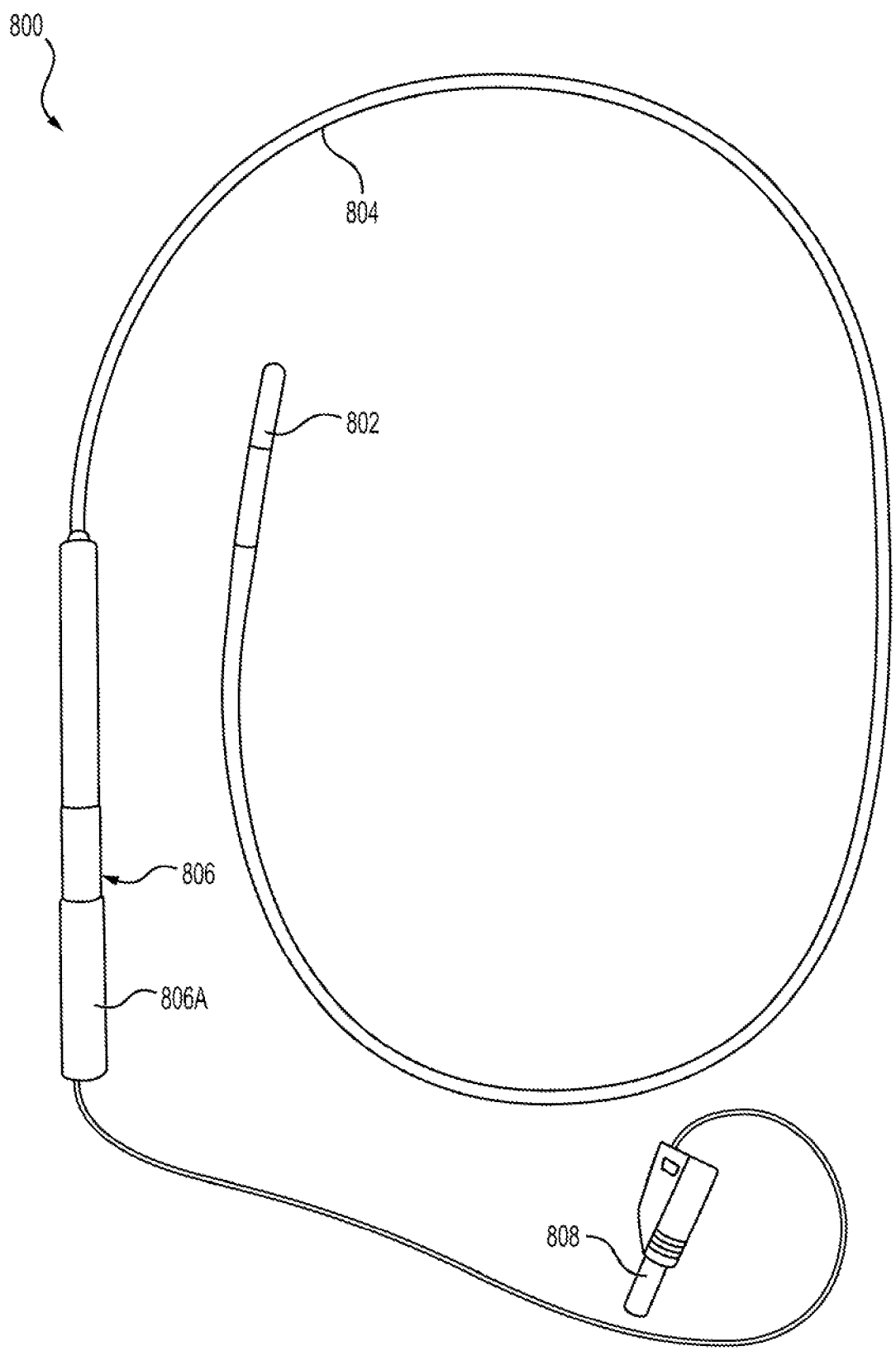
FIG. 14 is a perspective view of an alternative example ablation component.
Figure 15:
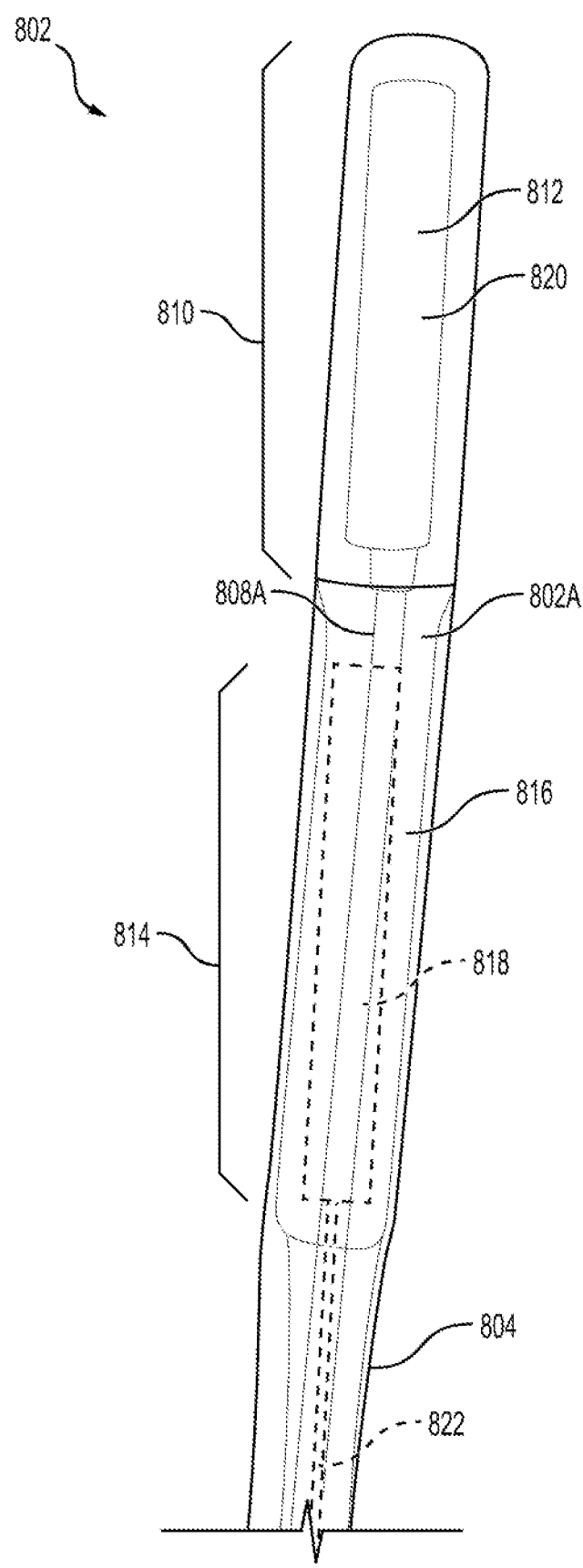
FIG. 15 is a detailed perspective view of an end effector of the ablation component of FIG. 14.

FIG. 14 is a perspective view of an alternative example ablation component 800, and FIG. 15 is a detailed perspective view of an end effector 802 of the ablation component 800, all according to at least some aspects of the present disclosure. Ablation component 800 is generally similar in structure and operation to ablation components described elsewhere herein, including ablation component 200, and repeated description of similar elements is omitted for brevity. Likewise, any feature described in connection with ablation component 800 may be utilized in connection with any other embodiment described elsewhere herein. The ablation component 800 may be similar to and/or may be utilized as the first ablation component 102 of FIG. 1, for example.

Referring to FIG. 14, in the illustrated embodiment, the ablation component 800 includes an end effector 802, an elongated connecting element 804, and a handle 806. Referring to FIGS. 14 and 15, an electrical connector 808 is configured to electrically couple the ablation component 200 to an electrosurgical generator, such as via an electrical conductor 808A extending longitudinally through the connecting element 804. It will be appreciated that similar connecting elements, handles, electrical conductors, and/or electrical connectors may be utilized in connection with other embodiments described herein, and the similar components described in connection with other embodiments herein may be utilized in connection with this embodiment.

Referring to FIG. 15, in the illustrated embodiment, the end effector 802 is disposed distally on the connecting element 804. The end effector 802 includes a distally positioned ablation portion 810, which includes an electrode 812. The end effector 802 also includes a proximally positioned flex zone 814. In this embodiment, the flex zone 814 includes a generally helical stiffener 816. The end effector 802 further includes a permanent magnet 818 disposed within a housing 802A. The magnet 818 is configured to cooperate with a magnetic element of a corresponding ablation component, such as the magnetic element 112 of the second ablation component 104 (FIG. 1). In the illustrated embodiment, the magnet 818 is diametrically magnetized.

In the illustrated embodiment, the magnet 818 is translatable (e.g., longitudinally repositionable) within the housing 802A generally between the ablation portion 810 and the flex zone 814, such as generally along a longitudinal axis of the magnet 818. For example, in the illustrated embodiment, the handle 806 includes an actuator 806A (FIG. 14), which is operable to translate the magnet 818 proximally and distally, such as via a mechanical linkage extending through the connecting element 804. In other example embodiments, the magnet 818 may translatable along other suitable axes. In this embodiment, the stiffener 816 of the flex zone 814 at least partially defines an internal cavity into which the magnet 818 may be retracted proximally. In the illustrated embodiment, the flex zone 814 is generally flexible, but the helical stiffener 816 keeps the inner diameter open to receive the magnet 818 therein when the magnet 818 is retracted proximally.

Referring to FIGS. 14 and 15, in the illustrated embodiment, the magnet 818 is movable proximally and distally by a mechanical linkage 822, which extends proximally within the connecting element 804 for actuation by a user, such as from the proximal handle 806. The mechanical linkage 822 may extend proximally to and/or may be operatively connected to an actuator on the handle 806 for operation by the user, for example. In the illustrated embodiment, the rotational orientation of the magnet (e.g., the orientation of the magnetic axis) remains substantially the same as the magnet 818 is repositioned proximally and/or distally. That is, the magnet 818 moves proximally and/or distally without substantial rotation relative to the housing 802A.

In the illustrated embodiment, prior to ablation, the magnet 818 may be moved into (or may be verified to already be in) a distal position generally adjacent the electrode 812. The magnet 818 may be used in connection with a cooperating magnet 112 (FIG. 1) to position the end effector 802 on the target tissue 18 (FIG. 1). In some embodiments, the magnetic attraction between the magnet 818 and the cooperating magnet 112 may at least partially compress the target tissue 18. After the desired ablation has been conducted, the magnet 818 may be retracted, such as to the position generally proximal to the electrode 812 as shown in FIG. 3. Such retraction may facilitate discontinuing and/or reducing magnetic attraction between the magnet 818 and the cooperating magnet 112.

Figure 16:
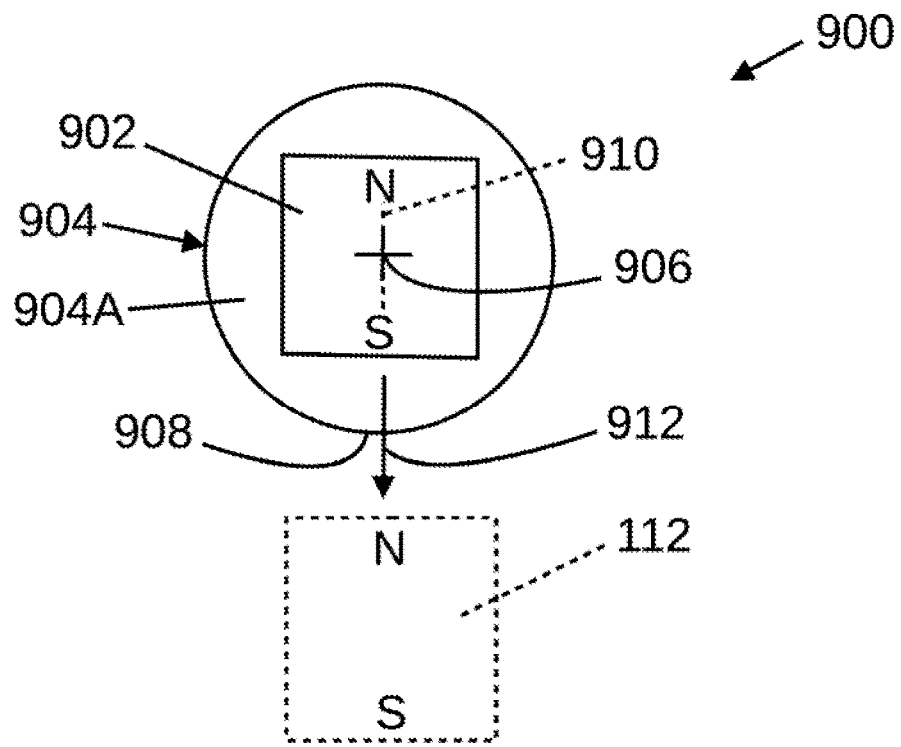
FIG. 16 is a simplified schematic view of an alternative example ablation component including a rotationally repositionable magnet in an engaged configuration.
Figure 17:
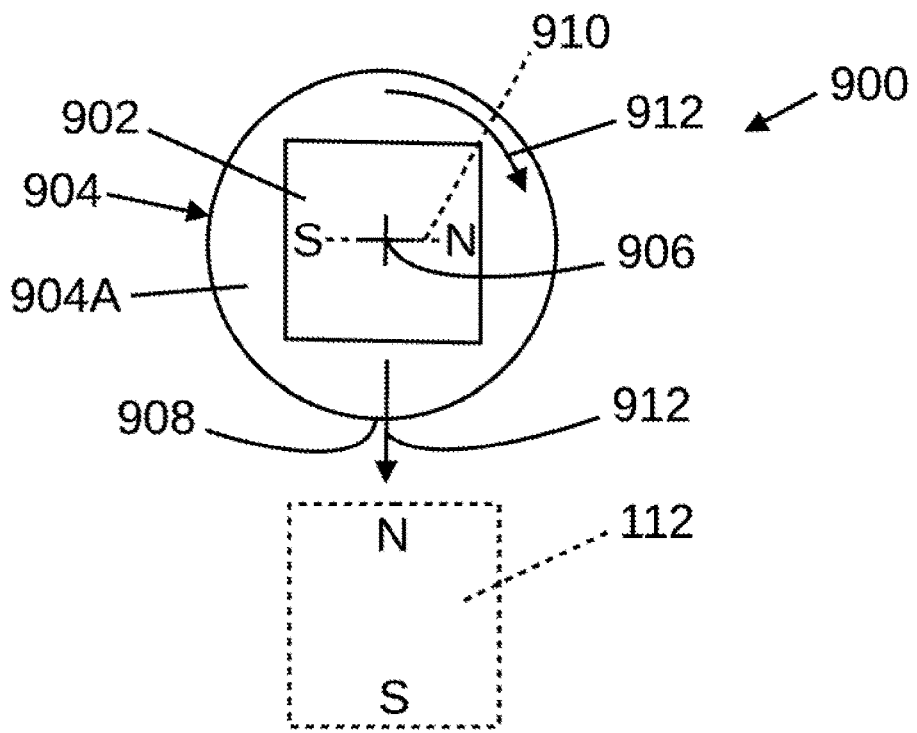
FIG. 17 is a simplified schematic view of the ablation component of FIG. 16 in a disengaged configuration.

FIG. 16 is a simplified schematic view of an alternative example ablation component 900 including a magnetic element comprising a rotationally repositionable magnet in an engaged configuration and FIG. 17 is a simplified schematic view of the ablation component 900 in a disengaged configuration, all according to at least some aspects of the present disclosure. Ablation component 900 is generally similar in structure and operation to ablation components described elsewhere herein and repeated description of similar elements is omitted for brevity. Likewise, any feature described in connection with ablation component 900 may be utilized in connection with any other embodiment described elsewhere herein. In the embodiment of FIGS. 16 and 17, however, a magnetic element comprising a permanent magnet 902 is rotationally repositionable relative to a housing 904A of the end effector 904 (or a tissue contacting surface thereof) between an engaged configuration and a disengaged configuration. In the illustrated embodiment, the magnet 902 is rotationally repositionable about the longitudinal axis 906 of the magnet 902. In alternative example embodiments, the magnet 902 may be rotationally repositionable about other suitable axes. In the illustrated embodiment, the magnet 902 is diametrically magnetized.

Referring to FIG. 16, which depicts the magnet 902 in an engaged configuration, the magnet 902 is rotationally oriented so that the North and South poles are oriented substantially towards and away from a target tissue contacting surface 908 of the end effector 904. That is, one of the North pole and the South pole is oriented substantially towards the tissue contacting surface 908 and the other of the North pole and the South pole is oriented substantially away from the tissue contacting surface 908. In this embodiment, the magnetic (North-South) axis 910 of the magnet 902 is disposed substantially coaxially with a direction 912 from the magnet 902 through the tissue contacting surface 908 (e.g., towards the cooperating magnetic element 112). Accordingly, in this orientation, the magnet 902 is arranged to attract the cooperating magnetic element 112.

Referring to FIG. 17, which depicts the magnet 902 in a disengaged configuration, the magnet 902 is oriented so that the magnetic axis 910 of the magnet 902 is oriented substantially perpendicular (e.g., at about 90 degrees) to the direction 912 from the magnet 902 through the tissue contacting surface 908 (e.g., towards the cooperating magnetic element 112). Accordingly, in this orientation, the magnet 902 is not arranged to attract the cooperating magnetic element 112. In the illustrated embodiment, the magnet 902 is rotationally repositionable without substantial translation, such as in a longitudinal direction.

Referring to FIGS. 16 and 17, in the illustrated embodiment, the magnet 902 can be repositioned from the engaged configuration (FIG. 16) to the disengaged configuration (FIG. 17) by rotating about 90 degrees about the longitudinal axis 906 of the end effector 904 in the direction of arrow 912. In some example embodiments, the magnet 902 may be further rotatable about another 90 degrees (e.g., about 180 degrees total) so that the magnetic axis 910 is once again substantially coaxial with the direction 912; however, because the polarity is reversed from the engaged configuration (FIG. 16), the magnet 902 may operate to repel the cooperating magnetic element 112. That is, because the magnetic fields are arranged with opposed orientations, the magnet 902 may repel the magnetic element 112.

Referring to FIGS. 16 and 17, prior to ablation, the magnet 902 may be moved into (or may be verified to already be in) the engaged configuration (FIG. 16). The magnet 902 may be used in connection with a cooperating magnet 112 to position the cooperating end effector on the target tissue 18 (FIG. 1). The magnetic attraction between the magnet 902 and the cooperating magnet 112 may at least partially compress the target tissue 18. After the desired ablation has been conducted, the magnet 902 may be rotated, such as to the disengaged configuration (FIG. 17). Such retraction may facilitate discontinuing magnetic attraction between the magnet 902 and the cooperating magnet 112.

Figure 18:
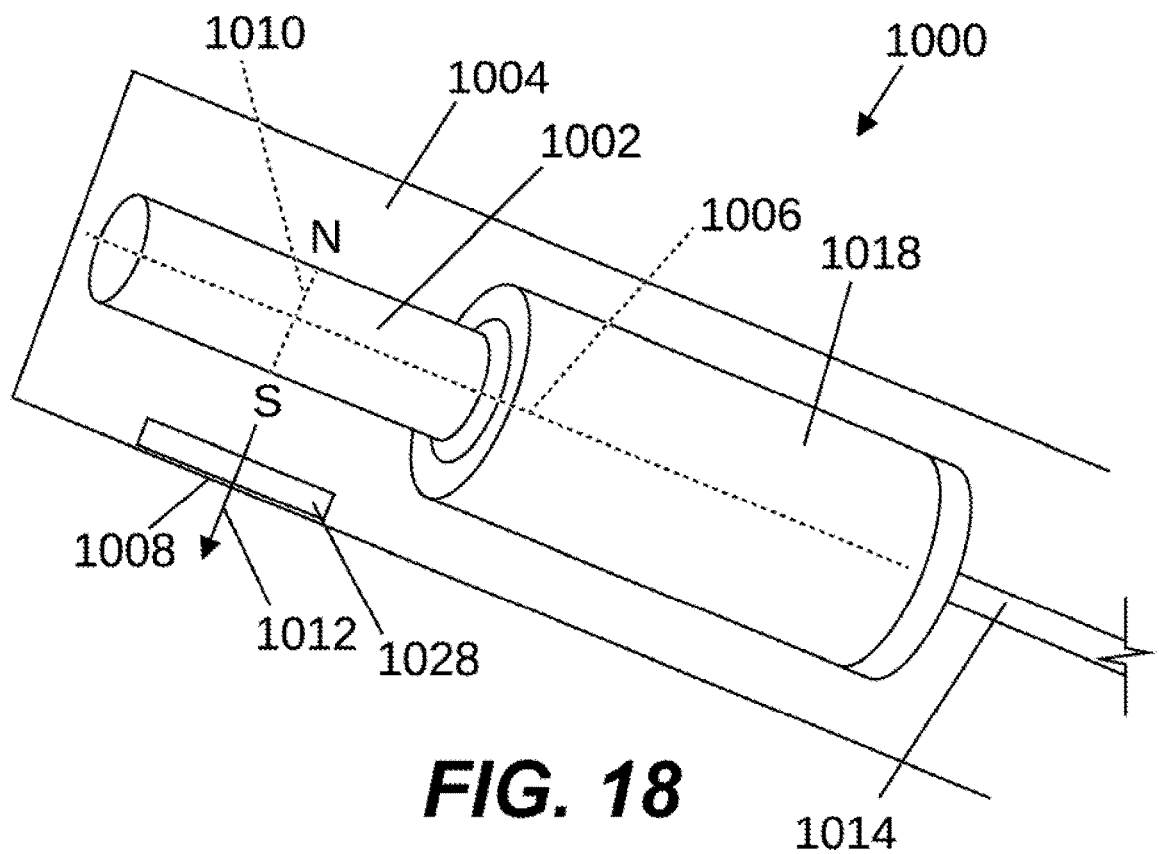
FIG. 18 is a simplified perspective view of an alternative example ablation component including a translationally and rotationally repositionable magnet in an engaged configuration.
Figure 19:
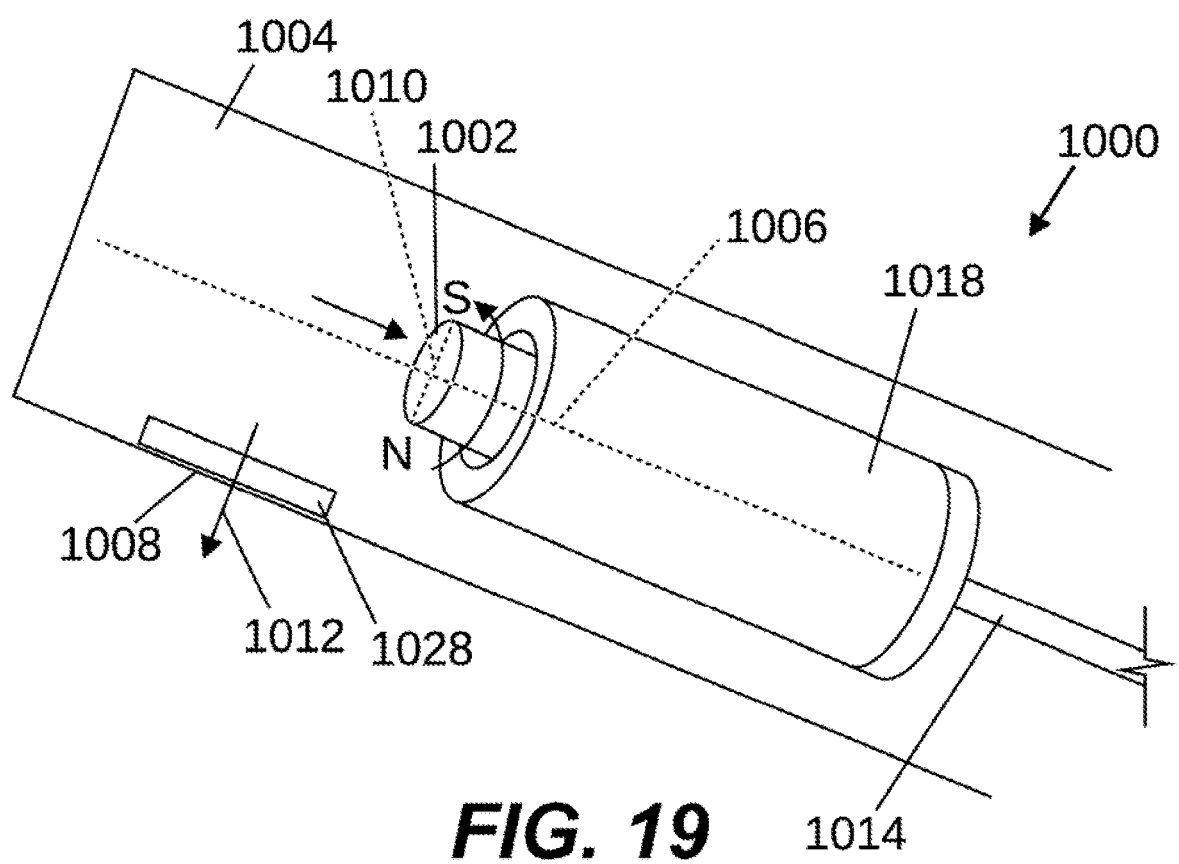
FIG. 19 is a simplified perspective view of the ablation component of FIG. 18 in a disengaged configuration.
Figure 20:
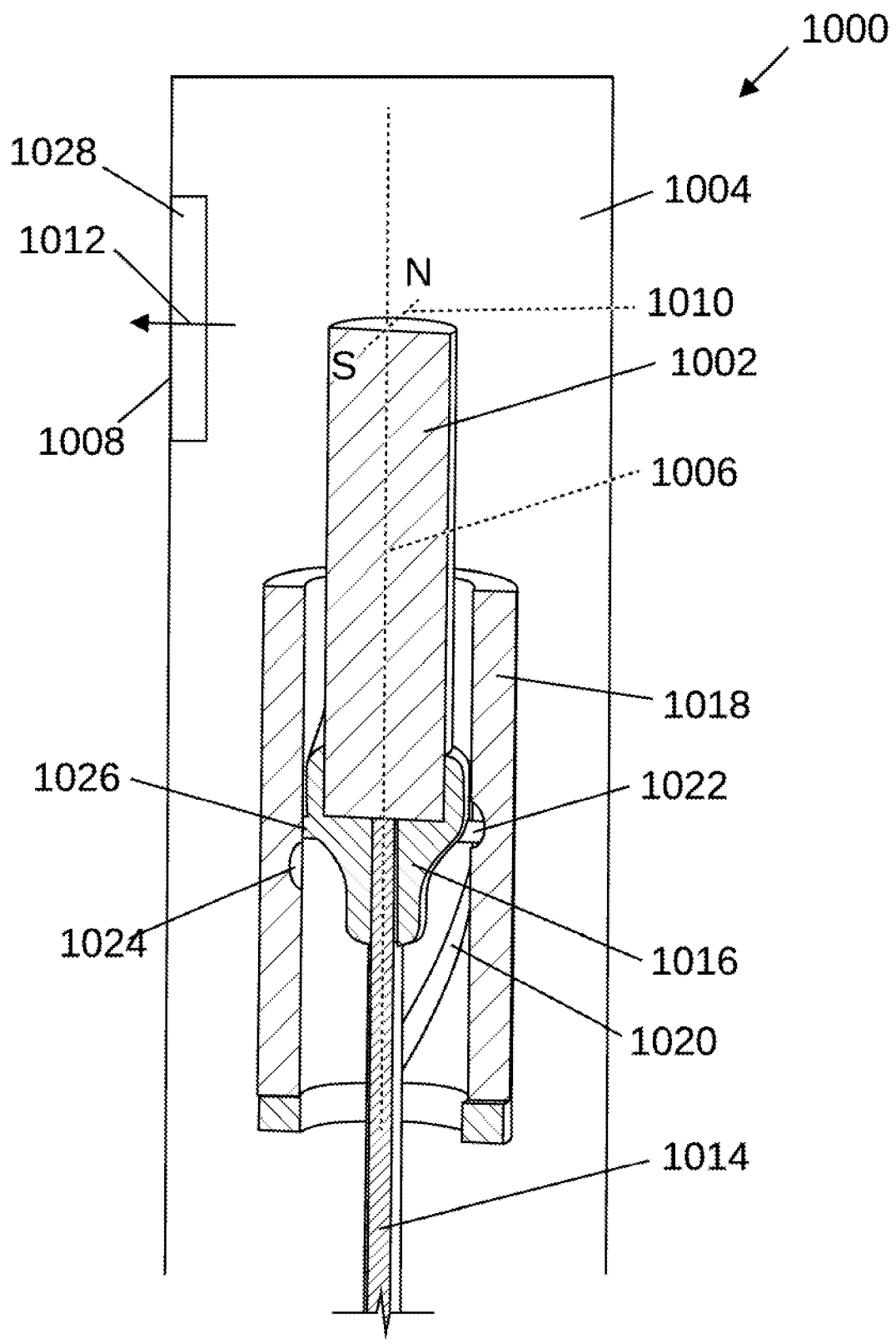
FIG. 20 is a simplified longitudinal section view of the ablation component of FIG. 18 in an intermediate configuration.

FIG. 18 is a simplified perspective view of an alternative example ablation component 1000 including a translationally and rotationally repositionable magnet in an engaged configuration, FIG. 19 is a simplified perspective view of the ablation component 1000 in a disengaged configuration, and FIG. 20 is a simplified longitudinal section view of the ablation component 1000 in an intermediate configuration, all according to at least some aspects of the present disclosure. The ablation component 1000 is generally similar in structure and operation to ablation components described elsewhere herein, including ablation component 900, and repeated description of similar elements is omitted for brevity. Likewise, any feature described in connection with ablation component 1000 may be utilized in connection with any other embodiment described elsewhere herein. In the embodiment of FIGS. 18-20, however, a magnetic element comprising a permanent magnet 1002 is simultaneously translationally and rotationally repositionable. In alternative embodiments, a permanent magnet may be sequentially translationally and rotationally repositionable (e.g., translate then rotate or rotate then translate). In the illustrated embodiment, the magnet 1002 is translationally and rotationally repositionable about the longitudinal axis 1006 of the magnet 1002. In alternative example embodiments, the magnet 1002 may be translationally repositionable along and/or rotationally repositionable about other suitable axes, such as a longitudinal axis of the end effector 1004. In the illustrated embodiment, the magnet 1002 is a diametrically magnetized, generally cylindrical permanent magnet with the generally circular cross section. Alternative embodiments may include magnets of any suitable shape, such as rectangular or square cross sections.

Referring to FIG. 18, which depicts the magnet 1002 in an engaged configuration, the magnet 1002 is rotationally positioned so that the North and South poles are oriented substantially towards and away from a tissue contacting surface 1008 of the end effector 1004. That is, one of the North pole and the South pole is oriented substantially towards the tissue contacting surface 1008 and the other of the North pole and the South pole is oriented substantially away from the tissue contacting surface 1008. Put another way, the magnetic axis 1010 of the magnet 1002 is disposed substantially parallel with a direction 1012 from the magnet 1002 through the ablation element 1028 (e.g., towards the cooperating magnetic element). Accordingly, in this position, the magnet 1002 is arranged to attract the cooperating magnetic element. Additionally, in the illustrated embodiment, the magnet 1002 is substantially laterally adjacent to the tissue contacting surface 1008 of the ablation element 1028 in the engaged configuration. In some alternative embodiments, the magnet 1002 may be at least partially laterally adjacent to the tissue contacting surface 1008 of the ablation element 1028 in the engaged configuration.

Referring to FIG. 19, which depicts the magnet 1002 in a disengaged configuration, the magnet is oriented so that the magnetic axis 1010 of the magnet 1002 is oriented parallel with the direction 1012, but the polarity is reversed from the engaged configuration (FIG. 18). Accordingly, in the disengaged configuration illustrated in FIG. 19, the magnet 1002 may operate to repel the cooperating magnetic element. In this embodiment, the orientation of the magnetic axis 1010 in the disengaged configuration is about 180 degrees from the orientation of the magnetic axis 1010 in the engaged configuration. Additionally, in the disengaged configuration in the illustrated embodiment, the magnet 1002 is retracted proximally so that it no longer lies substantially (or at least partially) laterally adjacent to the tissue contacting surface 1008. That is, the magnet 502 is substantially proximal to the tissue contacting surface 1008 proximate the ablation element 1028 in the disengaged configuration in this embodiment. It will be appreciated that alternative embodiments may include magnets that remain at least partially laterally adjacent the tissue contacting surface proximate the ablation elements in disengaged configurations.

In the illustrated embodiment, moving the magnet 502 from the engaged configuration of FIG. 18 to the disengaged configuration of FIG. 19 involves moving the magnet through the intermediate orientation of FIG. 20 in which the magnetic axis 1010 of the magnet 1002 is oriented at about 90 degrees to the direction 1012 from the magnet 1002 through the tissue contacting surface 1008 (e.g., similar to the orientation of the magnet 902 in FIG. 17). Some alternative example embodiments may be configured to operate between the engaged configuration of FIG. 18 and a disengaged configuration in which the magnetic axis 1010 of the magnet 1002 is oriented at about 90 degrees to the direction 1012 from the magnet 1002 through the tissue contacting surface 1008, similar to FIG. 17 and FIG. 20. That is, the disengaged configuration may be about 90 degrees from the engaged configuration.

Referring to FIG. 20, in the illustrated embodiment, the magnet 1002 is movable translationally and rotationally by a mechanical linkage 1014. The mechanical linkage 1014 may extend proximally to and/or may be operatively connected to an actuator on a handle for operation by a user, for example. In this embodiment, the magnet 1002 is operatively coupled to the linkage 1014 by a traveler 1016. The traveler 1016 is selectively movable within a housing 1018. Although FIG. 20 illustrates the housing 1018 as an internal component of the end effector 1004, in some alternative embodiments, the housing 1018 may be integrally formed as part of the end effector 1004. In this embodiment, the housing 1018 is generally tubular in shape and receives the traveler 1016 and magnet 1002 at least partially therein.

Referring to FIG. 20, in the illustrated embodiment, the radially inner surface of the housing 1018 includes a generally longitudinally oriented, generally helical groove 1020, which slidably receives a projection 1022 of the traveler. Accordingly, longitudinal movement of the traveler 1016 (and magnet 1002) results in rotation of the traveler 1016 (and magnet 1002) and/or rotational movement of the traveler 1016 (and magnet 1002) results in longitudinal movement of the traveler 1016 (and magnet 1002). In the illustrated embodiment, the housing 1018 includes a second generally helical grove 1024 and the traveler 1016 includes a second corresponding projection 1026, which are configured for operation in a similar manner in cooperation with the groove 1020 and projection 1022.

Referring to FIGS. 18-20, prior to ablation, the magnet 1002 may be moved into (or may be verified to already be in) the engaged position, such as generally adjacent the electrode 1028 (FIG. 18). The magnet 1002 may be used in connection with a cooperating magnet 112 (FIG. 1) to position the end effector 1004 on the target tissue 18 (FIG. 1). The magnetic attraction between the magnet 1002 and the cooperating magnet 112 may at least partially compress the target tissue 18. After the desired ablation has been conducted, the magnet 1002 may be rotated and longitudinally retracted, such as to the disengaged configuration (FIG. 19). Such retraction may facilitate discontinuing magnetic attraction between the magnet 1002 and the cooperating magnet 112 and removal of the end effector 1004 from the target tissue 18.

Figure 21:
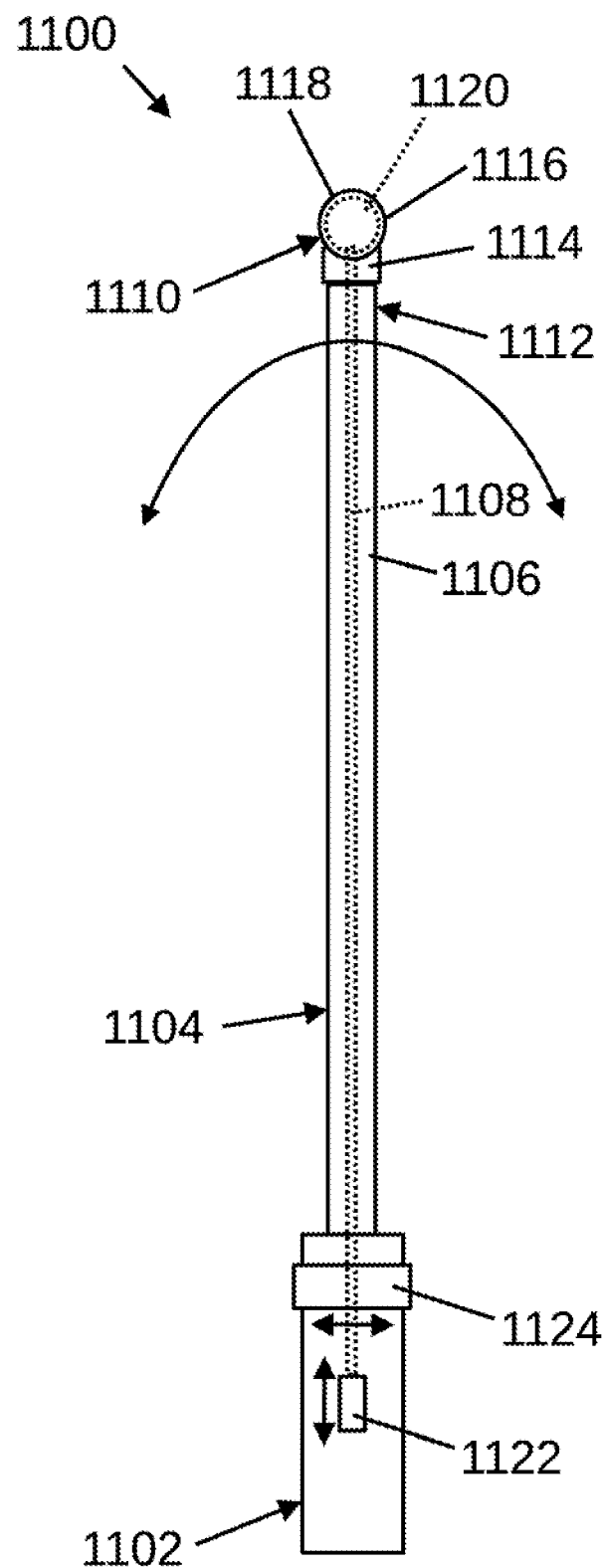
FIG. 21 is a simplified schematic illustration of an alternative example ablation component including a freely rotatable magnetic element in a retracted configuration.

FIG. 21 is a simplified schematic illustration of an alternative example ablation component 1100 including a freely rotatable magnetic element in a retracted configuration, according to at least some aspects of the present disclosure. The ablation component 1100 is generally similar in structure and operation to ablation components described elsewhere herein, and repeated description of similar elements is omitted for brevity. For example, the ablation component 1100 may be similar to and/or may be utilized as the second ablation component 102 of FIG. 1. Likewise, any feature described in connection with ablation component 1100 may be utilized in connection with any other embodiment described elsewhere herein.

Referring to FIG. 21, the ablation component 1100 may include a proximally disposed handle 1102, an elongated connecting element 1104, and/or a distally disposed end effector 2006. In the illustrated embodiment, the connecting element 1104 may include a first connecting element 1106 (e.g., generally in the form of a deflectable and/or steerable sheath) and a second connecting element 1108 (e.g., generally in the form of a flexible push/pull element). An end effector 1110 may be disposed generally distally on the second connecting element 1108. In some example embodiments, the first connecting element 1106 may include two or more zones having differing flexibilities, such as a relatively stiffer (e.g., more semi-rigid) proximal portion and a relatively flexible distal portion.

Figure 25:
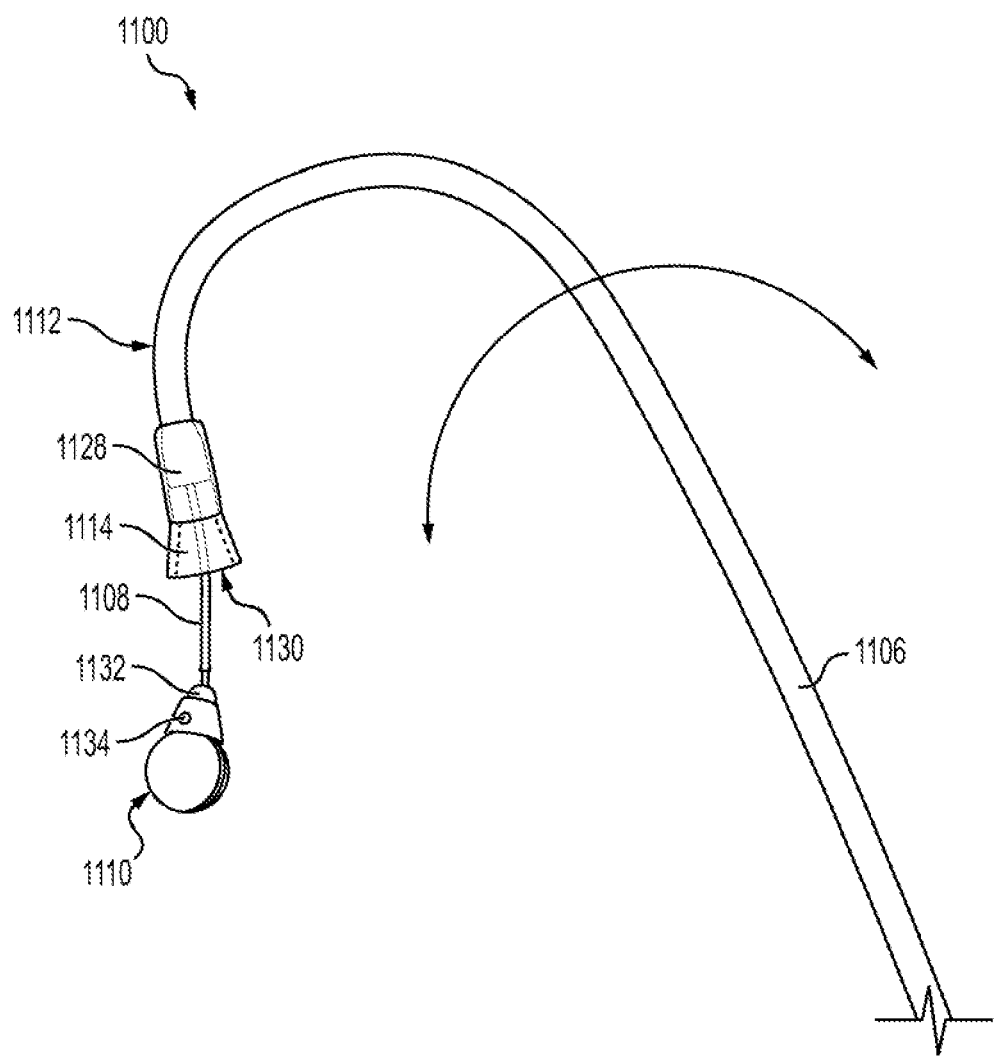
FIG. 25 is a perspective view of the distal end portion of the ablation component of FIG. 21 in a deployed configuration.

In the illustrated embodiment, the first connecting element 1106 may be generally tubular and/or may include a first connecting element distal portion 1112. In some example embodiments, the first connecting element distal portion 1112 may be relatively more flexible and/or may be deflectable or steerable. The second connecting element 1108 may be operatively coupled to the first connecting element distal portion 1112. For example, the second connecting element 1108 may be slidably disposed within the first connecting element 1106. The second connecting element 1108 and/or the end effector 1110 may be selectively repositionable relative to the first connecting element distal portion 1112, such as between a retracted configuration (FIG. 21) and a deployed configuration (FIG. 25, described below).

In the illustrated embodiment, an engagement element 1114 may operatively interpose the first connecting element distal portion 1112 and the end effector 1110. The end effector 1110 may include an end effector housing 1116, an ablation element 1118, and/or a magnetic element 1120. The handle 1102 may include a deployment actuator 1122 operative to reposition the second connecting element 1108 and/or the end effector 1110 between the retracted configuration and the deployed configuration. In some embodiments, such as those that include a steerable first connecting element 1106, the handle 1102 may include a steering/deflection actuator 1124, which may be disposed on the handle 1102 and/or may be operative to steer and/or deflect at least a portion of the first connecting element 1106. In some embodiments, the steering/deflection actuator 1124 may be generally in the form of a rotatable collar.

In some example embodiments, the first connecting element distal tip portion 1112 may be deflectable about 180 degrees. That is, the first connecting element distal tip portion 1112 may be deflected about 180 degrees into a generally J-shaped configuration. In some embodiments, the first connecting element distal portion 1112 may be deflectable unidirectionally. In alternative embodiments, the first connecting element distal portion 1112 may be steerable bidirectionally and/or in one or more planes. Some example embodiments may include one or more anti-kink elements within the first connecting element 1106, such as within the first connecting element distal portion 1112. For example, the first connecting element distal portion 1112 may be constructed with an elongated helical spring therein arranged to prevent kinking when the first connecting element distal portion 1112 is deflected.

Figure 22:
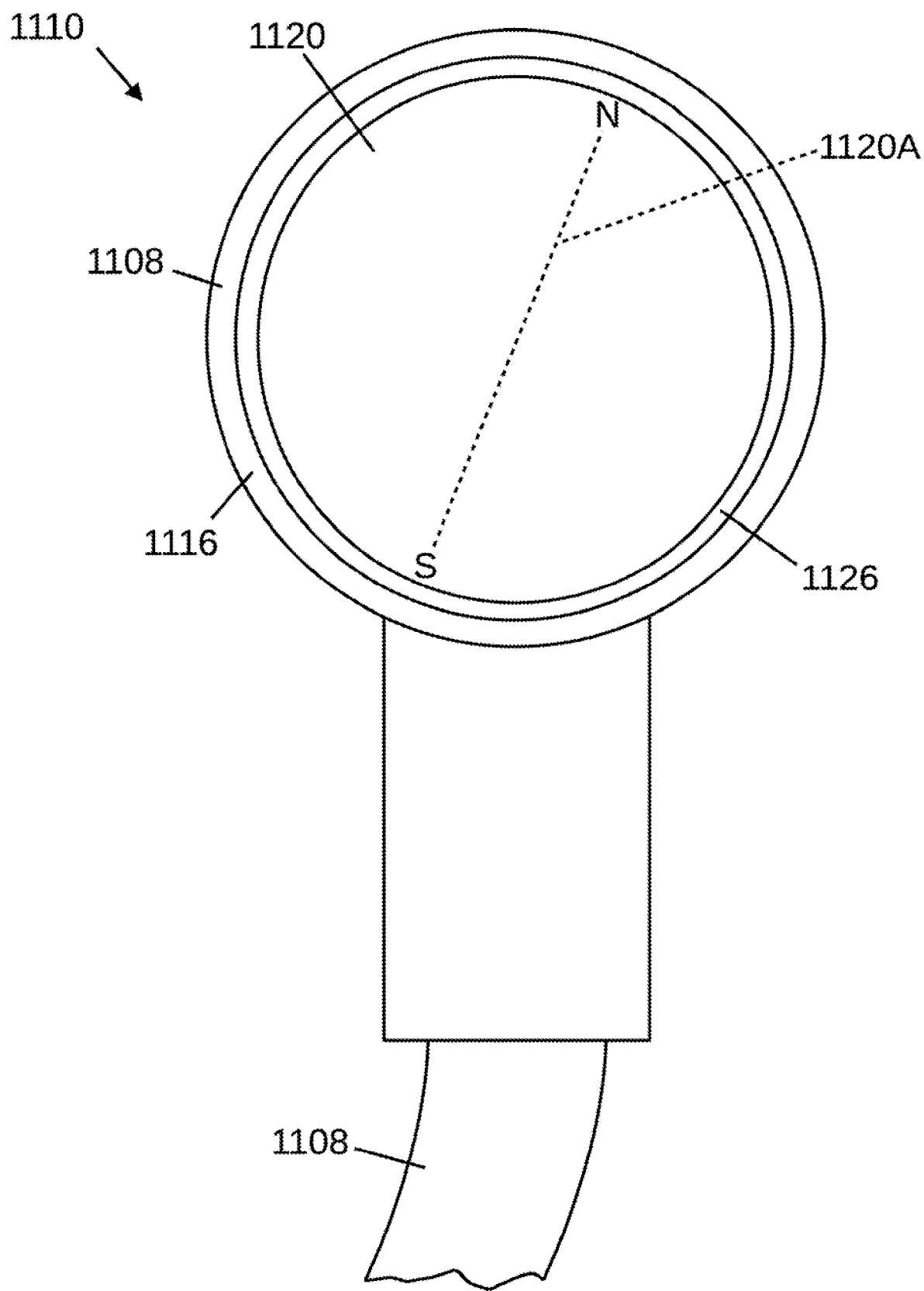
FIG. 22 is a simplified lateral cutaway view of the end effector of the ablation component of FIG. 21.

FIG. 22 is a simplified lateral cutaway view of the end effector 1110 of the ablation component 1100 of FIG. 21, according to at least some aspects of the present disclosure. In the illustrated embodiment, the magnetic element 1120 is movable relative to the housing 1116. Specifically, in this embodiment, the magnetic element 1120 is substantially freely rotatable relative to the housing 1116 about all three orthogonal axes (e.g., X, Y, Z and/or pitch, roll, yaw), while being constrained against substantial translation relative to the housing 1116. As used herein, "freely rotatable" may refer to a condition in which one element is rotatable, substantially without mechanical restraint (except for incidental friction), relative to another component about at least one axis of rotation. As used herein, "freely rotatable" may exclude a condition in which the rotation is controlled by a control element, such as an actuator and/or a mechanical linkage operated by a user. As used herein, "freely rotatable" may include a condition in which the rotatable element may be at least partially oriented and/or constrained by an externally applied magnetic field, such as due to close proximity of a cooperating magnetic element of a cooperating ablation component. Accordingly, in this embodiment, the magnetic element 1120 has three rotational degrees of freedom, substantially mechanically unconstrained, relative to the housing 1116. That is, the magnetic element 1120 is freely rotatable so that its magnetic axis 1120A may self-orient in any orientation relative to the housing 1116. As used herein, "self-orient" and related terms may refer to a movement of an element that is not affirmatively controlled or effected, such as by a user or control element. For example, self-orienting may include allowing the freely rotatable magnetic element 1120 to reorient itself due to an externally applied magnetic field (e.g., from a cooperating magnetic element of a cooperating ablation component), without externally applied mechanical interference.

In the illustrated embodiment, the magnetic element 1120 is in the form of a substantially spherical permanent magnet, such as a rare earth permanent magnet. The housing 1116 may be at least partially hollow and may at least partially define a substantially spherical interior 1126, which may be configured to rotatably house the magnetic element 1120 therein. In various embodiments, free rotation may be facilitated by forming the elements with specifically machined surface finishes, electroplating, lubricants, material selection (e.g., non-galling), and/or manufacturing to precise tolerances, or other suitable techniques.

In the illustrated embodiment, the ablation element 1108 (e.g., electrode) may form at least a portion of the housing 1116. For example, the housing 1116 may be constructed from a high magnetic permeability, non-ferrous material, which may also be electrically conductive. In the illustrated embodiment, the housing 1116 is constructed of copper and is configured to be electrically coupled to a source of radiofrequency energy (e.g., control unit 114 (FIG. 1)) to act as an electrode for performing ablation in cooperation with an ablation element of a cooperating ablation component. In some embodiments, the housing 1116 may be constructed from copper plated with nickel and/or gold.

In this embodiment, at least a portion of the exterior surface of the housing 1116 including the ablation element 1108 (e.g., electrode) has a generally bulbous shape, such as at least partially generally spherical. As used herein, "bulbous" may refer to an enlarged (with respect to adjacent structure(s)) and/or generally convexly rounded exterior surface. In other embodiments, the housing 1116 may include a generally dome-shaped tip with a substantially uniform diameter and/or cross section along its longitudinal length. In the illustrated embodiment, the ablation element 1108 is generally spherical and forms at least a portion of the housing 1116. In alternative embodiments, the ablation element 1108 (e.g., electrode) may be disposed on the housing 1116. As used herein, "ball electrode" may refer to an at least partially spherical electrode, at least a portion of which has an appearance generally similar to a ball. Further, in some embodiments, the ablation element 1108 may include two or more electrodes, such as a two or more elongated, generally parallel electrodes. Generally, other embodiments may utilize any suitable arrangement of ablation elements 1108 and/or other electrodes.

Figure 23:
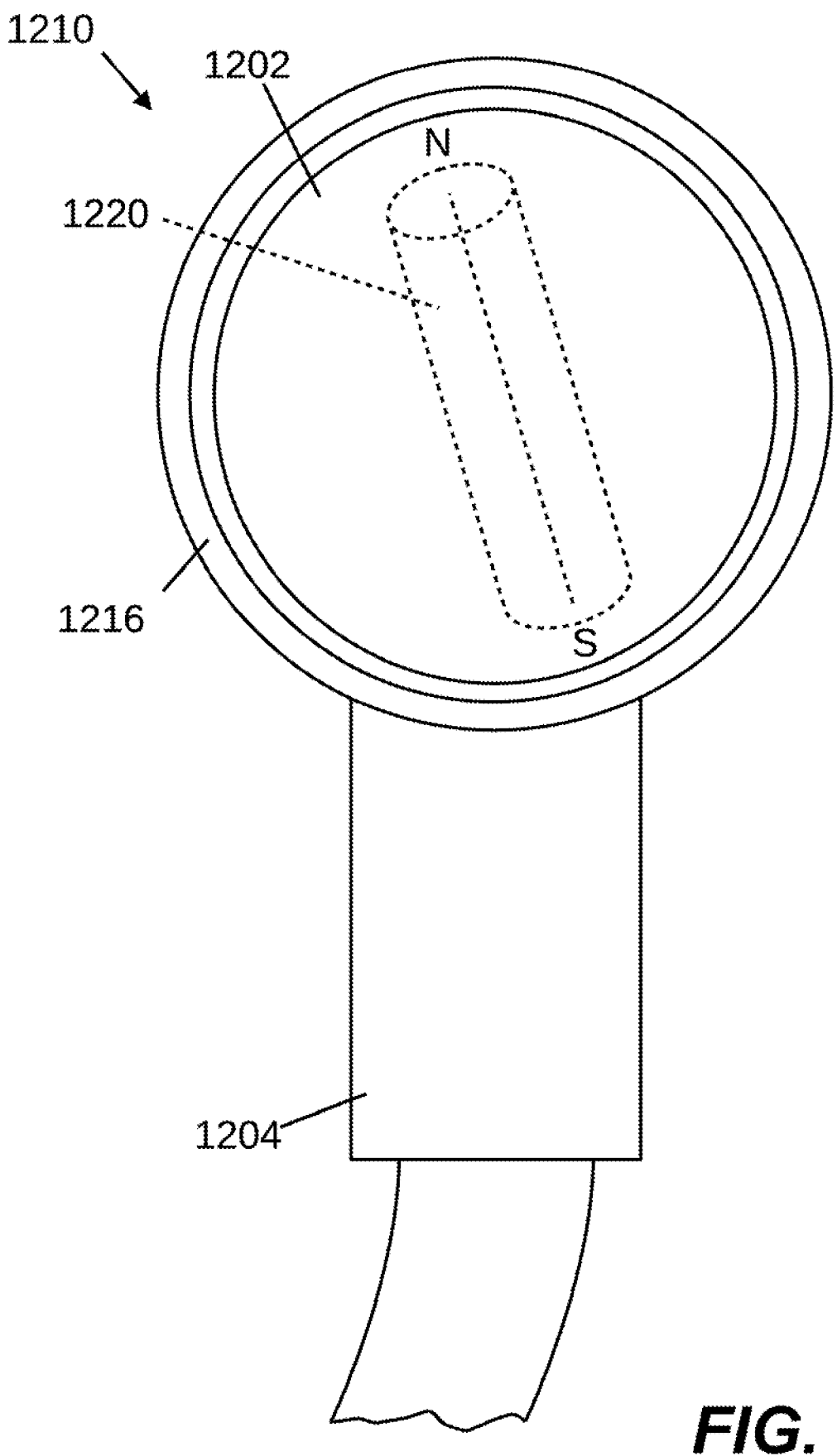
FIG. 23 is a simplified lateral cutaway view of an alternative end effector of the ablation component of FIG. 21.

FIG. 23 is a simplified lateral cutaway view of an alternative end effector 1210 of the ablation component 1100 of FIG. 21, according to at least some aspects of the present disclosure. End effector 1210 may be used in place of end effector 1110, described above. The end effector 1210 is generally similar in structure and operation to end effectors described elsewhere herein, such as end effector 1110, and repeated description of similar elements is omitted for brevity. Likewise, any feature described in connection with end effector 1210 may be utilized in connection with any other embodiment described elsewhere herein.

In the embodiment of FIG. 23, the magnetic element 1220 may be non-spherical (e.g., generally cylindrical), but may be disposed in a substantially spherical mount 1202. The mount 1202 is freely rotatably disposed within the housing 1216 of the end effector 1210 in a manner similar to the magnetic element 1120 and the housing 1116 of the end effector 1110 (FIG. 21).

Figure 24:
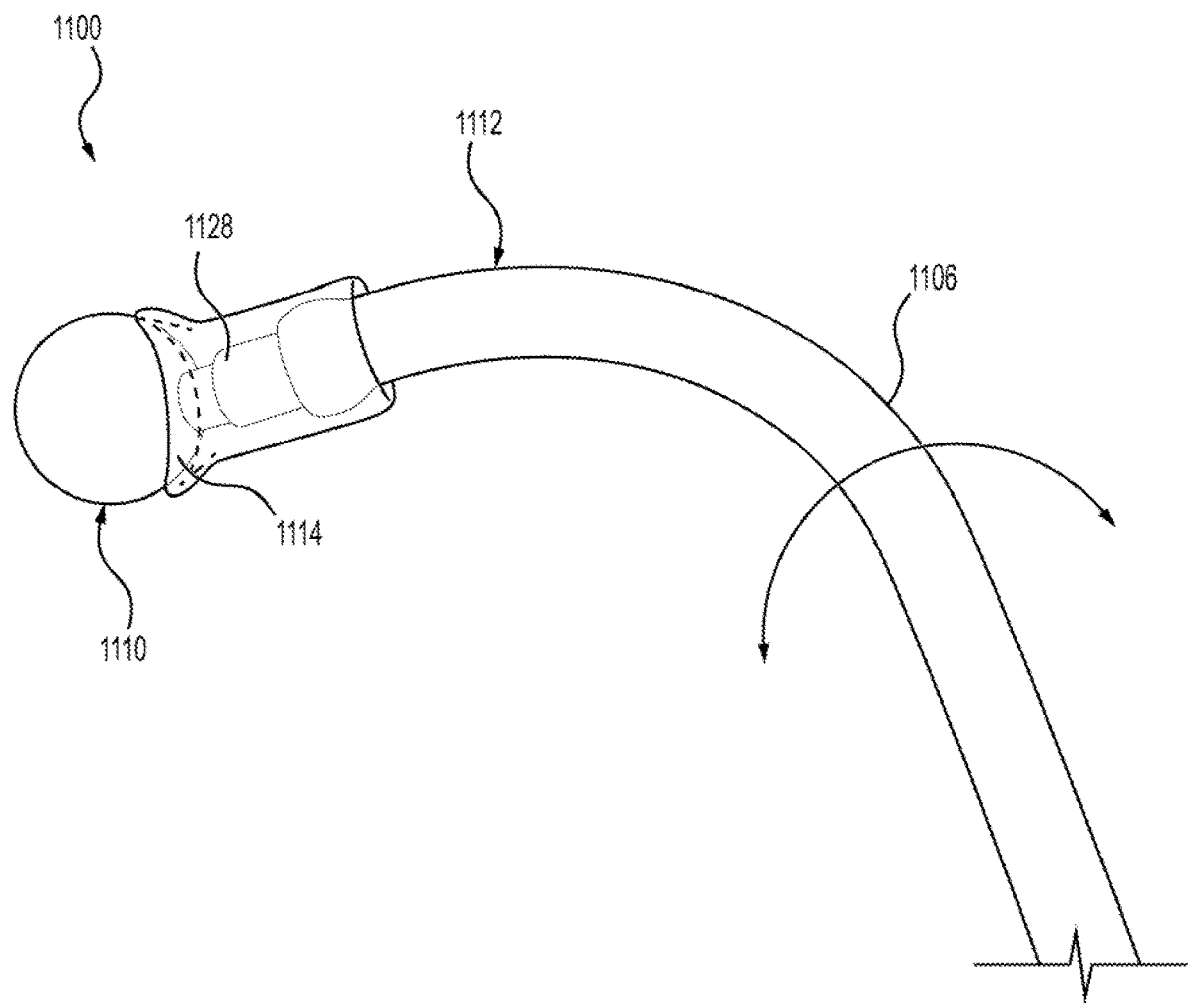
FIG. 24 is a perspective view of the distal end portion of the ablation component of FIG. 21 in a retracted configuration.

FIG. 24 is a perspective view of the distal end portion of the ablation component 1100 of FIG. 21 in a retracted configuration, and FIG. 25 is a perspective view of the distal end portion of the ablation component 1100 of FIG. 21 in a deployed configuration, all according to at least some aspects of the present disclosure. In the illustrated embodiment, in the retracted configuration (FIG. 24), the second connecting element 1108 may be disposed substantially within the first connecting element 1106 and/or the engagement element 1114 may operatively couple the end effector 1110 and the first connecting element distal portion 1112. In the deployed configuration (FIG. 25), at least a portion of the second connecting element 1108 may extend from the first connecting element distal portion 1112 and the engagement element 1114 may be disengaged from at least one of the end effector 1110 or the first connecting element distal portion 1112.

Referring to FIGS. 24 and 25, in the illustrated embodiment, the engagement element 1114 may be disposed at a distal end 1128 of the first connecting element 1106 distal portion 1112. Referring to FIG. 24, in the illustrated embodiment, in the retracted configuration, the end effector engages the engagement element 1114. In the retracted configuration, the end effector 1110 may be substantially mechanically coupled to the first connecting element distal portion 2012, such as by the engagement element 1114. Accordingly, the retracted configuration may facilitate precise positioning of the end effector 1110 using the connecting element 1104 (FIG. 21) when desired. Additionally, the retracted configuration may facilitate withdrawal of the end effector 1110 away from the target tissue following ablation, such as if substantial force is used to overcome magnetic attraction between the magnetic element 1120 and a cooperating magnetic element of a cooperating ablation component (see, e.g., FIG. 1). For example, when using a cooperating ablation component with a translationally repositionable magnetic element, it may be desirable to place the ablation component 1100 in the retracted configuration before translating the cooperating magnetic element for decoupling so as to prevent the end effector 1110 from translating along with the cooperating magnetic element. Further, in some circumstances, withdrawing the ablation component 1000 from the operative area in the retracted configuration may reduce the likelihood of injury due to a partially unconstrained end effector 1110.

Referring to FIG. 25, in the illustrated embodiment, in the deployed configuration, the end effector is disengaged from the engagement element 1114, but remains attached to the second connecting element 1108, which extends distally from the first engagement element 1106. In the deployed configuration, the portion of the second connecting element 1108 extending distally from the first connecting element 1106 distal portion 1112 may act as a tether for the end effector 1110. That is, the second connecting element 11108 may operatively (e.g., mechanically and/or electrically) connect to the end effector 1110; however, the second connecting element 1108 may be configured to allow the end effector 1110 to move substantially independently of the first connecting element distal portion 1112 (e.g., except for farther away from the first connecting element distal portion 1112 than permitted by the deployment length of the second connecting element 1108).

In the illustrated embodiment, the second connecting element 1108 may have substantially greater flexibility than the first connecting element distal portion 1112. Accordingly, in the deployed configuration, the end effector 1110 may be movable substantially more freely than in the retracted configuration (FIG. 24). Thus, the first connecting element distal portion 1112 may be at least partially mechanically decoupled from the end effector 1110. As a result, when the magnetic element 1120 (FIG. 21) of the end effector 1110 is magnetically coupled with a cooperating magnetic element of a cooperating ablation component (e.g., see FIG. 1), some movement of the first connecting element distal portion 1112 (e.g., of limited magnitude and in some directions) may exert sufficiently small forces on the end effector 1110 that the end effector 1110 may remain held in position by the attractive force between the magnetic element 1120 and a cooperating magnetic element of the cooperating ablation component. For example, when the connecting element 1104 (FIG. 21) extends into an interior chamber of the heart, such as through a heart valve, beating of the heart may cause substantial movement of the first connecting element distal portion 1112. When the ablation component 1110 is placed into the deployed configuration, the end effector 1110 may be able to remain in a desired location on the endocardial surface, held by magnetic attraction with an epicardial cooperating magnetic element, due to the partial mechanical decoupling of the end effector 1110 from the first connecting element distal portion 1112.

Referring to FIGS. 21 and 25, in some embodiments, the deployment actuator 1122 may be configured to extend the second connecting element 1108 and/or the end effector 1110 by a predetermined deployment distance between the retracted and deployed configurations. The deployment distance may be selected based upon an anticipated use of the device. For example, if the ablation component 1100 is intended to be used endocardially via vascular access, a deployment distance of about 5 mm to about 30 mm may provide sufficient mechanical decoupling between the first connecting element distal portion 1112 and the end effector 1110 while also limiting the likelihood that the end effector 1110 and/or the second connecting element 1108 may unintentionally engage the chordae tendineae. In the illustrated embodiment, the deployment distance may be fixed at the time of assembly. In some alternative embodiments, the deployment distance may be varied by an end user, either before deployment or while in the deployed configuration.

Referring to FIG. 25, in the illustrated embodiment, the engagement element 1114 may include a distally oriented, tapered opening 1130. The opening 1130 may be generally conical. Referring to FIGS. 24 and 25, in the retracted configuration, the opening 1130 may receive at least a portion of the end effector 1110 therein. Accordingly, in the retracted configuration, the end effector 1110 may be operatively coupled to the distal end portion 1112 of the first connecting element 1106. In some example embodiments, the engagement element 1114 may be substantially rigid. In some example embodiments, the engagement element 1114 may be at least partially flexible, such as to securely seat the end effector 1110 regardless of slight misalignment.

Figure 26:
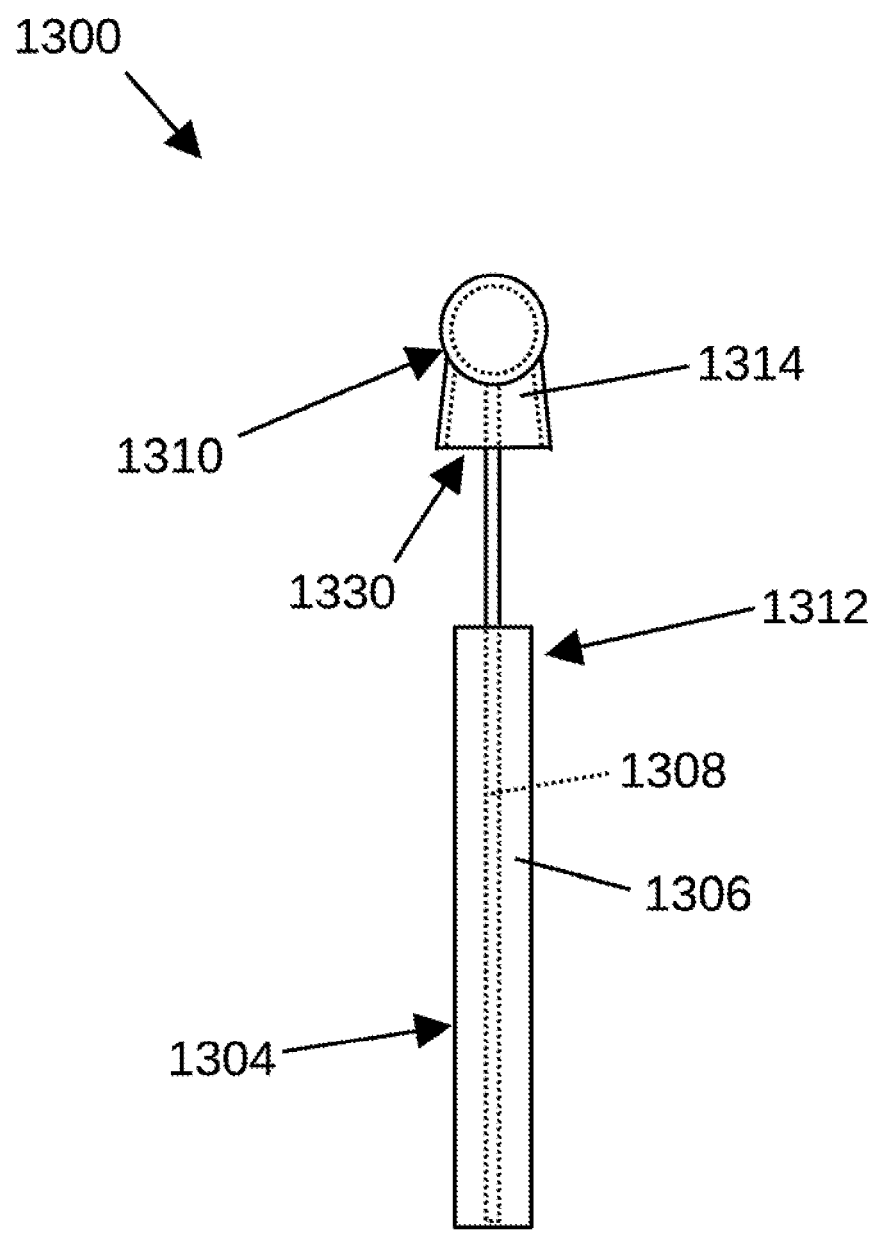
FIG. 26 is a detailed schematic view of the distal end portion of an alternative example ablation component 1300 in a deployed configuration.

FIG. 26 is a detailed schematic view of the distal end portion of an alternative example ablation component 1300 in a deployed configuration, according to at least some aspects of the present disclosure. The ablation component 1300 is generally similar in structure and operation to ablation components described elsewhere herein, including ablation component 1100, and repeated description of similar elements is omitted for brevity. Likewise, any feature described in connection with ablation component 1300 may be utilized in connection with any other embodiment described elsewhere herein.

In the illustrated embodiment, the ablation component 1300 may include a connecting element 1304 comprising a first connecting element 1306, a second connecting element 1308, and an end effector 1310. The end effector 1310 may include a magnetic element, such as a generally spherical permanent magnet, which may be freely rotatable about three axes of rotation within an end effector housing, as described above with reference to other similar embodiments. Unlike the embodiment of FIG. 21, described above, the embodiment of FIG. 26 includes an engagement element 1314 that is disposed on a proximal aspect of the end effector 1310. The engagement element 1314 is configured to selectively engage the first connecting element 1306 distal portion 1312 in a retracted configuration. In the illustrated embodiment, the engagement element 1314 is generally in the form of a proximally opening, generally tubular body having a generally cylindrical cutout configured to receive the first connecting element distal portion 1312 therein. Some embodiments may include a proximally oriented opening 1330, which may be tapered.

Figure 27:
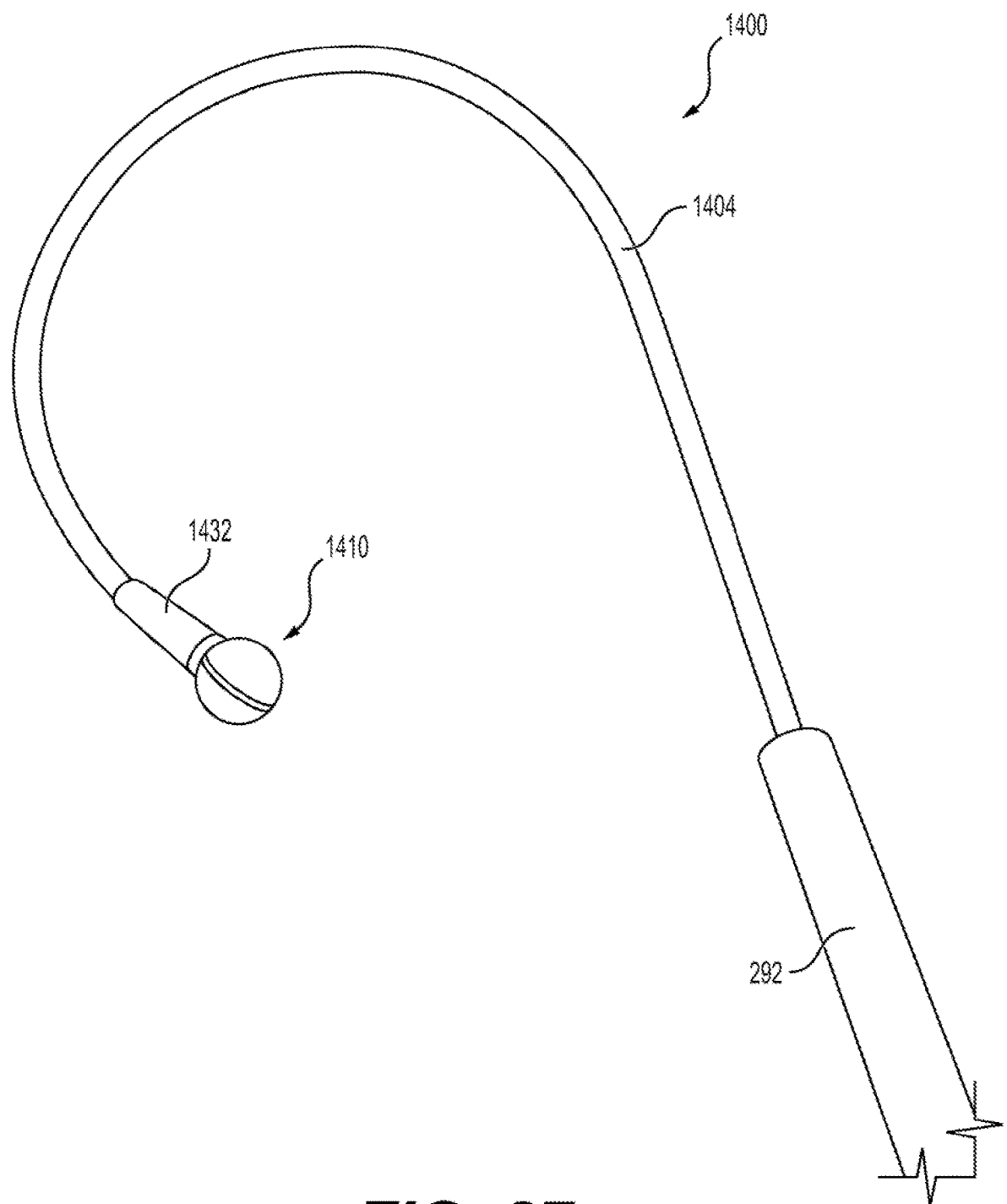
FIG. 27 is a perspective view of a distal end portion of an alternative example ablation component including a freely rotatable magnetic element.

FIG. 27 is a perspective view of a distal end portion of an alternative example ablation component 1400 including a freely rotatable magnetic element, according to at least some aspects of the present disclosure. The ablation component 1400 is generally similar in structure and operation to ablation components described elsewhere herein, including ablation component 1100, and repeated description of similar elements is omitted for brevity. Likewise, any feature described in connection with ablation component 1400 may be utilized in connection with any other embodiment described elsewhere herein. In FIG. 27, the ablation component 1400 is shown inserted through an example delivery device 292, which may be similar to delivery device 290, described above with reference to FIG. 2.

In the illustrated embodiment, the ablation component 1400 includes an end effector 1410 disposed distally on a connecting element 1404. The end effector 1410 may include a magnetic element, such as a generally spherical permanent magnet, which may be freely rotatable about three axes of rotation within an end effector housing, as described above with reference to other similar embodiments. In this embodiment, the connecting element may not include separate, relatively movable first and second connecting elements like those of ablation component 1100, described above. Instead, the end effector 1410 is disposed on the connecting element 1404. For example, the end effector 1410 may be directly fixedly coupled to the distal end of the connecting element 1404. In some embodiments, the connecting element 1404 may be generally flexible. In some embodiments, the connecting element 1404 may be steerable/deflectable. In this embodiment, the ablation component 1400 may not include an engagement element operatively interposing the end effector 1410 and the connecting element 1404.

FIGS. 28-31 are perspective views of alternative example end effectors 1500, 1520, 1540, 1560, all according to at least some aspects of the present disclosure. The alternative example end effectors 1500, 1520, 1540, 1560 are generally similar in structure and operation to end effectors described elsewhere herein, including end effectors 1110, 1210, 1310, 1410, and repeated description of similar elements is omitted for brevity. Likewise, any feature described in connection with end effectors 1500, 1520, 1540, 1560 may be utilized in connection with any other embodiment described elsewhere herein. Each of these end effectors 1500, 1520, 1540, 1560 may include a magnetic element, such as a generally spherical permanent magnet, which may be freely rotatable about three axes of rotation within an end effector housing, as described above with reference to other similar embodiments.

Referring to FIGS. 25, 27, and 28-31, various end effector features, shapes, and/or configurations may be utilized individually or in any combination with any embodiments according to at least some aspects of the present disclosure. Some example end effectors may be configured to facilitate desired heat transfer, such as by including one or more features operable as heat sinks. For example, some end effectors may include a proximally extending neck configured to transfer heat between the end effector and the surrounding fluid. For example, when used endocardially, the neck may transfer heat (e.g., from ablation) from the end effector housing into the blood. The size, shape, material, and/or other configuration of the neck may be configured to facilitate desired heat transfer and/or may be specifically configured for particular locations of use and/or procedures. In some example embodiments, at least a portion of the end effector housing may be electrically and/or thermally insulated, such as by an insulative coating (e.g., an externally disposed insulator) and/or by constructing at least a portion of the end effector from an insulating material (e.g., a polymer). Such insulation may reduce the amount of ablation energy (e.g., radiofrequency energy) that may be dissipated into non-target tissues and/or fluids. Also, such insulation may be used to achieve desired thermal performance of the ablation component.

Figure 28:
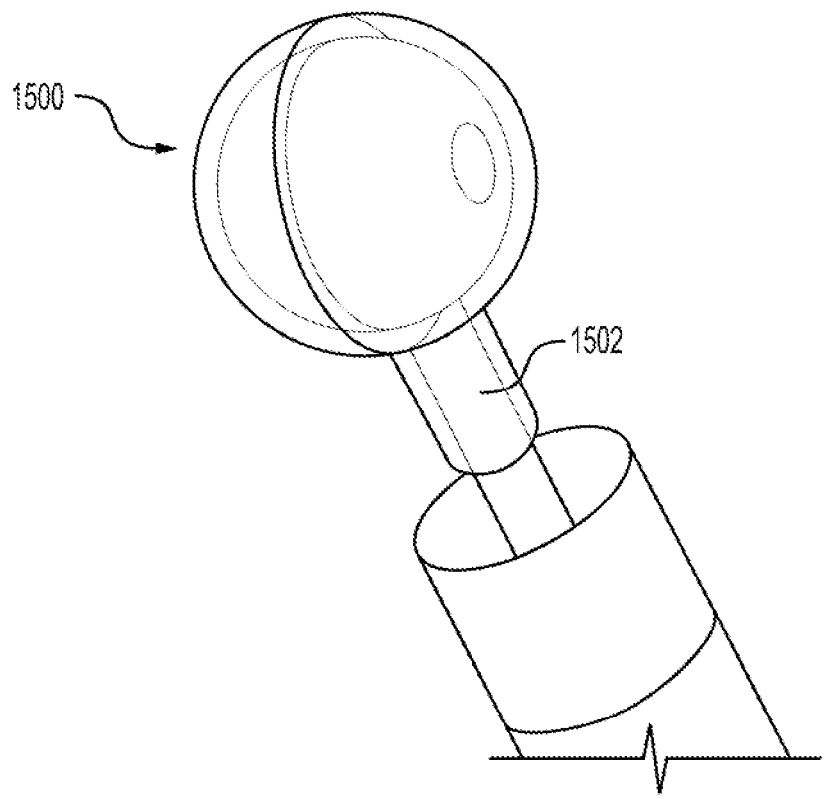
FIG. 28 is a perspective view of an alternative example end effector.
Figure 29:
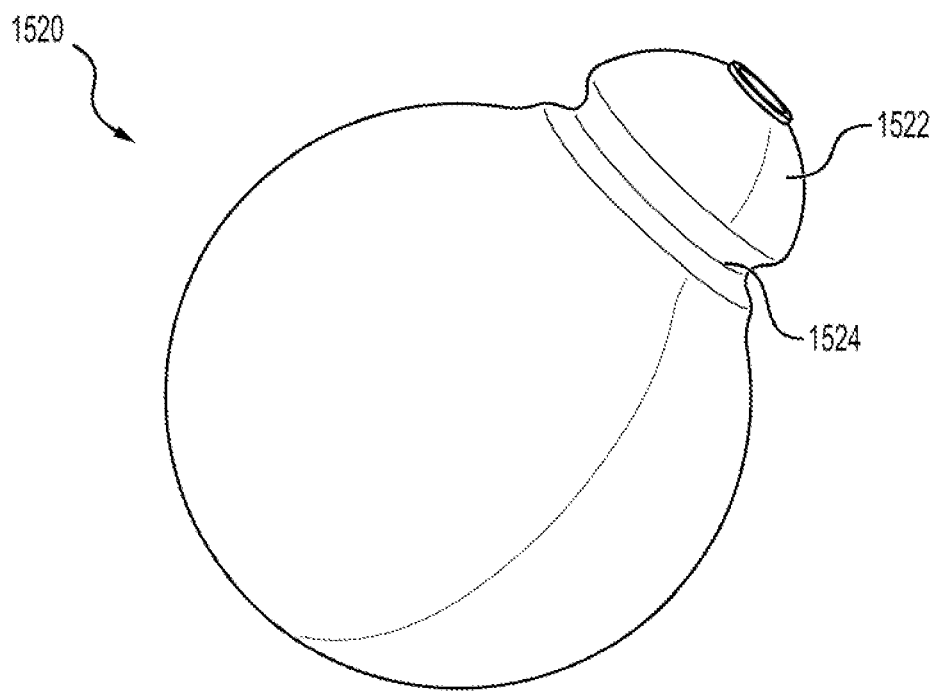
FIG. 29 is a perspective view of an alternative example end effector.
Figure 30:
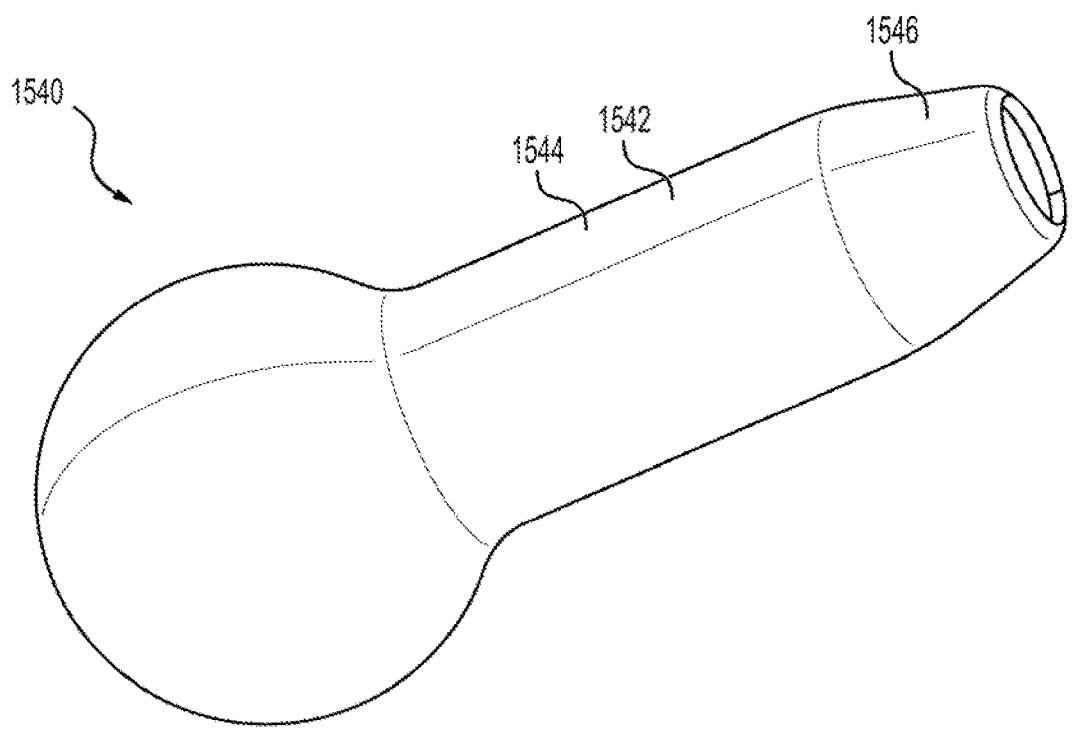
FIG. 30 is a perspective view of an alternative example end effector.
Figure 31:
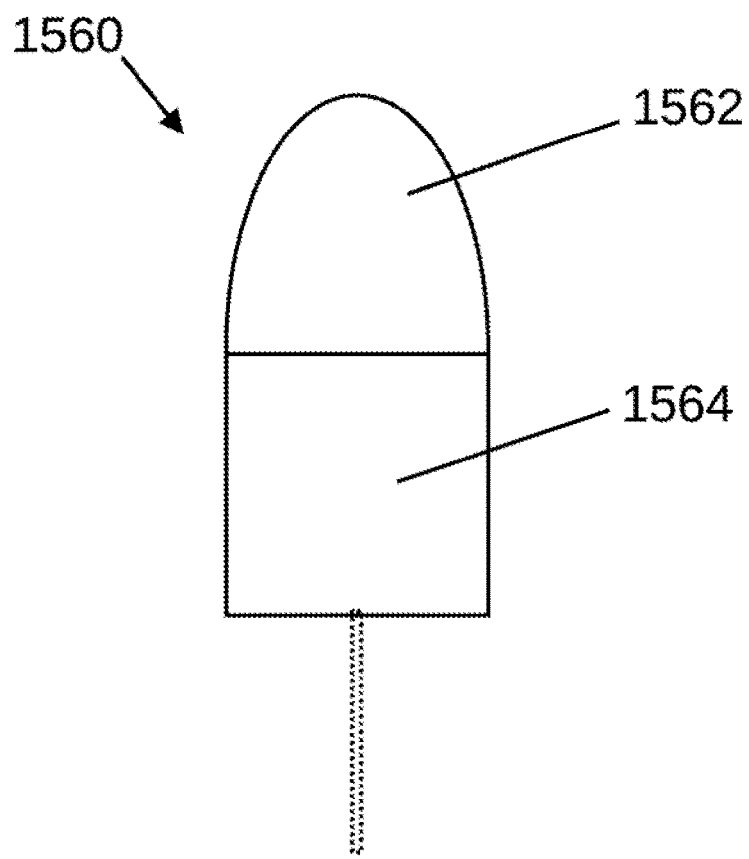
FIG. 31 is a perspective view of an alternative example end effector.

Referring to FIG. 25, the end effector 1110 includes a relatively short, proximally extending neck 1132. In the illustrated embodiment, the neck 1132 is constructed of copper and is partially covered by a circumferential insulator 1134, which may comprise a polymer. Referring to FIG. 27, the end effector 1410 includes a mid-length, relatively wide, generally cylindrical neck 1432. Referring to FIG. 28, the end effector 1500 includes an elongated, generally narrow, substantially uniform, cylindrical neck 1502. Referring to FIG. 29, the end effector 1520 includes a generally dome-shaped neck 1522 in the form of a relatively short, distally tapering cylinder, optionally with a circumferential recess 1524. Referring to FIG. 30, the end effector 1540 includes a neck 1542 having an elongated, substantially uniform, cylindrical distal portion 1544 followed by a proximal frustoconical portion 1546. Referring to FIG. 31, the end effector 1560 is generally bullet-shaped and/or semi-spherical. In particular, in this embodiment, the end effector 1560 includes a generally domed (e.g., semi spherical), bulbous distal portion 1562, which may include an ablation element, and a generally uniform cylindrical proximal portion 1564. In some example embodiments, the proximal portion 1564 may comprise an engagement element configured to receive the distal end portion of the first connecting element therein, such as in a generally cylindrical proximal opening similar to that shown in FIG. 26.

Figure 32:
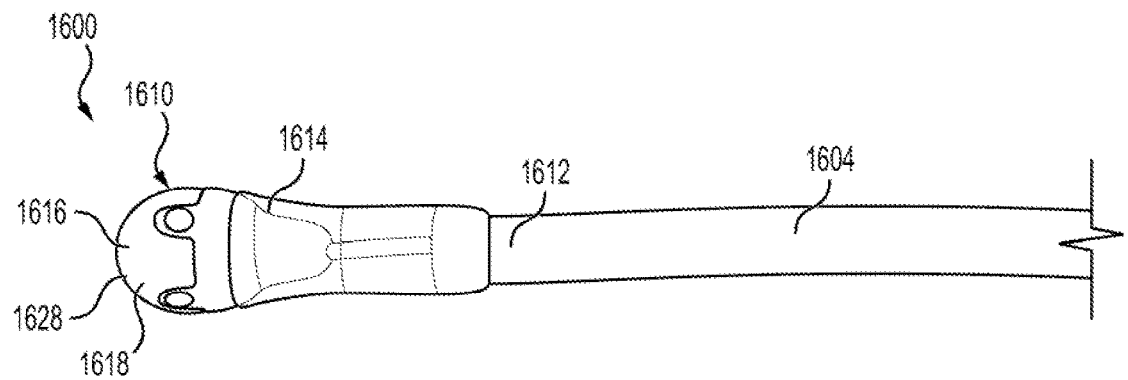
FIG. 32 is a perspective view of a distal end portion of an alternative example ablation component in a retracted configuration.
Figure 33:
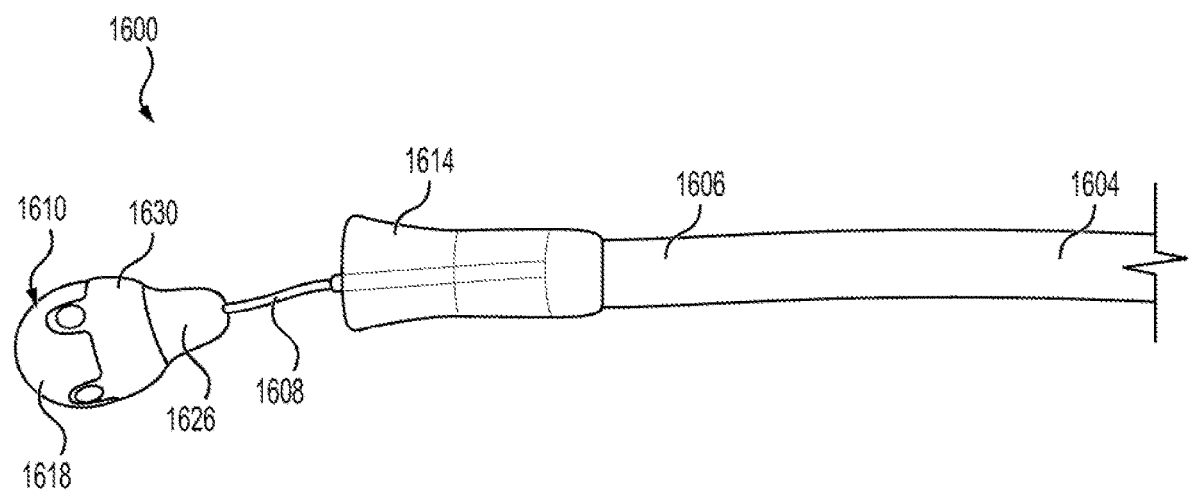
FIG. 33 is a perspective view of the ablation component of FIG. 32 in a deployed configuration.
Figure 34:
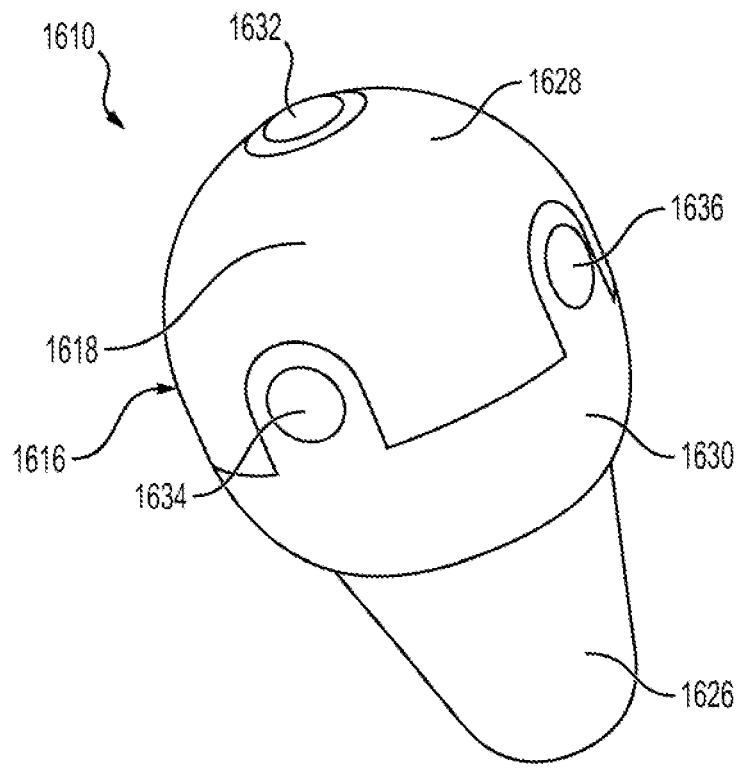
FIG. 34 is a detailed perspective view of an example end effector of the ablation component of FIG. 32.
Figure 35:
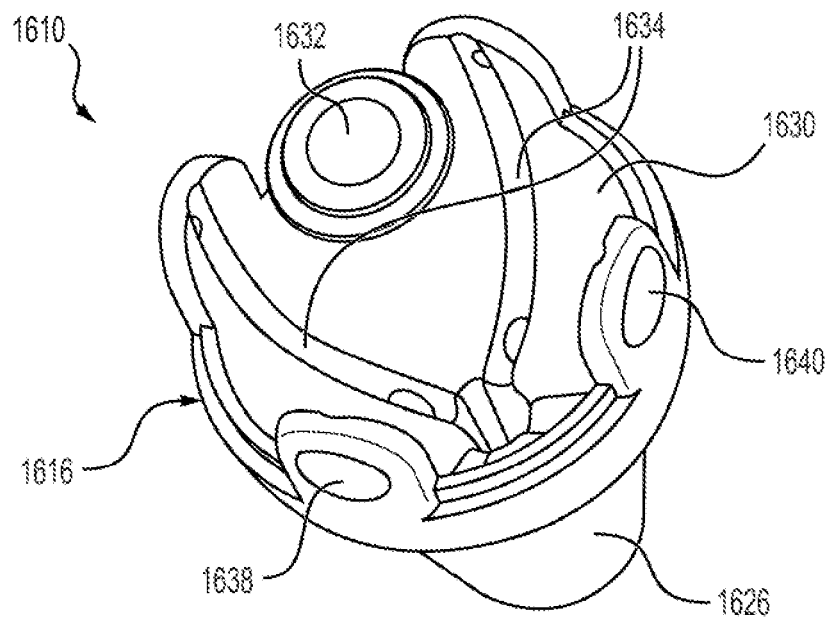
FIG. 35 is a detailed perspective partial view of the end effector of FIG. 34.

FIG. 32 is a perspective view of a distal end portion of an alternative example ablation component 1600 in a retracted configuration, FIG. 33 is a perspective view of the ablation component 1600 of FIG. 32 in a deployed configuration, FIG. 34 is a detailed perspective view of an example end effector 1610 of the ablation component 1600 of FIG. 32, and FIG. 35 is a detailed perspective partial view of the end effector 1610 of FIG. 34, all according to at least some aspects of the present disclosure. The ablation component 1600 is generally similar in structure and operation to ablation components described elsewhere herein, including ablation component 1100, and repeated description of similar elements is omitted for brevity. Likewise, any feature described in connection with ablation component 1600 may be utilized in connection with any other embodiment described elsewhere herein.

Referring to FIGS. 32 and 33, the illustrated ablation component 1600 may include an elongated connecting element 1604 and a distally disposed end effector 1610. The end effector 1610 may include a magnetic element, such as a generally spherical permanent magnet, which may be freely rotatable about three axes of rotation within an end effector housing, as described above with reference to other similar embodiments. In the illustrated embodiment, the connecting element 1604 may include a first connecting element 1606 (e.g., generally in the form of a deflectable sheath or catheter) and a second connecting element 1608 (e.g., generally in the form of a flexible push/pull element), which may be movable within and relative to the first connecting element 1606. The end effector 1610 may be disposed generally distally on the second connecting element 1608. An engagement element 1614 may operatively interpose a first connecting element distal portion 1612 and the end effector 1610.

Referring to FIGS. 32-35, in the illustrated embodiment, the end effector 1610 may include a housing 1616 that is at least partially generally spherical. The end effector 1610 may include a magnetic element, such as a generally spherical permanent magnet, which may be freely rotatable about three axes of rotation within the end effector housing 1616, as described above with reference to other similar embodiments. The end effector housing 1616 may include a generally bulbous tissue contacting surface, which may be at least partially generally spherical. At least a portion of the end effector housing 1616 may be constructed from a high magnetic permeability, non-ferrous, electrically conductive material, such as copper. In some embodiments, an ablation element may include a primary electrode 1618, and an electrically conductive portion of the end effector housing 1616 may form the primary electrode 1618.

Referring to FIGS. 33-35, in the illustrated embodiment, the end effector housing 1616 may include a proximally extending neck 1626 to which the second connecting element 1608 is coupled. In the embodiment illustrated in FIGS. 32-35, the neck 1626 is generally shaped as a relatively short, distally tapering cylinder. Various other neck configurations, such as those described elsewhere herein, may be utilized in alternative embodiments.

Referring to FIGS. 34 and 35, in the illustrated embodiment, a distal portion 1628 of the end effector housing 1616 comprises the primary electrode 1618. A proximal portion 1630 of the end effector housing 1616 may be constructed from a non-conductive material, such as a polymer. Together, the distal portion 1628 and the proximal portion 1630 define a generally spherical interior in which a generally spherical magnetic element (e.g., permanent magnet) may be freely rotatable, generally in the manner described elsewhere herein with reference to similar embodiments.

In the illustrated embodiment, the end effector 1610 may include one or more auxiliary electrodes 1632, 1634, 1636, 1638, 1640. For example, the illustrated embodiment includes one distal tip auxiliary electrode 1632 and four lateral auxiliary electrodes 1634, 1636, 1638, 1640, which may be generally evenly spaced apart circumferentially (e.g., at about 90 degrees of angular separation). As shown in FIG. 35, recesses 1634 may be formed in the proximal portion 1630 of the housing 1616 to allow routing of wires to the auxiliary electrodes 1632, 1634, 1636, 1638, 1640. In some example embodiments, the auxiliary electrodes 1632, 1634, 1636, 1638, 1640 may be electrically isolated from the primary electrode 3018, such as by insulators.

Figure 36:
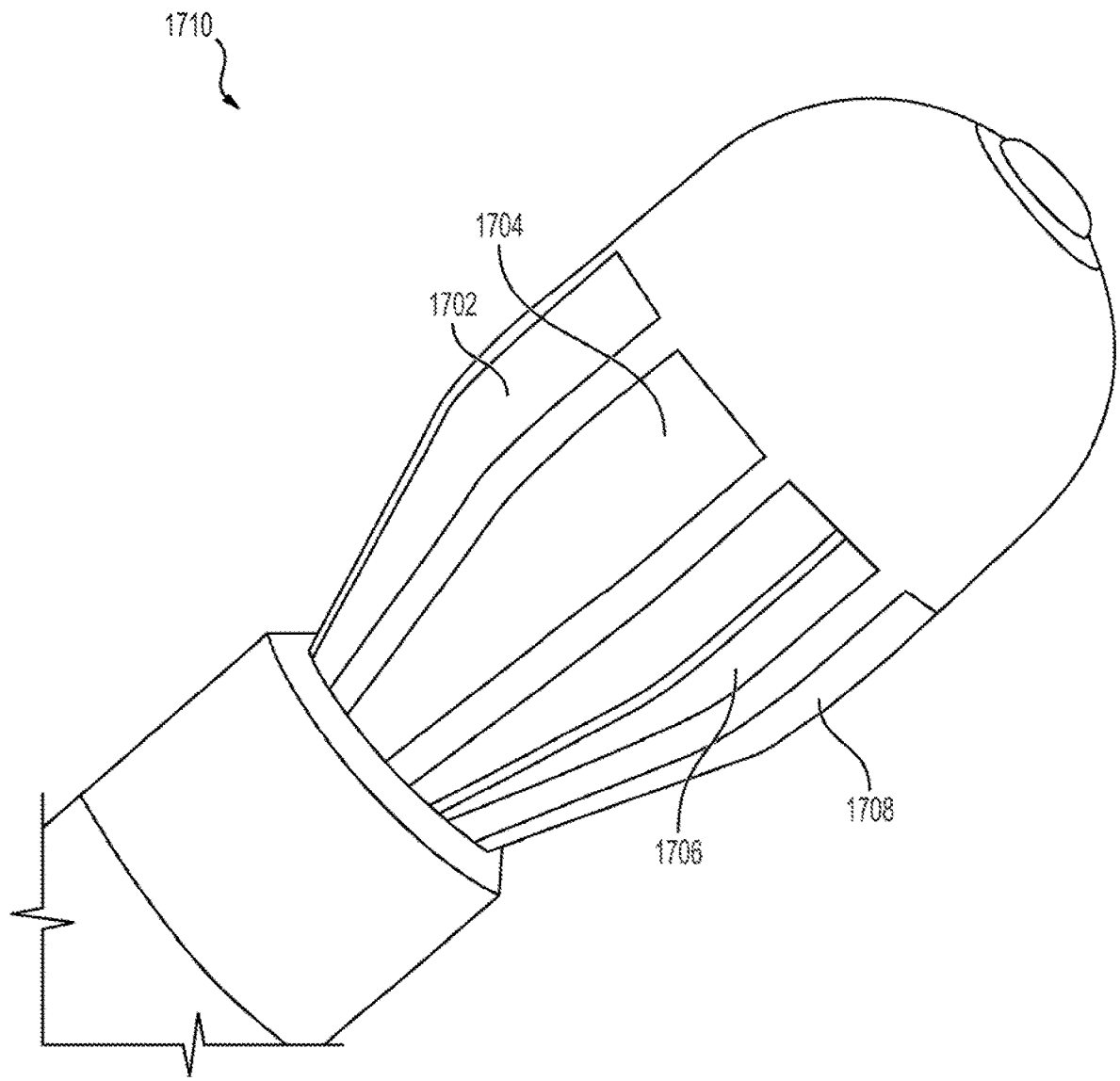
FIG. 36 is a detailed perspective view of an alternative end effector.

FIG. 36 is a detailed perspective view of an alternative end effector 1710, according to at least some aspects of the present disclosure. The end effector 1710 is generally similar in structure and operation to ablation components described elsewhere herein, including end effector 1610, and repeated description of similar elements is omitted for brevity. Likewise, any feature described in connection with end effector 1710 may be utilized in connection with any other embodiment described elsewhere herein. The end effector 1710 may include a magnetic element, such as a generally spherical permanent magnet, which may be freely rotatable about three axes of rotation within an end effector housing, as described above with reference to other similar embodiments. In the embodiment of FIG. 36, one or more lateral auxiliary electrodes 1702, 1704, 1706, 1708 are provided in the form of elongated electrodes, which may be generally longitudinally oriented about a proximal portion of the periphery of the end effector 1710.

Figure 37:
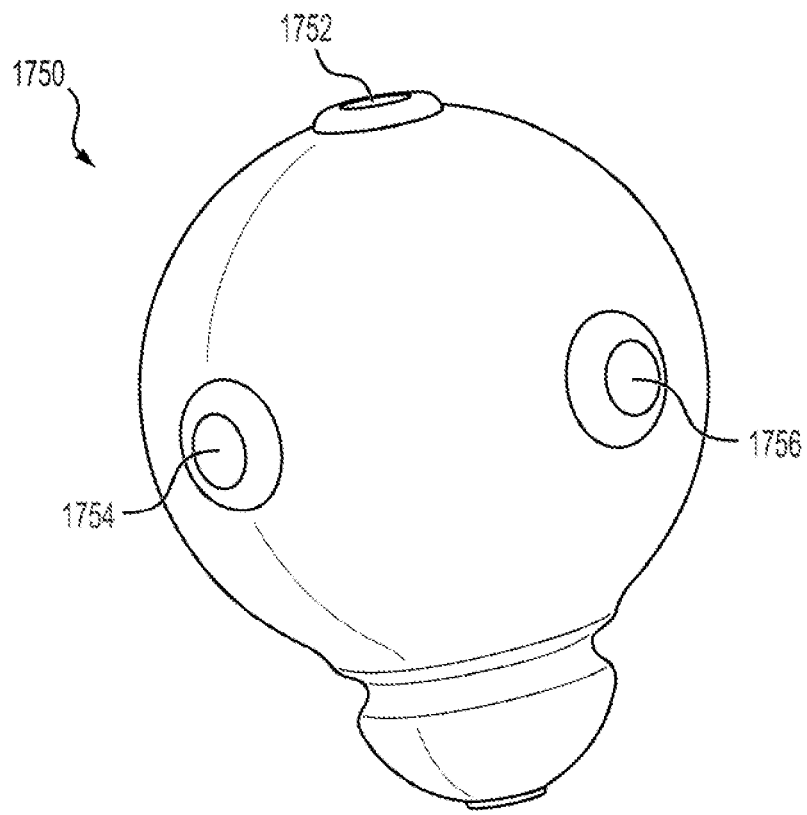
FIG. 37 is a detailed perspective view of an alternative end effector.
Figure 38:
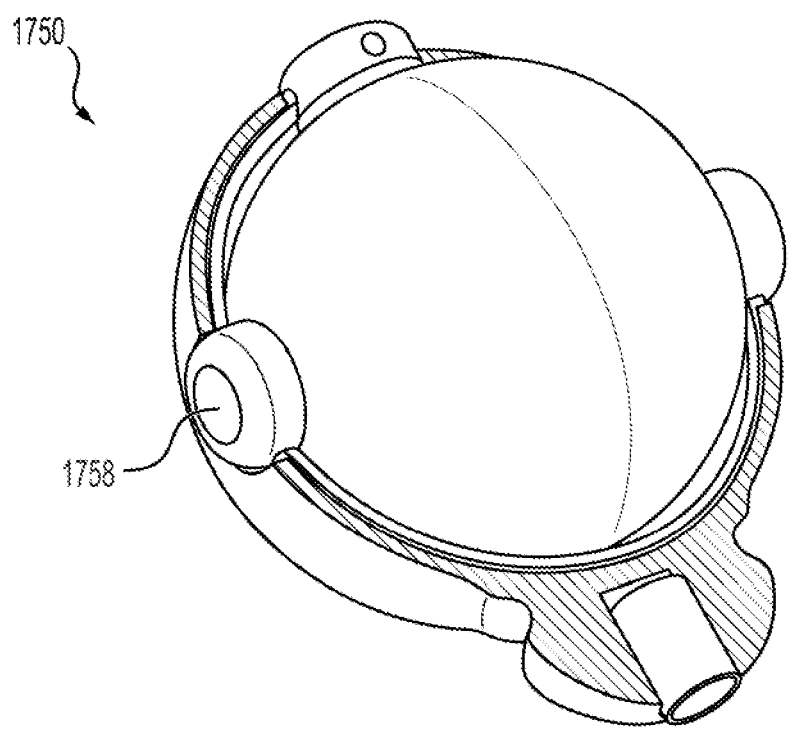
FIG. 38 is a detailed perspective cutaway view of the end effector of FIG. 37.

FIG. 37 is a detailed perspective view of an alternative end effector 1750, and FIG. 38 is a detailed perspective cutaway view of the end effector 1750, all according to at least some aspects of the present disclosure. The end effector 1750 is generally similar in structure and operation to ablation components described elsewhere herein, including end effectors 1520, 1710, and repeated description of similar elements is omitted for brevity. Likewise, any feature described in connection with end effector 1750 may be utilized in connection with any other embodiment described elsewhere herein. The end effector 1750 may include a magnetic element, such as a generally spherical permanent magnet, which may be freely rotatable about three axes of rotation within an end effector housing, as described above with reference to other similar embodiments. In the illustrated embodiment, the end effector 1750 is similar in shape to the end effector 1520 of FIG. 29, which includes a generally dome-shaped neck 1522 with a circumferential recess 1524. In the embodiment of FIGS. 37 and 38, however, the end effector 1750 includes a distal tip auxiliary electrode 1752 and four circumferentially spaced apart lateral auxiliary electrodes 1754, 1756, 1758 (the fourth lateral auxiliary electrode is not visible in FIGS. 37 and 38).

Figure 39:
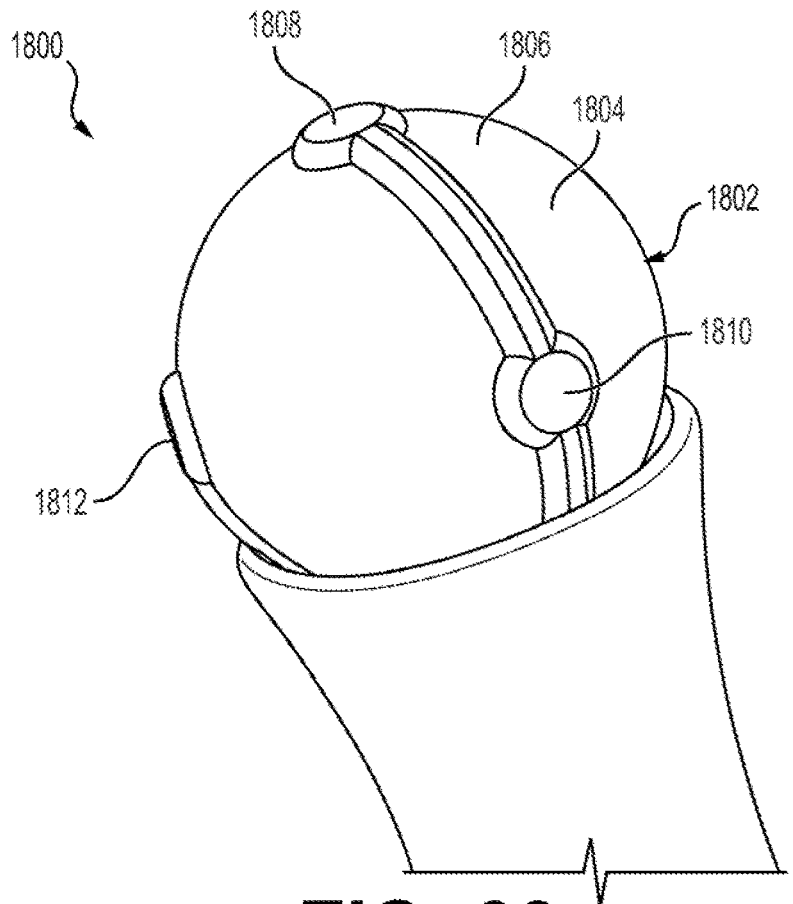
FIG. 39 is a detailed perspective view of a distal end portion of an alternative ablation component.
Figure 40:
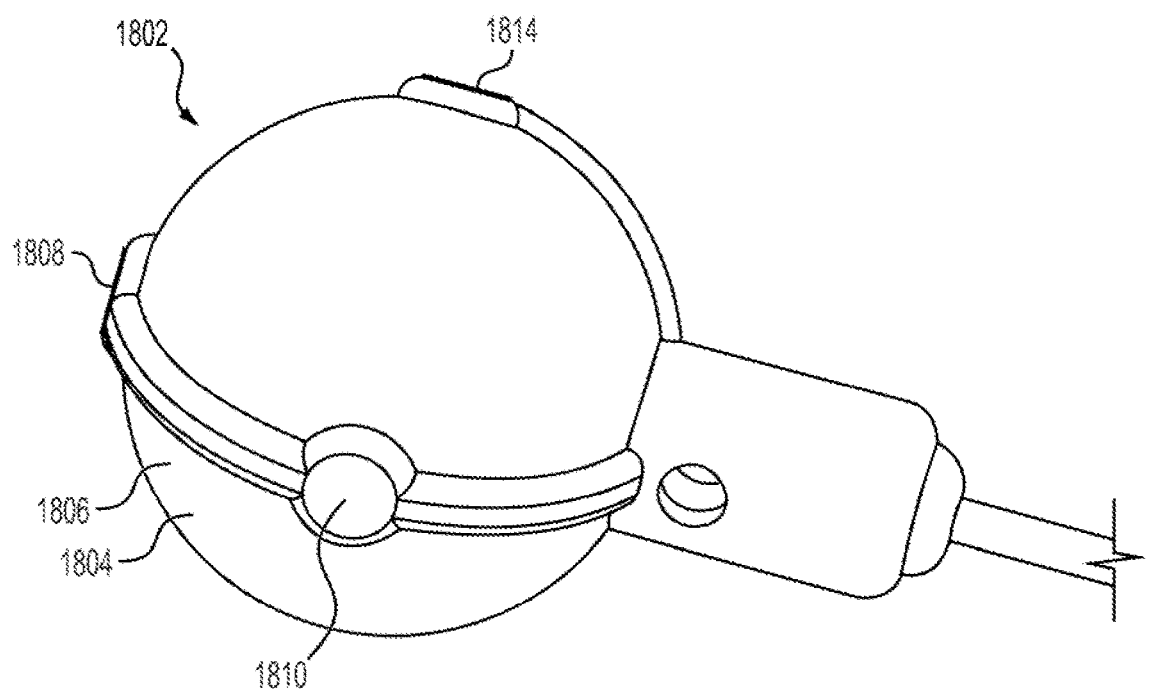
FIG. 40 is a detailed perspective view of an example end effector of the ablation component of FIG. 39.

FIG. 39 is a detailed perspective view of a distal end portion of an alternative ablation component 1800, and FIG. 40 is a detailed perspective view of an example end effector 1802 of the ablation component 1800 of FIG. 39, all according to at least some aspects of the present disclosure. The ablation component 1800 is generally similar in structure and operation to ablation components described elsewhere herein, including ablation component 1600, and repeated description of similar elements is omitted for brevity. Likewise, any feature described in connection with ablation component 1800 may be utilized in connection with any other embodiment described elsewhere herein. The end effector 1802 may include a magnetic element, such as a generally spherical permanent magnet, which may be freely rotatable about three axes of rotation within an end effector housing, as described above with reference to other similar embodiments.

In the illustrated embodiment, the end effector 1802 includes a generally spherical housing 1804 including a primary electrode 1806 as well as five auxiliary electrodes 1808, 1810, 1812, 1814 (the other lateral auxiliary electrode is similarly provided but is not visible in FIGS. 39 and 40). The auxiliary electrodes 1808, 1810, 1812 are disposed on the outer surface of the primary electrode 1806. Also disposed on the outer surface of the primary electrode 1806 are channels 1816, 1818, 1820, which allow routing of wires to the auxiliary electrodes 1808, 1810, 1812, 1814. In the illustrated embodiment, one channel 1816 operatively connects to both a distal tip auxiliary electrode 1808 and one of the lateral auxiliary electrodes 1810, while other channels 1818, 1820 operatively connect to individual lateral auxiliary electrodes.

Figure 41:
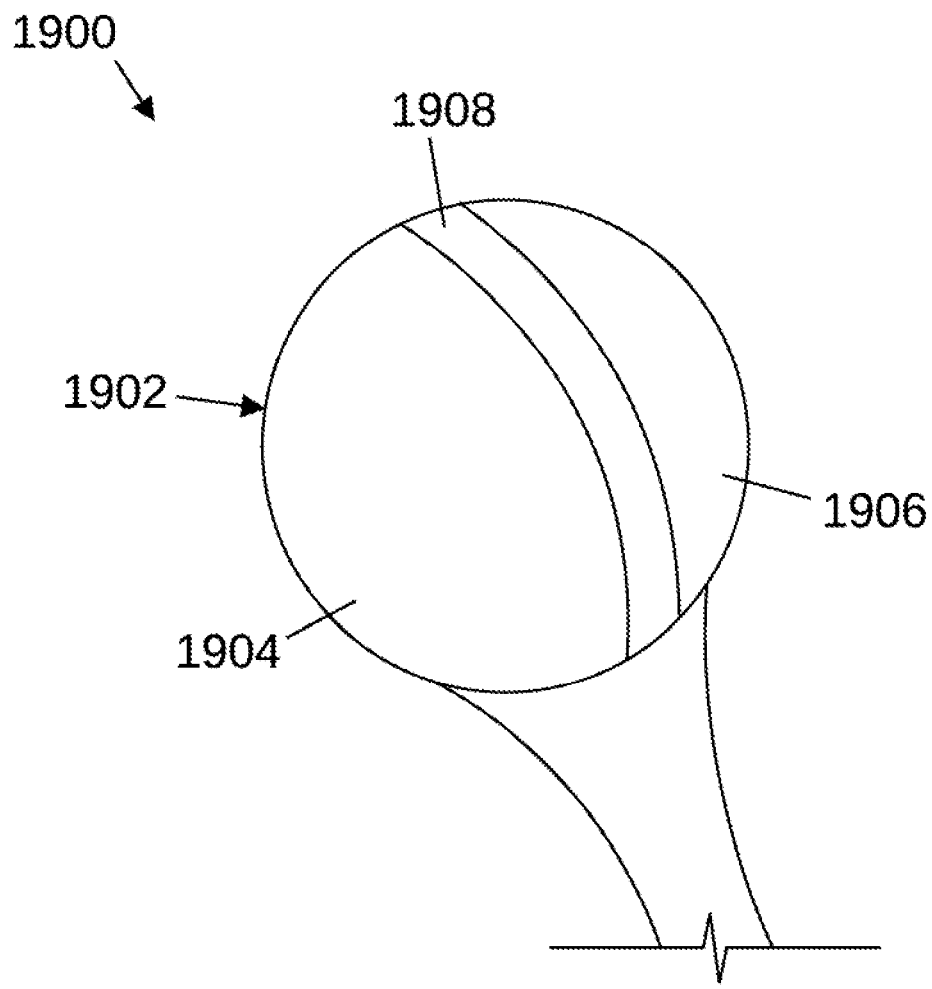
FIG. 41 is a detailed perspective view of an alternative example end effector.

FIG. 41 is a detailed perspective view of an alternative example end effector 1900, according to at least some aspects of the present disclosure. The end effector 1900 is generally similar in structure and operation to ablation components described elsewhere herein, including end effector 1610, and repeated description of similar elements is omitted for brevity. Likewise, any feature described in connection with end effector 1900 may be utilized in connection with any other embodiment described elsewhere herein.

In the illustrated embodiment, the end effector 1900 may include a magnetic element, such as a generally spherical permanent magnet, which may be freely rotatable about three axes of rotation within an end effector housing 1902, as described above with reference to other similar embodiments. The end effector housing 1902 may include a generally bulbous tissue contacting surface, which may be at least partially generally spherical. At least a portion of the end effector housing 1902 may be constructed from a high magnetic permeability, non-ferrous, electrically conductive material, such as copper. In some embodiments, an ablation element includes two or more primary electrodes 1904, 1906. In the illustrated embodiment, the end effector housing 1902 comprises the primary electrodes 1904, 1906, which are generally in the form of cooperating hemispheres. The primary electrodes may be electrically and/or mechanically separated by an insulator 1908, which may be in the form of a plastic spacer. In the illustrated embodiment, the primary electrodes 1904, 1906 are arranged laterally with respect to one another (e.g., one is on each lateral side of the longitudinal axis). In other embodiments, the generally hemispherical primary electrodes 1904, 1906 may be disposed in other relative arrangements, such as longitudinally with respect to one another. In some alternative embodiments, the generally spherical housing 1902 may comprise three or more partially spherical sections, which may be interposed by one or more spacers (e.g., insulators), and which may be disposed in any desired arrangement. In some embodiments, the primary electrodes 1904, 1906 may be utilized with one another for ablation of the target tissue from one side. In some embodiments, the primary electrodes 1904, 1906 may be utilized in cooperation with one or more cooperating electrodes positioned on an opposite side of the target tissue. In some such embodiments, the primary electrodes 1904, 1906 may be selectively switched on and off to create a desired ablation in the target tissue. Although not illustrated in FIG. 41, one or more auxiliary electrodes, such as those described above, may be utilized in connection this embodiment.

Figure 42:
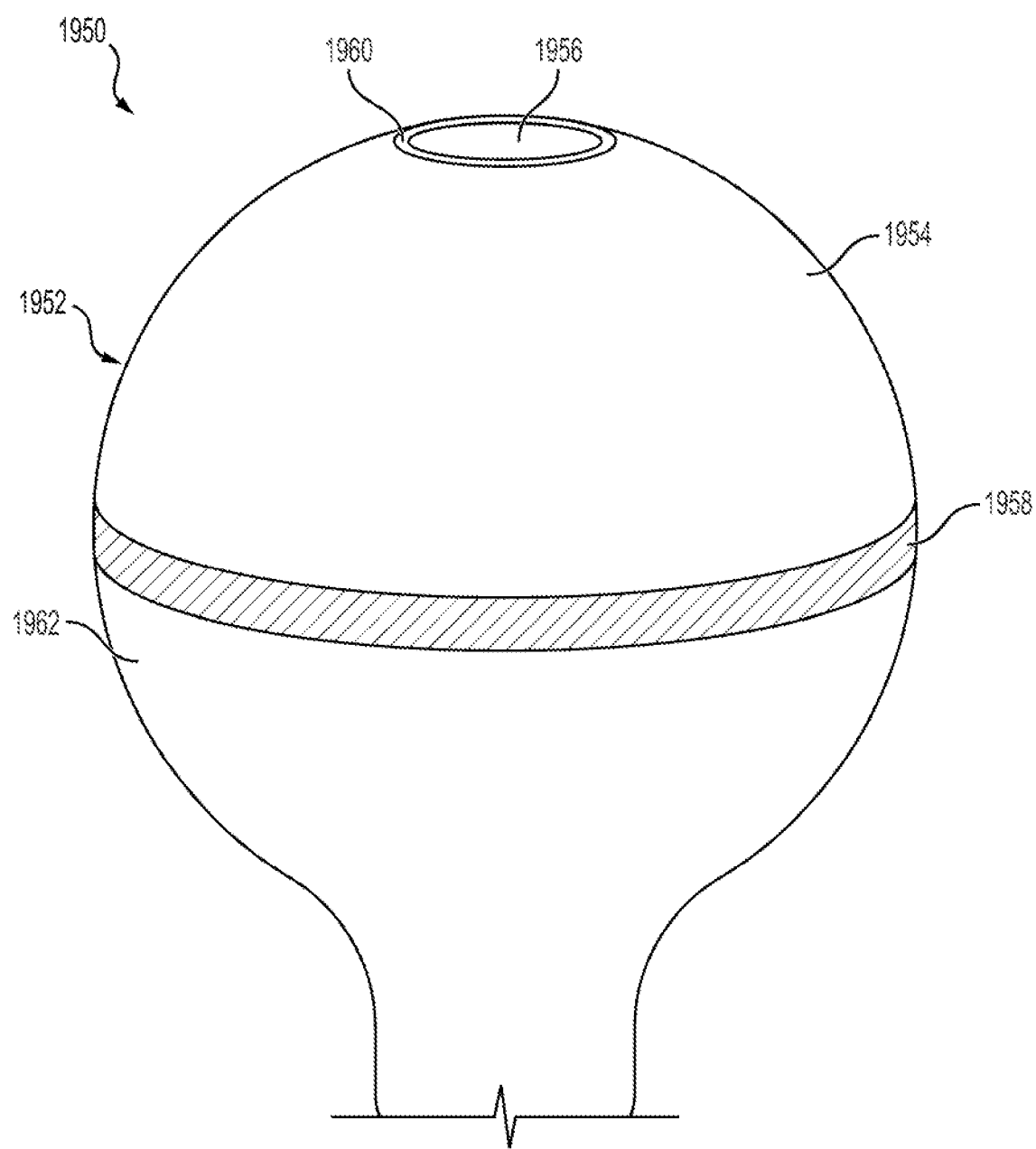
FIG. 42 is a detailed perspective view of an alternative example end effector.

FIG. 42 is a detailed perspective view of an alternative example end effector 1950, according to at least some aspects of the present disclosure. The end effector 1950 is generally similar in structure and operation to ablation components described elsewhere herein, including end effector 1610, and repeated description of similar elements is omitted for brevity. Likewise, any feature described in connection with end effector 1950 may be utilized in connection with any other embodiment described elsewhere herein.

In the illustrated embodiment, the end effector 1950 may include a magnetic element, such as a generally spherical permanent magnet, which may be freely rotatable about three axes of rotation within an end effector housing 1952, as described above with reference to other similar embodiments. The end effector housing 1952 may include a generally bulbous tissue contacting surface, which may be at least partially generally spherical. At least a portion of the end effector housing 1952 may be constructed from a high magnetic permeability, non-ferrous, electrically conductive material, such as copper. In some embodiments, an ablation element includes a distally disposed, generally hemispherical primary electrode 1954. The illustrated embodiment includes two auxiliary electrodes 1956, 1958 in addition to the primary electrode 1954. In this embodiment, one of the auxiliary electrodes 1956, 1958 includes a distal tip auxiliary electrode 1956 and the other includes a lateral auxiliary electrode 1958. The lateral auxiliary electrode 1958 may be generally in the form of a generally circular circumferential metal ring disposed proximally of the primary electrode 1954. In the illustrated embodiment the auxiliary electrodes 1956 are electrically isolated from the primary electrode 1954, such as by an interposed insulator 1960, which may be in the form of a plastic spacer. In the illustrated embodiment, a proximal portion 1962 of the end effector housing 1952 may be constructed of a non-conductive material, such as plastic. Generally, electrodes of any shape (e.g., generally hemispherical, generally circular, generally ring-shaped, etc.) may be used as primary and/or auxiliary electrodes in connection with any embodiment described herein, and may be oriented in any desired orientation on the end effector housing.

Figure 43:
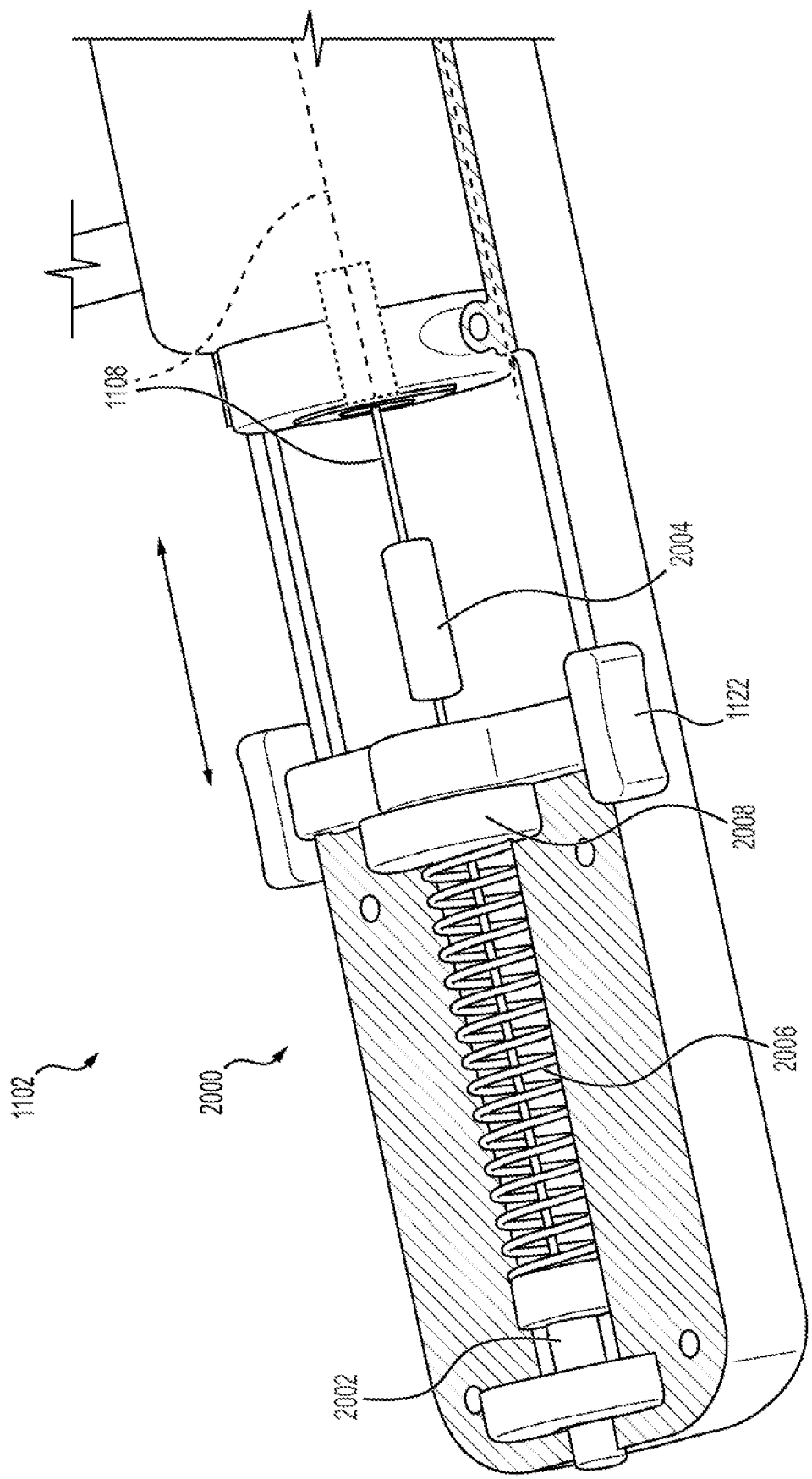
FIG. 43 is a detailed perspective partial cutaway view of an example end effector deployment mechanism in a retracted configuration.
Figure 44:
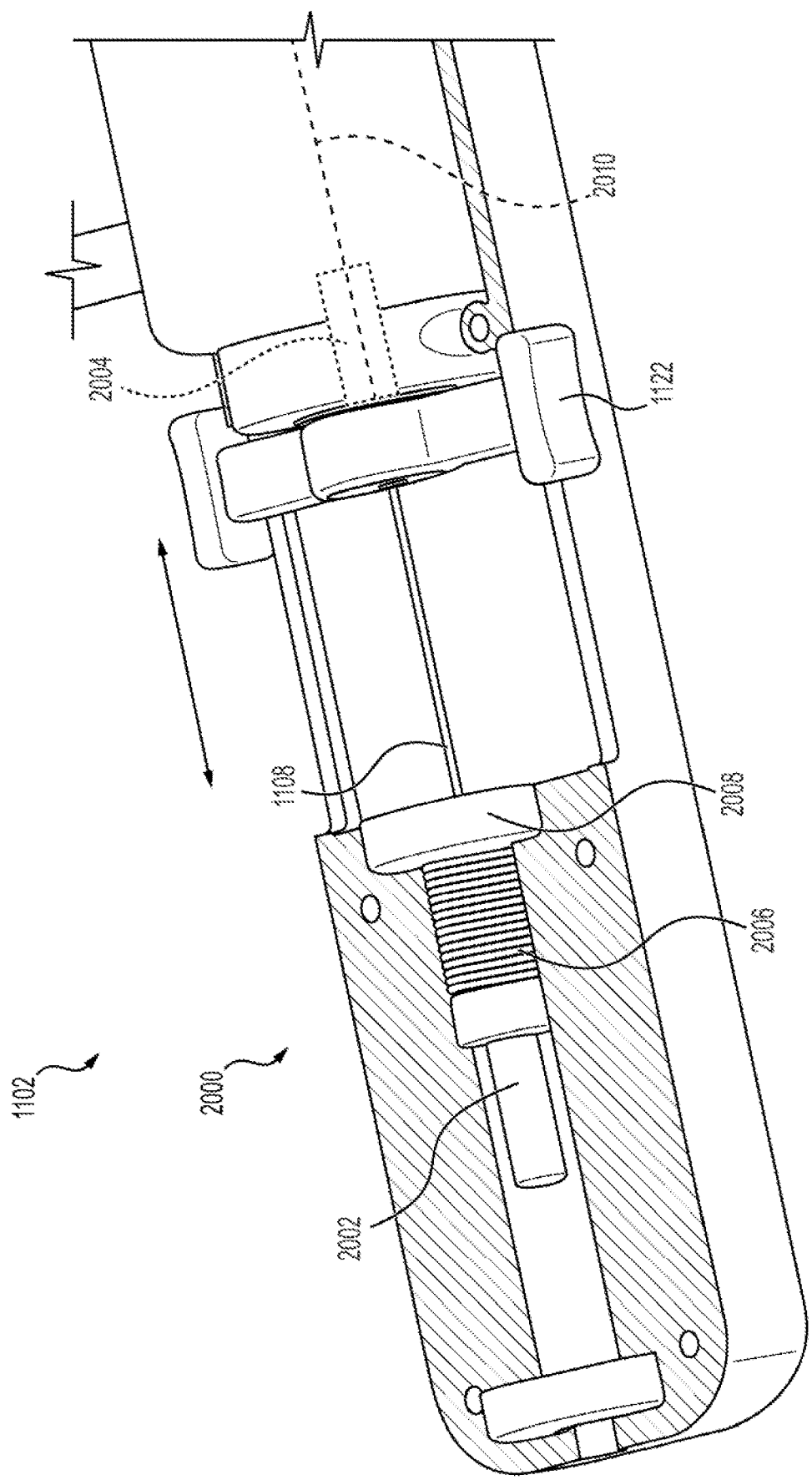
FIG. 44 is a detailed perspective partial cutaway view of the example deployment mechanism of FIG. 43 in a deployed configuration.

FIG. 43 is a detailed perspective partial cutaway view of an example end effector deployment mechanism 2000 in a retracted configuration, and FIG. 44 is a detailed perspective partial cutaway view of the example deployment mechanism 2000 of FIG. 43 in a deployed configuration, all according to at least some aspects of the present disclosure. The deployment mechanism 2000 is described with reference to the ablation component 1100 shown in FIGS. 21, 22, 24, and 25. It is to be understood, however, that the ablation component 1100 does not require the deployment mechanism 2000 and that the illustrated deployment mechanism 2000 may be used in connection with other embodiments, such as those in which an end effector may be deployed and/or retracted in a similar manner.

Referring so FIGS. 21, 22, 24, 25, 43, and 44, in some embodiments, the deployment mechanism 2000 may be disposed in the handle 1102 and may be configured to extend and/or retract the second connecting element 1108 (e.g., relative to the first connecting element 1106) to deploy and/or retract the end effector 1110. The illustrated deployment mechanism 2000 may include a first, proximal ferrule 2002 and a second, distal ferrule 2004. The ferrules 2002, 2004 may each be secured to the second connecting element 1108. A compression spring 2006 may act between a fixed stop 2008 (distally) and the proximal ferrule 2002 (proximally) so as to apply proximal tension on the second connecting element 1108. The deployment actuator 1122 may selectively engage the distal ferrule 2004.

Referring to FIG. 43, in the illustrated embodiment, in the retracted configuration, the deployment actuator 1122 may be in a proximal, retracted position. In this position, the deployment actuator 1122 may be disengaged from the distal ferrule 2004 and the proximal tension applied by the compression spring 2006 via the proximal ferrule 2002 may hold the second connecting element 20101108 in a proximal, retracted position.

Additionally, in the illustrated embodiment, in the retracted configuration, the compression spring 2006 is partially compressed. Accordingly, the spring 2006 maintains tension on the second connecting element 1108 even if the second connecting element 1108 is moved proximally a small amount. Similarly, the spring 2006 allows a small amount of distal movement of the second connecting element 1108 (e.g., if the second connecting element is pulled distally). This small proximal or distal movement of the second connecting element 1108 may occur, for example, when the first connecting element distal portion 1112 is deflected or straightened. Because the deployment mechanism 2000 is configured to apply continuous proximal tension on the second connecting element 1108 throughout such small movements of the second connecting element 1108, secure engagement between the engagement element 1114 and the end effector 1110 and/or the first connecting element distal portion 1112 can be maintained during deflection and/or straightening of the first connecting element distal portion 1112.

Referring to FIG. 44, in the illustrated embodiment, in the deployed configuration, the deployment actuator 1122 may be in a distal, deployed position. In this position, the deployment actuator 1122 may be engaged with the distal ferrule 2004. Specifically, the deployment actuator 1122 may hold the distal ferrule 2004 distally, such that it is not directly visible in the cutaway view of FIG. 43. Because the distal ferrule 2004 was moved distally by the deployment actuator 1122, and both the distal ferrule 2004 and proximal ferrule 2002 are securely attached to the second connecting element 1108, the compression spring 2006 is further compressed against the fixed stop 2008.

Figure 45:
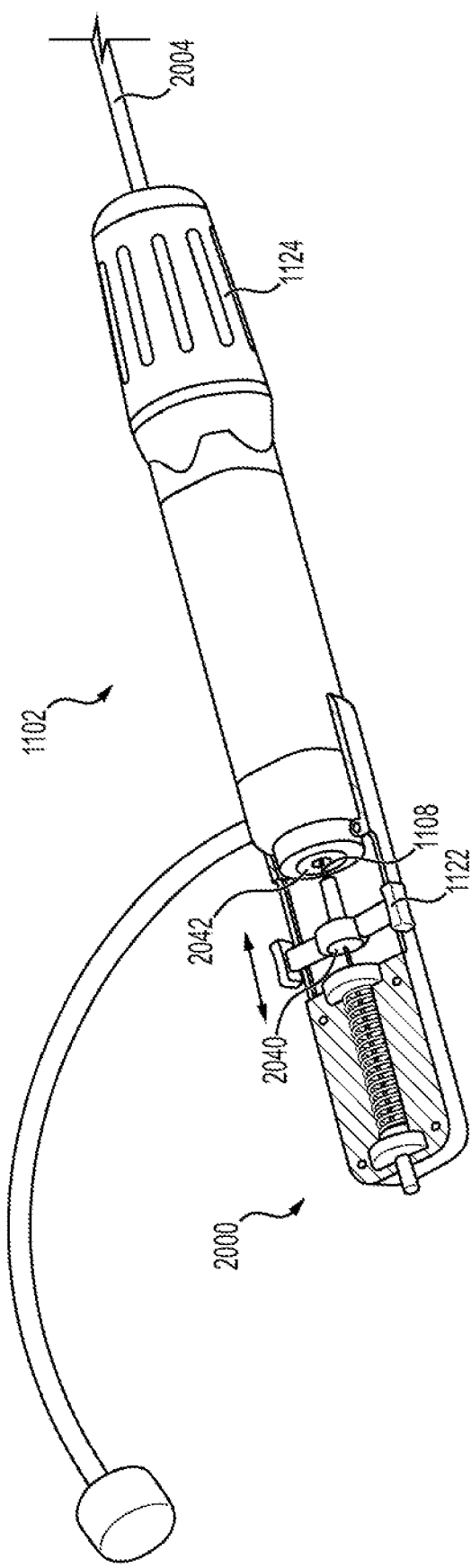
FIG. 45 is a detailed perspective partial cutaway view of the deployment mechanism of FIG. 43 in an intermediate position.
Figure 46:
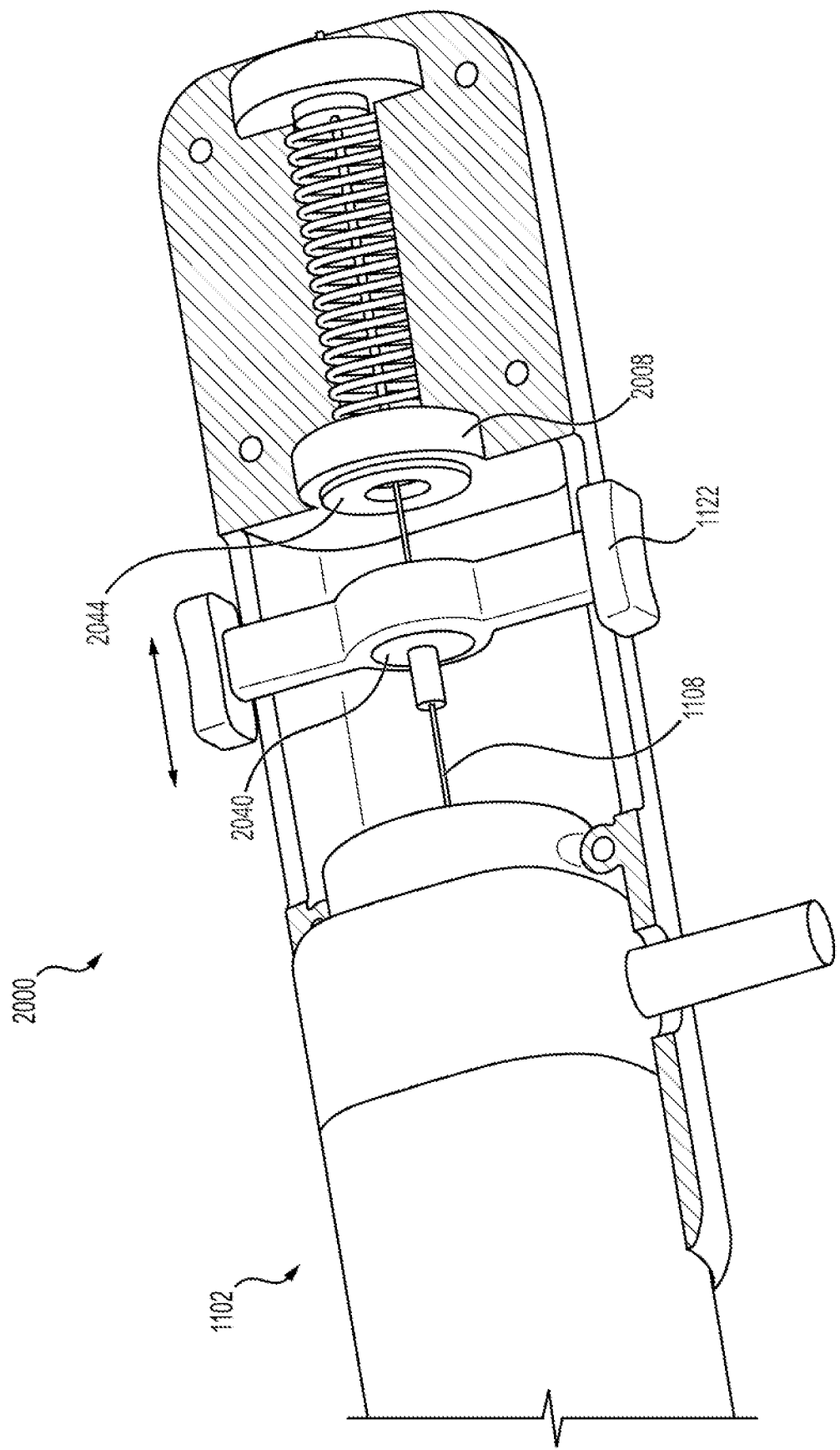
FIG. 46 is a detailed perspective partial cutaway view of the deployment mechanism of FIG. 43 in an intermediate position.

FIGS. 45 and 46 are detailed perspective partial cutaway views of the deployment mechanism 2000 in an intermediate position, all according to at least some aspects of the present disclosure. The deployment actuator 1122 may be held in the retracted (proximal) position and/or in the deployed (distal) position by one or more latch mechanisms. In particular, in the illustrated embodiment, the deployment actuator 1122 may be held in the retracted position and/or the deployed position by one or more magnetic latch mechanisms. Generally, example magnetic latch mechanisms may utilize magnet-to-magnet attraction and/or magnet-to-ferrous component attraction. Magnetic components may be selected to provide desired magnetic strength. In the illustrated embodiment, the deployment actuator 1122 may include a latch magnet 2040. Referring to FIG. 45, the proximal-facing interior surface at the distal end of the deployment mechanism 2000 may include a magnetic element 2042 configured to cooperate with the latch magnet 2040 in the deployed position. Referring to FIG. 46, the distal-facing surface of the fixed stop 2008 may include a magnetic element 2044 configured to cooperate with the latch magnet 2040 in the retracted position. In the illustrated embodiment, the magnetic elements 2042, 2044 may comprise ferromagnetic washers, which may be attracted by the latch magnet 2040. In some alternative embodiments, the magnetic elements 2042, 2044 may include permanent magnets. In still further alternative embodiments, mechanical latch mechanisms (e.g., catches, detents, etc.) may be utilized to hold the deployment actuator 1122 in the retracted position and/or deployed position.

Figure 47:
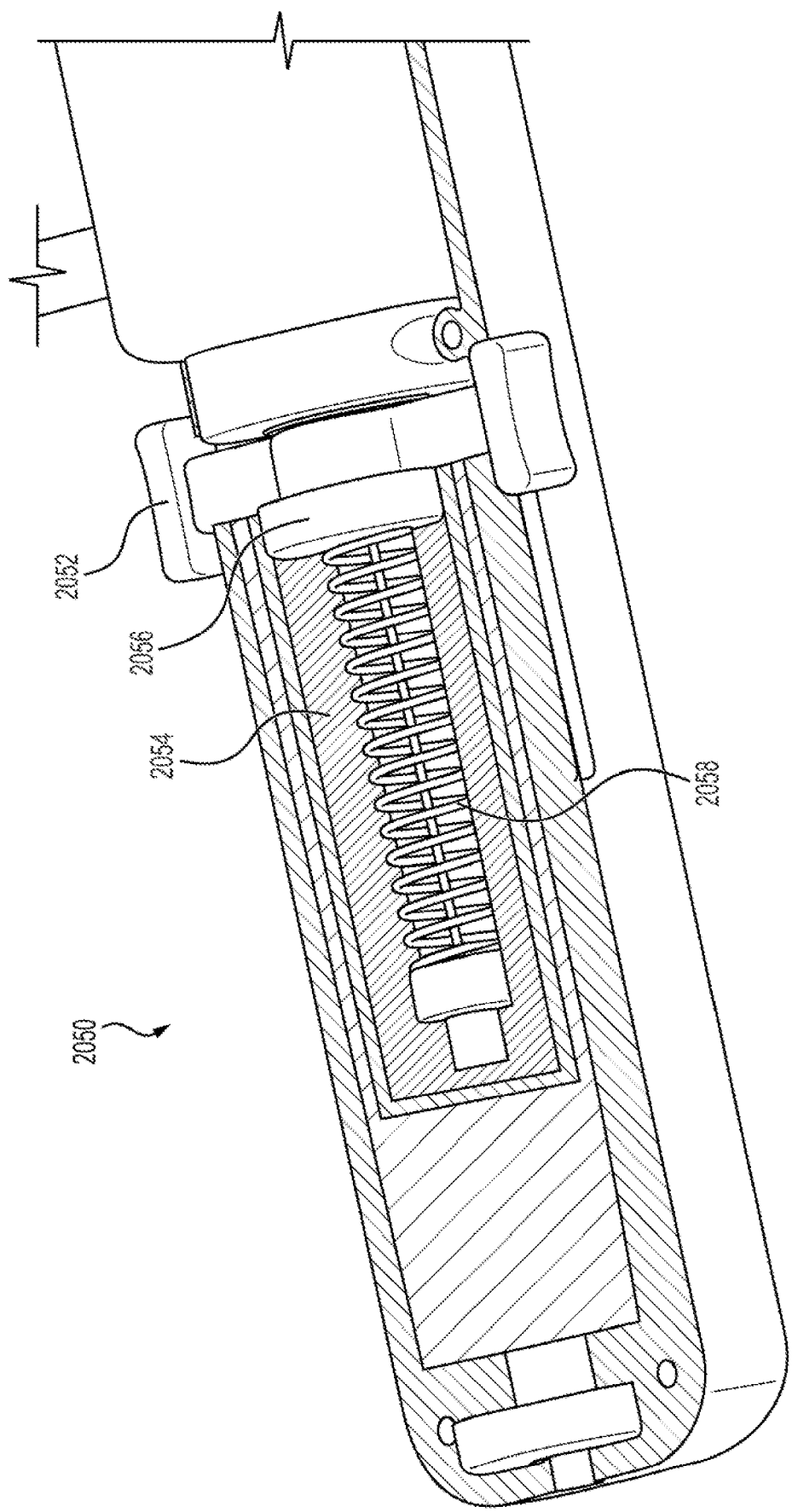
FIG. 47 is a detailed perspective cutaway view of an alternative deployment mechanism in a deployed configuration.

FIG. 47 is a detailed perspective cutaway view of an alternative deployment mechanism 2050 in a deployed configuration, according to at least some aspects of the present disclosure. Deployment mechanism 2050 is generally similar in structure and operation to other deployment mechanisms described herein, particularly deployment mechanism 2000, and repeated description of similar structures and operations is omitted for brevity. Likewise, any feature described in connection with deployment mechanism 2050 may be utilized in connection with any other embodiment described elsewhere herein.

In the illustrated embodiment, the deployment mechanism 2050 includes a deployment actuator 2052 that is configured to longitudinally translate a carriage 2054 between the retracted and deployed positions. The carriage 2054 includes the fixed stop 2056. Accordingly, unlike the deployment mechanism 2000 described above in which the fixed stop 2008 does not move with the deployment actuator 1122 (FIGS. 43-46), the fixed stop 2056 of the embodiment of FIG. 47 moves with the deployment actuator 2052. As a result, the spring 2058 is not substantially further compressed when the deployment actuator 2052 is moved from the retracted position to the deployed position.

Methods of using various example embodiments according to at least some aspects of the present disclosure, such as methods of creating a lesion, may include one or more of the operations described herein, in any order. This description of exemplary methods includes an overview for context followed by exemplary methods focusing on specific embodiments. It is to be understood that any operation described herein may be performed alone and/or in connection with any other portion of this or any other procedure. Further, it is to be understood that while this description of methods and operations references specific elements of some exemplary embodiments described elsewhere herein, the various methods and operations likewise pertain to other similar or related embodiments according to the present disclosure, regardless of whether such other embodiments are specifically referenced.

The following method focuses on, but is not limited to, ablation components similar to those illustrated in FIGS. 1-20. It is to be understood that any operation described in connection with this method may be used in connection with any operation of any other method described herein, such as operations described elsewhere herein focusing on ablation components similar to those illustrated in FIGS. 21-47.

Referring to FIG. 1, an example method of creating a lesion 16 may include placing a first ablation component 102 proximate a first surface 12 of a target tissue 18. The first ablation component 102 may include any ablation component described herein. The first ablation component 102 may include an end effector 102A including a housing 102B, a magnetic element 110, and a first ablation element 106. The method may include placing a second ablation component 104 proximate a second surface 14 of the target tissue 18. The second ablation component may include any ablation component described herein. The second ablation component 104 may include a magnetic element 112. The method may include positioning the end effector 102A and/or the second ablation component 104 using attractive magnetic coupling between the first ablation component magnet element 110 and the second ablation component magnetic element 112. The method may include creating a first lesion 16 in the target tissue 18 using the first ablation element 106 and/or an ablation element 108 of the second ablation component 104. In some example embodiments, creating the lesion 16 in the target tissue 18 using the ablation element 106 of the first ablation component 102 and/or the ablation element 108 of the second ablation component 104 may include one or more of radiofrequency (RF) energy ablation (monopolar and/or bipolar), pulsed field ablation, cryoablation, ultrasound ablation, or laser ablation, for example. Some or all of these operations may be repeated as desired to create a plurality of lesions. When all ablation operations are complete, the first ablation component 102 and the second ablation component 104 may be withdrawn from the operative area.

The method may include reducing the attractive magnetic coupling between the first ablation component magnetic element 110 and the second ablation component magnetic element 112, such as by repositioning the magnetic element 110 relative to the housing 102B (e.g., from an engaged position to a disengaged position). In some example embodiments, such as the ablation components 200, 1000, repositioning the magnetic element 220, 1002 relative to the housing 232, 1018 may include translationally repositioning the magnetic element 220, 1002 relative to the housing 232, 1018. In some embodiments, such as the ablation component 200, translationally repositioning the magnetic element 220 relative to the housing 232 may include translationally repositioning the magnetic element 220 relative to the housing 232 without substantial rotation. Translationally repositioning the magnetic element 220, 1002 relative to the housing 232, 1018 may include translationally repositioning the magnetic element 220, 1002 along a longitudinal axis 220A, 1006 of the magnetic element 220, 1002. In some embodiments, translationally repositioning the magnetic element 220, 1002 relative to the housing 232, 1018 may include translationally repositioning the magnetic element 220, 1002 from substantially laterally adjacent to a tissue contacting surface 224, 1008 of the end effector 202, 1004 to substantially not laterally adjacent to the tissue contacting surface 224, 1008.

In some example embodiments, such as ablation components 900, 1000, repositioning the magnetic element 902, 1002 relative to the housing 904A, 1018 may include rotationally repositioning the magnetic element 902, 1002 relative to the housing 904A, 1018. In some embodiments, rotationally repositioning the magnetic element 902 relative to the housing 904A may include rotationally repositioning the magnetic element 902 relative to the housing 904A without substantial translation. Rotationally repositioning the magnetic element 902, 1002 relative to the housing 904A, 1018 may include rotationally repositioning the magnetic element 902, 1002 about a longitudinal axis 906 of the end effector 904 and/or about a longitudinal axis 1006 of the magnetic element 1002. Rotationally repositioning the magnetic element 902, 1002 relative to the housing 904A, 1018 may include rotationally repositioning the magnetic element 902, 1002 from an orientation in which a magnetic axis 910, 1010 of the magnetic element 902, 1002 is substantially aligned with a direction 912, 1012 from the magnetic element 902, 1002 through a tissue contacting surface 908, 1008 of the end effector 904, 1004 for magnetic attraction with the magnetic element 112 of the second ablation component 104 to an orientation in which the magnetic axis 910, 1010 of the magnetic element 902, 1002 is substantially perpendicular to the direction 912, 1012 from the magnetic element 902, 1002 through the tissue contacting surface 908, 1008. Rotationally repositioning the magnetic element 902, 1002 relative to the housing 904A, 1018 may include rotationally repositioning the magnetic element 902, 1002 from an orientation in which a magnetic axis 910, 1010 of the magnetic element 902, 1002 is substantially aligned with a direction 912, 1012 from the magnetic element 902, 1002 through a tissue contacting surface 908, 1008 of the end effector 904, 1004 for magnetic attraction with the magnetic element 112 of the second ablation component 104 to an orientation in which the magnetic axis 910, 1010 of the magnetic element 902, 1002 is substantially aligned with the direction 912, 1012 from the magnetic element 902, 1002 through the tissue contacting surface 908, 1008 for magnetic repulsion of the magnetic element 112 of the second ablation component 104.

In some example embodiments, such as ablation component 1000, repositioning the magnetic element 1002 relative to the housing 1018 may include simultaneously translationally and rotationally repositioning the magnetic element 1002 relative to the housing 1018. Translationally repositioning the magnetic element 1002 relative to the housing 1018 may include translationally repositioning the magnetic element 1002 along a longitudinal axis 1006 of the magnetic element 1002. Rotationally repositioning the magnetic element 1002 relative to the housing 1018 may include rotationally repositioning the magnetic element 1002 about a longitudinal axis 1006 of the magnetic element 1002. In some embodiments, the magnetic element 1002 may be operatively coupled to a traveler 1016. The traveler 1016 may include a projection 1022 slidably disposed in a helical groove 1020. Simultaneously translationally and rotationally repositioning the magnetic element 1002 relative to the housing 1018 may include sliding the projection 1022 along the helical groove 1020.

In some example embodiments, such as ablation component 200, a method may include securing the ablation component 200 to the target tissue 18 (FIG. 1) by applying vacuum to a vacuum port 222 of the end effector 202. The method may include discontinuing applying vacuum to the vacuum port 222.

The following method focuses on, but is not limited to, ablation components similar to those illustrated in FIGS. 1 and 21-47. It is to be understood that any operation described in connection with this method may be used in connection with any operation of any other method described herein, such as operations described elsewhere herein focusing on ablation components similar to those illustrated in FIGS. 2-20.

Referring to FIG. 1, an example method of creating a lesion 16 in a target tissue 18 may include placing a first ablation component 102 on a first surface 12 of a target tissue 18. The first ablation component 102 may include a first ablation component end effector 102A, which may include a first ablation component end effector housing 102B and a first ablation component magnetic element 110. The method may include placing a second ablation component 104 on a second surface 14 of the target tissue 18. The second ablation component 104 may include a second ablation component ablation element 108 and a second ablation component permanent magnet 112. In some embodiments, such as the ablation component 1100 and similar embodiments, second ablation component permanent magnet 112, 1120 may be freely rotatable about at least one axis of rotation relative to a second ablation component end effector housing 104B, 1116. The method may include self-orienting the second ablation component permanent magnet 112, 1120 into a magnetically attractive orientation with the first ablation component magnetic element 110 by allowing the second ablation component permanent magnet 112, 1120 to rotate about the at least one axis of rotation. The method may include positioning one or both of the first ablation component end effector 102A, 1110 or the second ablation component end effector 104A using attractive magnetic coupling between the first ablation component magnetic element 110 and the second ablation component permanent magnet 112, 1120. The method may include creating a first lesion 16 in the target tissue 18 using the first ablation component ablation element 106 and/or the second ablation component ablation element 108, 1118. In some example embodiments, creating the lesion 16 in the target tissue 18 using the ablation element 106 of the first ablation component 102 and/or the ablation element 108, 1118 of the second ablation component 104, 1100 may include one or more of radiofrequency (RF) energy ablation (monopolar and/or bipolar), pulsed field ablation, cryoablation, ultrasound ablation, or laser ablation, for example. Some or all of these operations may be repeated as desired to create a plurality of lesions. When all ablation operations are complete, the first ablation component 102 and the second ablation component 104, 1100 may be withdrawn from the operative area.

In some example embodiments, such as ablation component 1100, self-orienting the second ablation component permanent magnet 1120 into the magnetically attractive orientation with the first ablation component magnetic element 110 may include self-orienting the second ablation component permanent magnet 1120 into the magnetically attractive orientation with the first ablation component magnetic element 110 without substantial translation of the second ablation component permanent magnet 1120 relative to the second ablation component end effector housing 1116.

In some example embodiments, such as ablation component 1100, the second ablation component permanent magnet 1120 may be freely rotatable about three axes of rotation relative to the second ablation component end effector housing 1116. Self-orienting the second ablation component permanent magnet 1120 into the magnetically attractive orientation with the first ablation component magnetic element 110 may include allowing the second ablation component permanent magnet 1120 to rotate about the three axes of rotation. In some example embodiments, the second ablation component permanent magnet 1120 may include a generally spherical second ablation component permanent magnet 1120 and the second ablation component end effector housing 1116 may include a generally spherical interior 1126. Allowing the second ablation component permanent magnet 1120 to rotate about the three axes of rotation may include allowing the generally spherical second ablation component permanent magnet 1120 to rotate about the three axes of rotation within the generally spherical interior 1126 of the second ablation component end effector housing 1116.

In some example embodiments, placing the second ablation component 104, 1110 on the second surface 14 of the target tissue 18 may include engaging a generally bulbous tissue contacting surface of the second ablation component 104, 1110 (e.g., electrode 1108) with the second surface 14 of the target tissue 18.

In some example embodiments, the second ablation component ablation element 108, 1108 may include a second ablation component electrode 108, 1108 and creating the first lesion 16 in the target tissue 18 using the second ablation component ablation element 108, 1108 includes applying radiofrequency ablation energy to the target tissue 18 using the second ablation component electrode 108, 1108. In some example embodiments, the first ablation component 102 may include a first ablation component ablation element 106 including a first ablation component electrode 106. Creating the first lesion 16 in the target tissue 18 using the second ablation component ablation element 108, 1108 may include applying bipolar radiofrequency ablation energy to the target tissue 18 using the first ablation component electrode 106 and the second ablation component electrode 108, 1108.

In some example embodiments, the method may include reducing the attractive magnetic coupling between the first ablation component magnetic element 110 and the second ablation component permanent magnet 112, 1120 and/or removing at least one of the first ablation component end effector 102A or the second ablation component end effector 104A, 1110 from the target tissue 18. In some example embodiments, the first ablation component magnetic element 110 may include a first ablation component permanent magnet 110 repositionably disposed relative to the first ablation component end effector housing 102B. The method may include reducing the attractive magnetic coupling between the first ablation component permanent magnet 110 and the second ablation component permanent magnet 112, 1120 by repositioning the first ablation component permanent magnet 110 relative to the first ablation component end effector housing 102B. For example, repositioning the first ablation component permanent magnet 110 relative to the first ablation component end effector housing 102B may include translationally repositioning the first ablation component permanent magnet 110 relative to the first ablation component end effector housing 102B. Translationally repositioning the first ablation component permanent magnet 110 relative to the first ablation component end effector housing 102B may include translationally repositioning the first ablation component permanent magnet 110 relative to the first ablation component end effector housing 102B without substantial rotation of the first ablation component permanent magnet 110 relative to the first ablation component end effector housing 102B.

In some example embodiments, repositioning the first ablation component permanent magnet 110 relative to the first ablation component end effector housing 102B may include rotationally repositioning the first ablation component permanent magnet 110 relative to the first ablation component end effector housing 102B. Rotationally repositioning the first ablation component permanent magnet 110 relative to the first ablation component end effector housing 102B may include rotationally repositioning the first ablation component permanent magnet 110 relative to the first ablation component end effector housing 102B without substantial translation of the first ablation component permanent magnet 110 relative to the first ablation component end effector housing 102B. In some example embodiments, repositioning the first ablation component permanent magnet 110 relative to the first ablation component end effector housing 102B may include simultaneously translationally and rotationally repositioning the first ablation component permanent magnet 110 relative to the first ablation component end effector housing 102B. In some example embodiments, such as ablation component 200, the method may include securing the first ablation component end effector 202 to the target tissue 18 by applying vacuum to a vacuum port 222 of the first ablation component end effector 202. The method may further include discontinuing applying vacuum to the vacuum port 2222.

The following method focuses on, but is not limited to, use of ablation components similar to those illustrated FIGS. 1-20 in connection with ablation components similar to those illustrated in FIGS. 1 and 21-47. It is to be understood that any operation described in connection with this method may be used in connection with any operation of any other method described herein.

Figure 48:
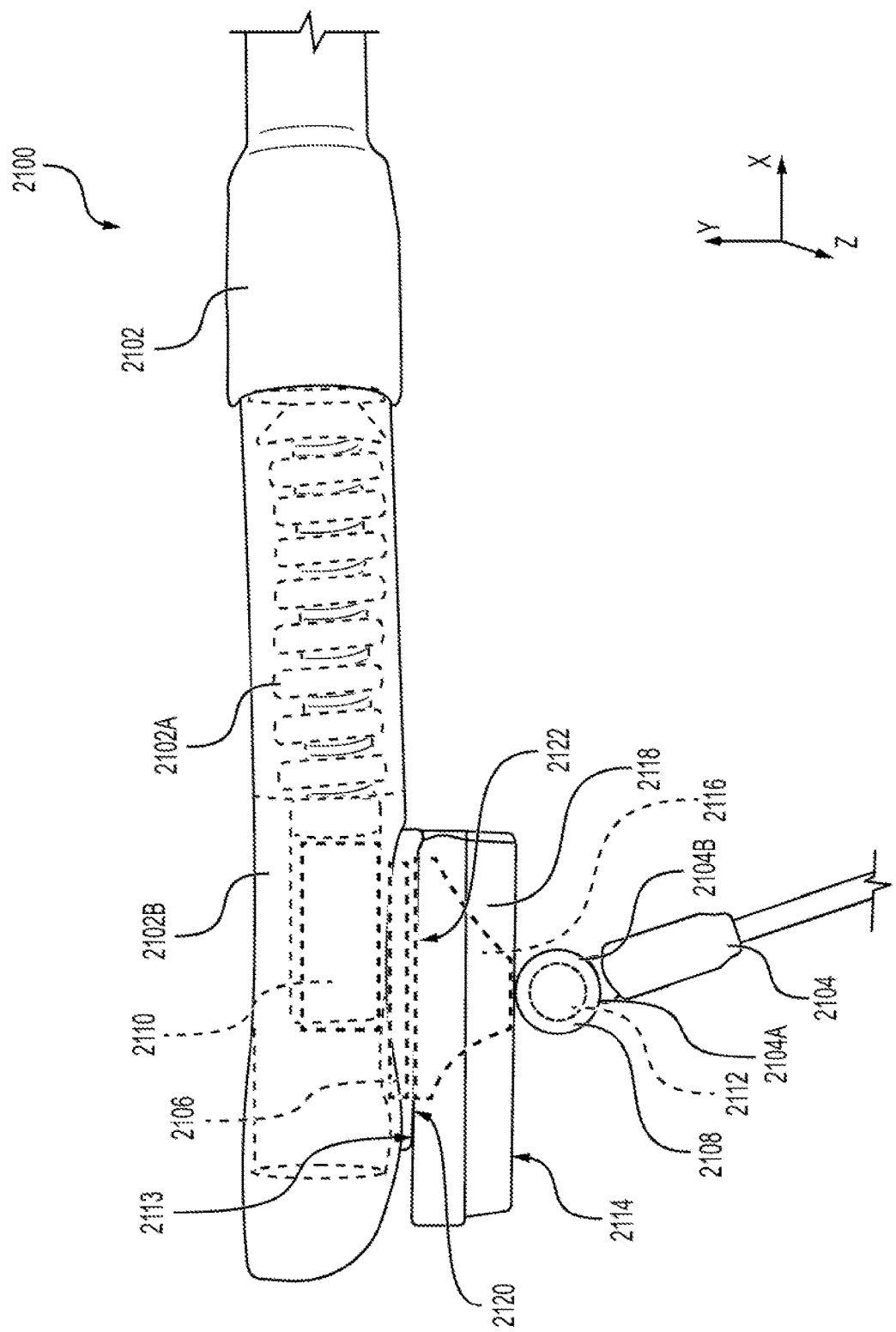
FIG. 48 is a perspective view of the distal end portion of an alternative example ablation system in use on a target tissue.

FIG. 48 is a perspective view of the distal end portion of an alternative example ablation system 2100 in use on a target tissue, according to at least some aspects of the present disclosure. In the illustrated embodiment, the ablation system 2100 includes a first ablation component 2102 configured to be positioned on a first side 2113 of a target tissue 2118, such as the epicardial surface 12 of the heart wall 18 (FIG. 1). The ablation system 2100 includes a second ablation component 2104 configured to be positioned on a second side 2114 of the target tissue 2118, such as the endocardial surface 14 of the heart wall 18 (FIG. 1). In the illustrated embodiment, each ablation component 2102, 2104 includes a respective end effector 2102A, 2104A comprising a respective housing 2102B, 2104B. Generally, the ablation system 2100 and ablation components 2102, 2104 may be similar in structure and operation to other ablation systems and ablation components described herein, and any suitable ablation components described herein may be used as the ablation components 2102, 2104. For example, the first ablation component 2102 may comprise the ablation component 200 (FIG. 3) or a related embodiment, and the second ablation component 2104 may comprise the ablation component 1100 (FIG. 21) or a related embodiment. Repeated description is omitted for brevity. Likewise, any feature or operation described in connection with the ablation system 2100 or ablation components 2102, 2104 may be utilized in connection with any other embodiment described elsewhere herein.

In the illustrated embodiment, the first ablation component 2102 may include at least one ablation element 2106, such as an electrode, and the second ablation component 2104 may include at least one ablation element 2108, such as an electrode. The ablation elements 2106, 2108 may be configured to cooperate to create a lesion 2116 in the target tissue 2118, such as a transmural lesion 2116 extending through the full thickness of the target tissue 2118. In other embodiments, only one of the first ablation component 2102 and the second ablation component 2104 may include an ablation element 2106, 2108.

In the illustrated embodiment, the first ablation 2102 component includes at least one magnetic element 2110 and the second ablation component 2104 includes at least one magnetic element 2112. The magnetic elements 2110, 2112 are configured to cooperate to facilitate positioning the first ablation component 2102 and/or the second ablation component 2104. For example, the magnetic elements 2110, 2112 may be configured for mutual attraction, such as to attract one another from a distance and/or align the ablation elements 2106, 2108 across the target tissue 2118 to create the lesion 2116 at the desired location. Some example ablation components 2102, 2104 may be configured to at least partially compress tissue therebetween. For example, the ablation components 2102, 2104 may be configured to cooperate to compress the target tissue 2118 therebetween using the magnetic attraction of the magnetic elements 2110, 2112, which may improve ablation outcomes in some circumstances. In the illustrated embodiment, the magnetic element 2110 is a diametrically magnetized, generally cylindrical permanent magnet. In other embodiments, bar magnets having generally square or rectangular cross sections may be used. In the illustrated embodiment, the magnetic element 212 is a generally spherical permanent magnet.

In some example embodiments, one or more of the magnetic elements 2110, 2112 may be movable relative to their respective housings 2102B, 2104B. For example, in the illustrated embodiment, the magnetic element 2110 of the first ablation component 1102 is selectively translationally repositionable relative to the housing 2102B, such as to facilitate decoupling of the magnetic element 2110 from the magnetic element 2112, such as when it may be desired to disengage one or both of the ablation components 2102, 2104 from the target tissue 2118. Generally, in various example embodiments, the magnetic element 2110 may be translationally and/or rotationally repositionable relative to the housing 2102B. Additionally, in the illustrated embodiment, the first ablation component 2102 includes a tissue contacting surface 2120 including a vacuum port 2122. Various embodiments may be configured to provide internal (e.g., closed circuit) fluid cooling and/or open circuit irrigation and/or cooling in connection with one or more of the housings 2102B, 2104B.

Figure 49:
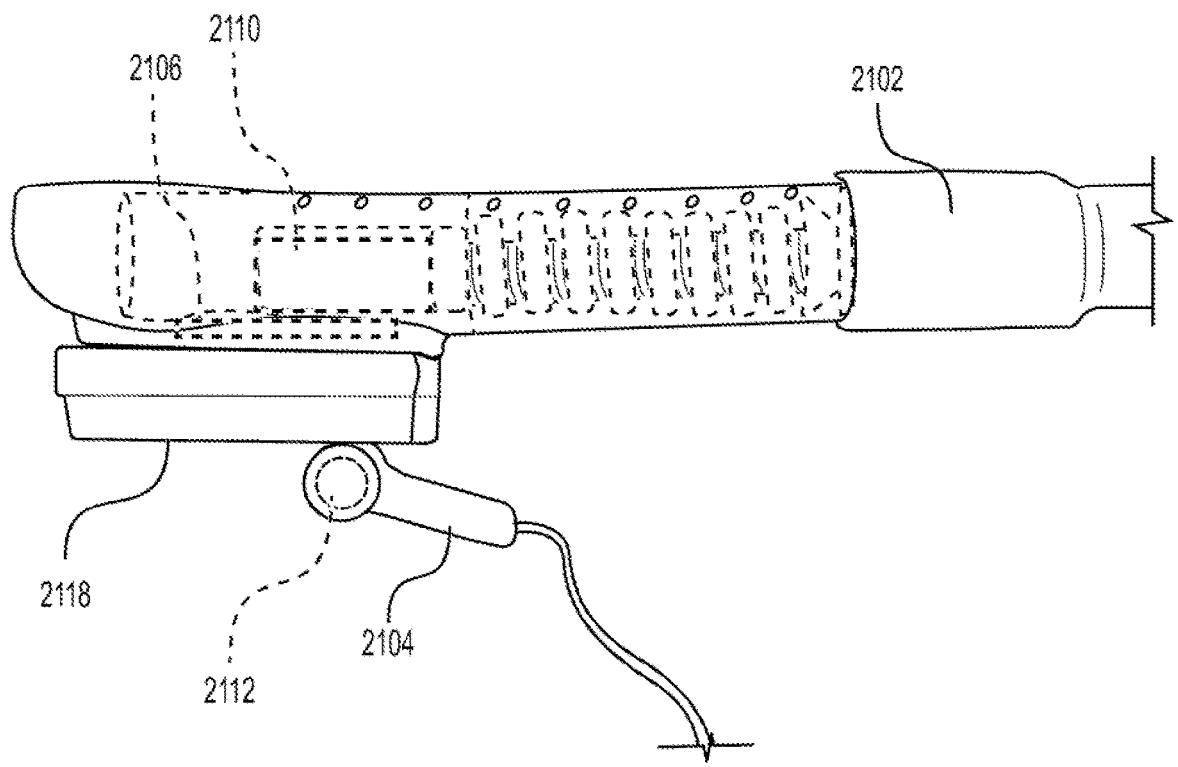
FIG. 49 is a perspective view of the distal end portion of the ablation system of FIG. 48.
Figure 50:
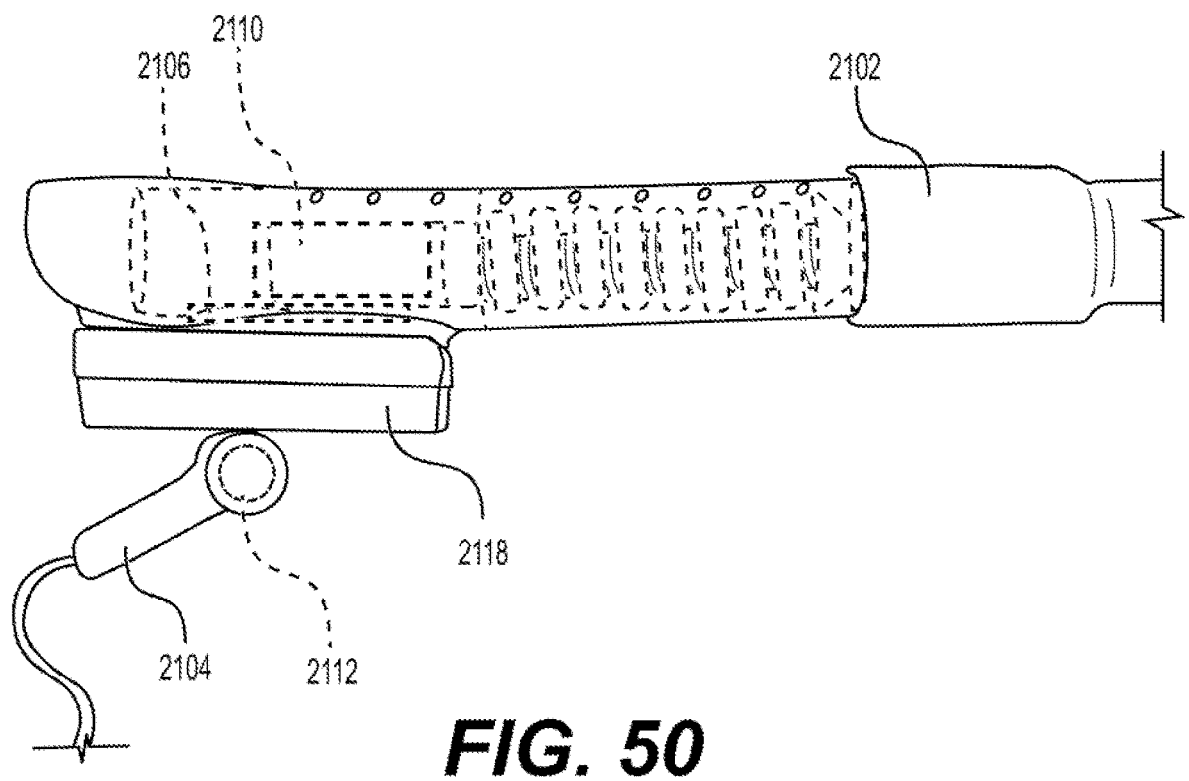
FIG. 50 is a perspective view of the distal end portion of the ablation system of FIG. 48.

FIGS. 49 and 50 are perspective views of the distal end portion of ablation system 1100 of FIG. 48, according to at least some aspects of the present disclosure. FIGS. 47-49 illustrate various angles at which the second ablation component 2104 can approach and/or magnetically cooperate with the first ablation component 2102. Generally, in this and similar embodiments, the second ablation component 2104 is configured to approach the target tissue 2118 from a wide range of approach angles (e.g., both in the plane of FIGS. 47-49 and generally perpendicular to the plane of FIGS. 47-49, or any plane therebetween). In particular, because the magnetic element 2112 of the second ablation component 2104 is freely rotatable in any direction, the magnetic element 2112 is configured to self-align into a magnetically attractive orientation with the cooperating magnetic element 2110 of the first ablation component 2102, regardless of the second ablation component's 2104 approach angle. Further, because the generally bulbous exterior surface of the housing 2104B comprising the ablation element (e.g., electrode) 2108 is configured to suitably contact the target tissue across a wide range of approach angles, ablation of the target tissue 2118 can be effectively performed regardless of approach angle. Additionally, in some embodiments comprising a tether configuration for the second ablation component 2104, the ability of the end effector 2104A of the second ablation component 2104 to move generally independently of other portions of the second ablation component 2104 may provide additional freedom of movement to facilitate magnetic attraction and cooperation between the first ablation component 2102 and the second ablation component 2014.

FIGS. 51-59 are various views illustrating an example ablation procedure using the first ablation component 2102 and second ablation component 2104, all according to at least some aspects of the present disclosure. It is to be understood that any operation described herein may be performed alone and/or in connection with any other portion of this or any other procedure. Further, it is to be understood that while this description of methods and operations references specific elements of some exemplary embodiments described elsewhere herein, the various methods and operations likewise pertain to other similar or alternative embodiments according to the present disclosure, regardless of whether such other embodiments are specifically referenced.

Figure 51:
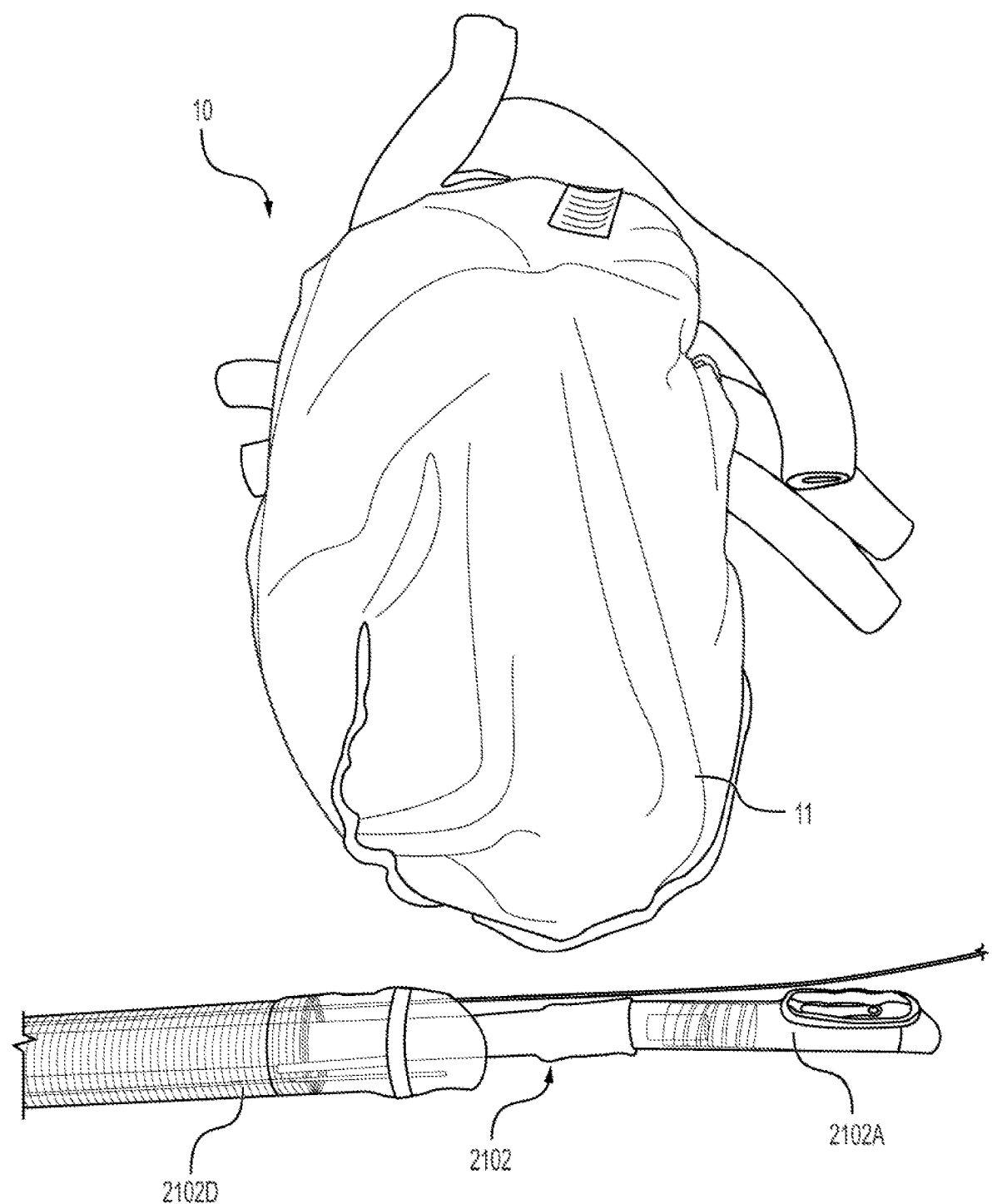
FIG. 51 is a perspective view of a heart illustrating an operation involving approaching the heart with the first ablation component of FIG. 48.
Figure 52:
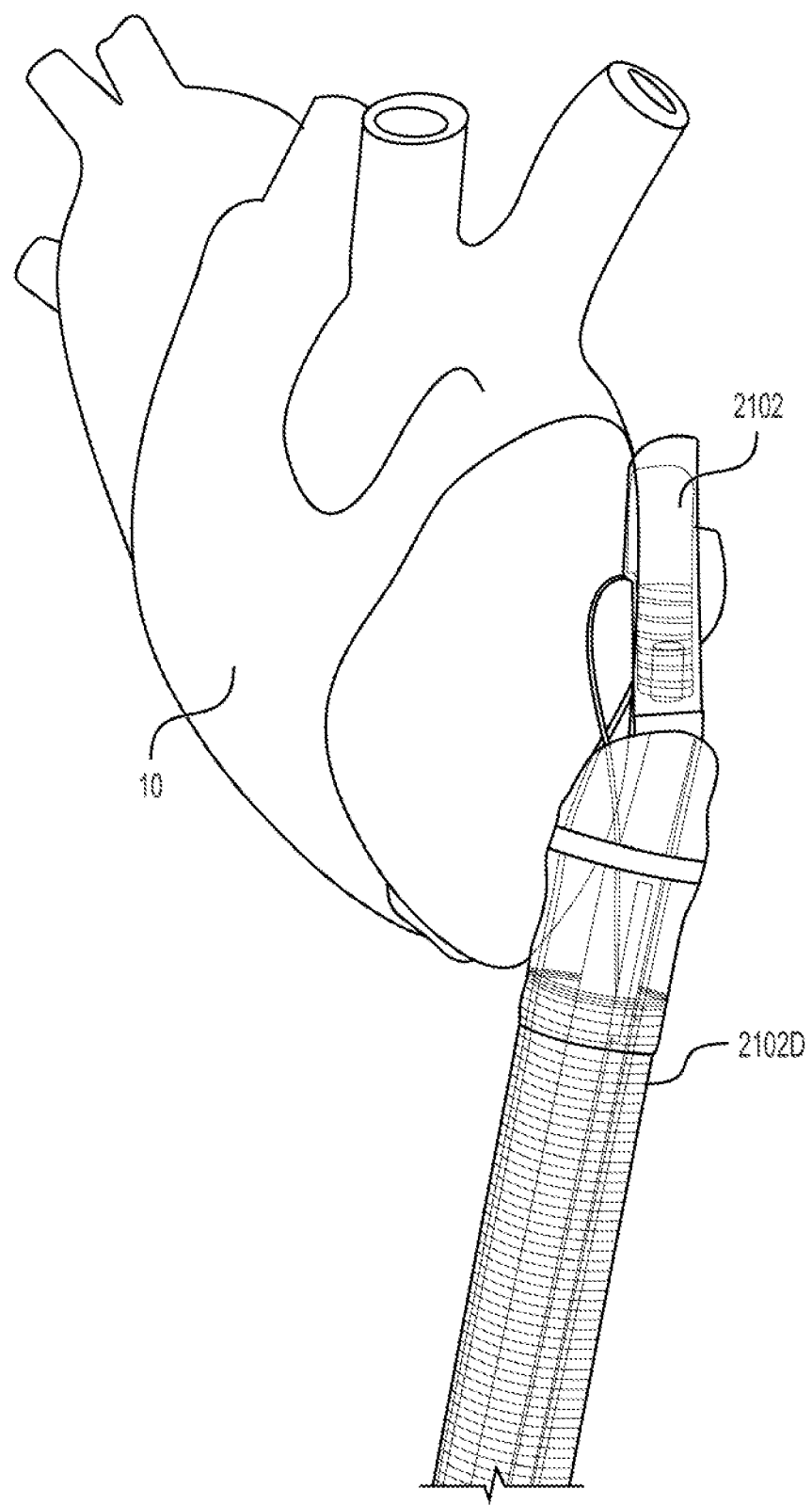
FIG. 52 is a perspective view of the heart illustrating an operation involving positioning the first ablation component of FIG. 48 on the heart.
Figure 53:
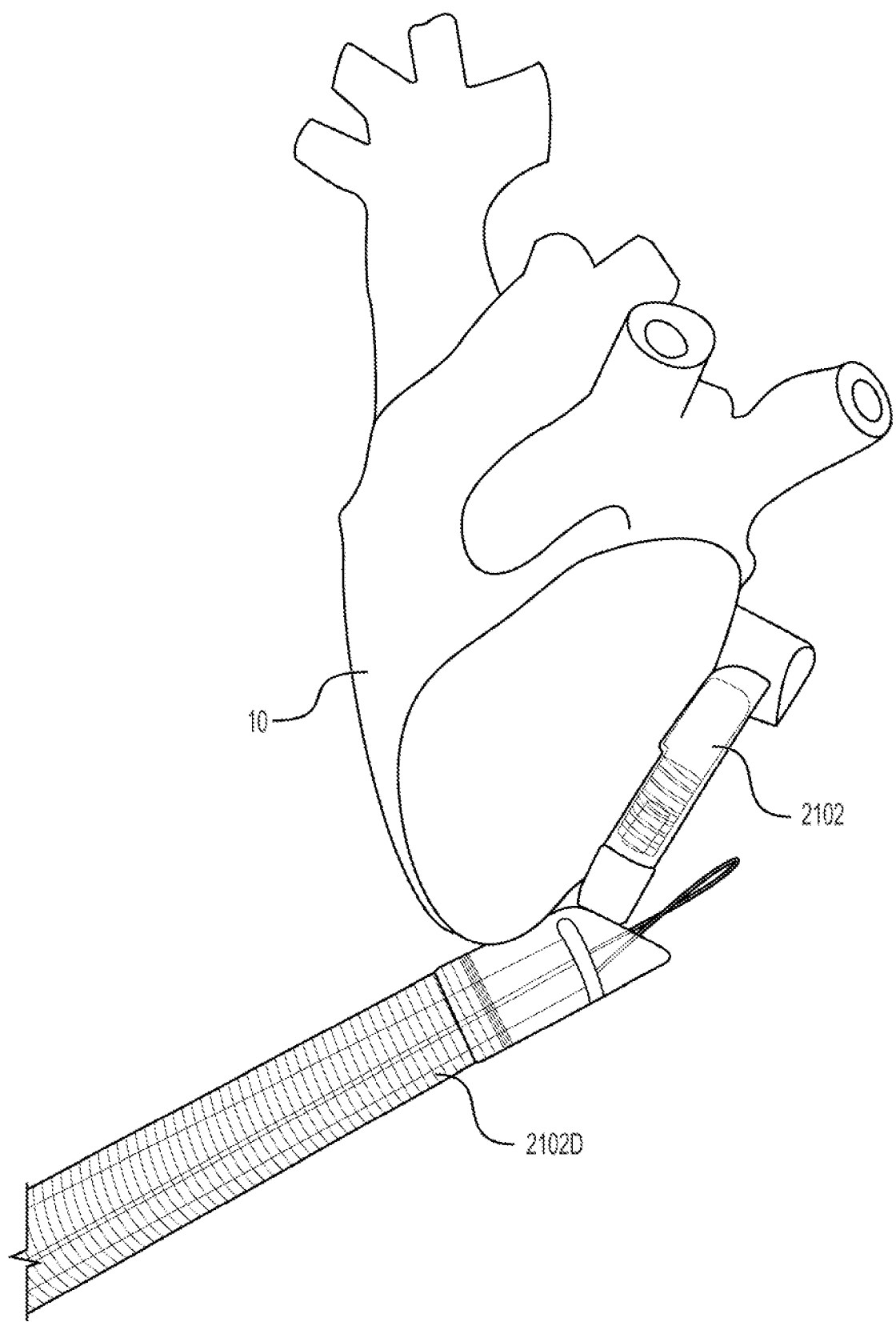
FIG. 53 is a perspective view of the heart illustrating an operation involving positioning the first ablation component of FIG. 48 on the heart.

FIGS. 51-53 are perspective views of a heart 10 illustrating operations involving approaching the heart 10 with the first ablation component 2102 and positioning the first ablation component 2102 on the heart 10, all according to at least some aspects of the present disclosure. Referring to FIG. 51, a heart 10 is disposed within a pericardium 11. The distal end portion, including the end effector 2102A, of the ablation device 2102 is routed proximate the heart 10. For example, suitable open, minimally invasive, or percutaneous access may be obtained. Optionally, a delivery device 2102D may be used to direct the first ablation component 2102.

Referring to FIG. 52, shown without the pericardium, the first ablation component 2102 may be placed proximate the epicardial (exterior) surface 12 of the heart 10, and the first ablation component 2102 may be positioned at a desired ablation location. The delivery device 2102D may be positioned to facilitate positioning of the end effector 2102A proximate the desired ablation site on the heart 10. If desired, the ablation component 2102 may be articulated to facilitate positioning. In the illustrated embodiment, the end effector 2102 may be held generally against the heart 10 by overlying tissues, such as the pericardium 11. Referring to FIG. 53, also shown without the pericardium, vacuum may be applied to the vacuum port of the end effector 2102A to fix the first ablation component 1102 on the on the epicardial surface 12.

Figure 54:
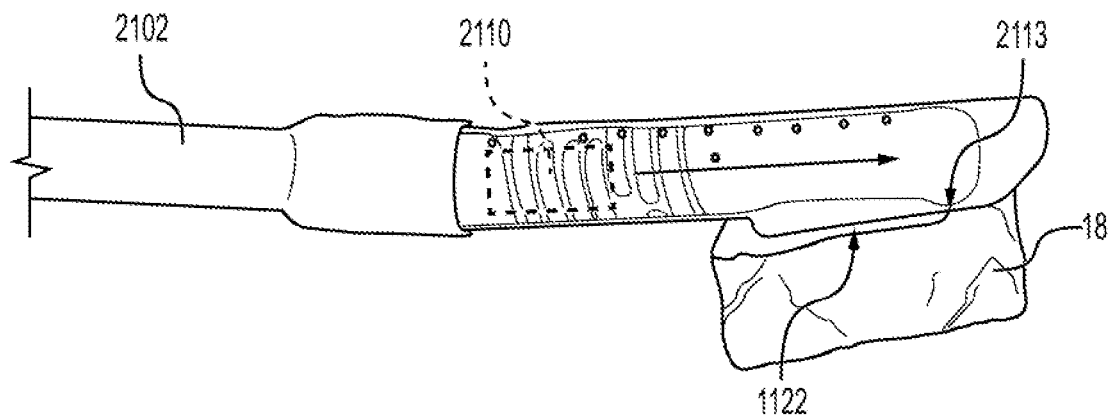
FIG. 54 is a perspective cross section view of an example procedure using the ablation system of FIG. 48 on a heart wall.
Figure 55:
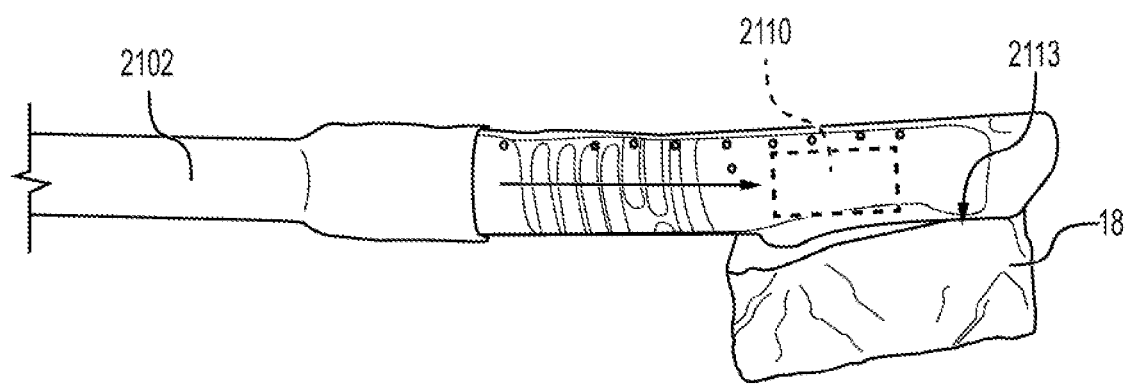
FIG. 55 is a perspective cross section view of an example procedure using the ablation system of FIG. 48 on a heart wall.

FIGS. 54-59 are perspective cross section views of an example procedure using the ablation system 2100 on a heart 10 wall 18, all according to at least some aspects of the present disclosure. Referring to FIGS. 54 and 55, after the first ablation component 2102 is positioned as desired on the heart wall 18, and is optionally vacuum fixed thereon, the first ablation component magnetic element 2110 may be repositioned to an engaged configuration, or may be confirmed to already be in the engaged configuration. In the illustrated embodiment, the first ablation component magnetic element 2110 is moved distally from the proximal disengaged configuration (FIG. 54) to the distal engaged configuration (FIG. 55). In other embodiments, the first ablation component magnetic element 2110 may be in the engaged configuration when the first ablation component is placed proximate the first surface 2113, thus making repositioning the first ablation component permanent magnet 2110 unnecessary.

Figure 56:
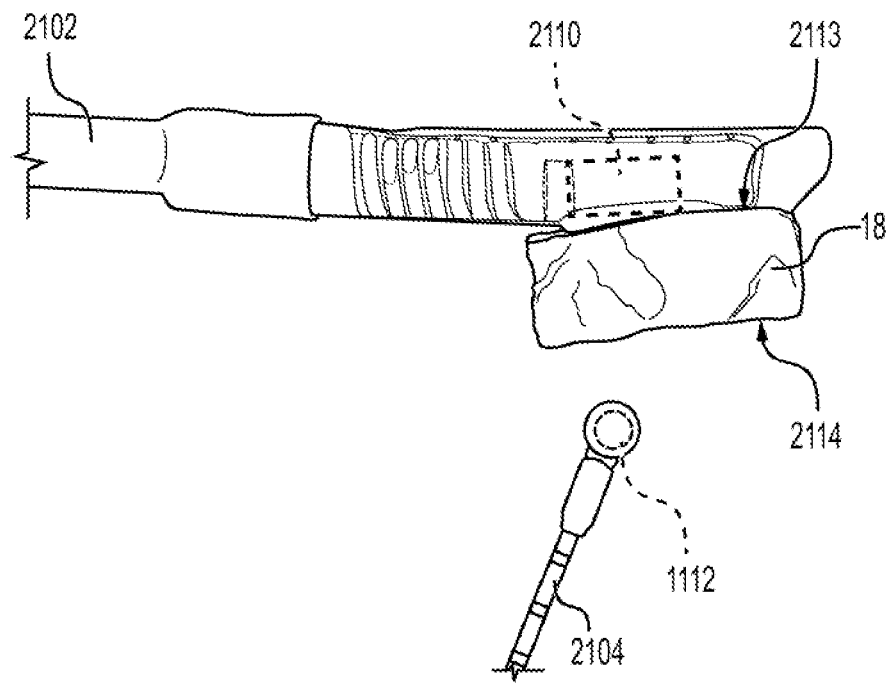
FIG. 56 is a perspective cross section view of an example procedure using the ablation system of FIG. 48 on a heart wall.

Referring to FIG. 56, the second ablation component 2104 is placed proximate the second surface 2114 of the target tissue 18. For example, suitable vascular access or surgical endocardial access (such as purse string access) may be obtained, and the second ablation component 2104 may be placed proximate the endocardium.

Figure 57:
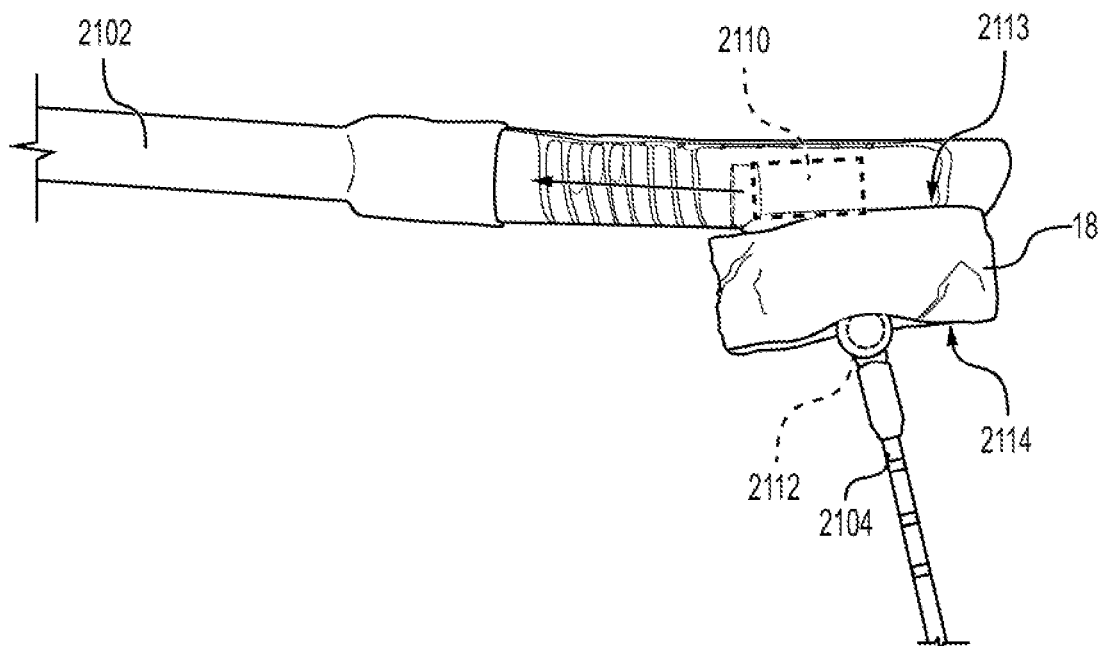
FIG. 57 is a perspective cross section view of an example procedure using the ablation system of FIG. 48 on a heart wall.

Referring to FIG. 57, cooperative magnetic attraction between the first ablation component magnetic element 2110 and the second ablation component magnetic element 2112 is used to facilitate positioning the first ablation component 2102 and/or the second ablation component 2104 at the desired ablation location on the target tissue 18. In some embodiments configured for sensing, stimulating, mapping, and/or pacing, any one or more electrodes (e.g., primary and/or auxiliary) associated with either ablation component 2102, 2104 may be used for sensing, stimulating, mapping, and/or pacing, such as to identify a desired ablation location, to confirm placement of either or both of the ablation components 2102, 2104, and/or (after ablation) to assess an effectiveness of an ablation or a need for further ablations.

In embodiments constructed with a tether configuration, second ablation component 2104 may be reconfigured to a deployed (e.g., extended) configuration. The magnetic attraction between the first ablation component magnetic element 2110 and the second ablation component magnetic element 2112 compresses the target tissue 18. Bipolar radiofrequency ablation energy is delivered to the electrodes of the first ablation component 2102 and the second ablation component 2104 to create a first lesion in the target tissue 18.

Figure 58:
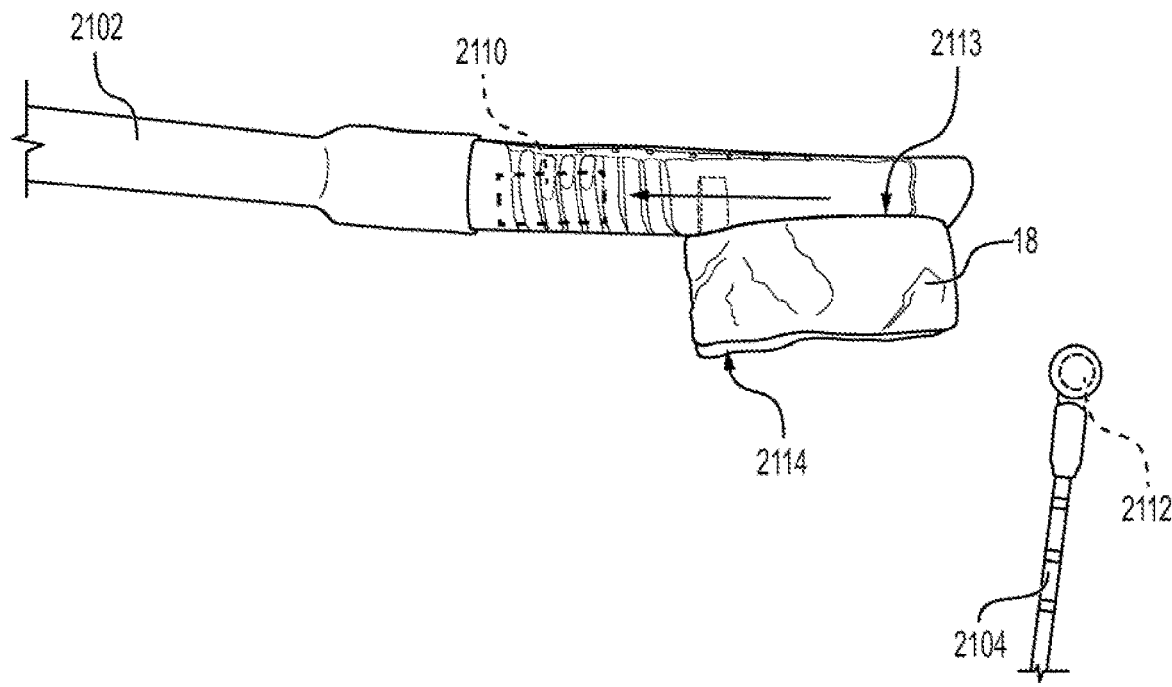
FIG. 58 is a perspective cross section view of an example procedure using the ablation system of FIG. 48 on a heart wall.

Referring to FIG. 58, the first ablation component magnetic element 2110 is moved proximally from the distal engaged configuration (FIG. 57) to the proximal disengaged configuration (FIG. 58). This reduces the attractive magnetic coupling between the first ablation component magnetic element 2110 and the second ablation component magnetic element 2112, and the second ablation component 2104 is moved away from ablation site on the target tissue 18. In the illustrated embodiment, this operation was performed with the second ablation component 2104 remaining in the deployed configuration. In other circumstances, the second ablation component 2104 may be reconfigured to the retracted configuration before the first ablation component 2102 is reconfigured to the disengaged configuration.

Figure 59:
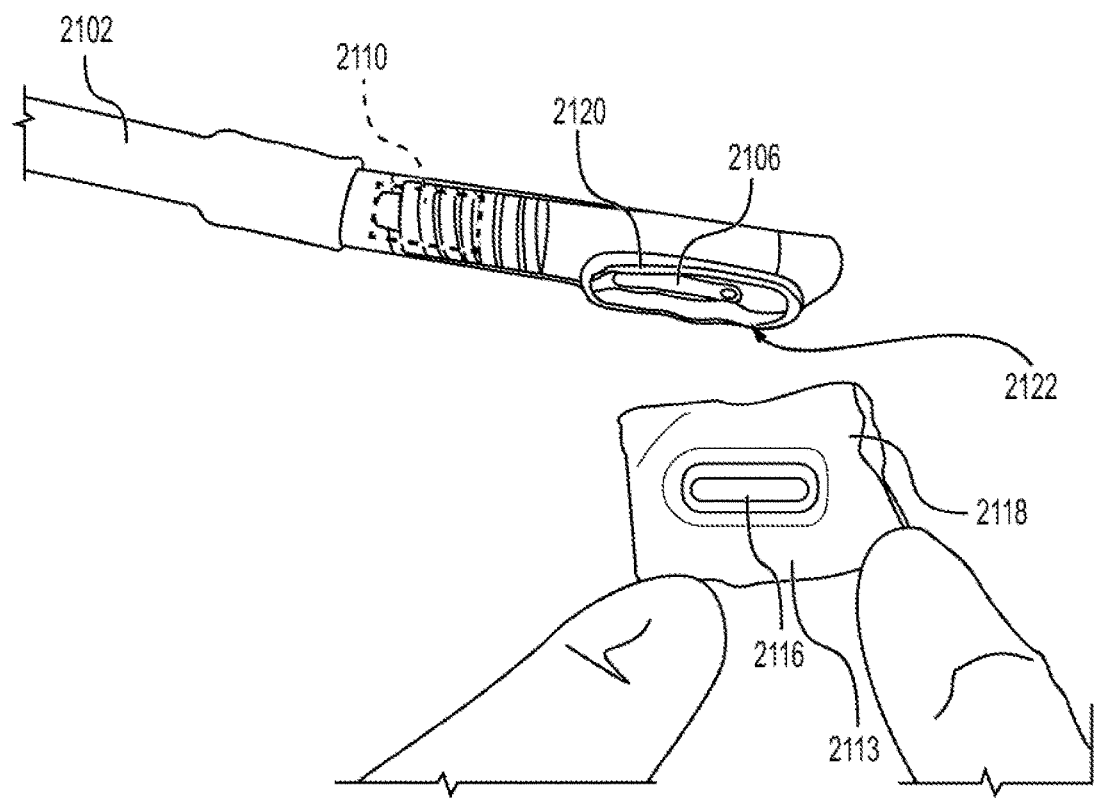
FIG. 59 is a perspective cross section view of an example procedure using the ablation system of FIG. 48 on a heart wall.

Referring to FIG. 59, the vacuum applied to the vacuum port 2122 of the first ablation component 2102 is discontinued, and the first ablation component 2102 is removed from the first surface of the target tissue 18. In some circumstances, the vacuum applied to the vacuum port 2122 of the first ablation component 2102 may be discontinued before the first ablation component magnetic element 2110 is moved to the disengaged configuration. In other circumstances, the vacuum applied to the vacuum port 2122 of the first ablation component 2102 may be discontinued after the first ablation component permanent magnet 2110 is moved to the disengaged configuration. In FIG. 59, the first ablation component ablation element 2106 and the corresponding lesion 16 on the first side 2113 of the target tissue 18 are visible.

Various operations may be repeated as desired to create additional lesions. The ablation components 2102, 2104 may be withdrawn from the operative site upon completion of the desired ablations.

Figure 60:
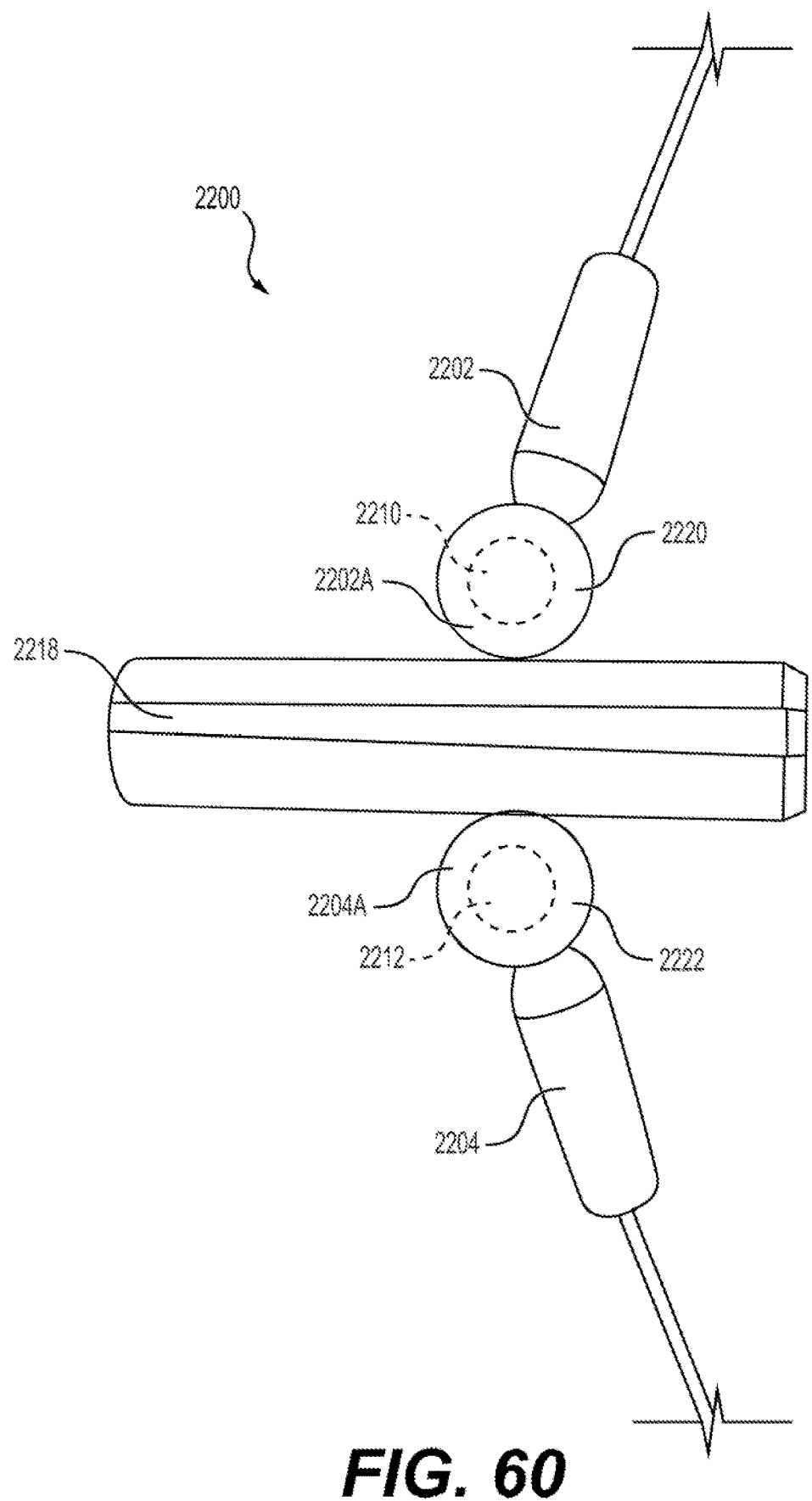
FIG. 60 is a perspective view of a distal end portion of an alternative ablation system in use on a target tissue.

FIG. 60 is a perspective view of a distal end portion of an alternative ablation system 2200 in use on a target tissue 2218, according to at least some aspects of the present disclosure. Generally, the ablation system 2200 and ablation components 2202, 2204 may be similar in structure and operation to other ablation systems and ablation components described herein, such as ablation systems 100, 2100, and any suitable ablation components described herein may be used as the ablation components 2202, 2204. For example, the first and second ablation components 2202, 2204 may comprise the ablation component 1100 (FIG. 21) or a related embodiment. Repeated description is omitted for brevity. Likewise, any feature or operation described in connection with the ablation system 2200 or ablation components 2202, 2204 may be utilized in connection with any other embodiment described elsewhere herein.

In the illustrated embodiment, each of the first ablation component 2202 and the second ablation component 2204 includes a respective freely rotatable (about three axes of rotation) magnetic element (e.g., permanent magnet) 2210, 2212. In this embodiment, each of the first ablation component magnetic element 2210 and the second ablation component magnetic element 2212 is configured to self-orient into a magnetically attractive orientation with the cooperating magnetic element 2210, 2212 of the cooperating ablation component 2202, 2204, regardless of target tissue approach angle. Further, because the generally bulbous exterior surface of each end effector housing 2202A, 2204A comprising the respective ablation element (e.g., electrode) 2220, 2222 is configured to suitably contact the target tissue 2218 across a wide range of approach angles, ablation of the target tissue 2218 can be effectively performed regardless of approach angle on both sides of the target tissue 2218.

The embodiment of FIG. 60 may be used, for example, in conducting ablation on an atrial or ventricular septum, for example. Such a procedure may be generally similar to the ablation procedure described above, except endocardial access may be obtained to each side of the target tissue 2218 (e.g., septum), and a respective ablation component 2202, 2204 may be routed to each side of the target tissue 2218. Additionally, rather than having one cooperating magnetic element with a fixed orientation and one freely rotatable magnetic element, the embodiment of FIG. 60 may utilize two ablation components 2202, 2204, each comprising a respective freely rotatable (self-orienting) magnetic element 2210, 2212. Ablation energy, such as bipolar and/or monopolar radiofrequency ablation energy may be applied to the target tissue using the first and second ablation components 2202, 2204. In a particular example, the target tissue may include a ventricular septum. The first side of the target tissue may include a right ventricular surface of the ventricular septum and the second side of the target tissue may include a left ventricular surface of the ventricular septum. The ablation energy may be applied to create a transmural lesion in the ventricular septum.

Figure 61:
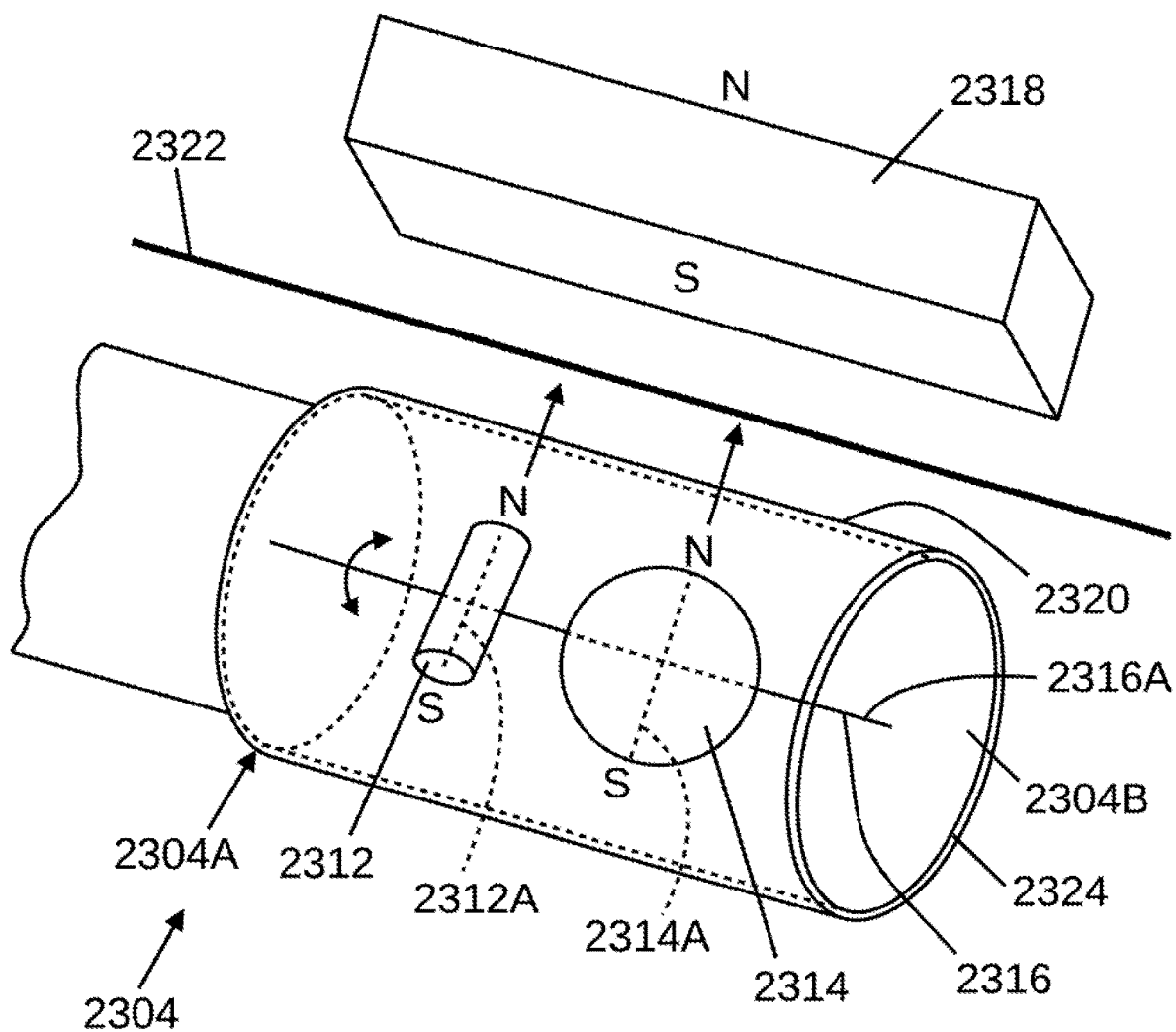
FIG. 61 is a simplified cross section view of an alternative example ablation component.

FIG. 61 is a simplified cross section view of an alternative example ablation component 2304 according to at least some aspects of the present disclosure. The ablation component 2304 is generally similar in structure and operation to ablation components described elsewhere herein, and repeated description of similar elements is omitted for brevity. Likewise, any feature described in connection with ablation component 2304 may be utilized in connection with any other embodiment described elsewhere herein. In some embodiments, the ablation component 2304 may be substituted for the second ablation component 104, as well as other ablation components described herein. In the ablation component 2304, one or more magnetic elements 2312, 2314 are rotatably mounted for rotation about an axis of rotation 2316, which may be defined by an axle 2316A. Accordingly, the magnetic elements 2312, 2314 have one rotational degree of freedom relative to the housing 2304B.

In the illustrated embodiment, the axis 2316 is oriented generally parallel with a longitudinal axis of the end effector 2304A of the ablation component 2304. The respective magnetic axes 2312A, 2314A of the individual magnetic elements 2312, 2314 are oriented generally perpendicular to the axis of rotation 2316. When used in connection with one or more cooperating magnetic elements 2318 (e.g., of a cooperating ablation component), the magnetic elements 2312, 2314 may cause a lateral surface 2320 of the end effector 2304A to engage the target tissue 2322. In the illustrated embodiment, which may have a generally longitudinally oriented, generally cylindrical end effector 2304A, the ablation element 2324 (e.g., an electrode) may extend over substantially the entire (e.g., about 360 degree) outer radius of the end effector 2304A.

In this embodiment, the ablation component 2304 is configured to approach the target tissue 2322 from a wide range of approach angles relative to the axis of rotation 2316 of the magnetic elements 2312, 2314. In particular, because the magnetic elements 2312, 2314 are freely rotatable about the axis of rotation 2316, the magnetic elements 2312, 2314 are configured to self-align into a magnetically attractive orientation with the cooperating magnetic element 2318 of the cooperating ablation component, regardless of approach angle relative to the axis of rotation 2316. Further, because the generally right circular cylindrical exterior surface 2320 of the housing 2304B comprising the ablation element (e.g., electrode) 2324 is configured to suitably contact the target tissue across a wide range of approach angles relative to the axis of rotation 2316, ablation of the target tissue 2322 can be effectively performed regardless of approach angle relative to the axis of rotation 2316.

Figure 62:
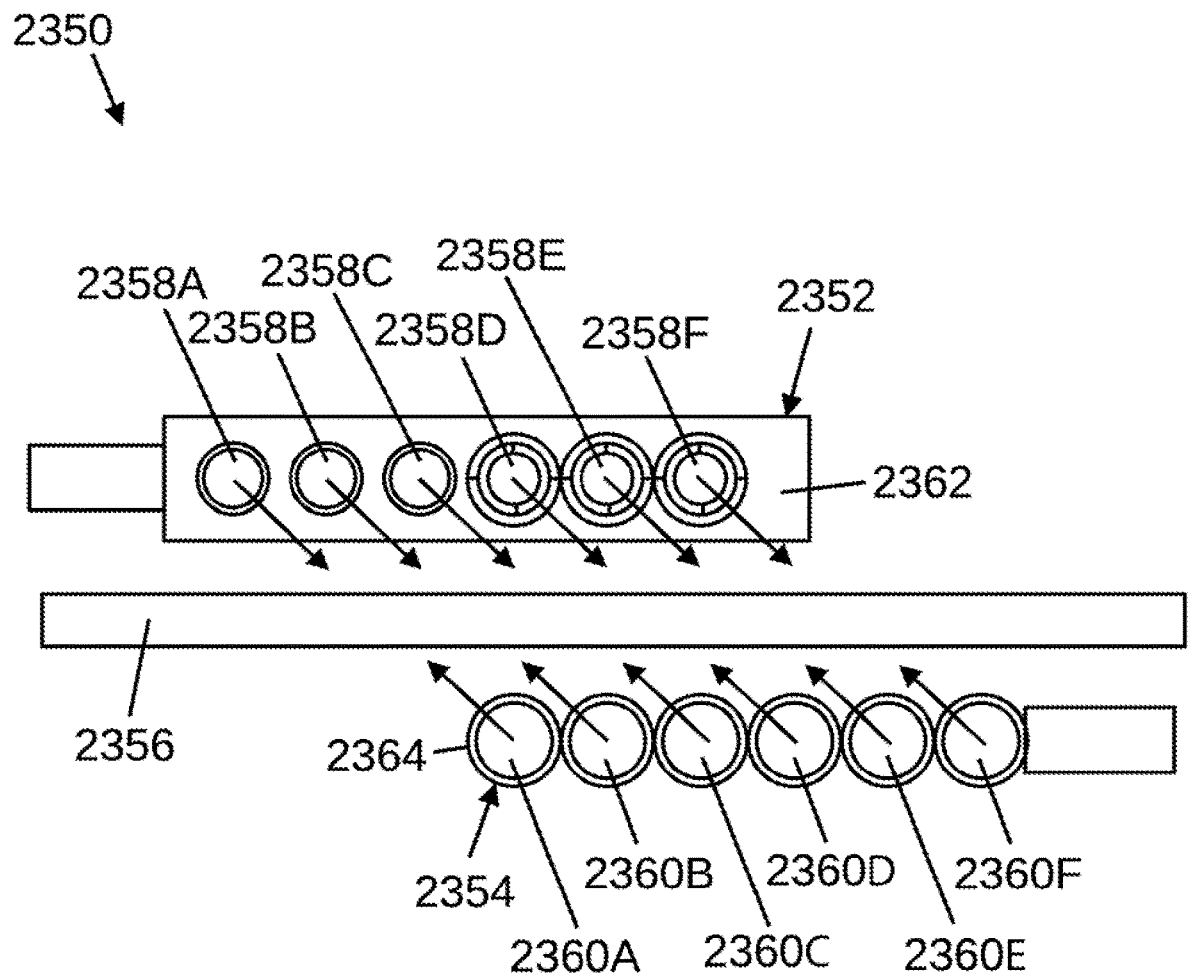
FIG. 62 is a simplified cross section view of an alternative ablation system.

FIG. 62 is a simplified cross section view of an alternative ablation system 2350, according to at least some aspects of the present disclosure. The ablation system 2350 is generally similar in structure and operation to ablation systems described elsewhere herein, and repeated description of similar elements is omitted for brevity. Likewise, any feature described in connection with ablation system 2350 may be utilized in connection with any other embodiment described elsewhere herein. In the illustrated embodiment, the ablation system 2350 includes a first ablation component 2352 and a second ablation component 2354 on opposite sides of a target tissue 2356.

In the illustrated embodiment, the first ablation component 2352 includes a plurality of magnetic elements 2358A, 2358B, 2358C, 2358D, 2358E, 2358F, and the second ablation component 2354 includes a respective plurality of cooperating magnetic elements 2360A, 2360B, 2360C, 2360D, 2360E, 2360F. In the illustrated embodiment, magnetic elements 2358A-C and 2360A-F are freely rotatable spherical magnetic elements generally similar to those described elsewhere herein. The magnetic elements 2358D-F are gimbal-mounted permanent magnets. In this embodiment, each magnetic element 2358D-F is rotatably mounted using two gimbals, thus having two rotational degrees of freedom. It will be appreciated that either configuration may be utilized throughout either ablation component 2352, 2354, or both ablation components 2352, 2354 may include a both configurations (or other suitable configurations).

In the illustrated embodiment, the magnetic elements 2358A-C are disposed within a contiguous, smooth end effector housing 2362 of the first ablation component 2352. In contrast, the second ablation component 2354 includes an end effector 2364 in which individual housings of the magnetic elements 2360A-F are exposed.

In this embodiment, the magnetic elements 2358A-C and 2360A-F are configured for mutual attraction across the target tissue 2356. In some embodiments, because of the in-line arrangement of the magnetic elements 2358A-C and 2360A-F, the ablation components 2352, 2354 may be configured to self-align in a generally parallel manner on opposite sides of the target tissue 2356.

Figure 63:
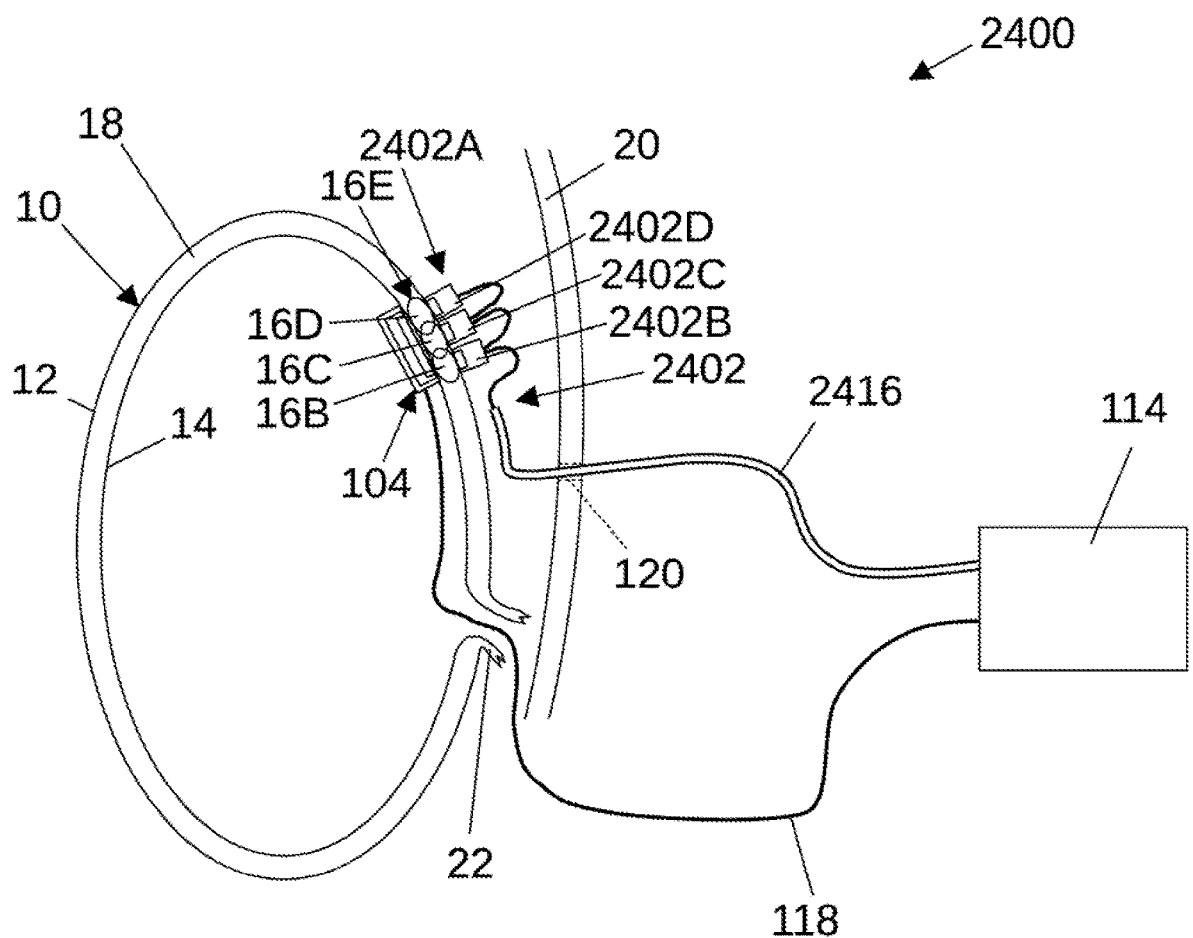
FIG. 63 is a simplified schematic view of an alternative example ablation system including a first ablation component including a plurality of independently positionable end effector units in use on a heart.

FIG. 63 is a simplified schematic view of an alternative example ablation system 2400 including a first ablation component 2402 including a plurality of independently positionable end effector units 2402B, 2402C, 2402D in use on a heart 10, according to at least some aspects of the present disclosure. As used herein, "independently positionable" may refer to two or more individual units that can be positioned and/or oriented substantially independently of one another and includes, for example, units that may be tethered or otherwise connected to one another by flexible members, provided that such tethers or connections permit at least some substantially independent positioning and/or orientating of the individual units. In the illustrated embodiment, the first ablation component 2402 of the ablation system 2400 is configured to be positioned on the first side 12 of the target tissue 18, such as the epicardial surface 12 of the heart wall 18. In the illustrated embodiment, the first ablation component 2402 includes an end effector 2402A, which includes the plurality of independently positionable end effector units 2402B, 2402C, 2402D. The ablation system 2400 includes a second ablation component 104 configured to be positioned on a second side 14 of the target tissue 18, such as the endocardial surface 14 of the heart wall 18. The second ablation component 104 and the end effector units 2402B, 2402C, 2402D of first ablation component 2402 may be configured to cooperate to create one or more lesions 16B, 16C, 16D in the target tissue, such as transmural lesions extending through the full thickness of the heart wall 18. In some embodiments, the end effector units 2402B, 2402C, 2402D may be positioned to cooperate with the second ablation component 104 so that the lesions 16B, 16C, 16D are at least partially overlapping so as to form a contiguous, larger, composite lesion 16E. Generally, the ablation system 2400 and ablation components 2402, 104 may be similar in structure and operation to other ablation systems and ablation components described herein, and repeated description is omitted for brevity. Likewise, any feature described in connection with ablation system 2400 may be utilized in connection with any other embodiment described elsewhere herein.

It will be understood that although a generic second ablation component 104 is illustrated in FIG. 63, an ablation component 2402 including a plurality of independently positionable end effector units 2402B, 2402C, 2401D may be utilized in connection with any cooperating ablation component, such as may be described elsewhere herein. For example, an ablation component 2402 may be used cooperatively with an ablation component including a translationally and/or rotationally repositionable magnetic element, such as described elsewhere herein.

Further, although the first ablation component 24102 including the end effector 2402A including the independently positionable end effector units 2402B, 2402C, 2402D is shown in FIG. 63 on the epicardial surface 12 of the heart 10, a similar ablation component including a plurality of independently positionable end effector units may be utilized on the endocardial surface 14 of the heart 10 and may operate cooperatively with any ablation component described herein on the opposite, epicardial surface 12 of the heart. Further, in some embodiments, one or more ablation components comprising independently positionable end effector units may be utilized for endocardial-endocardial ablation (e.g., of a septum), wherein one or both of the ablation components includes the independently positionable end effector units. In some example embodiments, first and second ablation components, each on a opposite side of the target tissue, may each include a plurality of independently positionable end effector units, similar to the first ablation component 2402 of FIG. 63.

Figure 64:
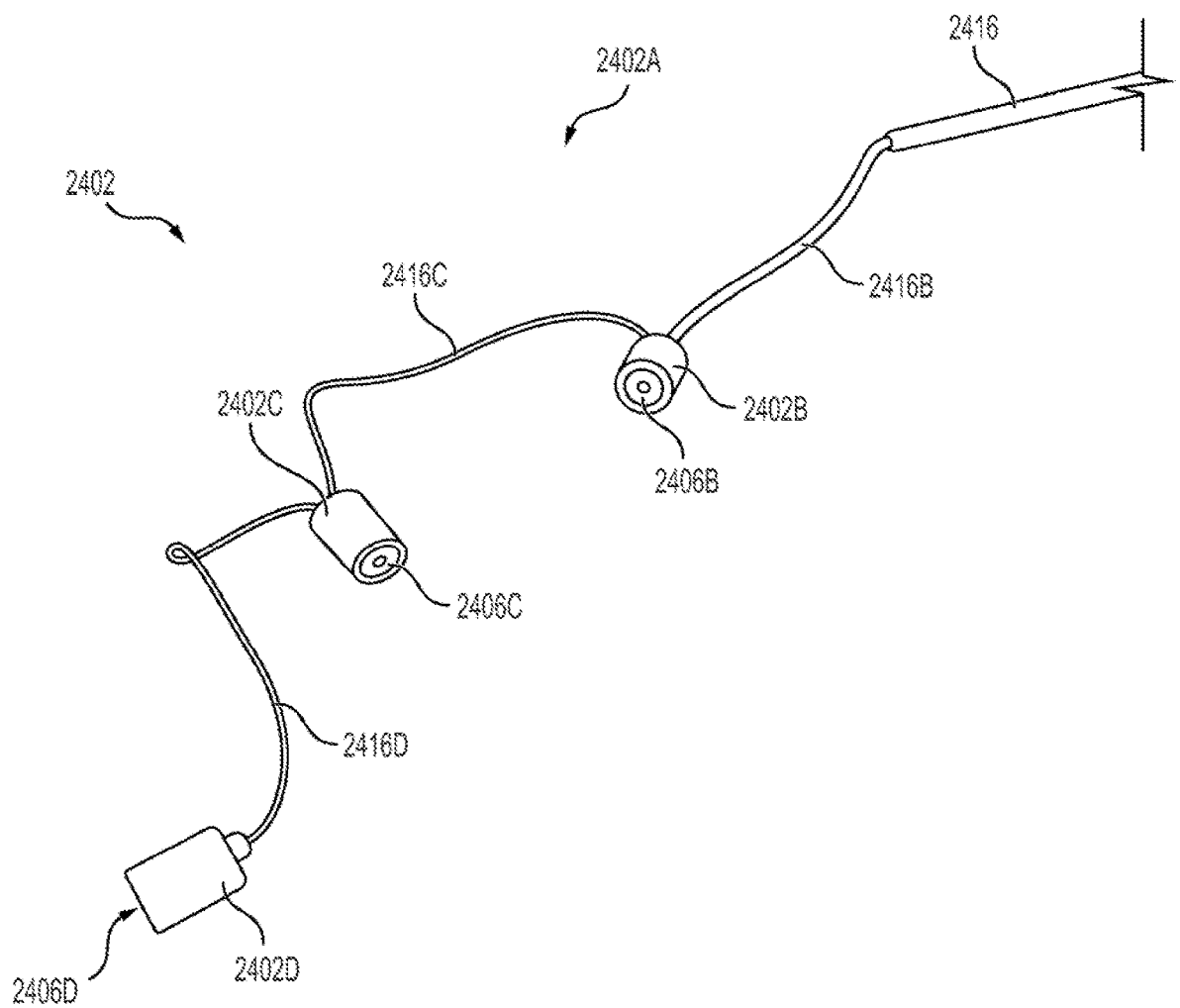
FIG. 64 is a perspective view of the end effector of the first ablation component of FIG. 63 in a deployed configuration.
Figure 65:
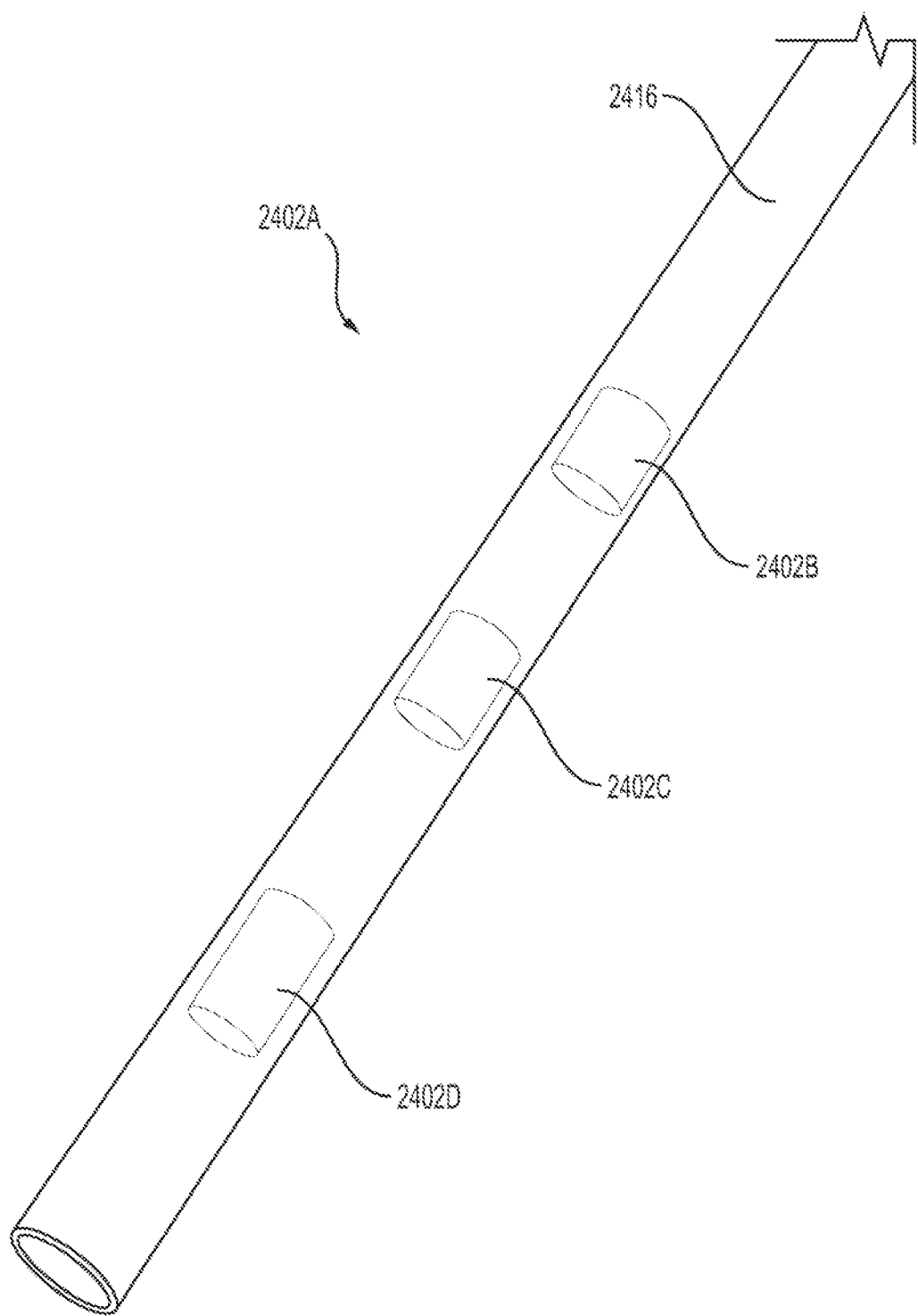
FIG. 65 is a perspective view of the end effector of the first ablation component of FIG. 63 in a stowed configuration.
Figure 66:
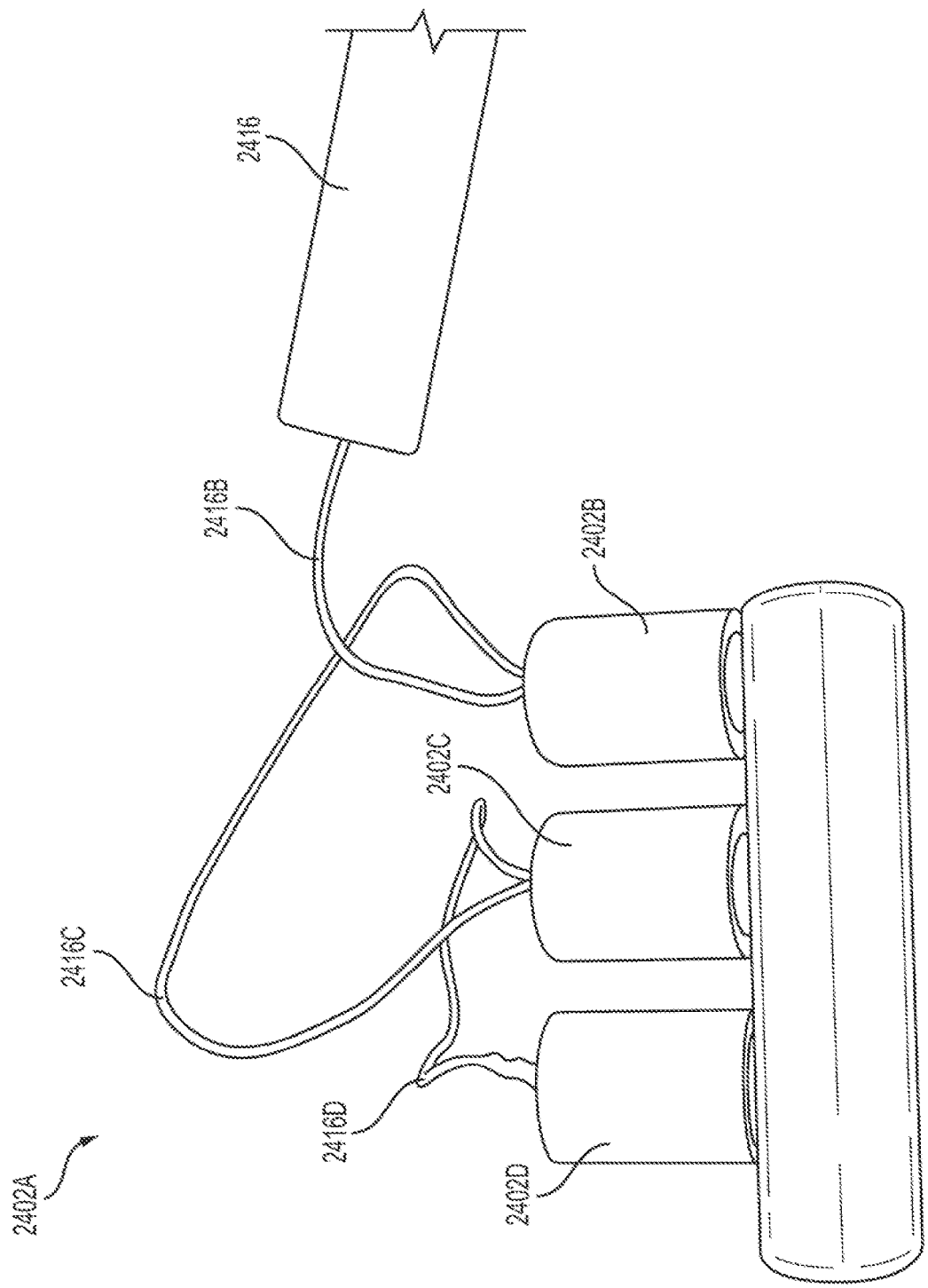
FIG. 66 is a perspective view of the end effector of the first ablation component of FIG. 63 illustrating the independently positionable end effector units in use with a cooperating magnetic element.

FIG. 64 is a perspective view of the end effector 2402A of the first ablation component 2402 of FIG. 63 in a deployed configuration, FIG. 65 is a perspective view of the end effector 2402A of the first ablation component 2402 of FIG. 63 in a stowed configuration, and FIG. 66 is a perspective view of the end effector 2402A of the first ablation component 2402 of FIG. 63 illustrating the independently positionable end effector units 2402B, 2402C, 2402D in use with a cooperating magnetic element, all according to at least some aspects of the present disclosure. Referring to FIGS. 63-66, in the illustrated embodiment, the first ablation component 2402 includes a connecting element 2416, which operatively couples the end effector 2402A to the control unit 114. The connecting element 2416 may include or be used in connection with one or more electrical conductors, fluidic conduits, mechanical force transmission components (e.g., mechanical linkages), catheters, wires, steerable portions, sheaths, trocars, hemostatic components, etc. In the illustrated embodiment, the connecting element 2416 is generally tubular and at least partially defines an interior lumen configured to selectively receive the end effector units 2402B, 2402C, 2402D.

Although FIGS. 63-66 illustrate an example embodiment including three independently positionable end effector units 2402B, 2402C, 2402D, various alternative example embodiments may include two or more (e.g., two, three, four, five, etc.) independently positionable end effector units. Further, although FIGS. 62-65 illustrate an example embodiment in which the independently positionable end effector units 2402B, 2402C, 2402D are substantially identical, various alternative example embodiments may include one or more independently positionable end effector units that differ in at least one respect from one or more other independently positionable end effector units.

Referring to FIGS. 64 and 66, the first ablation component 2402 may include end effector unit connecting elements 2416B, 2416C, 2416D operatively coupled to the end effector units 2402B, 2402C, 2402D. In the embodiment illustrated in FIGS. 63-66, a first end effector unit connecting element 2416B extends between the connecting element 2416 and a first end effector unit 2402B. A second end effector unit connecting element 2416C extends between the first end effector unit 2402B and a second end effector unit 2402C. A third end effector unit connecting element 2416C extends between the second end effector unit 2401C and a third end effector unit 2402D. Accordingly, the end effector unit connecting elements 2416B, 2416C, 2416D operatively couple the independently positionable end effector units 2402B, 2402C, 2402D in a daisy chain (e.g., sequential, one after the other) arrangement. Each end effector unit connecting element 2416B, 2416C, 2416D may include one or more electrical conductors, fluidic conduits, mechanical force transmission components (e.g., mechanical linkages), catheters, wires, steerable portions, sheaths, trocars, hemostatic components, etc.

Referring to FIGS. 63 and 64, in the illustrated embodiment, each end effector unit 2402B, 2402C, 2402D includes a respective ablation element, such as a respective electrode 2406B, 2406C, 2406D. In this embodiment, the electrodes 2406B, 2406C, 2406D may include axially magnetized, generally cylindrical permanent magnets positioned so that an axial end face at least partially defines a tissue-contacting surface. Accordingly, in this embodiment, the electrodes also comprise respective magnetic elements, similar to those described elsewhere herein. In some alternative embodiments, the electrodes 2406B, 2406C, 2406D may be provided separately from the magnetic elements, similar to those described elsewhere herein. In still further embodiments, other types of ablation elements may be utilized, such as ablation elements associated with alternative ablation modalities as may be discussed elsewhere herein.

Figure 67:
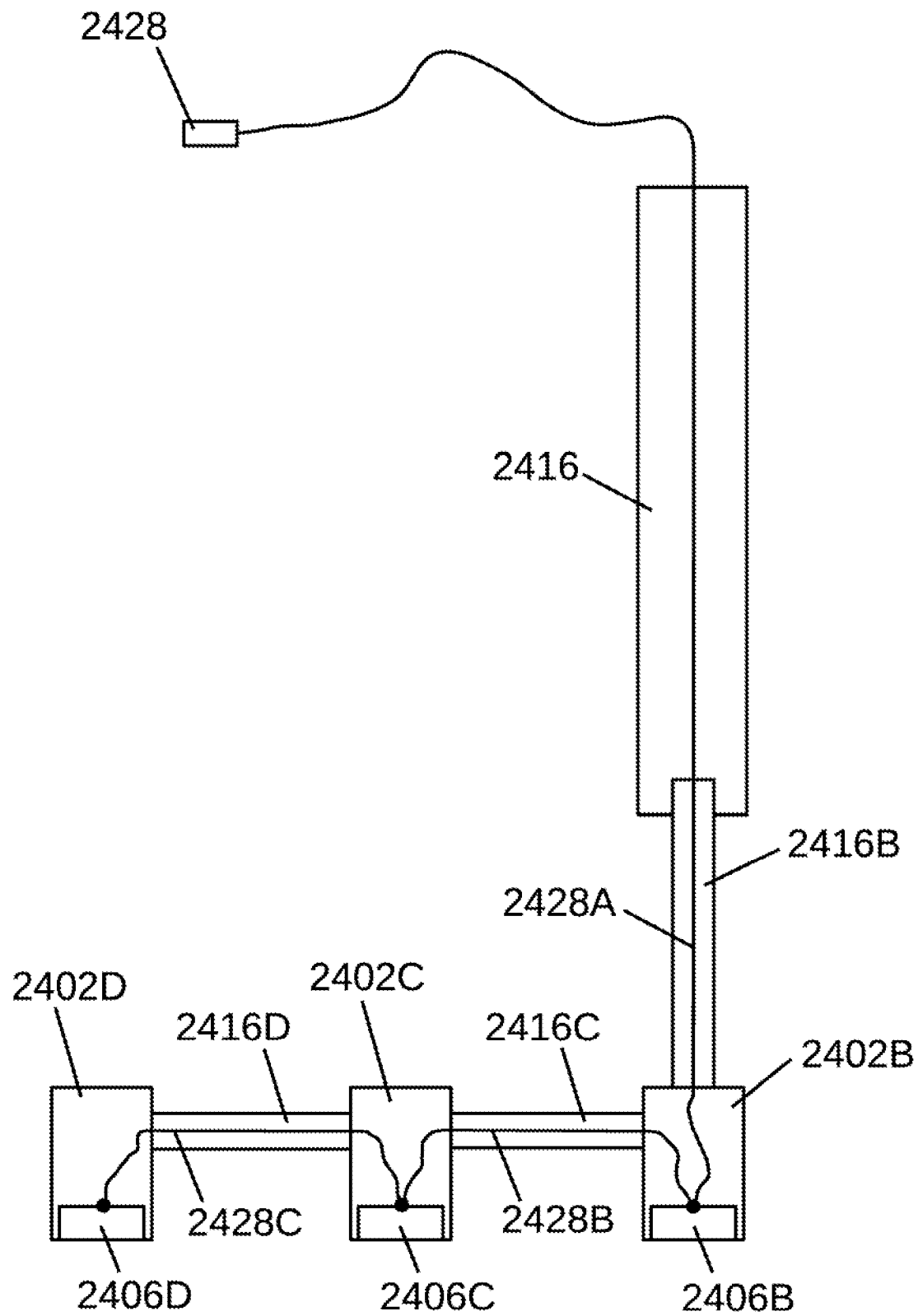
FIG. 67 is a simplified schematic diagram illustrating an example electrical configuration of the ablation component of FIG. 63.

FIG. 67 is a simplified schematic diagram illustrating an example electrical configuration of the ablation component 2402 of FIGS. 62-65, according to at least some aspects of the present disclosure. In the illustrated embodiment, the electrodes 2406B, 2406C, 2406D of the end effector units 2402B, 2402C, 2402D are electrically connected in a parallel configuration. That is, all three of the electrodes 2406B, 2406C, 2406D are simultaneously electrically connected to the proximally positioned electrical connector 2428, which is configured to electrically couple the ablation component 2400 to an electrosurgical generator 114 (FIG. 31) and/or an electrophysiological sensing, stimulating, mapping, and/or pacing unit. For example, one or more electrical conductors 2428A may electrically couple the electrical connector 2428 and the electrode 2406B of the first end effector unit 2402B, such as by extending generally longitudinally through the connecting element 2416 and/or the first end effector unit connecting element 2416B. An electrical conductor 2428B may electrically couple the electrode 2406B of the first end effector unit 2402B and the electrode 2406C of the second end effector unit 2402C, such as by extending through and/or forming at least a portion of the second end effector unit connecting element 2416C. An electrical conductor 2428C may electrically couple the electrode 2406C of the second end effector unit 2402C and the electrode 2406D of the third end effector unit 2402D, such as by extending through and/or forming at least a portion of the third end effector unit connecting element 2416D.

Referring to FIGS. 64 and 65, some example embodiments may be reconfigurable between a stowed configuration (FIG. 65) and a deployed configuration (FIG. 64). For example, the stowed configuration may be utilized while the first ablation component 2402 is routed to the target tissue 18 and/or when removing the first ablation component 2402 from the operative site. The deployed configuration may be utilized to facilitate positioning of individual end effector units 2402B, 2402C, 2402D and/or ablation of the target tissue 18.

Referring to FIG. 65, in the illustrated embodiment, in the stowed configuration, the end effector units 2402B, 2402C, 2402D are received substantially within the first ablation component connecting element 2416. For example, the end effector units 2402B, 2402C, 2402D may be received within the interior lumen of the connecting element 2416. In the stowed configuration, the end effector unit connecting elements 2416B, 2416C, 2416D are also received substantially within the connecting element 2416.

Referring to FIG. 64, in the illustrated embodiment, in the deployed configuration, the end effector units 2402B, 2402C, 2402D may be disposed substantially outside of the connecting element 2416. In the deployed configuration, the first end effector unit connecting element 2416B may extend at least partially within the connecting element 2416 and/or may extend at least partially outside the connecting element 2416 (e.g., to the first end effector unit 2402B). In the deployed configuration, the second end effector unit connecting element 2416C and/or the third end effector unit connecting element 2416D may be disposed substantially outside of the connecting element 2416.

Referring to FIGS. 63-67, some example methods of using the ablation system 2400 may include one or more of the following operations, in any order. An example method of creating a lesion 16 in a target tissue 18 may include placing a second ablation component 104 proximate a second surface 14 of a target tissue 18. The second ablation component 104 may include a second ablation component magnetic element 112 (FIG. 1), which may act as a cooperating magnetic element. The method may include placing a first ablation component 2402 proximate a first surface 12 of the target tissue 18. The first ablation component 2402 may include a first ablation component connecting element 2416 and a first ablation component end effector 2402A extending distally from the first ablation component connecting element 2416. The first ablation component end effector 2402A may include a first end effector unit 2402B and a second end effector unit 2402C. Some embodiments may include a third end effector unit 2402D and/or further end effector units. The end effector units 2402B, 2402C, 2402D may be independently positionable and/or may be coupled in a daisy chain arrangement, such as by one or more end effector unit connecting elements 2416B, 2416C, 2416D. The first end effector unit 2402B may include a first end effector unit magnetic element 2406B and/or a first end effector unit ablation element 2406B. The second end effector unit 2402C may include a second end effector unit magnetic element 2406C and/or a second end effector unit ablation element 2406C. The third end effector unit 2402D and further end effector units may be similarly constructed. The method may include attractively magnetically coupling the first end effector unit magnetic element 2406B with the second ablation component magnetic element 112 and/or attractively magnetically coupling the second end effector unit magnetic element 2406C with the second ablation component magnetic element 112. Similarly, the third end effector unit magnetic element 2406D may be attractively magnetically coupled with the second ablation component magnetic element 112. The attractive magnetic coupling may facilitate positioning of the ablation components 2402, 104 and/or compression of the target tissue 18 as described elsewhere herein. The method may include creating a first lesion 16B in the target tissue using the first end effector unit ablation element 2406B and/or creating a second lesion 16C in the target tissue 18 using the second end effector unit ablation element 2406C. Similarly, a third lesion 16C may be created using the third end effector unit ablation element 2406D.

In some embodiments, the first lesion 16B and the second lesion 16C (and/or the third lesion 16D and further lesions) may overlap and form a contiguous composite lesion 16. In some embodiments, creating the first lesion 16B and creating the second lesion 16C (and/or the third lesion 16D and further lesions) may be performed simultaneously. In some embodiments, the second ablation component 104 may include a second ablation component ablation element 108 (FIG. 1). Creating the first lesion 16B in the target tissue 18 using the first end effector unit ablation element 2406B may include creating the first lesion 16B in the target tissue 18 by applying bipolar radiofrequency ablation energy to the target tissue 18 using the first end effector unit ablation element 2406B and the second ablation component ablation element 108. Creating the second lesion 16C in the target tissue 18 using the second end effector unit ablation element 2106C may include creating the second lesion 16C in the target tissue 18 by applying bipolar radiofrequency ablation energy to the target tissue 18 using the second end effector unit ablation element 2406C and the second ablation component ablation element 108. Further lesions may be created similarly with further end effector units.

In some embodiments, the method may include independently positioning the first end effector unit 2402B and the second end effector unit 2402C at respective target locations on the first surface 12 of the target tissue 18. For example, one or more end effector units 2402B, 2402C, 2402D may be positioned using one or more surgical tools positioned at the operative site, such as forceps.

In some embodiments, placing the first ablation component 2402 proximate the first surface 12 of the target tissue 18 may include placing the first ablation component end effector 2402A proximate the first surface 12 of the target tissue 18 while the first ablation component end effector 2402A is in a stowed configuration. In the stowed configuration, the first end effector unit 2402B and the second end effector unit 2402C (and/or the third end effector unit 2402D and further units) may be received substantially within the first ablation component connecting element 2416. The method may include reconfiguring the first ablation component end effector 2402A from the stowed configuration to a deployed configuration. In the deployed configuration, the first end effector unit 2402B and the second end effector unit 2402C (and/or the third end effector unit 2402D and further units) may be disposed substantially outside of the first ablation component connecting element 2416. Reconfiguring the first ablation component 2402 from the stowed configuration to the deployed configuration may include removing the first end effector unit 2402B from the first ablation component connecting element 2416 and/or removing the second end effector unit 2402C from the first ablation component connecting element 2416. Similarly, the third end effector unit 2402D and further units may be removed from the first ablation component connecting element 2416. The method may include, after creating the first lesion 16B and creating the second lesion 16C, reconfiguring the first ablation component end effector 2402A from the deployed configuration to the stowed configuration. The method may include, after reconfiguring the first ablation component end effector 2402A from the deployed configuration to the stowed configuration, withdrawing the first ablation component end effector 2402A from proximate the target tissue 18.

In some embodiments, the method may include reducing the attractive magnetic coupling between the magnetic element 2406B and a cooperating magnetic element, and between the magnetic element 2406C and the cooperating magnetic element by repositioning the cooperating magnetic element relative to its respective end effector housing, generally as described elsewhere herein. For example, the attractive magnetic coupling may be reduced by rotationally and/or translationally repositioning the cooperating magnetic element relative to the respective end effector housing.

In some embodiments, at least one of (i) attractively magnetically coupling the magnetic element 2406B with a cooperating magnetic element, and (ii) attractively magnetically coupling the magnetic element 2106C with the cooperating magnetic element may include rotatably self-orienting the cooperating magnetic element into a magnetically attractive orientation with at least one of the magnetic element 2106B and the magnetic element 2106C. For example, the cooperating magnetic element may be freely rotatable about one or more axes of rotation with various degrees of rotational freedom as discussed elsewhere herein.

In some example embodiments according at least some aspects of the present disclosure, one or more auxiliary electrodes may be used for sensing, stimulating, mapping, and/or pacing, for example. Such sensing, stimulating, mapping, and/or pacing may be conducted, for example, for diagnostic purposes and/or in connection with identifying a target location for a future ablation and/or for assessing the effectiveness of a prior ablation. In some example embodiments, a primary electrode or ablation electrode may be used for non-ablation purposes, such as sensing, stimulating, mapping, and/or pacing, instead of or in addition to one or more auxiliary electrodes. Accordingly, various example methods of using devices comprising one or more electrodes may include operations pertaining to sensing, stimulating, mapping, and/or pacing, using one or more auxiliary and/or primary electrodes, before, after, or separately from delivering ablation energy, such as by delivering radiofrequency energy using a primary electrode. Likewise, any example embodiment described herein as including an electrode may be used for sensing, stimulating, mapping, and/or pacing, using one or more auxiliary and/or primary electrodes, before, after, or separately from delivering ablation energy.

Various example embodiments useful for sensing, stimulating, mapping, and/or pacing may be arranged for use of individual electrodes, pairs of electrodes, and/or three or more electrodes simultaneously and/or sequentially. For example, some devices (e.g., ablation components) configured for sensing, stimulating, mapping, and/or pacing may be coupled to a control unit including one or more external devices configured for sensing, stimulating, mapping, and/or pacing. Such sensing, stimulating, mapping and/or pacing devices may be configured to selectively connect to individual and/or a plurality of electrodes, or such sensing, stimulating, mapping, and/or pacing devices may be configured to connect to all available electrodes. In some example embodiments, sensing, stimulating, mapping, and/or pacing may be performed individually by an epicardial component. That is one or more electrodes on an epicardial component may be used for sensing, stimulating, mapping, and/or pacing. Similarly, in some example embodiments, sensing, stimulating, mapping, and/or pacing may be performed individually by an endocardial component. That is, one or more electrodes on an endocardial component may be used for sensing, stimulating, mapping, and/or pacing.

In some example embodiments, one or more epicardial components may be used cooperatively with one or more endocardial components for sensing, stimulating, mapping, and/or pacing. For example, sensing, stimulating, mapping, and/or pacing may be performed using one or more electrodes of one or more epicardial components in cooperation with one or more electrodes of one or more endocardial components. More generally, sensing, stimulating, mapping, and/or pacing may be performed across the thickness of a target tissue using components positioned on both sides of the target tissue. In some circumstances, cooperatively sensing, stimulating, mapping, and/or pacing on opposite surfaces of a target tissue may provide three dimensional information about a location of interest in the target tissue, such as a potential future ablation lesion location.

Although various example embodiments described herein are referred to as ablation components, these embodiments or similar embodiments may be useful for sensing, stimulating, mapping, and/or pacing in addition to or separately from ablation operations. Further, any component described herein may be constructed without an ablation element, and such component may include one or more electrodes which may be used for sensing, stimulating, mapping, and/or pacing.

Figure 68:
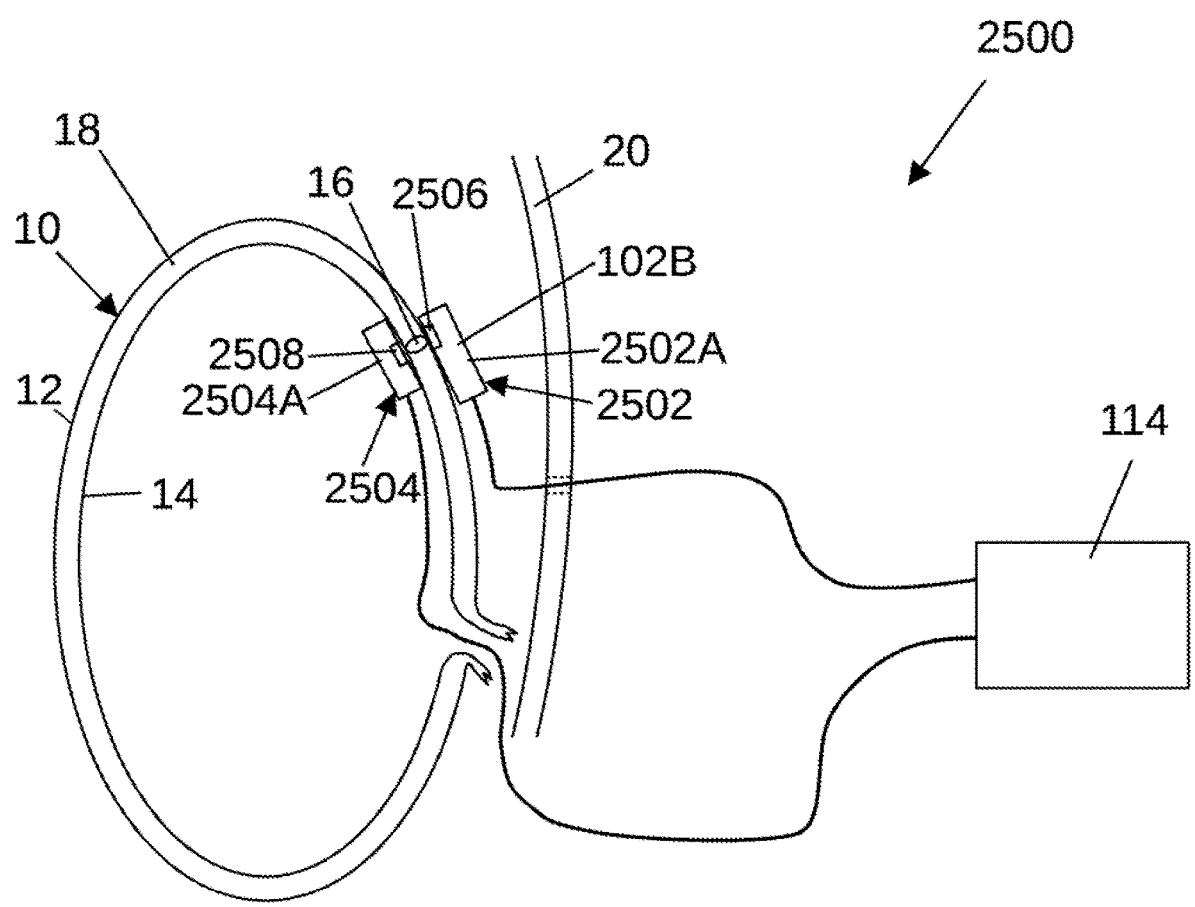
FIG. 68 is a simplified schematic view of a further alternative example ablation system; all in accordance with at least some aspects of the present disclosure.

For example, FIG. 68 is a simplified schematic view of an example system 2500 in use on a heart 10, according to at least some aspects of the present disclosure. The system 2500 and its components may be generally similar in structure and operation to other devices described elsewhere herein, such as the ablation system 100 of FIG. 1, and repeated description is omitted for brevity. Likewise, any feature described in connection with system 2500 may be utilized in connection with any other embodiment described elsewhere herein.

The example system 2500 may include a first component 2502 configured to be positioned on a first side of a target tissue (e.g., the heart wall 18) and/or a second component 2504 configured to be positioned on a second side of the target tissue. Generally, each of the components 2502, 2504 may comprise and/or may be similar to any ablation component described herein. For example and without limitation, in some embodiments, the first component 2502 may comprise an ablation component such as those described herein with reference to FIGS. 2-20 and/or the second ablation component 2504 may comprise an ablation component such as those described herein with reference to FIGS. 21-47. In some embodiments, each of the first component 2502 and the second component 2504 may comprise an ablation component such as those described herein with reference to FIGS. 2-20. In some embodiments, each of the first component 2502 and the second component 2504 may comprise an ablation component such as those described herein with reference to FIGS. 21-47.

Alternatively, and as illustrated in FIG. 68, the first component 2502 and/or the second component 2504 may not include an ablation component and/or a magnetic element. In the illustrated embodiment, the first component may include a first component end effector 2502A configured to be positioned on the first side 12 of a heart tissue (wall) 18. The first component end effector 2502A may include a first component electrode 2506. The second component may include a second component end effector 2504A configured to be positioned on the second side 14 of the heart tissue 18 opposite the first side 12. The second component end effector may include a second component electrode 2508. The first component 2502 and the second component 2504 may be configured for cooperative use of the first component electrode 2506 and the second component electrode 2508 for at least one of sensing, pacing, stimulation, and mapping. As used herein, "cooperative use" may include coordinated use of two or more elements to achieve a result or obtain information that would not be available through use of one of the elements alone, or through use of the two or elements in an uncoordinated manner.

In the illustrated embodiment, the system 2500 may include a control unit 114 configured for cooperative use of the first component electrode 2506 and the second component electrode 2508 for at least one of sensing, pacing, stimulation, and mapping. Cooperative use of the first component electrode 2506 and the second component electrode 2508 for the at least one of sensing, pacing, stimulation, and mapping may include cooperative sensing using the first component electrode 2506 and the second component electrode 2508. Cooperative use of the first component electrode 2506 and the second component electrode 2508 for the at least one of sensing, pacing, stimulation, and mapping may include cooperative pacing using the first component electrode 2506 and the second component electrode 2508. Cooperative use of the first component electrode 2506 and the second component electrode 2508 for the at least one of sensing, pacing, stimulation, and mapping may include cooperative stimulation using the first component electrode 2506 and the second component electrode 2508. Cooperative use of the first component electrode 2506 and the second component electrode 2508 for the at least one of sensing, pacing, stimulation, and mapping may include cooperative mapping using the first component electrode 2506 and the second component electrode 2508.

In some embodiments, cooperative use of the first component electrode 2506 and the second component electrode 2508 for the at least one of sensing, pacing, stimulation, and mapping may include delivery of an electrical current to the heart tissue 18 using one of the first component electrode 2506 and the second component electrode 2508 and detection of at least one electrical parameter associated with the heart tissue 18 using the other of the first component electrode 2506 and the second component electrode 2508.

In the illustrated embodiment, the first component end effector 2502A may be configured to be positioned on an epicardial surface 12 of the heart 10. in some embodiments, the first component end effector 2502A may be configured to be positioned on an 14 endocardial surface of the heart 10. In the illustrated embodiment, the second component end effector 2504A may be configured to be positioned on an epicardial surface 12 of the heart 10. in some embodiments, the second component end effector 2504A may be configured to be positioned on an endocardial surface 14 of the heart 10.

In some example embodiments, at least one of the first component end effector 2502A and the second component end effector 2504A may include an ablation element, such as those described elsewhere herein, which may comprise or may be separate from the electrodes 2506, 2508.

In some example embodiments, the first component end effector 2502A may include a first component magnetic element, such as described elsewhere here. In some example embodiments, the second component end effector 2504A may include a second component magnetic element, such as described elsewhere herein. The first component magnetic element and the second component magnetic element may be configured for cooperative magnetic attraction across the heart tissue as described elsewhere herein.

Some example methods of using a system 2500 may include placing the first component 2502 proximate a first surface 12 of a heart tissue 18, the first component 2502 including a first component end effector 2502A including a first component electrode 2506. The method may include placing a second component 2504 proximate a second surface 14 of the heart tissue 18 opposite the first surface 12, the second component 2504 including a second component end effector 2504A including a second component electrode 2508. The method may include cooperatively using the first component electrode 2506 and the second component electrode 2508 for at least one of sensing, pacing, stimulation, and mapping.

In some embodiments, cooperatively using the first component electrode 2506 and the second component electrode 2508 for the at least one of sensing, pacing, stimulation, and mapping may include delivering an electrical current to the heart tissue 18 using one of the first component electrode 2506 and the second component electrode 2508 and/or detecting at least one electrical parameter associated with the heart tissue 18 using the other of the first component 2506 electrode and the second component electrode 2508.

In some embodiments, the method may include creating a lesion 16 in the heart tissue 18. Creating the lesion 16 in the heart tissue 18 may include creating the lesion 16 in the heart tissue 18 using at least one of the first component end effector 2502A and the second component end effector 2504A. Creating the lesion 16 in the heart tissue 18 using the at least one of the first component end effector 2502A and the second component end effector 2504A may include delivering ablation energy to the heart tissue 18 using at least one of the first component electrode 2506 and the second component electrode 2508.

In some embodiments, cooperatively using the first component electrode 2506 and the second component electrode 2508 for the at least one of sensing, pacing, stimulation, and mapping may include identifying a target location in the heart tissue 18 for a future ablation. In some embodiments, cooperatively using the first component electrode and the second component electrode for the at least one of sensing, pacing, stimulation, and mapping may include assessing an ablation.

It is an aspect of the present disclosure to provide a first ablation component 102, 200 configured for use on a first side 12 of a target tissue 18 in connection with a cooperating second ablation component 104 on an opposite, second side 14 of the target tissue 18. The first ablation component 102, 200, 900 may include a first ablation component end effector 102A, 202, 904 configured to be positioned on a first side 12 of a target tissue 18. The first ablation component end effector 102A, 202, 904 may include a first ablation component end effector housing 102B, 232, a tissue contacting surface 224, 908 configured to engage the first side 12 of the target tissue 18, and/or a first ablation component ablation element 106, 228, the first ablation component ablation element 106, 228 being selectively operable to cause ablation of the target tissue 18, and/or a first ablation component permanent magnet 110, 220, 902 repositionably disposed relative to the first ablation component end effector housing 102B, 232. The first ablation component permanent magnet 110, 220, 902 may be repositionable relative to the first ablation component end effector housing 102B, 232 between an engaged configuration and a disengaged configuration. The first ablation component permanent magnet 110, 220, 902 may define a magnetic axis 236, 910. The first ablation component 102, 200, 900 may include a mechanical linkage 234 operatively coupled to reposition the first ablation component permanent magnet 110, 220, 902 relative to the first ablation component end effector housing 102B, 232 between the engaged configuration and the disengaged configuration. In the engaged configuration, the first ablation component permanent magnet 110, 220, 902 may be positioned to magnetically attract a cooperating second ablation component magnetic element 112 positioned on an opposite, second side 14 of the target tissue 18 substantially adjacent the tissue contacting surface 224. In the disengaged configuration, the first ablation component permanent magnet 110, 220, 902 may not be positioned to magnetically attract the cooperating second ablation component magnetic element 112 positioned on the opposite, second side 14 of the target tissue 18 substantially adjacent the tissue contacting surface 224. At least one of a location of the first ablation component permanent magnet 110, 220, 902 relative to the first ablation component end effector housing 102B, 232 and an orientation of the magnetic axis 236, 910 relative to the first ablation component end effector housing 102B, 232 may differ between the engaged configuration and the disengaged configuration.

In a detailed embodiment, the first ablation component permanent magnet 110, 220 may be translationally repositionable relative to the first ablation component end effector housing 102B, 232 between the engaged configuration and the disengaged configuration.

In a detailed embodiment, the first ablation component permanent magnet 902 may be rotationally repositionable relative to the first ablation component end effector housing between the engaged configuration and the disengaged configuration.

It is an aspect of the present disclosure to provide a first ablation component 2402 for use on a first side 12 of a target tissue 18 in connection with a cooperating second ablation component 104 on an opposite, second side 14 of the target tissue 18. The first ablation component 2402 may include a first ablation component end effector 2402A operatively coupled to a first ablation component connecting element 2416. The first ablation component end effector 2402A may include a first end effector unit 2402B including a first end effector unit ablation element, a second end effector unit 2402C including a second end effector unit ablation element, a first end effector unit connecting element 2416B operatively coupling the first end effector unit and the first ablation component connecting element 2416, and/or a second end effector unit connecting element 2416C operatively coupling the first end effector unit 2402B and the second end effector unit 2402C. The first end effector unit 2402B and the second end effector unit 2402C may be independently positionable.

In a detailed embodiment, the first ablation component end effector 2402 may include a third end effector unit 2402D and a third end effector unit connecting element 2416D operatively coupling the second end effector unit 2402C and the third end effector unit 2402D. The first end effector unit 2402B, the second end effector unit 2402C, and the third end effector 2402D unit may be independently positionable.

In a detailed embodiment, the first end effector unit 2402B and the second end effector unit 2402C may be substantially identical. In another detailed embodiment, the first end effector unit 2402B may differ from the second end effector unit 2402C.

In a detailed embodiment, the first end effector unit 2402B may include a first end effector unit magnetic element arranged for cooperative magnetic attraction with a second ablation component magnetic element 112 of the cooperating second ablation component 104. The second end effector unit 2402C may include a second end effector unit magnetic element arranged for cooperative magnetic attraction with the second ablation component magnetic element 112.

In a detailed embodiment, at least one of the first end effector unit magnetic element and the second end effector unit magnetic element includes an axially magnetized, generally cylindrical permanent magnet.

In a detailed embodiment, the first end effector unit ablation element may include a first end effector unit ablation electrode 2406B and the second end effector unit ablation element may include a second end effector unit ablation electrode 2406C. In some embodiments, the first end effector unit ablation electrode and the second end effector unit ablation electrode may be electrically connected in parallel. In some embodiments, the first end effector unit ablation electrode may include a first end effector unit magnetic element arranged for cooperative magnetic attraction with a second ablation component magnetic element of the cooperating second ablation component. The second end effector unit ablation electrode may include a second end effector unit magnetic element arranged for cooperative magnetic attraction with the second ablation component magnetic element.

In a detailed embodiment, the first end effector unit connecting element may include a first electrical conductor 2428A electrically interposing a proximally disposed electrical connector 2428 and the first end effector unit ablation electrode 2406B. The second end effector unit connecting element 2416C may include a second electrical conductor 2428B electrically interposing the first end effector unit ablation electrode 2406B and the second end effector unit ablation electrode 2406C.

In a detailed embodiment, the first ablation component end effector 2402 may include a third end effector unit 2402D and third end effector unit connecting element 2416D operatively coupling the second end effector unit 2402C and the third end effector unit 2402D. The first end effector unit 2402B, the second end effector unit 2402C, and the third end effector 2402D unit may be independently positionable. The third end effector unit connecting element 2416D may include a third electrical conductor 2428C electrically interposing the second end effector unit ablation electrode 2406C and the third end effector unit ablation electrode 2406D.

In a detailed embodiment, the first ablation component end effector 2402 may be reconfigurable between a stowed configuration and a deployed configuration. In the stowed configuration, the first end effector unit 2402B and the second end effector unit 2402C may be received substantially within the first ablation component connecting element 2416. In the stowed configuration, the first end effector unit connecting element 2416B and the second end effector unit connecting element 2416C may be received substantially within the first ablation component connecting element 2416. In the deployed configuration, the first end effector unit 2402B and the second end effector unit 2402C may be disposed substantially outside of the first ablation component connecting element 2416. In the deployed configuration, the first end effector unit connecting element 2416B may extend at least partially within the first ablation component connecting element 2416 and at least partially outside the first ablation component connecting element 2416. In the deployed configuration, the second end effector unit connecting element 2416C may be disposed substantially outside of the first ablation component connecting element 2416.

In a detailed embodiment, an ablation system 2400 may include the first ablation component 2402 and the second ablation component 104. The second ablation component 104 may include a second ablation component permanent magnet 112 repositionably disposed relative to a second ablation component end effector housing between an engaged configuration and a disengaged configuration.

In a detailed embodiment, the first end effector unit 2402B may include a first end effector unit magnetic element arranged for cooperative magnetic attraction with a second ablation component magnetic element 112 of the cooperating second ablation component 104. The second end effector unit 2402C may include a second end effector unit magnetic element arranged for cooperative magnetic attraction with the second ablation component magnetic element 112. The second ablation component may include a second ablation component permanent magnet that is configured to rotatably self-orient into a magnetically attractive orientation with at least one of the first end effector unit magnetic element and the second end effector unit magnetic element.

It is an aspect of the present disclosure to provide an ablation system 100 including a first ablation component 102 and a second ablation component 104. The first ablation component 102 may include any ablation component described herein, and may include a first ablation component magnetic element 110. The second ablation component 104 may include a second ablation component connecting element 118 and a second ablation component end effector 104A extending distally from the second ablation component connecting element 118. In some embodiments, such as the ablation system 2400, the second ablation component end effector 104, 2402A may include a plurality of independently positionable end effector units 2402B, 2402C, 2402D coupled in a daisy chain arrangement.

In a detailed embodiment, each end effector unit 2402B, 2402C, 2402D may include a respective end effector magnetic element. The second ablation component magnetic elements may be configured for cooperative magnetic attraction with the first ablation component magnetic element 110.

It is an aspect of the present disclosure to provide a method of creating a lesion 16 in a target tissue 18, including placing a second ablation component 104 proximate a second surface 14 of a target tissue. The second ablation component 104 may include a second ablation component magnetic element 112. The method may include placing a first ablation component 102, 2402 proximate a first surface 12 of the target tissue. The first ablation component 102, 2402 may include a first ablation component connecting element 116, 2416 and a first ablation component end effector 102A, 2402A extending distally from the first ablation component connecting element 116, 2416. The first ablation component end effector 2402A may include a first end effector unit 2402B and a second end effector unit 2402C. The first end effector unit 2402B and the second end effector unit 2402C may be independently positionable and may be coupled in a daisy chain arrangement. The first end effector unit 2402B may include a first end effector unit magnetic element and a first end effector unit ablation element. The second end effector 2402C unit may include a second end effector unit magnetic element and a second end effector unit ablation element. The method may include attractively magnetically coupling the first end effector unit magnetic element with the second ablation component 104 magnetic element 112 and attractively magnetically coupling the second end effector unit magnetic element with the second ablation component 104 magnetic element 112. The method may include creating a first lesion 16B in the target tissue using the first end effector unit ablation element and creating a second lesion 16C in the target tissue using the second end effector unit ablation element.

In a detailed embodiment, the first lesion 16B and the second lesion 16C may overlap and form a contiguous composite lesion 16E. Creating the first lesion 16B and the creating the second lesion 16C operations may be performed simultaneously or sequentially.

In a detailed embodiment, the second ablation component 104 comprises a second ablation component ablation element 108. Creating the first lesion 16B in the target tissue 18 using the first end effector unit ablation element comprises creating the first lesion 16B in the target tissue 18 by applying bipolar radiofrequency ablation energy to the target tissue 18 using the first end effector unit ablation element and the second ablation component ablation element 108.

In a detailed embodiment, creating the second lesion 16C in the target tissue 18 using the second end effector unit ablation element comprises creating the second lesion 16C in the target tissue 18 by applying bipolar radiofrequency ablation energy to the target tissue using the second end effector unit ablation element and the second ablation component ablation element 108.

In a detailed embodiment, the method may include independently positioning the first end effector unit 2402B and the second end effector unit 2402C at respective target locations on the first surface 12 of the target tissue 18.

In a detailed embodiment, placing the first ablation component 2402 proximate the first surface 12 of the target tissue 18 comprises placing the first ablation component end effector 2402A proximate the first surface 12 of the target tissue 18 while the first ablation component end effector 2402A is in a stowed configuration. In the stowed configuration, the first end effector unit 2402B and the second end effector unit 2402C may be received substantially within the first ablation component connecting element 2416.

In a detailed embodiment, the method may include reconfiguring the first ablation component end effector 2402A from the stowed configuration to a deployed configuration. In the deployed configuration, the first end effector unit 2402B and the second end effector unit 2402C may be disposed substantially outside of the first ablation component connecting element 2416. Reconfiguring the first ablation component 2402 from the stowed configuration to the deployed configuration may include removing the first end effector unit 2402B from the first ablation component connecting element 2416 and removing the second end effector unit 2402C from the first ablation component connecting element 2416.

In a detailed embodiment, the method may include, after creating the first lesion 16B and creating the second lesion 16C, reconfiguring the first ablation component end effector 2402A from the deployed configuration to the stowed configuration. The method may include, after reconfiguring the first ablation component end effector 2402A from the deployed configuration to the stowed configuration, withdrawing the first ablation component end effector 2402A from proximate the target tissue 18.

In a detailed embodiment, the method may include reducing the attractive magnetic coupling between the first end effector unit magnetic element and the second ablation component magnetic element 112 and between the second end effector unit magnetic element and the second ablation component magnetic element 112 by repositioning the second ablation component magnetic element 112 relative to a second ablation component end effector housing 104A.

In a detailed embodiment, attractively magnetically coupling the first end effector unit magnetic element with the second ablation component magnetic element 112 and/or attractively magnetically coupling a second end effector unit magnetic element with the second ablation component magnetic element 112 comprises rotatably self-orienting the second ablation component magnetic element 112 into a magnetically attractive orientation with at least one of the first end effector unit magnetic element and the second end effector unit magnetic element.

It is an aspect of the present disclosure to provide a method, including placing a first ablation component 102 proximate a first surface 12 of a target tissue 18, the first ablation component 102 comprising a first ablation component end effector 102A comprising a first ablation component end effector housing 102B, a first ablation component permanent magnet 110, and a first ablation component ablation element 106. The method may include placing a second ablation component 104 proximate a second surface 14 of the target tissue 18, the second ablation component 104 comprising a second ablation component magnetic element 112. The method may include positioning one or both of the first ablation component end effector 102A or the second ablation component 104 using attractive magnetic coupling between the first ablation component permanent magnet 110 and the second ablation component magnetic element 112. The method may include creating a first lesion 16 in the target tissue using the first ablation component ablation element 106. The method may include reducing the attractive magnetic coupling between the first ablation component permanent magnet 110 and the second ablation component magnetic 112 element by repositioning the first ablation component permanent magnet 110 relative to the first ablation component end effector housing 102B. In some embodiments, the second ablation component may include a plurality of independently positionable end effector units 2402B, 2402C, 2402D coupled in a daisy chain arrangement, each of the end effector units 2402B, 2402C, 2402D comprising a respective end effector unit magnetic element 2406B, 2406C, 2406D. The second ablation component magnetic element 112 may include the end effector magnetic elements. Using attractive magnetic coupling between the first ablation component permanent magnet 110 and the second ablation component magnetic element 112 may include using attractive magnetic coupling between the first ablation component permanent magnet 110 and respective end effector unit magnetic elements 2406B, 2406C, 2406D of individual ones of the plurality of independently positionable end effector units 2402B, 2402C, 2402D.

In a detailed embodiment, each of the end effector units 2402B, 2402C, 2402D comprises a respective end effector unit ablation element 2406B, 2406C, 2406D. Creating the first lesion 16 in the target tissue 18 using the first ablation component ablation element 106 may include applying bipolar radiofrequency ablation energy to the first ablation component ablation element 106 and at least one of the end effector unit ablation elements 2406B, 2406C, 2406D.

It is an aspect of the present disclosure to provide a method including placing a first ablation component 102 on a first surface 12 of a target tissue 18, the first ablation component 102 comprising a first ablation component end effector 102A comprising a first ablation component end effector housing 102B and a first ablation component magnetic element 110. The method may include placing a second ablation component 104 on a second surface 14 of the target tissue 18, the second ablation component 104 comprising a second ablation component ablation element 108 and a second ablation component permanent magnet 112 which is freely rotatable about at least one axis of rotation relative to a second ablation component end effector housing 104B. The method may include self-orienting the second ablation component permanent magnet 112 into a magnetically attractive orientation with the first ablation component magnetic element 110 by allowing the second ablation component permanent magnet 112 to rotate about the at least one axis of rotation. The method may include positioning one or both of the first ablation component end effector 102A or the second ablation component end effector 104A using attractive magnetic coupling between the first ablation component magnetic element 110 and the second ablation component permanent magnet 112. The method may include creating a first lesion 16 in the target tissue 18 using the second ablation component ablation element 108. In some embodiments, the first ablation component end effector housing 102B may include a plurality of independently positionable end effector units 2402B, 2402C, 2402D coupled in a daisy chain arrangement, each of the end effector units 2402B, 2402C, 2402D comprising a respective end effector unit magnetic element 2406B, 2406C, 2406D. The first ablation component magnetic element 110 may include the end effector magnetic elements 2406B, 2406C, 2406D. Using attractive magnetic coupling between the first ablation component magnetic element 110 and the second ablation component permanent magnet 112 may include using attractive magnetic coupling between the second ablation component permanent magnet 112 and respective end effector unit magnetic elements 2406B, 2406C, 2406D of individual ones of the plurality of independently positionable end effector units 2402B, 2402C, 2402D.

In a detailed embodiment, each of the end effector units 2402B, 2402C, 2402D comprises a respective end effector unit ablation element 2406B, 2406C, 2406D. Creating the first lesion 16 in the target tissue 18 using the second ablation component ablation element 108 comprises applying bipolar radiofrequency ablation energy to the second ablation component ablation element 108 and at least one of the end effector unit ablation elements 2406B, 2406C, 2406D.

It is an aspect of the present disclosure to provide a method of making an ablation system, an ablation component, and/or any constituent component thereof as described herein. For example, a method of making an ablation system may include providing a first ablation component and a second ablation component as described herein. A method of making an ablation component may include assembling an end effector and a connecting element as described herein. A method of making an end effector may include assembling a housing, a magnetic element, and an ablation element as described herein. Generally, such methods may involve any exemplary embodiments described herein, in any combination.

It will be appreciated that any example ablation components described herein may be constructed using suitable rigid, flexible, malleable, and/or steerable connecting elements.

Various example embodiments including a plurality of electrodes are described herein. And, more generally, any embodiment described herein may be provided with multiple electrodes, unless explicitly stated otherwise. While some embodiments may have been described in connection with particular exemplary uses of particular individual electrodes, it is to be understood that any electrode on any embodiment may be used for any purpose, regardless of how it may be described in a specific example. For example, an electrode described as a primary or ablation electrode may be used for pacing, stimulating, mapping, and/or sensing in some circumstances. Similarly, an electrode described as an auxiliary or pacing, stimulating, mapping, and/or sensing electrode may be used for ablation in some circumstances.

It is within the scope of this disclosure to conduct procedures involving any portions of the heart using apparatus and/or methods disclosed herein. For example, procedures involving the right atrium may be performed in connection with treatment for inappropriate sinus tachycardia (e.g., crista line, inferior vena cava, and/or superior vena cava), atrial fibrillation (e.g., Cox maze lesions—right side), and/or Wolff-Parkinson-White Syndrome. Procedures involving the right ventricle may be performed in connection with treatment for ventricular tachycardia (e.g., right ventricle posterior wall, right ventricle lateral free wall, right ventricle anterior, septum, right ventricle papillary muscles, and/or right ventricle outflow tract), partial ventricular contractors (e.g., right ventricle outflow tract septum, basal right ventricle, and/or right ventricle outflow tract free wall), and/or Brugada Syndrome (e.g., right ventricle outflow tract), for example. Procedures involving the left atrium may be performed in connection with treatment for atrial fibrillation (e.g., ligament of Marshall, roof and floor lines, left atrium posterior wall, isthmus line, and/or autonomics (ganglionated plexus)) and/or left atrial appendage isolation (e.g., left atrial appendage ostium). Procedures involving the left ventricle may be performed in connection with syncope (e.g., autonomics (ganglionated plexus)), atrial tachycardia (e.g., anywhere in the left ventricle), atrial flutter (e.g., mitral valve), Wolff-Parkinson-White Syndrome (e.g., atrioventricular groove), partial ventricular contractions (e.g., left ventricle outflow tract and/or aortic root), hypertension (e.g., anywhere in the left ventricle), and/or ventricular tachycardia (e.g., left ventricle posterior wall, left ventricle lateral free wall, left ventricle anterior, septum, left ventricle papillary muscles, and/or left ventricle summit), for example. Procedures involving the right ventricle/left ventricle septum may be performed in connection with ventricular tachycardia (e.g., combined right ventricle and left ventricle lesion), for example. It will be understood that the foregoing list is merely exemplary and is not to be considered limiting.

Some example embodiments described herein and illustrated in the accompanying drawings may include and/or may be utilized in connection with commercially available devices or components thereof. For example, some sheaths, catheters, etc. described above may include commercially available surgical devices or components thereof and/or may include modified versions of commercially available surgical devices or components thereof.

Unless specifically indicated, it will be understood that the description of any structure, function, and/or methodology with respect to any illustrative embodiment herein may apply to any other illustrative embodiments. More generally, it is within the scope of the present disclosure to utilize any one or more features of any one or more example embodiments described herein in connection with any other one or more features of any other one or more other example embodiments described herein. Accordingly, any combination of any of the features or embodiments described herein is within the scope of this disclosure.

It is an aspect of the present disclosure to provide any ablation system described herein, as well as an ablation system comprising any one or more ablation components, or constituent elements thereof, described herein. Further, it is an aspect of the present disclosure to separately provide, alone or in any combination, any one or more constituent elements of any ablation system described herein. For example, it is an aspect of the present disclosure to separately provide any ablation component described herein. Similarly, it is an aspect of the present disclosure to separately provide, alone or in any combination, any one or more constituent elements of any ablation component, or any constituent element thereof, described herein. For example, it is an aspect of the present disclosure to separately provide any end effector, connecting element, handle, and/or other constituent element of any ablation component described herein.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

What is claimed is:

1. An ablation system, comprising:
 a first ablation component comprising
  a first ablation component end effector configured to be positioned on a first side of a target tissue, the first ablation component end effector comprising
   a first ablation component end effector housing,
   a first ablation component tissue contacting portion configured to engage the first side of the target tissue,
   a first ablation component ablation element, wherein the first ablation component ablation element is selectively operable to cause ablation of the target tissue, and
   a first ablation component permanent magnet, wherein the first ablation component permanent magnet is translationally repositionable relative to the first ablation component end effector housing between an engaged configuration and a disengaged configuration; and
  a mechanical linkage operatively coupled to translationally reposition the first ablation component permanent magnet relative to the first ablation component end effector housing between the engaged configuration and the disengaged configuration; and
 a second ablation component configured for cooperative operation with the first ablation component, the second ablation component comprising
  a second ablation component end effector configured to be positioned on a second side of the target tissue opposite the first side of the target tissue, the second ablation component end effector comprising
   a second ablation component end effector housing,
   a second ablation component tissue contacting portion configured to engage the second side of the target tissue,
   a second ablation component ablation element, wherein the second ablation component is selectively operable to cause ablation of the target tissue, and
   a second ablation component permanent magnet, wherein the second ablation component permanent magnet is freely rotatable about at least one axis of rotation relative to the second ablation component end effector housing without substantial translation relative to the second ablation component end effector housing, and wherein the second ablation component permanent magnet is configured to rotatably self-orient into a magnetically attractive orientation with the first ablation component permanent magnet;
 wherein, in the engaged configuration, the first ablation component permanent magnet is configured to magnetically attract the second ablation component permanent magnet with the second ablation component end effector positioned on the second side of the target tissue substantially adjacent the first ablation component tissue contacting portion; and
 wherein, in the disengaged configuration, with the second ablation component end effector positioned on the second side of the target tissue substantially adjacent the first ablation component tissue contacting portion, magnetic attraction between the first ablation component permanent magnet and the second ablation component permanent magnet is reduced as compared to the engaged configuration.

2. The ablation system of claim 1, wherein the first ablation component permanent magnet is translationally repositionable relative to the first ablation component end effector housing between the engaged configuration and the disengaged configuration without substantial rotation.

3. The ablation system of claim 1,
 wherein the first ablation component end effector comprises at least one vacuum port disposed on the first ablation component tissue contacting portion, the vacuum port configured to be fluidically coupled to a vacuum source; and
 wherein the vacuum port is configured so that, upon application of vacuum to the vacuum port, the vacuum port releasably secures the first ablation component tissue contacting portion to the target tissue.

4. The ablation system of claim 1,
 wherein the first ablation component ablation element comprises a first ablation component ablation electrode; and wherein the first ablation component is configured to deliver radio frequency ablation energy to the target tissue via the first ablation component ablation electrode.

5. The ablation system of claim 1,
wherein the first ablation component end effector comprises an outwardly extending, generally circumferential first ablation component end effector skirt; and
wherein the first ablation component tissue contacting portion comprises the first ablation component end effector skirt.

6. The ablation system of claim 5, wherein the first ablation component ablation element is disposed within a perimeter at least partially defined by the first ablation component end effector skirt.

7. The ablation system of claim 1, the first ablation component end effector comprises at least one opening configured to deliver an irrigation fluid to the first side of the target tissue proximate the first ablation component ablation element.

8. The ablation system of claim 1,
wherein the first ablation component ablation element comprises a first ablation component ablation electrode;
wherein the first ablation component ablation electrode comprises at least one internal channel; and
wherein the at least one internal channel is operatively coupled to a source of cooling fluid.

9. The ablation system of claim 1,
wherein the first ablation component comprises a first ablation component connecting element;
wherein the first ablation component end effector is disposed distally on the first ablation component connecting element;
wherein the first ablation component comprises a first ablation component handle disposed proximally on the first ablation component connecting element; and
wherein the first ablation component handle comprises a first ablation component magnet actuator operatively connected to the first ablation component permanent magnet via the mechanical linkage to reposition the first ablation component permanent magnet between the engaged configuration and the disengaged configuration.

10. The ablation system of claim 1, wherein the first ablation component comprises at least one first ablation component auxiliary electrode.

11. The ablation system of claim 1, wherein the second ablation component permanent magnet is freely rotatable about three axes of rotation relative to the second ablation component end effector housing.

12. The ablation system of claim 1, wherein the second ablation component comprises at least one second ablation component auxiliary electrode.

13. The ablation system of claim 1,
wherein the second ablation component end effector housing is at least partially generally spherical; and
wherein the second ablation component end effector housing comprises a distal portion constructed from a conductive material and a proximal portion constructed from a non-conductive material.

14. The ablation system of claim 1,
wherein the second ablation component comprises a second ablation component connecting element;
wherein the second ablation component end effector is disposed distally on the second ablation component connecting element; and
wherein the second ablation component connecting element comprises
a generally tubular first connecting element, the first connecting element comprising a first connecting element distal portion;
a second connecting element operatively coupled to the first connecting element distal portion, wherein the second ablation component end effector is disposed distally on the second connecting element; and
an engagement element configured to selectively engage the second ablation component end effector with the first connecting element distal portion;
wherein the second connecting element is selectively repositionable relative to the first connecting element distal portion between (i) a retracted configuration in which the second connecting element is disposed substantially within the first connecting element and the engagement element operatively couples the second ablation component end effector and the first connecting element distal portion, and (ii) a deployed configuration in which at least a portion of the second connecting element extends from the first connecting element distal portion and the engagement element is disengaged from at least one of the second ablation component end effector or the first connecting element distal portion.

15. The ablation system of claim 14, wherein the second connecting element portion has greater flexibility than the first connecting element distal portion.

16. The ablation system of claim 14, further comprising a second ablation component handle disposed proximally on the first connecting element, the second ablation component handle comprising a deployment actuator operable to reposition the second connecting element relative to the first connecting element distal portion.

17. The ablation system of claim 16,
wherein the first connecting element distal portion is steerable; and
wherein the second ablation component handle comprises a steering actuator operable to steer the first connecting element distal portion.

18. The ablation system of claim 14,
wherein the engagement element is disposed at a distal end of the first connecting element distal portion; and
wherein, in the retracted configuration, the engagement element is configured to receive at least a portion of the end effector therein.

19. The ablation system of claim 18, wherein the engagement element comprises a distally oriented opening.

20. A method of creating a lesion in a target tissue, the method comprising:
placing a first ablation component proximate a first surface of a target tissue, the first ablation component comprising a first ablation component end effector comprising a first ablation component end effector housing, a first ablation component permanent magnet which is translationally repositionable within the first ablation component end effector housing, and a first ablation component ablation element;
placing a second ablation component proximate a second surface of the target tissue opposite the first surface of the target tissue, the second ablation component comprising a second ablation component end effector comprising a second ablation component end effector housing, a second ablation component permanent magnet which is freely rotatable about at least one axis of rotation relative to the second ablation component end effector housing, and a second ablation component ablation element;

self-orienting the second ablation component permanent magnet into a magnetically attractive orientation with the first ablation component permanent magnet by allowing the second ablation component permanent magnet to rotate about the at least one axis of rotation without substantial translation relative to the second ablation component end effector housing;

positioning one or both of the first ablation component end effector and the second ablation component end effector on the target tissue using attractive magnetic coupling between the first ablation component permanent magnet and the second ablation component permanent magnet;

creating a first lesion in the target tissue using at least one of the first ablation component ablation element and the second ablation component ablation element; and reducing the attractive magnetic coupling between the first ablation component permanent magnet and the second ablation component permanent magnet by translationally repositioning the first ablation component permanent magnet within the first ablation component end effector housing from an engaged configuration to a disengaged configuration.

21. The method of claim 20, further comprising removing at least one of the first ablation component end effector and the second ablation component end effector from the target tissue.

22. The method of claim 20, wherein translationally repositioning the first ablation component permanent magnet within the first ablation component end effector housing comprises translationally repositioning the first ablation component permanent magnet within the first ablation component end effector housing without substantial rotation of the first ablation component permanent magnet relative to the first ablation component end effector housing.

23. The method of claim 20, wherein translationally repositioning the first ablation component permanent magnet within the first ablation component end effector housing comprises translationally repositioning the first ablation component permanent magnet along a longitudinal axis of the first ablation component permanent magnet.

24. The method of claim 20, wherein translationally repositioning the first ablation component permanent magnet within the first ablation component end effector housing comprises translationally repositioning the first ablation component permanent magnet from substantially laterally adjacent to a first ablation component tissue contacting portion of the first ablation component end effector housing to substantially not laterally adjacent to the first ablation component tissue contacting portion.

25. The method of claim 20,
wherein the first ablation component comprises a first ablation component connecting element, wherein the first ablation component end effector is disposed distally on the first ablation component connecting element;
wherein the first ablation component comprises a first ablation component handle disposed proximally on the first ablation component connecting element;
wherein the first ablation component handle comprises a first ablation component magnet actuator operatively connected to the first ablation component permanent magnet to translationally reposition the first ablation component permanent magnet within the first ablation component end effector housing between the engaged configuration and the disengaged configuration; and
wherein translationally repositioning the first ablation component permanent magnet within the first ablation component end effector housing from the engaged configuration to the disengaged configuration comprises translationally repositioning the first ablation component permanent magnet within the first ablation component end effector housing from the engaged configuration to the disengaged configuration by operating the first ablation component magnet actuator.

26. The method of claim 20, further comprising securing the first ablation component end effector to the target tissue by applying vacuum to a vacuum port of the first ablation component end effector.

27. The method of claim 20,
wherein the first ablation component ablation element comprises a first ablation component ablation electrode;
wherein the second ablation component ablation element comprises a second ablation component ablation electrode; and
wherein creating the first lesion in the target tissue using the at least one of the first ablation component ablation element and the second ablation component ablation element comprises creating the first lesion in the target tissue by applying bipolar radiofrequency energy to the target tissue using the first ablation component ablation element and the second ablation component ablation element.

28. The method of claim 20,
wherein the first ablation component comprises at least one electrode; and
wherein the method comprises at least one of pacing, sensing, stimulating, and mapping using the at least one electrode.

29. The method of claim 28,
wherein the at least one electrode comprises at least one of a first ablation component ablation electrode and a first ablation component auxiliary electrode; and
wherein the at least one of pacing, sensing, stimulating, and mapping using the at least one electrode comprises at least one of pacing, sensing, stimulating, and mapping using the at least one of the first ablation component ablation electrode and the first ablation component auxiliary electrode.

30. The method of claim 20, wherein placing the first ablation component proximate the first surface of the target tissue comprises steering a distal portion of a first ablation component connecting element, the first ablation component end effector disposed distally on the first ablation component connecting element.

31. The method of claim 20,
wherein the second ablation component permanent magnet is freely rotatable about three axes of rotation relative to the second ablation component end effector housing; and
wherein self-orienting the second ablation component permanent magnet into the magnetically attractive orientation with the first ablation component permanent magnet comprises allowing the second ablation component permanent magnet to rotate about the three axes of rotation.

32. The method of claim 31,
wherein the second ablation component permanent magnet comprises a generally spherical second ablation component permanent magnet;

wherein the second ablation component end effector housing comprises a generally spherical interior; and wherein allowing the second ablation component permanent magnet to rotate about the three axes of rotation comprises allowing the generally spherical second ablation component permanent magnet to rotate about the three axes of rotation within the generally spherical interior of the second ablation component end effector housing.

33. The method of claim 20, wherein positioning the one or both of the first ablation component end effector and the second ablation component end effector on the target tissue comprises engaging a generally bulbous tissue contacting surface of the second ablation component end effector with the second surface of the target tissue.

34. The method of claim 20,
wherein the second ablation component comprises at least one electrode; and
wherein the method comprises at least one of pacing, sensing, stimulating, and mapping using the at least one electrode.

35. The method of claim 34,
wherein the at least one electrode comprises at least one of a second ablation component ablation electrode and a second ablation component auxiliary electrode; and
wherein the at least one of pacing, sensing, stimulating, and mapping using the at least one electrode comprises at least one of pacing, sensing, stimulating, and mapping using the at least one of the second ablation component ablation electrode and the second ablation component auxiliary electrode.

36. The method of claim 20, wherein placing the second ablation component proximate the second surface of the target tissue comprises steering a distal portion of a second ablation component connecting element, the second ablation component end effector disposed distally on the second ablation component connecting element.

37. The method of claim 20,
wherein the second ablation component comprises a second ablation component connecting element, the second ablation component connecting element comprising a generally tubular first connecting element comprising a first connecting element distal portion, and a second connecting element operatively coupled to the first connecting element distal portion;
wherein the second ablation component end effector is disposed distally on the second connecting element; and wherein the method further comprises repositioning the second connecting element and the second ablation component end effector from a retracted configuration in which the second connecting element is disposed substantially within the first connecting element to a deployed configuration in which at least a portion of the second connecting element extends from the first connecting element distal portion.

38. The method of claim 37, wherein creating the first lesion in the target tissue using the at least one of the first ablation component ablation element and the second ablation component ablation element is performed while the second connecting element and the second ablation component end effector are in the deployed configuration.

39. The method of claim 37,
wherein the second ablation component comprises a second ablation component handle disposed proximally on the first connecting element, the second ablation component handle comprising a deployment actuator operable to reposition the second connecting element relative to the first connecting element distal portion; and
wherein repositioning the second connecting element and the second ablation component end effector from the retracted configuration to the deployed configuration comprises operating the deployment actuator.

40. The method of claim 37, wherein the method further comprises repositioning the second connecting element and the second ablation component end effector from the deployed configuration to the retracted configuration.

41. The method of claim 37, wherein repositioning the second connecting element and the second ablation component end effector from the retracted configuration to the deployed configuration comprises disengaging the second ablation component end effector from an engagement element configured to selectively engage the second ablation component end effector with the first connecting element distal portion.

42. The method of claim 41, wherein repositioning the second connecting element and the second ablation component end effector from the deployed configuration to the retracted configuration comprises engaging the second ablation component end effector with the engagement element.

43. The method of claim 42, further comprising discontinuing applying vacuum to the vacuum port.

\* \* \* \* \*